(12) United States Patent
Do et al.

(10) Patent No.: US 10,874,750 B2
(45) Date of Patent: Dec. 29, 2020

(54) GENE THERAPY CONSTRUCTS AND METHODS OF USE

(71) Applicant: Amicus Therapeutics, Inc., Cranbury, NJ (US)

(72) Inventors: Hung Do, Cranbury, NJ (US); Steven Tuske, Cranbury, NJ (US); Russell Gotschall, Cranbury, NJ (US); Ce Feng Liu, Cranbury, NJ (US)

(73) Assignee: Amicus Therapeutics, Inc., Cranbury, NJ (US)

( * ) Notice: Subject to any disclaimer, the term of this patent is extended or adjusted under 35 U.S.C. 154(b) by 0 days.

(21) Appl. No.: 16/399,979

(22) Filed: Apr. 30, 2019

(65) Prior Publication Data

US 2019/0343968 A1    Nov. 14, 2019

Related U.S. Application Data

(60) Provisional application No. 62/744,068, filed on Oct. 10, 2018, provisional application No. 62/688,640, filed on Jun. 22, 2018, provisional application No. 62/664,741, filed on Apr. 30, 2018.

(51) Int. Cl.

| | |
|---|---|
| *A61K 48/00* | (2006.01) |
| *C07K 16/40* | (2006.01) |
| *C12N 15/52* | (2006.01) |
| *C12N 15/86* | (2006.01) |
| *C07K 16/38* | (2006.01) |
| *C07K 19/00* | (2006.01) |

(52) U.S. Cl.
CPC .......... *A61K 48/0066* (2013.01); *C07K 16/38* (2013.01); *C07K 16/40* (2013.01); *C07K 19/00* (2013.01); *C12N 15/52* (2013.01); *C12N 15/86* (2013.01); *C07K 2317/92* (2013.01); *C07K 2319/02* (2013.01); *C07K 2319/03* (2013.01); *C12N 2840/105* (2013.01); *C12Y 301/02022* (2013.01)

(58) Field of Classification Search
CPC .............. A61K 48/005; A61K 48/0066; A61K 48/0075; C07K 14/65; C07K 16/38; C07K 16/40; C12N 15/86
See application file for complete search history.

(56) References Cited

U.S. PATENT DOCUMENTS

| | | |
|---|---|---|
| 6,326,193 B1 | 12/2001 | Liu et al. |
| 7,355,018 B2 | 4/2008 | Glass |
| 7,396,811 B2 | 7/2008 | Lebowitz et al. |
| 7,560,424 B2 | 7/2009 | Lebowitz et al. |
| 7,629,309 B2 | 12/2009 | Lebowitz et al. |
| 7,785,856 B2 | 8/2010 | Lebowitz et al. |
| 7,858,576 B2 | 12/2010 | Lebowitz et al. |
| 8,207,114 B2 | 6/2012 | Lebowitz et al. |
| 8,492,337 B2 | 7/2013 | Lebowitz et al. |
| 8,492,338 B2 | 7/2013 | Lebowitz et al. |
| 9,206,235 B2 | 12/2015 | Martini et al. |
| 9,279,007 B2 | 3/2016 | Do |
| 9,469,683 B2 | 10/2016 | Lebowitz et al. |
| 9,493,753 B2 | 11/2016 | Ishihara |
| 9,545,450 B2 | 1/2017 | Do |
| 9,814,762 B2 | 11/2017 | Lebowitz et al. |
| 2001/0007755 A1 | 7/2001 | Borel et al. |
| 2003/0072761 A1 | 4/2003 | Lebowitz |
| 2006/0121018 A1 | 6/2006 | Lebowitz |
| 2008/0241118 A1 | 10/2008 | Lebowitz |
| 2009/0117091 A1 | 5/2009 | Lebowitz et al. |
| 2009/0202511 A1 | 8/2009 | Galindo et al. |
| 2009/0203575 A1 | 8/2009 | Lebowitz et al. |
| 2010/0104589 A1 | 4/2010 | Govindan et al. |
| 2018/0125949 A1 | 5/2018 | Lebowitz et al. |

FOREIGN PATENT DOCUMENTS

| | | | | |
|---|---|---|---|---|
| CN | 102066422 A | 5/2011 | | |
| EP | 1436316 B1 | 1/2008 | | |
| EP | 1974752 B1 | 9/2012 | | |
| EP | 3115372 A1 | 1/2017 | | |
| EP | 3187508 A1 | 7/2017 | | |
| EP | 2925776 B1 | 5/2018 | | |
| WO | WO-0129058 A1 | 4/2001 | | |
| WO | WO-0196584 A2 | 12/2001 | | |
| WO | WO-03032727 A1 | 4/2003 | | |
| WO | WO-2004064750 A2 | 8/2004 | | |
| WO | WO-2004098648 A1 | 11/2004 | | |
| WO | WO-2009137721 A2 | 11/2009 | | |
| WO | WO-2014085621 A1 * | 6/2014 | ............. | C07K 14/65 |
| WO | WO-2014143734 A2 * | 9/2014 | ............. | A61K 38/47 |
| WO | WO-2015060722 A1 | 4/2015 | | |
| WO | WO-2015085238 A1 | 6/2015 | | |

OTHER PUBLICATIONS

Doerfler et al. Targeted approaches to induce immune tolerance for Pompe disease therapy. Mol Ther Methods Clin Dev 3:15053 (2016).
Ferreira et al. Tuning gene expression with synthetic upstream open reading frames. PNAS USA 110(28):11284-11289 (2013).
Heldermon et al. Disease correction by combined neonatal intracranial AAV and systemic lentiviral gene therapy in Sanfilippo Syndrome type B mice. Gene Therapy 20(9):913-921 (2013).
Hocquemiller et al. Adeno-Associated Virus-Based Gene Therapy for CNS Diseases. Human Gene Therapy 27(7):478-496 (2016).
PCT/US2019/030076 Invitation to Pay Additional Fees dated Aug. 19, 2019.
Puzzo et al. Rescue of Pompe disease in mice by AAV-mediated liver delivery of secretable acid alpha-glucosidase. Sci Trans Med 9(418):pii:eaam6375 (2017).

(Continued)

*Primary Examiner* — Antonio Galisteo Gonzalez
(74) *Attorney, Agent, or Firm* — Margareta K. Sorenson; Hyun Joon Chung

(57) ABSTRACT

Provided herein are improved gene therapy vectors and methods of use, in some embodiments, comprising sequences for improved expression and cellular targeting of a therapeutic protein.

19 Claims, 21 Drawing Sheets

Specification includes a Sequence Listing.

(56) References Cited

OTHER PUBLICATIONS

Puzzo et al. Supplementary Materials for: Rescue of Pompe disease in mice by AAV-mediated liver delivery of secretable acid alpha-glucosidase. Sci Trans Med 9(418):pii:eaam6375 (2017).
PCT/US2019/030076 International Search Report and Written Opinion dated Oct. 11, 2019.
CFP UniProtKB—A0A059PIU2 (A0A059PIU2_AEQVI) (last viewed on Jul. 10, 2015).
Ciplys et al. Generation of human ER chaperone BiP in yeast *Saccharomyces cerevisiae*. Microbial Cell Factories 13:22 (9 pgs) (2014).
Deng et al. Aspirin and salicylate bind to immunoglobulin heavy chain binding protein (BiP) and inhibit its ATPase activity in human fibroblasts. FASEB J. 15(13):2463-2470 (2001).
Devos et al. Practical limits of function prediction. Proteins: Structure, Function and Genetics 41:98-107 (2000).
Fernandez et al. Distinct molecular events during secretory granule biogenesis revealed by sensitivities to Brefeldin A. Molecular Biology of the Cell 8:2171-2185 (Nov. 1997).
Freiden et al. Interconversion of three differentially modified and assembled forms of BiP, The EMBO Journal 11(1):63-70 (1992).
Guo et al. Protein tolerance to random amino acid change. PNAS 101.25 (2004): 9205-9210.
Hill et al. Functional Analysis of conserved Histidines in ADP-Giucose Pyrophosphorylase from *Escherichia coli*. Biochem. Biophys. Res. Comm. 244:573-577 (1998).
Hochstrasser. Ubiquitin-dependent protein degradation. Annu. Rev. Genet. 30:405-439 (1996).
June et al. Engineering lymphocyte subsets: tools, trials and tribulations. Nat Rev Immunol 9.10:704-716 (2009).
Kilian et al. Identification and characterization of a new conserved motif within the presequence of proteins targeted into complex diatom plastids. The Plant Journal 41:175-183 (2005).
Kisselev. Polypeptide release factors in prokaryotes and eukaryotes: same function, different structure. Structure 10(1):8-9 (2002).
Lazar et al. Transforming growth factor alpha: mutation of aspartic acid 47 and leucine 48 results in different biological activities. Mol Cell Biol. 8:1247-1252 (1988).
Lock et al. Rapid, simple, and versatile manufacturing of recombinant adeno-associated viral vectors at scale. Hum Gene Ther 21(10):1259-1271 (2010).
Lu et al. Anti-Citrullinated Protein Antibodies Bing Surface-Expressed Citrullinated Grp78 on Monocyte/Macrophages and Stimulate Tumor Necrosis Factor .alpha. Production, Arthritis & Rheumatism 62(5):1213-1223 (2010).
Martoglio et al. Signal sequences: more than just greasy peptides. Trends in Cell biology 8(10):410-415 (1998).
Milone et al. Chimeric receptors containing CD137 signal transduction domains mediate enhanced survival of T cells and increased antileukemic efficacy in vivo. Mol. Ther. 17:1453-1464 (2009).
PCT/US2011/061862 International Search Report and Written Opinion dated May 30, 2012.
PCT/US2012/039705 International Search Report and Written Opinion dated Dec. 7, 2012.
Punt et al. Analysis of the role of the gene bipA, encoding the major endoplasmic reticulum chaperone protein in the secretion of homologous and heterologous proteins in black Aspergilli. Applied Mircobiology and Biotechnology 50:447-454 (1998).
RecName: Full=78 kDa glucose-regulated protein, UniProt:Q354T7, Oct. 3, 2006, 2 pages.
Tuske et al. Development of a novel gene therapy for Pompe disease: Engineered acid alpha-glucosidase transgene for improved expression and muscle targeting. Poster. American Society of Gene & Cell Therapy Annual Meeting in Washington DC. (Apr. 30, 2019).
Tuske et al. Development of a Novel Gene Therapy for Pompe Disease: Engineered Acid Alpha-Glucosidase Transgene for Improved Expression and Muscle Targeting. Molecular Therapy 27(4S1 (Abstract 518) (Apr. 15, 2019).
Wacey et al. Disentangling the perturbational effects of amino acid substitutions in the DNA-binding domain of p53. Hum Genet 104:15-22 (1999).
Whisstock et al. Prediction of protein function from protein sequence and structure. Quarterly Reviews of Biophysics 36(3):307-340 (2003).
Witkowski et al. Conversion of a beta-ketoacyl synthase to a malonyl decarboxylase by replacement of the active-site cysteine with glutamine. Biochemistry 38:11643-11650 (1999).
Wu et al. Targeting to the endoplasmic reticulum improves the folding of recombinant human telomerase reverse transcriptase. Protein Expr. Purif. 56(1):8-19 (2007).

\* cited by examiner

SEQUENCE LISTING

<160> NUMBER OF SEQ ID NOS: 48

<210> SEQ ID NO 1
<211> LENGTH: 67
<212> TYPE: PRT
<213> ORGANISM: Homo sapiens

<400> SEQUENCE: 1

Ala Tyr Arg Pro Ser Glu Thr Leu Cys Gly Gly Glu Leu Val Asp Thr
1               5                   10                  15

Leu Gln Phe Val Cys Gly Asp Arg Gly Phe Tyr Phe Ser Arg Pro Ala
            20                  25                  30

Ser Arg Val Ser Arg Arg Ser Arg Gly Ile Val Glu Glu Cys Cys Phe
        35                  40                  45

Arg Ser Cys Asp Leu Ala Leu Leu Glu Thr Tyr Cys Ala Thr Pro Ala
    50                  55                  60

Lys Ser Glu
65

<210> SEQ ID NO 2
<211> LENGTH: 67
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Ala Tyr Arg Pro Ser Glu Thr Leu Cys Gly Gly Glu Leu Val Asp Thr
1               5                   10                  15

Leu Gln Phe Val Cys Gly Asp Arg Gly Ser Tyr Phe Ser Arg Pro Ala
            20                  25                  30

Ser Arg Val Ser Arg Arg Ser Arg Gly Ile Val Glu Glu Cys Cys Phe
        35                  40                  45

Arg Ser Cys Asp Leu Ala Leu Leu Glu Thr Tyr Cys Ala Thr Pro Ala
    50                  55                  60

Lys Ser Glu
65

<210> SEQ ID NO 3
<211> LENGTH: 67
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Ala Tyr Arg Pro Ser Glu Thr Leu Cys Gly Gly Glu Leu Val Asp Thr
1               5                   10                  15

Leu Gln Phe Val Cys Gly Asp Arg Gly Phe Leu Phe Ser Arg Pro Ala
            20                  25                  30

Ser Arg Val Ser Arg Arg Ser Arg Gly Ile Val Glu Glu Cys Cys Phe
        35                  40                  45

Arg Ser Cys Asp Leu Ala Leu Leu Glu Thr Tyr Cys Ala Thr Pro Ala
    50                  55                  60

Lys Ser Glu
65

<210> SEQ ID NO 4

```
<211> LENGTH: 67
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Ala Tyr Arg Pro Ser Glu Thr Leu Cys Gly Gly Glu Leu Val Asp Thr
1               5                   10                  15

Leu Gln Phe Val Cys Gly Asp Arg Gly Phe Tyr Phe Ser Arg Pro Ala
            20                  25                  30

Ser Arg Val Ser Arg Arg Ser Arg Gly Ile Leu Glu Glu Cys Cys Phe
        35                  40                  45

Arg Ser Cys Asp Leu Ala Leu Leu Glu Thr Tyr Cys Ala Thr Pro Ala
    50                  55                  60

Lys Ser Glu
65

<210> SEQ ID NO 5
<211> LENGTH: 67
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Ala Tyr Arg Pro Ser Glu Thr Leu Cys Gly Gly Glu Leu Val Asp Thr
1               5                   10                  15

Leu Gln Phe Val Cys Gly Asp Arg Gly Phe Tyr Phe Ser Arg Pro Ala
            20                  25                  30

Ser Arg Val Ser Arg Arg Ser Arg Gly Ile Val Glu Glu Cys Cys Thr
        35                  40                  45

Arg Ser Cys Asp Leu Ala Leu Leu Glu Thr Tyr Cys Ala Thr Pro Ala
    50                  55                  60

Lys Ser Glu
65

<210> SEQ ID NO 6
<211> LENGTH: 67
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Ala Tyr Arg Pro Ser Glu Thr Leu Cys Gly Gly Glu Leu Val Asp Thr
1               5                   10                  15

Leu Gln Phe Val Cys Gly Asp Arg Gly Phe Tyr Phe Ser Arg Pro Ala
            20                  25                  30

Ser Arg Val Ser Arg Arg Ser Arg Gly Ile Val Glu Glu Cys Cys Phe
        35                  40                  45

Ser Ser Cys Asp Leu Ala Leu Leu Glu Thr Tyr Cys Ala Thr Pro Ala
    50                  55                  60

Lys Ser Glu
65

<210> SEQ ID NO 7
<211> LENGTH: 67
```

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Ala Tyr Arg Pro Ser Glu Thr Leu Cys Gly Gly Glu Leu Val Asp Thr
1               5                   10                  15

Leu Gln Phe Val Cys Gly Asp Arg Gly Phe Tyr Phe Ser Arg Pro Ala
            20                  25                  30

Ser Arg Val Ser Arg Arg Ser Arg Gly Ile Val Glu Glu Cys Cys Phe
        35                  40                  45

Arg Ile Cys Asp Leu Ala Leu Leu Glu Thr Tyr Cys Ala Thr Pro Ala
    50                  55                  60

Lys Ser Glu
65

<210> SEQ ID NO 8
<211> LENGTH: 67
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Ala Tyr Arg Pro Ser Glu Thr Leu Cys Gly Gly Glu Leu Val Asp Thr
1               5                   10                  15

Leu Gln Phe Val Cys Gly Asp Arg Gly Phe Tyr Phe Ser Arg Pro Ala
            20                  25                  30

Ser Arg Val Ser Arg Arg Ser Arg Gly Ile Val Glu Glu Cys Cys Phe
        35                  40                  45

Arg Ser Cys Asp Leu Arg Leu Leu Glu Thr Tyr Cys Ala Thr Pro Ala
    50                  55                  60

Lys Ser Glu
65

<210> SEQ ID NO 9
<211> LENGTH: 67
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Ala Tyr Arg Pro Ser Glu Thr Leu Cys Gly Gly Glu Leu Val Asp Thr
1               5                   10                  15

Leu Gln Phe Val Cys Gly Asp Arg Gly Phe Tyr Phe Ser Arg Pro Ala
            20                  25                  30

Ser Arg Val Ser Arg Arg Ser Arg Gly Ile Val Glu Glu Cys Cys Phe
        35                  40                  45

Arg Ser Cys Asp Leu Ala Arg Leu Glu Thr Tyr Cys Ala Thr Pro Ala
    50                  55                  60

Lys Ser Glu
65

<210> SEQ ID NO 10
<211> LENGTH: 67
<212> TYPE: PRT

<213> ORGANISM: Artificial Sequence
<220> FEATURE:
<223> OTHER INFORMATION: Description of Artificial Sequence: Synthetic polypeptide

<400> SEQUENCE: 10

```
Ala Tyr Arg Pro Ser Glu Thr Leu Cys Gly Gly Glu Leu Val Asp Thr
1               5                   10                  15
Leu Gln Phe Val Cys Gly Asp Arg Gly Ser Leu Phe Ser Arg Pro Ala
            20                  25                  30
Ser Arg Val Ser Arg Arg Ser Arg Gly Ile Leu Glu Glu Cys Cys Thr
        35                  40                  45
Ser Ile Cys Asp Leu Arg Arg Leu Glu Thr Tyr Cys Ala Thr Pro Ala
    50                  55                  60
Lys Ser Glu
65
```

<210> SEQ ID NO 11
<211> LENGTH: 61
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 11

```
Thr Leu Cys Gly Gly Glu Leu Val Asp Thr Leu Gln Phe Val Cys Gly
1               5                   10                  15
Asp Arg Gly Phe Leu Phe Ser Arg Pro Ala Ser Arg Val Ser Arg Arg
            20                  25                  30
Ser Arg Gly Ile Val Glu Glu Cys Cys Phe Arg Ser Cys Asp Leu Ala
        35                  40                  45
Leu Leu Glu Thr Tyr Cys Ala Thr Pro Ala Arg Ser Glu
    50                  55                  60
```

<210> SEQ ID NO 12
<211> LENGTH: 190
<212> TYPE: DNA
<213> ORGANISM: Cripavirus sp.

<400> SEQUENCE: 12

```
aaaaatgtga tcttgcttgt aaatacaatt ttgagaggtt aataaattac aagtagtgct    60
atttttgtat ttaggttagc tatttagctt tacgttccag gatgcctagt ggcagcccca   120
caatatccag gaagccctct ctgcggtttt tcagattagg tagtcgaaaa acctaagaaa   180
tttacctgct                                                          190
```

<210> SEQ ID NO 13
<211> LENGTH: 18
<212> TYPE: PRT
<213> ORGANISM: Homo sapiens

<400> SEQUENCE: 13

```
Met Lys Leu Ser Leu Val Ala Ala Met Leu Leu Leu Leu Ser Ala Ala
1               5                   10                  15
Arg Ala
```

<210> SEQ ID NO 14
<211> LENGTH: 28
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 14

Met Lys Leu Ser Leu Val Ala Ala Met Leu Leu Leu Ser Leu Val
1               5                   10                  15

Ala Ala Met Leu Leu Leu Leu Ser Ala Ala Arg Ala
            20                  25

<210> SEQ ID NO 15
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Met Lys Leu Ser Leu Val Ala Ala Met Leu Leu Leu Trp Val Ala
1               5                   10                  15

Leu Leu Leu Leu Ser Ala Ala Arg Ala
            20                  25

<210> SEQ ID NO 16
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Met Lys Leu Ser Leu Val Ala Ala Met Leu Leu Leu Ser Leu Val
1               5                   10                  15

Ala Leu Leu Leu Leu Ser Ala Ala Arg Ala
            20                  25

<210> SEQ ID NO 17
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Met Lys Leu Ser Leu Val Ala Ala Met Leu Leu Leu Ala Leu Val
1               5                   10                  15

Ala Leu Leu Leu Leu Ser Ala Ala Arg Ala
            20                  25

<210> SEQ ID NO 18
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gly Gly Gly Gly Ser Gly Gly Gly Gly
1               5

<210> SEQ ID NO 19
```

<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Gly Gly Gly Gly Ser
1               5

<210> SEQ ID NO 20
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Gly Gly Gly Ser Gly Gly Gly Gly Ser
1               5

<210> SEQ ID NO 21
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Gly Gly Gly Gly Ser Gly Gly Gly Ser
1               5

<210> SEQ ID NO 22
<211> LENGTH: 952
<212> TYPE: PRT
<213> ORGANISM: Homo sapiens

<400> SEQUENCE: 22

Met Gly Val Arg His Pro Pro Cys Ser His Arg Leu Leu Ala Val Cys
1               5                   10                  15

Ala Leu Val Ser Leu Ala Thr Ala Ala Leu Leu Gly His Ile Leu Leu
                20                  25                  30

His Asp Phe Leu Leu Val Pro Arg Glu Leu Ser Gly Ser Ser Pro Val
            35                  40                  45

Leu Glu Glu Thr His Pro Ala His Gln Gln Gly Ala Ser Arg Pro Gly
        50                  55                  60

Pro Arg Asp Ala Gln Ala His Pro Gly Arg Pro Arg Ala Val Pro Thr
65                  70                  75                  80

Gln Cys Asp Val Pro Pro Asn Ser Arg Phe Asp Cys Ala Pro Asp Lys
                85                  90                  95

Ala Ile Thr Gln Glu Gln Cys Glu Ala Arg Gly Cys Cys Tyr Ile Pro
            100                 105                 110

Ala Lys Gln Gly Leu Gln Gly Ala Gln Met Gly Gln Pro Trp Cys Phe
        115                 120                 125

Phe Pro Pro Ser Tyr Pro Ser Tyr Lys Leu Glu Asn Leu Ser Ser Ser
    130                 135                 140

Glu Met Gly Tyr Thr Ala Thr Leu Thr Arg Thr Thr Pro Thr Phe Phe
145                 150                 155                 160

Pro Lys Asp Ile Leu Thr Leu Arg Leu Asp Val Met Met Glu Thr Glu

```
                165                 170                 175
Asn Arg Leu His Phe Thr Ile Lys Asp Pro Ala Asn Arg Arg Tyr Glu
            180                 185                 190

Val Pro Leu Glu Thr Pro His Val His Ser Arg Ala Pro Ser Pro Leu
            195                 200                 205

Tyr Ser Val Glu Phe Ser Glu Glu Pro Phe Gly Val Ile Val Arg Arg
            210                 215                 220

Gln Leu Asp Gly Arg Val Leu Leu Asn Thr Thr Val Ala Pro Leu Phe
225                 230                 235                 240

Phe Ala Asp Gln Phe Leu Gln Leu Ser Thr Ser Leu Pro Ser Gln Tyr
                245                 250                 255

Ile Thr Gly Leu Ala Glu His Leu Ser Pro Leu Met Leu Ser Thr Ser
                260                 265                 270

Trp Thr Arg Ile Thr Leu Trp Asn Arg Asp Leu Ala Pro Thr Pro Gly
                275                 280                 285

Ala Asn Leu Tyr Gly Ser His Pro Phe Tyr Leu Ala Leu Glu Asp Gly
                290                 295                 300

Gly Ser Ala His Gly Val Phe Leu Leu Asn Ser Asn Ala Met Asp Val
305                 310                 315                 320

Val Leu Gln Pro Ser Pro Ala Leu Ser Trp Arg Ser Thr Gly Gly Ile
                325                 330                 335

Leu Asp Val Tyr Ile Phe Leu Gly Pro Glu Pro Lys Ser Val Val Gln
                340                 345                 350

Gln Tyr Leu Asp Val Val Gly Tyr Pro Phe Met Pro Pro Tyr Trp Gly
                355                 360                 365

Leu Gly Phe His Leu Cys Arg Trp Gly Tyr Ser Ser Thr Ala Ile Thr
                370                 375                 380

Arg Gln Val Val Glu Asn Met Thr Arg Ala His Phe Pro Leu Asp Val
385                 390                 395                 400

Gln Trp Asn Asp Leu Asp Tyr Met Asp Ser Arg Arg Asp Phe Thr Phe
                405                 410                 415

Asn Lys Asp Gly Phe Arg Asp Phe Pro Ala Met Val Gln Glu Leu His
                420                 425                 430

Gln Gly Gly Arg Arg Tyr Met Met Ile Val Asp Pro Ala Ile Ser Ser
                435                 440                 445

Ser Gly Pro Ala Gly Ser Tyr Arg Pro Tyr Asp Glu Gly Leu Arg Arg
450                 455                 460

Gly Val Phe Ile Thr Asn Glu Thr Gly Gln Pro Leu Ile Gly Lys Val
465                 470                 475                 480

Trp Pro Gly Ser Thr Ala Phe Pro Asp Phe Thr Asn Pro Thr Ala Leu
                485                 490                 495

Ala Trp Trp Glu Asp Met Val Ala Glu Phe His Asp Gln Val Pro Phe
                500                 505                 510

Asp Gly Met Trp Ile Asp Met Asn Glu Pro Ser Asn Phe Ile Arg Gly
                515                 520                 525

Ser Glu Asp Gly Cys Pro Asn Asn Glu Leu Glu Asn Pro Pro Tyr Val
                530                 535                 540

Pro Gly Val Val Gly Gly Thr Leu Gln Ala Ala Thr Ile Cys Ala Ser
545                 550                 555                 560

Ser His Gln Phe Leu Ser Thr His Tyr Asn Leu His Asn Leu Tyr Gly
                565                 570                 575

Leu Thr Glu Ala Ile Ala Ser His Arg Ala Leu Val Lys Ala Arg Gly
                580                 585                 590
```

Thr Arg Pro Phe Val Ile Ser Arg Ser Thr Phe Ala Gly His Gly Arg
            595                 600                 605

Tyr Ala Gly His Trp Thr Gly Asp Val Trp Ser Ser Trp Glu Gln Leu
610                 615                 620

Ala Ser Ser Val Pro Glu Ile Leu Gln Phe Asn Leu Leu Gly Val Pro
625                 630                 635                 640

Leu Val Gly Ala Asp Val Cys Gly Phe Leu Gly Asn Thr Ser Glu Glu
                645                 650                 655

Leu Cys Val Arg Trp Thr Gln Leu Gly Ala Phe Tyr Pro Phe Met Arg
                660                 665                 670

Asn His Asn Ser Leu Leu Ser Leu Pro Gln Glu Pro Tyr Ser Phe Ser
                675                 680                 685

Glu Pro Ala Gln Gln Ala Met Arg Lys Ala Leu Thr Leu Arg Tyr Ala
690                 695                 700

Leu Leu Pro His Leu Tyr Thr Leu Phe His Gln Ala His Val Ala Gly
705                 710                 715                 720

Glu Thr Val Ala Arg Pro Leu Phe Leu Glu Phe Pro Lys Asp Ser Ser
                725                 730                 735

Thr Trp Thr Val Asp His Gln Leu Leu Trp Gly Glu Ala Leu Leu Ile
                740                 745                 750

Thr Pro Val Leu Gln Ala Gly Lys Ala Glu Val Thr Gly Tyr Phe Pro
                755                 760                 765

Leu Gly Thr Trp Tyr Asp Leu Gln Thr Val Pro Val Glu Ala Leu Gly
770                 775                 780

Ser Leu Pro Pro Pro Ala Ala Pro Arg Glu Pro Ala Ile His Ser
785                 790                 795                 800

Glu Gly Gln Trp Val Thr Leu Pro Ala Pro Leu Asp Thr Ile Asn Val
                805                 810                 815

His Leu Arg Ala Gly Tyr Ile Ile Pro Leu Gln Gly Pro Gly Leu Thr
                820                 825                 830

Thr Thr Glu Ser Arg Gln Gln Pro Met Ala Leu Ala Val Ala Leu Thr
                835                 840                 845

Lys Gly Gly Glu Ala Arg Gly Glu Leu Phe Trp Asp Asp Gly Glu Ser
850                 855                 860

Leu Glu Val Leu Glu Arg Gly Ala Tyr Thr Gln Val Ile Phe Leu Ala
865                 870                 875                 880

Arg Asn Asn Thr Ile Val Asn Glu Leu Val Arg Val Thr Ser Glu Gly
                885                 890                 895

Ala Gly Leu Gln Leu Gln Lys Val Thr Val Leu Gly Val Ala Thr Ala
                900                 905                 910

Pro Gln Gln Val Leu Ser Asn Gly Val Pro Val Ser Asn Phe Thr Tyr
                915                 920                 925

Ser Pro Asp Thr Lys Val Leu Asp Ile Cys Val Ser Leu Leu Met Gly
                930                 935                 940

Glu Gln Phe Leu Val Ser Trp Cys
945                 950

<210> SEQ ID NO 23
<211> LENGTH: 982
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

```
Met Lys Leu Ser Leu Val Ala Ala Met Leu Leu Leu Ser Ala Ala
1               5                   10                  15

Arg Ala Ser Arg Thr Leu Cys Gly Gly Glu Leu Val Asp Thr Leu Gln
            20                  25                  30

Phe Val Cys Gly Asp Arg Gly Phe Leu Phe Ser Arg Pro Ala Ser Arg
            35                  40                  45

Val Ser Arg Arg Ser Arg Gly Ile Val Glu Glu Cys Cys Phe Arg Ser
        50                  55                  60

Cys Asp Leu Ala Leu Leu Glu Thr Tyr Cys Ala Thr Pro Ala Arg Ser
65                  70                  75                  80

Glu Gly Gly Gly Ser Gly Gly Gly Ser Arg Pro Gly Pro Arg
                85                  90                  95

Asp Ala Gln Ala His Pro Gly Arg Pro Arg Ala Val Pro Thr Gln Cys
                100                 105                 110

Asp Val Pro Pro Asn Ser Arg Phe Asp Cys Ala Pro Asp Lys Ala Ile
            115                 120                 125

Thr Gln Glu Gln Cys Glu Ala Arg Gly Cys Cys Tyr Ile Pro Ala Lys
130                 135                 140

Gln Gly Leu Gln Gly Ala Gln Met Gly Gln Pro Trp Cys Phe Phe Pro
145                 150                 155                 160

Pro Ser Tyr Pro Ser Tyr Lys Leu Glu Asn Leu Ser Ser Ser Glu Met
                165                 170                 175

Gly Tyr Thr Ala Thr Leu Thr Arg Thr Thr Pro Thr Phe Phe Pro Lys
                180                 185                 190

Asp Ile Leu Thr Leu Arg Leu Asp Val Met Met Glu Thr Glu Asn Arg
            195                 200                 205

Leu His Phe Thr Ile Lys Asp Pro Ala Asn Arg Arg Tyr Glu Val Pro
        210                 215                 220

Leu Glu Thr Pro His Val His Ser Arg Ala Pro Ser Pro Leu Tyr Ser
225                 230                 235                 240

Val Glu Phe Ser Glu Glu Pro Phe Gly Val Ile Val Arg Arg Gln Leu
                245                 250                 255

Asp Gly Arg Val Leu Leu Asn Thr Thr Val Ala Pro Leu Phe Phe Ala
                260                 265                 270

Asp Gln Phe Leu Gln Leu Ser Thr Ser Leu Pro Ser Gln Tyr Ile Thr
            275                 280                 285

Gly Leu Ala Glu His Leu Ser Pro Leu Met Leu Ser Thr Ser Trp Thr
290                 295                 300

Arg Ile Thr Leu Trp Asn Arg Asp Leu Ala Pro Thr Pro Gly Ala Asn
305                 310                 315                 320

Leu Tyr Gly Ser His Pro Phe Tyr Leu Ala Leu Glu Asp Gly Gly Ser
                325                 330                 335

Ala His Gly Val Phe Leu Leu Asn Ser Asn Ala Met Asp Val Val Leu
                340                 345                 350

Gln Pro Ser Pro Ala Leu Ser Trp Arg Ser Thr Gly Gly Ile Leu Asp
            355                 360                 365

Val Tyr Ile Phe Leu Gly Pro Glu Pro Lys Ser Val Gln Gln Tyr
        370                 375                 380

Leu Asp Val Val Gly Tyr Pro Phe Met Pro Pro Tyr Trp Gly Leu Gly
385                 390                 395                 400

Phe His Leu Cys Arg Trp Gly Tyr Ser Ser Thr Ala Ile Thr Arg Gln
                405                 410                 415
```

```
Val Val Glu Asn Met Thr Arg Ala His Phe Pro Leu Asp Val Gln Trp
            420                 425                 430

Asn Asp Leu Asp Tyr Met Asp Ser Arg Arg Asp Phe Thr Phe Asn Lys
        435                 440                 445

Asp Gly Phe Arg Asp Phe Pro Ala Met Val Gln Glu Leu His Gln Gly
    450                 455                 460

Gly Arg Arg Tyr Met Met Ile Val Asp Pro Ala Ile Ser Ser Ser Gly
465                 470                 475                 480

Pro Ala Gly Ser Tyr Arg Pro Tyr Asp Glu Gly Leu Arg Arg Gly Val
                485                 490                 495

Phe Ile Thr Asn Glu Thr Gly Gln Pro Leu Ile Gly Lys Val Trp Pro
            500                 505                 510

Gly Ser Thr Ala Phe Pro Asp Phe Thr Asn Pro Thr Ala Leu Ala Trp
        515                 520                 525

Trp Glu Asp Met Val Ala Glu Phe His Asp Gln Val Pro Phe Asp Gly
    530                 535                 540

Met Trp Ile Asp Met Asn Glu Pro Ser Asn Phe Ile Arg Gly Ser Glu
545                 550                 555                 560

Asp Gly Cys Pro Asn Asn Glu Leu Glu Asn Pro Pro Tyr Val Pro Gly
                565                 570                 575

Val Val Gly Gly Thr Leu Gln Ala Ala Thr Ile Cys Ala Ser Ser His
            580                 585                 590

Gln Phe Leu Ser Thr His Tyr Asn Leu His Asn Leu Tyr Gly Leu Thr
        595                 600                 605

Glu Ala Ile Ala Ser His Arg Ala Leu Val Lys Ala Arg Gly Thr Arg
    610                 615                 620

Pro Phe Val Ile Ser Arg Ser Thr Phe Ala Gly His Gly Arg Tyr Ala
625                 630                 635                 640

Gly His Trp Thr Gly Asp Val Trp Ser Ser Trp Glu Gln Leu Ala Ser
                645                 650                 655

Ser Val Pro Glu Ile Leu Gln Phe Asn Leu Leu Gly Val Pro Leu Val
            660                 665                 670

Gly Ala Asp Val Cys Gly Phe Leu Gly Asn Thr Ser Glu Glu Leu Cys
        675                 680                 685

Val Arg Trp Thr Gln Leu Gly Ala Phe Tyr Pro Phe Met Arg Asn His
    690                 695                 700

Asn Ser Leu Leu Ser Leu Pro Gln Glu Pro Tyr Ser Phe Ser Glu Pro
705                 710                 715                 720

Ala Gln Gln Ala Met Arg Lys Ala Leu Thr Leu Arg Tyr Ala Leu Leu
                725                 730                 735

Pro His Leu Tyr Thr Leu Phe His Gln Ala His Val Ala Gly Glu Thr
            740                 745                 750

Val Ala Arg Pro Leu Phe Leu Glu Phe Pro Lys Asp Ser Ser Thr Trp
        755                 760                 765

Thr Val Asp His Gln Leu Leu Trp Gly Glu Ala Leu Leu Ile Thr Pro
    770                 775                 780

Val Leu Gln Ala Gly Lys Ala Glu Val Thr Gly Tyr Phe Pro Leu Gly
785                 790                 795                 800

Thr Trp Tyr Asp Leu Gln Thr Val Pro Val Glu Ala Leu Gly Ser Leu
                805                 810                 815

Pro Pro Pro Pro Ala Ala Pro Arg Glu Pro Ala Ile His Ser Glu Gly
            820                 825                 830
```

-continued

Gln Trp Val Thr Leu Pro Ala Pro Leu Asp Thr Ile Asn Val His Leu
            835                 840                 845

Arg Ala Gly Tyr Ile Ile Pro Leu Gln Gly Pro Gly Leu Thr Thr Thr
    850                 855                 860

Glu Ser Arg Gln Gln Pro Met Ala Leu Ala Val Ala Leu Thr Lys Gly
865                 870                 875                 880

Gly Glu Ala Arg Gly Glu Leu Phe Trp Asp Asp Gly Glu Ser Leu Glu
                885                 890                 895

Val Leu Glu Arg Gly Ala Tyr Thr Gln Val Ile Phe Leu Ala Arg Asn
            900                 905                 910

Asn Thr Ile Val Asn Glu Leu Val Arg Val Thr Ser Glu Gly Ala Gly
        915                 920                 925

Leu Gln Leu Gln Lys Val Thr Val Leu Gly Val Ala Thr Ala Pro Gln
    930                 935                 940

Gln Val Leu Ser Asn Gly Val Pro Val Ser Asn Phe Thr Tyr Ser Pro
945                 950                 955                 960

Asp Thr Lys Val Leu Asp Ile Cys Val Ser Leu Met Gly Glu Gln
                965                 970                 975

Phe Leu Val Ser Trp Cys
            980

<210> SEQ ID NO 24
<211> LENGTH: 306
<212> TYPE: PRT
<213> ORGANISM: Homo sapiens

<400> SEQUENCE: 24

Met Ala Ser Pro Gly Cys Leu Trp Leu Leu Ala Val Ala Leu Leu Pro
1               5                   10                  15

Trp Thr Cys Ala Ser Arg Ala Leu Gln His Leu Asp Pro Pro Ala Pro
            20                  25                  30

Leu Pro Leu Val Ile Trp His Gly Met Gly Asp Ser Cys Cys Asn Pro
        35                  40                  45

Leu Ser Met Gly Ala Ile Lys Lys Met Val Glu Lys Lys Ile Pro Gly
    50                  55                  60

Ile Tyr Val Leu Ser Leu Glu Ile Gly Lys Thr Leu Met Glu Asp Val
65                  70                  75                  80

Glu Asn Ser Phe Phe Leu Asn Val Asn Ser Gln Val Thr Thr Val Cys
                85                  90                  95

Gln Ala Leu Ala Lys Asp Pro Lys Leu Gln Gln Gly Tyr Asn Ala Met
            100                 105                 110

Gly Phe Ser Gln Gly Gly Gln Phe Leu Arg Ala Val Ala Gln Arg Cys
        115                 120                 125

Pro Ser Pro Pro Met Ile Asn Leu Ile Ser Val Gly Gly Gln His Gln
    130                 135                 140

Gly Val Phe Gly Leu Pro Arg Cys Pro Gly Glu Ser Ser His Ile Cys
145                 150                 155                 160

Asp Phe Ile Arg Lys Thr Leu Asn Ala Gly Ala Tyr Ser Lys Val Val
                165                 170                 175

Gln Glu Arg Leu Val Gln Ala Glu Tyr Trp His Asp Pro Ile Lys Glu
            180                 185                 190

Asp Val Tyr Arg Asn His Ser Ile Phe Leu Ala Asp Ile Asn Gln Glu
        195                 200                 205

Arg Gly Ile Asn Glu Ser Tyr Lys Lys Asn Leu Met Ala Leu Lys Lys
    210                 215                 220

```
Phe Val Met Val Lys Phe Leu Asn Asp Ser Ile Val Asp Pro Val Asp
225                 230                 235                 240

Ser Glu Trp Phe Gly Phe Tyr Arg Ser Gly Gln Ala Lys Glu Thr Ile
            245                 250                 255

Pro Leu Gln Glu Thr Ser Leu Tyr Thr Gln Asp Arg Leu Gly Leu Lys
        260                 265                 270

Glu Met Asp Asn Ala Gly Gln Leu Val Phe Leu Ala Thr Glu Gly Asp
    275                 280                 285

His Leu Gln Leu Ser Glu Glu Trp Phe Tyr Ala His Ile Ile Pro Phe
290                 295                 300

Leu Gly
305

<210> SEQ ID NO 25
<211> LENGTH: 387
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Met Ala Ser Pro Gly Cys Leu Trp Leu Leu Ala Val Ala Leu Leu Pro
1               5                   10                  15

Trp Thr Cys Ala Ser Arg Ala Leu Gln His Leu Ser Arg Thr Leu Cys
            20                  25                  30

Gly Gly Glu Leu Val Asp Thr Leu Gln Phe Val Cys Gly Asp Arg Gly
        35                  40                  45

Phe Leu Phe Ser Arg Pro Ala Ser Arg Val Ser Arg Arg Ser Arg Gly
    50                  55                  60

Ile Val Glu Glu Cys Cys Phe Arg Ser Cys Asp Leu Ala Leu Leu Glu
65                  70                  75                  80

Thr Tyr Cys Ala Thr Pro Ala Arg Ser Glu Gly Gly Gly Ser Gly
                85                  90                  95

Gly Gly Gly Ser Arg Pro Arg Ala Val Pro Thr Gln Asp Pro Pro Ala
            100                 105                 110

Pro Leu Pro Leu Val Ile Trp His Gly Met Gly Asp Ser Cys Cys Asn
        115                 120                 125

Pro Leu Ser Met Gly Ala Ile Lys Lys Met Val Glu Lys Lys Ile Pro
130                 135                 140

Gly Ile Tyr Val Leu Ser Leu Glu Ile Gly Lys Thr Leu Met Glu Asp
145                 150                 155                 160

Val Glu Asn Ser Phe Phe Leu Asn Val Asn Ser Gln Val Thr Thr Val
                165                 170                 175

Cys Gln Ala Leu Ala Lys Asp Pro Lys Leu Gln Gln Gly Tyr Asn Ala
            180                 185                 190

Met Gly Phe Ser Gln Gly Gly Gln Phe Leu Arg Ala Val Ala Gln Arg
        195                 200                 205

Cys Pro Ser Pro Pro Met Ile Asn Leu Ile Ser Val Gly Gly Gln His
    210                 215                 220

Gln Gly Val Phe Gly Leu Pro Arg Cys Pro Gly Glu Ser Ser His Ile
225                 230                 235                 240

Cys Asp Phe Ile Arg Lys Thr Leu Asn Ala Gly Ala Tyr Ser Lys Val
                245                 250                 255

Val Gln Glu Arg Leu Val Gln Ala Glu Tyr Trp His Asp Pro Ile Lys
```

```
            260                 265                 270
Glu Asp Val Tyr Arg Asn His Ser Ile Phe Leu Ala Asp Ile Asn Gln
        275                 280                 285

Glu Arg Gly Ile Asn Glu Ser Tyr Lys Lys Asn Leu Met Ala Leu Lys
    290                 295                 300

Lys Phe Val Met Val Lys Phe Leu Asn Asp Ser Ile Val Asp Pro Val
305                 310                 315                 320

Asp Ser Glu Trp Phe Gly Phe Tyr Arg Ser Gly Gln Ala Lys Glu Thr
                325                 330                 335

Ile Pro Leu Gln Glu Thr Ser Leu Tyr Thr Gln Asp Arg Leu Gly Leu
            340                 345                 350

Lys Glu Met Asp Asn Ala Gly Gln Leu Val Phe Leu Ala Thr Glu Gly
        355                 360                 365

Asp His Leu Gln Leu Ser Glu Glu Trp Phe Tyr Ala His Ile Ile Pro
    370                 375                 380

Phe Leu Gly
385

<210> SEQ ID NO 26
<211> LENGTH: 387
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Met Lys Leu Ser Leu Val Ala Ala Met Leu Leu Leu Leu Trp Val Ala
1               5                   10                  15

Leu Leu Leu Leu Ser Ala Ala Arg Ala Ala Ala Ser Arg Thr Leu Cys
                20                  25                  30

Gly Gly Glu Leu Val Asp Thr Leu Gln Phe Val Cys Gly Asp Arg Gly
            35                  40                  45

Phe Leu Phe Ser Arg Pro Ala Ser Arg Val Ser Arg Arg Ser Arg Gly
    50                  55                  60

Ile Val Glu Glu Cys Cys Phe Arg Ser Cys Asp Leu Ala Leu Leu Glu
65                  70                  75                  80

Thr Tyr Cys Ala Thr Pro Ala Arg Ser Glu Gly Gly Gly Gly Ser Gly
                85                  90                  95

Gly Gly Gly Ser Arg Pro Arg Ala Val Pro Thr Gln Asp Pro Pro Ala
            100                 105                 110

Pro Leu Pro Leu Val Ile Trp His Gly Met Gly Asp Ser Cys Cys Asn
        115                 120                 125

Pro Leu Ser Met Gly Ala Ile Lys Lys Met Val Glu Lys Lys Ile Pro
    130                 135                 140

Gly Ile Tyr Val Leu Ser Leu Glu Ile Gly Lys Thr Leu Met Glu Asp
145                 150                 155                 160

Val Glu Asn Ser Phe Phe Leu Asn Val Asn Ser Gln Val Thr Thr Val
                165                 170                 175

Cys Gln Ala Leu Ala Lys Asp Pro Lys Leu Gln Gln Gly Tyr Asn Ala
            180                 185                 190

Met Gly Phe Ser Gln Gly Gly Gln Phe Leu Arg Ala Val Ala Gln Arg
        195                 200                 205

Cys Pro Ser Pro Pro Met Ile Asn Leu Ile Ser Val Gly Gly Gln His
    210                 215                 220
```

```
Gln Gly Val Phe Gly Leu Pro Arg Cys Pro Gly Glu Ser Ser His Ile
225                 230                 235                 240

Cys Asp Phe Ile Arg Lys Thr Leu Asn Ala Gly Ala Tyr Ser Lys Val
            245                 250                 255

Val Gln Glu Arg Leu Val Gln Ala Glu Tyr Trp His Asp Pro Ile Lys
        260                 265                 270

Glu Asp Val Tyr Arg Asn His Ser Ile Phe Leu Ala Asp Ile Asn Gln
    275                 280                 285

Glu Arg Gly Ile Asn Glu Ser Tyr Lys Lys Asn Leu Met Ala Leu Lys
290                 295                 300

Lys Phe Val Met Val Lys Phe Leu Asn Asp Ser Ile Val Asp Pro Val
305                 310                 315                 320

Asp Ser Glu Trp Phe Gly Phe Tyr Arg Ser Gly Gln Ala Lys Glu Thr
            325                 330                 335

Ile Pro Leu Gln Glu Thr Ser Leu Tyr Thr Gln Asp Arg Leu Gly Leu
        340                 345                 350

Lys Glu Met Asp Asn Ala Gly Gln Leu Val Phe Leu Ala Thr Glu Gly
    355                 360                 365

Asp His Leu Gln Leu Ser Glu Glu Trp Phe Tyr Ala His Ile Ile Pro
370                 375                 380

Phe Leu Gly
385

<210> SEQ ID NO 27
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27 gccrccatgg                                                          10

<210> SEQ ID NO 28
<211> LENGTH: 7
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(3)
<223> OTHER INFORMATION: a, c, t, g, unknown or other

<400> SEQUENCE: 28 annatga                                                             7

<210> SEQ ID NO 29
<211> LENGTH: 7
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29 aagatga                                                             7

<210> SEQ ID NO 30
<211> LENGTH: 60
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Leu Cys Gly Gly Glu Leu Val Asp Thr Leu Gln Phe Val Cys Gly Asp
1               5                   10                  15

Arg Gly Phe Leu Phe Ser Arg Pro Ala Ser Arg Val Ser Arg Arg Ser
            20                  25                  30

Arg Gly Ile Val Glu Glu Cys Cys Phe Arg Ser Cys Asp Leu Ala Leu
        35                  40                  45

Leu Glu Thr Tyr Cys Ala Thr Pro Ala Arg Ser Glu
    50                  55                  60

<210> SEQ ID NO 31
<211> LENGTH: 63
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Ser Arg Thr Leu Cys Gly Gly Glu Leu Val Asp Thr Leu Gln Phe Val
1               5                   10                  15

Cys Gly Asp Arg Gly Phe Leu Phe Ser Arg Pro Ala Ser Arg Val Ser
            20                  25                  30

Arg Arg Ser Arg Gly Ile Val Glu Glu Cys Cys Phe Arg Ser Cys Asp
        35                  40                  45

Leu Ala Leu Leu Glu Thr Tyr Cys Ala Thr Pro Ala Arg Ser Glu
    50                  55                  60

<210> SEQ ID NO 32
<211> LENGTH: 17
<212> TYPE: PRT
<213> ORGANISM: Gaussia princeps

<400> SEQUENCE: 32

Met Gly Val Lys Val Leu Phe Ala Leu Ile Cys Ile Ala Val Ala Glu
1               5                   10                  15

Ala

<210> SEQ ID NO 33
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Gly Gly Ser Gly Ser Gly Ser Thr Ser
1               5

<210> SEQ ID NO 34
<211> LENGTH: 63
<212> TYPE: PRT
<213> ORGANISM: Artificial Sequence
<220> FEATURE:
<223> OTHER INFORMATION: Description of Artificial Sequence: Synthetic
      polypeptide
```

-continued

<400> SEQUENCE: 34

Ser Arg Thr Leu Cys Gly Gly Glu Leu Val Asp Thr Leu Gln Phe Val
1               5                   10                  15

Cys Gly Asp Arg Gly Phe Leu Phe Ser Arg Pro Ala Ser Arg Val Ser
            20                  25                  30

Arg Arg Ser Arg Gly Ile Val Glu Glu Cys Cys Phe Arg Ser Cys Asp
        35                  40                  45

Leu Ala Leu Leu Glu Thr Tyr Cys Ala Thr Pro Ala Lys Ser Glu
    50                  55                  60

<210> SEQ ID NO 35
<211> LENGTH: 67
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Ala Tyr Arg Pro Ser Arg Thr Leu Cys Gly Gly Glu Leu Val Asp Thr
1               5                   10                  15

Leu Gln Phe Val Cys Gly Asp Arg Gly Phe Tyr Phe Ser Arg Pro Ala
            20                  25                  30

Ser Arg Val Ser Arg Arg Ser Arg Gly Ile Val Glu Glu Cys Cys Phe
        35                  40                  45

Arg Ser Cys Asp Leu Ala Leu Leu Glu Thr Tyr Cys Ala Thr Pro Ala
    50                  55                  60

Lys Ser Glu
65

<210> SEQ ID NO 36
<211> LENGTH: 189
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 36
tctagaacac tgtgcggagg ggagcttgta gacactcttc agttcgtgtg tggagatcgc      60
gggttcctct ctctcgccc cgcttccaga gtttcacgga ggtctagggg tatagtagag     120
gagtgttgtt tcaggtcctg tgacttggcg ctcctcgaga cctattgcgc gacgccagcc    180
aggtccgaa                                                            189

<210> SEQ ID NO 37
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Gly Gly Gly Gly Ser Gly Gly Gly Gly Ser
1               5                   10

<210> SEQ ID NO 38
<211> LENGTH: 2954
<212> TYPE: DNA
<213> ORGANISM: Artificial Sequence
<220> FEATURE:

<223> OTHER INFORMATION: Description of Artificial Sequence: Synthetic
polynucleotide
<220> FEATURE:
<221> NAME/KEY: modified_base
<222> LOCATION: (869)..(869)
<223> OTHER INFORMATION: a, c, t, g, unknown or other

<400> SEQUENCE: 38

| | | | | | |
|---|---|---|---|---|---|
| gcaagatgaa | gctctccctg | gtggccgcga | tgctgctgct | gctcagcgcg | gcgcgggcct | 60 |
| ctagaacact | gtgcggaggg | gagcttgtag | acactcttca | gttcgtgtgt | ggagatcgcg | 120 |
| ggttcctctt | ctctcgcccc | gcttccagag | tttcacggag | gtctaggggt | atagtagagg | 180 |
| agtgttgttt | caggtcctgt | gacttggcgc | tcctcgagac | ctattgcgcg | acgccagcca | 240 |
| ggtccgaagg | gggcggtggc | tcaggtggtg | gaggtagcag | accagggccc | cgggatgccc | 300 |
| aggcacaccc | cggccgtccc | agagcagtgc | ccacacagtg | cgacgtcccc | ccaacagcc | 360 |
| gcttcgattg | cgcccctgac | aaggccatca | cccaggaaca | gtgcgaggcc | cgcggctgtt | 420 |
| gctacatccc | tgcaaagcag | gggctgcagg | gagcccagat | ggggcagccc | tggtgcttct | 480 |
| tcccacccag | ctaccccagc | tacaagctgg | agaacctgag | ctcctctgaa | atgggctaca | 540 |
| cggccaccct | gacccgtacc | accccacct | tcttccccaa | ggacatcctg | acctgcggc | 600 |
| tggacgtgat | gatggagact | gagaaccgcc | tccacttcac | gatcaaagat | ccagctaaca | 660 |
| ggcgctacga | ggtgcccttg | gagacccgc | atgtccacag | ccgggcaccg | tccccactct | 720 |
| acagcgtgga | gttctccgag | gagcccttcg | gggtgatcgt | gcgccggcag | ctggacggcc | 780 |
| gcgtgctgct | gaacacgacg | gtggcgcccc | tgttctttgc | ggaccagttc | cttcagctgt | 840 |
| ccacctcgct | gccctcgcag | tatatcacng | gcctcgccga | gcacctcagt | cccctgatgc | 900 |
| tcagcaccag | ctggaccagg | atcaccctgt | ggaaccggga | ccttgcgccc | acgcccggtg | 960 |
| cgaacctcta | cgggtctcac | cctttctacc | tggcgctgga | ggacggcggg | tcggcacacg | 1020 |
| gggtgttcct | gctaaacagc | aatgccatgg | atgtggtcct | gcagccgagc | cctgcccta | 1080 |
| gctggaggtc | gacaggtggg | atcctggatg | tctacatctt | cctgggccca | gagcccaaga | 1140 |
| gcgtggtgca | gcagtacctg | gacgttgtgg | gataccgtt | catgccgcca | tactggggcc | 1200 |
| tgggcttcca | cctgtgccgc | tgggctact | cctccaccgc | tatcacccgc | caggtggtgg | 1260 |
| agaacatgac | cagggcccac | ttcccccctgg | acgtccagtg | gaacgacctg | gactacatgg | 1320 |
| actcccggag | ggacttcacg | ttcaacaagg | atggcttccg | ggacttcccg | gccatggtgc | 1380 |
| aggagctgca | ccagggcggc | cggcgctaca | tgatgatcgt | ggatcctgcc | atcagcagct | 1440 |
| cgggccctgc | cgggagctac | aggccctacg | acgagggtct | gcggagggg | gttttcatca | 1500 |
| ccaacgagac | cggccagccg | ctgattggga | aggtatggcc | cgggtccact | gccttccccg | 1560 |
| acttcaccaa | ccccacagcc | ctggcctggt | gggaggacat | ggtggctgag | ttccatgacc | 1620 |
| aggtgccctt | cgacggcatg | tggattgaca | tgaacgagcc | ttccaacttc | atcagggct | 1680 |
| ctgaggacgg | ctgccccaac | aatgagctgg | agaaccacc | ctacgtgcct | ggggtggttg | 1740 |
| gggggaccct | ccaggcggcc | accatctgtg | cctccagcca | ccagtttctc | tccacacact | 1800 |
| acaacctgca | caacctctac | ggcctgaccg | aagccatcgc | ctcccacagg | gcgctggtga | 1860 |
| aggctcgggg | gacacgccca | tttgtgatct | cccgctcgac | ctttgctggc | cacggccgat | 1920 |
| acgccggcca | ctggacgggg | gacgtgtgga | gctcctggga | gcagctcgcc | tcctccgtgc | 1980 |
| cagaaatcct | gcagttttaac | ctgctgggg | tgcctctggt | cggggccgac | gtctgcggct | 2040 |
| tcctgggcaa | cacctcagag | gagctgtgtg | tgcgctggac | ccagctgggg | gccttctacc | 2100 |

```
ccttcatgcg gaaccacaac agcctgctca gtctgcccca ggagccgtac agcttcagcg      2160
agccggccca gcaggccatg aggaaggccc tcaccctgcg ctacgcactc ctcccccacc      2220
tctacacact gttccaccag gcccacgtcg cggggagac cgtggcccgg ccctcttcc        2280 tggagttccc caaggactct agcacctgga ctgtggacca ccagctcctg tgggggagg       2340 ccctgctcat cacccagtg ctccaggccg ggaaggccga agtgactggc tacttcccct       2400
tgggcacatg gtacgacctg cagacggtgc cagtagaggc ccttggcagc ctcccacccc      2460
cacctgcagc tccccgtgag ccagccatcc acagcgaggg gcagtgggtg acgctgccgg      2520
cccccctgga caccatcaac gtccacctcc gggctgggta catcatcccc ctgcagggcc      2580
ctggcctcac aaccacagag tcccgccagc agcccatggc cctggctgtg ccctgacca      2640 agggtgggga ggcccgaggg gagctgttct gggacgatgg agagagcctg gaagtgctgg      2700
agcgaggggc ctacacacag gtcatcttcc tggccaggaa taacacgatc gtgaatgagc      2760
tggtacgtgt gaccagtgag ggagctggcc tgcagctgca gaaggtgact gtcctgggcg      2820
tggccacggc gccccagcag gtcctctcca acggtgtccc tgtctccaac ttcacctaca      2880
gccccgacac caaggtcctg gacatctgtg tctcgctgtt gatgggagag cagtttctcg      2940
tcagctggtg ttag                                                       2954
```

<210> SEQ ID NO 39
<211> LENGTH: 3139
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 39

```
aaaaatgtga tcttgcttgt aaatacaatt ttgagaggtt aataaattac aagtagtgct        60
atttttgtat ttaggttagc tatttagctt tacgttccag gatgcctagt ggcagcccca       120
caatatccag gaagccctct ctgcggtttt tcagattagg tagtcgaaaa acctaagaaa       180
tttacctgct atgaagctct ccctggtggc cgcgatgctg ctgctgctca gcgcggcgcg       240
ggcctctaga acactgtgcg gaggggagct tgtagacact cttcagttcg tgtgtggaga       300 tcgcggggttc ctcttctctc gccccgcttc cagagtttca cggaggtcta ggggtatagt      360
agaggagtgt tgtttcaggt cctgtgactt ggcgctcctc gagacctatt gcgcgacgcc      420
agccaggtcc gaaggggcg gtggctcagg tggtggaggt agcagaccag gccccggga        480 tgcccaggca caccccggcc gtcccagagc agtgcccaca cagtgcgacg tccccccaa       540 cagccgcttc gattgcgccc ctgacaaggc catcacccag gaacagtgcg aggcccgcgg      600
ctgttgctac atccctgcaa agcagggct gcagggagcc cagatgggc agccctggtg       660 cttcttccca cccagctacc ccagctacaa gctggagaac ctgagctcct ctgaaatggg      720
ctacacggcc accctgaccc gtaccacccc caccttcttc cccaaggaca tcctgacct       780 gcggctggac gtgatgatgg agactgagaa ccgcctccac ttcacgatca agatccagc      840 taacaggcgc tacgaggtgc ccttggagac cccgcatgtc cacagccggg caccgtcccc    900
actctacagc gtggagttct ccgaggagcc cttcggggtg atcgtgcgcc ggcagctgga     960
cggccgcgtg ctgctgaaca cgacggtggc gcccctgttc tttgcggacc agttccttca     1020
gctgtccacc tcgctgccct cgcagtatat cacaggcctc gccgagcacc tcagtcccct    1080
gatgctcagc accagctgga ccaggatcac cctgtggaac cgggaccttg cgcccacgcc    1140
```

```
cggtgcgaac ctctacgggt ctcacccttt ctacctggcg ctggaggacg gcgggtcggc    1200
acacggggtg ttcctgctaa acagcaatgc catggatgtg gtcctgcagc cgagccctgc    1260
ccttagctgg aggtcgacag gtgggatcct ggatgtctac atcttcctgg gcccagagcc    1320
caagagcgtg gtgcagcagt acctggacgt tgtgggatac ccgttcatgc cgccatactg    1380
gggcctgggc ttccacctgt gccgctgggg ctactcctcc accgctatca cccgccaggt    1440
ggtggagaac atgaccaggg cccacttccc cctggacgtc cagtggaacg acctggacta    1500
catggactcc cggagggact tcacgttcaa caaggatggc ttccgggact cccggccat     1560 ggtgcaggag ctgcaccagg gcggccggcg ctacatgatg atcgtggatc ctgccatcag    1620
cagctcgggc cctgccggga gctacaggcc ctacgacgag ggtctgcgga ggggggtttt    1680
catcaccaac gagaccggcc agccgctgat tgggaaggta tggcccgggt ccactgcctt    1740
ccccgacttc accaaccccca cagccctggc ctggtgggag gacatggtgg ctgagttcca    1800
tgaccaggtg cccttcgacg gcatgtggat tgacatgaac gagccttcca acttcatcag    1860
gggctctgag gacggctgcc ccaacaatga gctggagaac ccaccctacg tgcctggggt    1920
ggttgggggg accctccagg cggccaccat ctgtgcctcc agccaccagt ttctctccac    1980
acactacaac ctgcacaacc tctacggcct gaccgaagcc atcgcctccc acaggggcgct    2040 ggtgaaggct cgggggacac gcccatttgt gatctcccgc tcgacctttg ctggccacgg    2100
ccgatacgcc ggccactgga cggggacgt gtggagctcc tgggagcagc tcgcctcctc    2160
cgtgccagaa atcctgcagt ttaacctgct gggggtgcct ctggtcgggg ccgacgtctg    2220
cggcttcctg ggcaacacct cagaggagct gtgtgtgcgc tggacccagc tgggggcctt    2280
ctaccccttc atgcggaacc acaacagcct gctcagtctg ccccaggagc cgtacagctt    2340
cagcgagccg gcccagcagg ccatgaggaa ggccctcacc ctgcgctacg cactcctccc    2400
ccacctctac acactgttcc accaggccca cgtcgcgggg gagaccgtgg cccggccct     2460 cttcctggag ttccccaagg actctagcac ctggactgtg gaccaccagc tcctgtgggg    2520
ggaggccctg ctcatcaccc cagtgctcca ggccgggaag gccgaagtga ctggctactt    2580
cccccttggg c acatggtacg acctgcagac ggtgccagta gaggcccttg gcagcctccc    2640 acccccaccct gcagctcccc gtgagccagc catccacagc gagggggcagt gggtgacgct    2700 gccggccccc ctggacacca tcaacgtcca cctccgggct gggtacatca tcccctgca    2760 gggccctggc ctcacaacca cagagtcccg ccagcagccc atggccctgg ctgtggccct    2820
gaccaagggt ggggaggccc gaggggagct gttctgggac gatggagaga gcctggaagt    2880
gctggagcga ggggcctaca cacaggtcat cttcctggcc aggaataaca cgatcgtgaa    2940
tgagctggta cgtgtgacca gtgagggagc tggcctgcag ctgcagaagg tgactgtcct    3000
gggcgtggcc acggcgcccc agcaggtcct ctccaacggt gtccctgtct ccaacttcac    3060
ctacagcccc gacaccaagg tcctggacat ctgtgtctcg ctgttgatgg gagagcagtt    3120
tctcgtcagc tggtgttag                                               3139
```

<210> SEQ ID NO 40
<211> LENGTH: 921
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 40

```
atggcatcac cgggttgcct ctggttgttg gccgttgcgt tgcttccgtg acatgtgca      60 tcaagagctc ttcaacatct ggatccccca gctcccctgc cgctcgtaat ctggcacggg    120
atgggggatt catgttgtaa cccgttgtca atgggcgcga taaaaaagat ggttgaaaag    180
aagattccag gcatctacgt tctgtccctg gaaatcggta agacactgat ggaagacgtg    240
gagaactcct tctttctcaa cgtcaatagt caggtcacta ccgtctgtca agcattggca    300 aaggaccctda aacttcagca ggggtacaat gcgatgggg ttagccaggg cggacagttt    360
cttagagccg tcgcacagcg ctgtccatct cccccgatga ttaaccttat atctgtcggg    420
ggacaacacc agggtgtttt tggtcttcct cgctgtcctg gtgaaagctc ccacatctgt    480
gatttcatac gcaaaacgtt gaacgcagga gcttatagta aagtcgtcca agaacggctt    540
gttcaagcgg agtattggca tgacccaata aagaagacg tttataggaa tcactctatc     600
ttcttggccg atatcaacca agaacgcgga atcaacgaaa gctacaaaaa gaatcttatg    660
gctctcaaga aatttgttat ggtgaaattc cttaatgact ctatagtaga tcctgtcgat    720
tcagaatggt tcgggttcta caggtctggc caggcgaagg agactattcc cctccaagaa    780
acgtctctct atacacaaga cagactcgga ctgaaagaga tggataatgc gggccagttg    840
gtcttcttgg ctacgaagg cgatcatctc caactctccg aagagtggtt ctatgcccat    900
ataatcccgt cctgggcta a                                              921
```

<210> SEQ ID NO 41
<211> LENGTH: 1164
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 41

```
atggcatccc ccggatgttt gtggctgctg gcggttgcgc ttctgccatg gacgtgcgcc     60
tcccgagccc tccaacacct gtccaggaca ctttgcggcg gagagttggt cgatacgctt    120
caattcgtgt gtggggatag aggcttcctt ttttctcggc ccgctagccg cgtgtcccga    180
aggtcccggg gtatcgttga ggaatgctgt ttccggtcct gcgatcttgc actgttggag    240
acatactgtg ctacgcctgc gagaagcgag ggtggagggg gttctggagg tggagggagc    300
cggcctcggg cggttcccac ccaggatcct ccagctcctc tgcctctggt catctggcat    360
gggatggggg actcatgttg taacccgctg agtatggggg caattaaaaa atggttgaa    420 aagaaaattc caggtatttta tgtcctctct cttgaaatcg gtaagacact tatggaggat    480
gtggaaaact ccttttttcct taatgtcaat tctcaggtca aacagtttg tcaggctctg    540 gcgaaggatc ctaagctgca gcaaggctac aacgccatgg ttttttccca gggaggccaa    600
tttctcagag cggtagctca gcgatgtcca tcaccaccga tgataaatct gatcagtgtc    660
ggcggacaac accagggagt tttcgggctg cccaggtgtc cggggaatc tagtcacata    720 tgtgacttca ttcgcaagac ccttaacgcc ggcgcttact caaaggtggt tcaagaacgg    780
cttgtgcagg ctgaatactg gcacgatccc atcaaggaag atgtatatag gaaccacagt    840
atctttctgg cagacataaa tcaggaaagg ggtattaacg aaagctacaa gaaaaatctc    900
atggccctga gaaatttgt aatggttaag ttttgaacg attctatagt agatcctgtt    960
gactccgagt ggttcgggtt ctatcgatct ggtcaagcca aggagacgat tccgcttcag   1020
gaaacttcac tgtacacaca ggatcggctg ggactcaagg agatggacaa tgcgggccag   1080
```

```
ttggtgtttc tggctacaga gggagaccat ctccagttga gtgaagaatg gttctatgca    1140
catattatcc cattcctcgg ctaa                                           1164
```

<210> SEQ ID NO 42
<211> LENGTH: 1164
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 42

```
atgaagctct ccctggtggc cgcgatgctg ctgctgctct gggtggcact gctgctgctc     60
agcgcggcga gggccgccgc gagtcgcacg ttgtgtggag gtgaactcgt cgacacccct    120
cagttcgtat gtggagatcg cggtttcctc ttctcacgcc cagcttccag agtttcccga    180
agatcacgag gaatagttga ggagtgctgt tttcggtctt gtgatctggc tctcctcgag    240
acttattgtg ctacgccggc ccgctctgaa ggaggtggtg gcagtggagg aggagggagt    300
cggcctaggg cagtcccaac ccaggacccg ccggcgccgc tgccgttggt gatctggcat    360
gggatgggga cagctgttg caatccctta agcatgggtg ctattaaaaa aatggtggag    420
aagaaaatac ctggaattta cgtcttatct ttagagattg ggaagaccct gatggaggac    480
gtggagaaca gcttcttctt gaatgtcaat tcccaagtaa caacagtgtg tcaggcactt    540
gctaaggatc ctaaattgca gcaaggctac aatgctatgg gattctccca gggaggccaa    600
tttctgaggg cagtggctca gagatgccct tcacctccca tgatcaatct gatctcggtt    660
gggggacaac atcaaggtgt ttttggactc cctcgatgcc aggagagag ctctcacatc    720 tgtgacttca tccgaaaaac actgaatgct ggggcgtact ccaaagttgt tcaggaacgc    780
ctcgtgcaag ccgaatactg gcatgacccc ataaaggagg atgtgtatcg caaccacagc    840
atcttcttgg cagatataaa tcaggagcgg ggtatcaatg agtcctacaa gaaaaacctg    900
atggccctga agaagtttgt gatggtgaaa ttcctcaatg attccattgt ggaccctgta    960
gattcggagt ggtttggatt ttacagaagt ggccaagcca aggaaaccat tcccttacag   1020
gagacctccc tgtacacaca ggaccgcctg ggctaaagg aaatgacaa tgcaggacag   1080 ctagtgtttc tggctacaga aggggaccat cttcagttgt ctgaagaatg gttttatgcc   1140
cacatcatac cattccttgg atga                                          1164
```

<210> SEQ ID NO 43
<211> LENGTH: 72
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

```
Gly Gly Gly Gly Ser Gly Gly Gly Gly Ser Arg Thr Leu Cys Gly Gly
1               5                   10                  15

Glu Leu Val Asp Thr Leu Gln Phe Val Cys Gly Asp Arg Gly Phe Leu
            20                  25                  30

Phe Ser Arg Pro Ala Ser Arg Val Ser Arg Arg Ser Arg Gly Ile Val
        35                  40                  45

Glu Glu Cys Cys Phe Arg Ser Cys Asp Leu Ala Leu Leu Glu Thr Tyr
    50                  55                  60

Cys Ala Thr Pro Ala Arg Ser Glu
65                  70
```

<210> SEQ ID NO 44
<211> LENGTH: 8
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 44 gcaagatg                                                                  8

<210> SEQ ID NO 45
<211> LENGTH: 2864
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 45

```
gcaagatggg agtgaggcac ccgccctgct cccaccggct cctggccgtc tgcgccctcg    60
tgtccttggc aaccgctgca ctcctggggc acatcctact ccatgatttc ctgctggttc   120
cccgagagct gagtggctcc tccccagtcc tggaggagac tcacccagct caccagcagg   180
gagccagtag accagggccc cgggatgccc aggcacaccc cggccgtccc agagcagtgc   240
ccacacagtg cgacgtcccc cccaacagcc gcttcgattg cgccctgac aaggccatca    300 cccaggaaca gtgcgaggcc cgcggctgtt gctacatccc tgcaaagcag gggctgcagg   360
gagcccagat ggggcagccc tggtgcttct cccacccag ctaccccagc tacaagctgg    420
agaacctgag ctcctctgaa atgggctaca cggccaccct gacccgtacc accccacct    480 tcttccccaa ggacatcctg accctgcggc tggacgtgat gatggagact gagaaccgcc   540
tccacttcac gatcaaagat ccagctaaca ggcgctacga ggtgcccttg agacccgc     600 atgtccacag ccgggcaccg tccccactct acagcgtgga gttctccgag agcccttcg    660 gggtgatcgt gcgccggcag ctggacggcc gcgtgctgct gaacacgacg gtggcgcccc   720
tgttctttgc ggaccagttc cttcagctgt ccacctcgct gccctcgcag tatatcacag   780
gcctcgccga gcacctcagt ccctgatgc tcagcaccag ctggaccagg atcaccctgt    840
ggaaccggga ccttgcgccc acgcccggtg cgaacctcta cgggtctcac cctttctacc   900
tggcgctgga ggacggcggg tcggcacacg gggtgttcct gctaaacagc aatgccatgg   960
atgtggtcct gcagccgagc cctgccctta gctggaggtc gacaggtggg atcctggatg  1020
tctacatctt cctgggccca gagcccaaga gcgtggtgca gcagtacctg gacgttgtgg  1080 gataccgtt catgccgcca tactggggcc tgggcttcca cctgtgccgc tggggctact   1140
cctccaccgc tatcacccgc caggtggtgg agaacatgac cagggcccac ttccccctgg  1200
acgtccagtg gaacgacctg gactacatgg actcccggag ggacttcacg ttcaacaagg  1260
atggcttccg ggacttcccg gccatggtgc aggagctgca ccagggcggc cggcgctaca  1320
tgatgatcgt ggatcctgcc atcagcagct cgggccctgc cggagctac aggccctacg   1380 acgagggtct gcggagggg gttttcatca ccaacgagac cggccagccg ctgattggga   1440
aggtatggcc cggtccact gccttccccg acttcaccaa ccccacagcc ctggcctggt   1500
gggaggacat ggtggctgag ttccatgacc aggtgccctt cgacggcatg tggattgaca  1560
tgaacgagcc ttccaacttc atcagggggct ctgaggacgg ctgccccaac aatgagctgg  1620
```

```
agaacccacc ctacgtgcct ggggtggttg gggggacccct ccaggcggcc accatctgtg    1680
cctccagcca ccagtttctc tccacacact acaacctgca caacctctac ggcctgaccg    1740
aagccatcgc ctcccacagg gcgctggtga aggctcgggg gacacgccca tttgtgatct    1800
cccgctcgac ctttgctggc cacggccgat acgccggcca ctggacgggg gacgtgtgga    1860
gctcctggga gcagctcgcc tcctccgtgc cagaaatcct gcagtttaac ctgctggggg    1920
tgcctctggt cggggccgac gtctgcggct tcctgggcaa cacctcagag gagctgtgtg    1980
tgcgctggac ccagctgggg gccttctacc ccttcatgcg gaaccacaac agcctgctca    2040
gtctgcccca ggagccgtac agcttcagcg agccggccca gcaggccatg aggaaggccc    2100
tcaccctgcg ctacgcactc ctccccccacc tctacacact gttccaccag gcccacgtcg    2160
cgggggagac cgtggcccgg cccctcttcc tggagttccc caaggactct agcacctgga    2220
ctgtggacca ccagctcctg tgggggagg ccctgctcat caccccagtg ctccaggccg    2280
ggaaggccga agtgactggc tacttcccct tgggcacatg gtacgacctg cagacggtgc    2340
cagtagaggc ccttggcagc tcccacccccc cacctgcagc tccccgtgag ccagccatcc    2400
acagcgaggg gcagtgggtg acgctgccgg ccccccctgga caccatcaac gtccacctcc    2460
gggctgggta catcatcccc ctgcagggcc ctggcctcac aaccacagag tcccgccagc    2520
agcccatggc cctggctgtg gccctgacca agggtgggga ggcccgaggg gagcttttct    2580
gggacgatgg agagagcctg gaagtgctgg agcgaggggc ctacacacag gtcatcttcc    2640
tggccaggaa taacacgatc gtgaatgagc tggtacgtgt gaccagtgag ggagctggcc    2700
tgcagctgca gaaggtgact gtcctgggcg tggccacggc gccccagcag gtcctctcca    2760
acggtgtccc tgtctccaac ttcacctaca gccccgacac caaggtcctg gacatctgtg    2820
tctcgctgtt gatgggagag cagtttctcg tcagctggtg ttag                     2864
```

<210> SEQ ID NO 46
<211> LENGTH: 892
<212> TYPE: PRT
<213> ORGANISM: Homo sapiens

<400> SEQUENCE: 46

```
Ser Arg Pro Gly Pro Arg Asp Ala Gln Ala His Pro Gly Arg Pro Arg
1               5                   10                  15

Ala Val Pro Thr Gln Cys Asp Val Pro Pro Asn Ser Arg Phe Asp Cys
                20                  25                  30

Ala Pro Asp Lys Ala Ile Thr Gln Glu Gln Cys Glu Ala Arg Gly Cys
            35                  40                  45

Cys Tyr Ile Pro Ala Lys Gln Gly Leu Gln Gly Ala Gln Met Gly Gln
        50                  55                  60

Pro Trp Cys Phe Phe Pro Ser Tyr Pro Ser Tyr Lys Leu Glu Asn
65                  70                  75                  80

Leu Ser Ser Ser Glu Met Gly Tyr Thr Ala Thr Leu Thr Arg Thr Thr
                85                  90                  95

Pro Thr Phe Phe Pro Lys Asp Ile Leu Thr Leu Arg Leu Asp Val Met
            100                 105                 110

Met Glu Thr Glu Asn Arg Leu His Phe Thr Ile Lys Asp Pro Ala Asn
        115                 120                 125

Arg Arg Tyr Glu Val Pro Leu Glu Thr Pro His Val His Ser Arg Ala
    130                 135                 140

Pro Ser Pro Leu Tyr Ser Val Glu Phe Ser Glu Glu Pro Phe Gly Val
```

```
            145                 150                 155                 160
        Ile Val Arg Arg Gln Leu Asp Gly Arg Val Leu Leu Asn Thr Thr Val
                            165                 170                 175
        Ala Pro Leu Phe Phe Ala Asp Gln Phe Leu Gln Leu Ser Thr Ser Leu
                            180                 185                 190
        Pro Ser Gln Tyr Ile Thr Gly Leu Ala Glu His Leu Ser Pro Leu Met
                            195                 200                 205
        Leu Ser Thr Ser Trp Thr Arg Ile Thr Leu Trp Asn Arg Asp Leu Ala
                            210                 215                 220
        Pro Thr Pro Gly Ala Asn Leu Tyr Gly Ser His Pro Phe Tyr Leu Ala
        225                 230                 235                 240
        Leu Glu Asp Gly Gly Ser Ala His Gly Val Phe Leu Leu Asn Ser Asn
                            245                 250                 255
        Ala Met Asp Val Val Leu Gln Pro Ser Pro Ala Leu Ser Trp Arg Ser
                            260                 265                 270
        Thr Gly Gly Ile Leu Asp Val Tyr Ile Phe Leu Gly Pro Glu Pro Lys
                            275                 280                 285
        Ser Val Val Gln Gln Tyr Leu Asp Val Val Gly Tyr Pro Phe Met Pro
                            290                 295                 300
        Pro Tyr Trp Gly Leu Gly Phe His Leu Cys Arg Trp Gly Tyr Ser Ser
        305                 310                 315                 320
        Thr Ala Ile Thr Arg Gln Val Val Glu Asn Met Thr Arg Ala His Phe
                            325                 330                 335
        Pro Leu Asp Val Gln Trp Asn Asp Leu Asp Tyr Met Asp Ser Arg Arg
                            340                 345                 350
        Asp Phe Thr Phe Asn Lys Asp Gly Phe Arg Asp Phe Pro Ala Met Val
                            355                 360                 365
        Gln Glu Leu His Gln Gly Gly Arg Arg Tyr Met Met Ile Val Asp Pro
                            370                 375                 380
        Ala Ile Ser Ser Ser Gly Pro Ala Gly Ser Tyr Arg Pro Tyr Asp Glu
        385                 390                 395                 400
        Gly Leu Arg Arg Gly Val Phe Ile Thr Asn Glu Thr Gly Gln Pro Leu
                            405                 410                 415
        Ile Gly Lys Val Trp Pro Gly Ser Thr Ala Phe Pro Asp Phe Thr Asn
                            420                 425                 430
        Pro Thr Ala Leu Ala Trp Trp Glu Asp Met Val Ala Glu Phe His Asp
                            435                 440                 445
        Gln Val Pro Phe Asp Gly Met Trp Ile Asp Met Asn Glu Pro Ser Asn
                            450                 455                 460
        Phe Ile Arg Gly Ser Glu Asp Gly Cys Pro Asn Asn Glu Leu Glu Asn
        465                 470                 475                 480
        Pro Pro Tyr Val Pro Gly Val Val Gly Gly Thr Leu Gln Ala Ala Thr
                            485                 490                 495
        Ile Cys Ala Ser Ser His Gln Phe Leu Ser Thr His Tyr Asn Leu His
                            500                 505                 510
        Asn Leu Tyr Gly Leu Thr Glu Ala Ile Ala Ser His Arg Ala Leu Val
                            515                 520                 525
        Lys Ala Arg Gly Thr Arg Pro Phe Val Ile Ser Arg Ser Thr Phe Ala
                            530                 535                 540
        Gly His Gly Arg Tyr Ala Gly His Trp Thr Gly Asp Val Trp Ser Ser
        545                 550                 555                 560
        Trp Glu Gln Leu Ala Ser Ser Val Pro Glu Ile Leu Gln Phe Asn Leu
                            565                 570                 575
```

-continued

Leu Gly Val Pro Leu Val Gly Ala Asp Val Cys Gly Phe Leu Gly Asn
                580                 585                 590

Thr Ser Glu Glu Leu Cys Val Arg Trp Thr Gln Leu Gly Ala Phe Tyr
            595                 600                 605

Pro Phe Met Arg Asn His Asn Ser Leu Leu Ser Leu Pro Gln Glu Pro
        610                 615                 620

Tyr Ser Phe Ser Glu Pro Ala Gln Gln Ala Met Arg Lys Ala Leu Thr
625                 630                 635                 640

Leu Arg Tyr Ala Leu Leu Pro His Leu Tyr Thr Leu Phe His Gln Ala
                645                 650                 655

His Val Ala Gly Glu Thr Val Ala Arg Pro Leu Phe Leu Glu Phe Pro
            660                 665                 670

Lys Asp Ser Ser Thr Trp Thr Val Asp His Gln Leu Leu Trp Gly Glu
        675                 680                 685

Ala Leu Leu Ile Thr Pro Val Leu Gln Ala Gly Lys Ala Glu Val Thr
    690                 695                 700

Gly Tyr Phe Pro Leu Gly Thr Trp Tyr Asp Leu Gln Thr Val Pro Val
705                 710                 715                 720

Glu Ala Leu Gly Ser Leu Pro Pro Pro Ala Ala Pro Arg Glu Pro
                725                 730                 735

Ala Ile His Ser Glu Gly Gln Trp Val Thr Leu Pro Ala Pro Leu Asp
            740                 745                 750

Thr Ile Asn Val His Leu Arg Ala Gly Tyr Ile Ile Pro Leu Gln Gly
        755                 760                 765

Pro Gly Leu Thr Thr Thr Glu Ser Arg Gln Gln Pro Met Ala Leu Ala
    770                 775                 780

Val Ala Leu Thr Lys Gly Gly Glu Ala Arg Gly Glu Leu Phe Trp Asp
785                 790                 795                 800

Asp Gly Glu Ser Leu Glu Val Leu Glu Arg Gly Ala Tyr Thr Gln Val
                805                 810                 815

Ile Phe Leu Ala Arg Asn Asn Thr Ile Val Asn Glu Leu Val Arg Val
            820                 825                 830

Thr Ser Glu Gly Ala Gly Leu Gln Leu Gln Lys Val Thr Val Leu Gly
        835                 840                 845

Val Ala Thr Ala Pro Gln Gln Val Leu Ser Asn Gly Val Pro Val Ser
    850                 855                 860

Asn Phe Thr Tyr Ser Pro Asp Thr Lys Val Leu Asp Ile Cys Val Ser
865                 870                 875                 880

Leu Leu Met Gly Glu Gln Phe Leu Val Ser Trp Cys
                885                 890

<210> SEQ ID NO 47
<211> LENGTH: 7
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47 caccatg                                                            7

<210> SEQ ID NO 48
<211> LENGTH: 201
<212> TYPE: DNA
<213> ORGANISM: Homo sapiens

```
<400> SEQUENCE: 48
gcttaccgcc ccagtgagac cctgtgcggc ggggagctgg tggacaccct ccagttcgtc        60
tgtggggacc gcggcttcta cttcagcagg cccgcaagcc gtgtgagccg tcgcagccgt       120
ggcatcgttg aggagtgctg tttccgcagc tgtgacctgg ccctcctgga gacgtactgt       180 gctaccccg ccaagtccga g                                                   201
```

GENE THERAPY CONSTRUCTS AND METHODS OF USE

CROSS-REFERENCE

This application claims the benefit of U.S. Provisional Application No. 62/664,741, filed Apr. 30, 2018; U.S. Provisional Application No. 62/688,640, filed Jun. 22, 2018; and U.S. Provisional Application No. 62/744,068, filed Oct. 10, 2018, each of which application is incorporated herein by reference in its entirety.

SEQUENCE LISTING

The instant application contains a Sequence Listing which has been filed electronically in ASCII format and is hereby incorporated by reference in its entirety. Said ASCII copy, created on Jul. 9, 2019, is named 36003-701_201_SL.txt and is 68,536 bytes in size.

BACKGROUND

Genetic disorders arise via heritable or de novo mutations occurring in gene coding regions of the genome. In some cases, such genetic disorders are treated by administration of a protein encoded by the gene mutated in the individual having the genetic disorder. Such treatment has challenges however, as administration of the protein does not always result in the protein reaching the organs, cells, or organelle where it is needed. Furthermore, this treatment also often requires biweekly infusions, which are not needed with gene therapy, where a single treatment can offer lasting relief. Therefore, gene therapy has the potential to offer improved results over currently available treatments for genetic disorders.

SUMMARY

Provided herein are compositions and methods for treatment of genetic disorders using gene therapy. Also provided herein are gene therapy vector components and methods to be used in gene therapy for improving protein expression and increasing cellular uptake or delivery and intracellular or sub-cellular targeting of therapeutic proteins provided by gene therapy vectors.

In certain aspects, there are provided gene therapy vectors, for example, gene therapy vectors comprising a nucleic acid construct comprising, in 5' to 3' order: (a) a translation initiation sequence, and (b) a nucleic acid sequence encoding a therapeutic protein. In some embodiments, the translation initiation sequence comprises a Kozak sequence. In some embodiments, the translation initiation sequence and the nucleic acid sequence encoding the therapeutic protein may overlap, such that the last three nucleotides of the translation initiation sequence are also the start codon for the therapeutic protein. In some embodiments, the Kozak sequence comprises the sequence $AX_1X_2ATGA$ (SEQ ID NO: 28), wherein each of $X_1$ and $X_2$ is any nucleotide. In some embodiments, $X_1$ comprises A. In some embodiments, $X_2$ comprises G. In some embodiments, the Kozak sequence comprises a nucleic acid sequence at least 85% identical to AAGATGA (SEQ ID NO: 29). In some embodiments, the Kozak sequence differs from the sequence of AAGATGA (SEQ ID NO: 29) by one or two nucleotides. In some embodiments, the Kozak sequence comprises AAGATGA (SEQ ID NO: 29). In some embodiments the Kozak sequence comprises a nucleic acid sequence at least 85% identical to GCAAGATG (SEQ ID NO: 44), wherein the last three nucleotides (ATG) are also the start codon for the therapeutic protein. In some embodiments the Kozak sequence differs from the sequence of GCAAGATG (SEQ ID NO: 44) by one or two nucleotides. In some embodiments, the Kozak sequence comprises GCAAGATG (SEQ ID NO: 44). In some embodiments the Kozak sequence comprises a nucleic acid sequence at least 85% identical to CACCATG (SEQ ID NO: 47). In some embodiments the Kozak sequence differs from the sequence of CACCATG (SEQ ID NO: 47) by one or two nucleotides. In some embodiments, the Kozak sequence comprises CACCATG (SEQ ID NO: 47). In some embodiments, the nucleic acid construct further comprises a nucleic acid sequence encoding a signal peptide capable of increasing secretion of the therapeutic protein as compared to the therapeutic protein without the signal peptide. In some embodiments, the signal peptide is selected from a binding immunoglobulin protein (BiP) signal peptide and a *Gaussia* signal peptide. In some embodiments, the BiP signal peptide comprises an amino acid sequence at least 90% identical to an amino acid sequence selected from the group consisting of SEQ ID NOs: 13-17. In some embodiments, the signal peptide differs from a sequence selected from the group consisting of SEQ ID Nos: 13-17 by 5 or fewer, 4 or fewer, 3 or fewer, 2 or fewer, or 1 amino acid. In some embodiments, the BiP signal peptide comprises an amino acid sequence selected from the group consisting of SEQ ID NOs: 13-17. In some embodiments, the *Gaussia* signal peptide comprises an amino acid sequence at least 90% identical to SEQ ID NO: 32. In some embodiments, the signal peptide differs from the sequence of SEQ ID NO: 32 by 5 or fewer, 4 or fewer, 3 or fewer, 2 or fewer, or 1 amino acid. In some embodiments, the *Gaussia* signal peptide comprises an amino acid sequence of SEQ ID NO: 32. In some embodiments, the nucleic acid construct further comprises an internal ribosomal entry sequence (IRES). In some embodiments, the IRES is a cricket paralysis virus (CrPV) IRES. In some embodiments, the IRES comprises a nucleic acid sequence at least 90% identical to SEQ ID NO: 12. In some embodiments, the IRES comprises SEQ ID NO: 12.

In additional aspects, there are provided gene therapy vectors comprising a nucleic acid construct comprising, in 5' to 3' order: (a) a nucleic acid sequence encoding a signal peptide, and (b) a nucleic acid sequence encoding a therapeutic protein, wherein the signal peptide is capable of increasing secretion of the therapeutic protein as compared to the therapeutic protein without the signal peptide. In some embodiments, the signal peptide is selected from a binding immunoglobulin protein (BiP) signal peptide and a *Gaussia* signal peptide. In some embodiments, the BiP signal peptide comprises an amino acid sequence at least 90% identical to an amino acid sequence selected from the group consisting of SEQ ID NOs: 13-17. In some embodiments, the signal peptide differs from a sequence selected from the group consisting of SEQ ID Nos: 13-17 by 5 or fewer, 4 or fewer, 3 or fewer, 2 or fewer, or 1 amino acid. In some embodiments, the BiP signal peptide comprises an amino acid sequence selected from the group consisting of SEQ ID NOs: 13-17. In some embodiments, the signal peptide comprises a *Gaussia* signal peptide. In some embodiments, the *Gaussia* signal peptide comprises an amino acid sequence at least 90% identical to SEQ ID NO: 32. In some embodiments, the signal peptide differs from the sequence of SEQ ID NO: 32 by 5 or fewer, 4 or fewer, 3 or fewer, 2 or fewer, or 1 amino acid. In some embodiments, the *Gaussia* signal peptide comprises SEQ ID NO: 32. In some embodiments, the nucleic acid construct further comprises a translation initiation sequence. In some embodiments, the translation initiation sequence comprises a Kozak sequence comprising AX₁X₂ATGA (SEQ ID NO: 28), wherein each of X₁ and X₂ is any nucleotide. In some embodiments, X₁ comprises A. In some embodiments, X₂ comprises G. In some embodiments, the Kozak sequence comprises a nucleic acid sequence at least 85% identical to AAGATGA (SEQ ID NO: 29). In some embodiments, the Kozak sequence differs from the sequence of AAGATGA (SEQ ID NO: 29) by one or two nucleotides. In some embodiments, the Kozak sequence comprises AAGATGA (SEQ ID NO: 29). In some embodiments the Kozak sequence comprises a nucleic acid sequence at least 85% identical to GCAAGATG (SEQ ID NO: 44). In some embodiments the Kozak sequence differs from the sequence of GCAAGATG (SEQ ID NO: 44) by one or two nucleotides. In some embodiments, the Kozak sequence comprises GCAAGATG (SEQ ID NO: 44). In some embodiments the Kozak sequence comprises a nucleic acid sequence at least 85% identical to CACCATG (SEQ ID NO: 47). In some embodiments the Kozak sequence differs from the sequence of CACCATG (SEQ ID NO: 47) by one or two nucleotides. In some embodiments, the Kozak sequence comprises CACCATG (SEQ ID NO: 47). In some embodiments, the nucleic acid construct further comprises an internal ribosomal entry sequence (IRES). In some embodiments, the IRES comprises an IRES selected from the group consisting of a cricket paralysis virus (CrPV) IRES, a picornavirus IRES, an Aphthovirus IRES, a Kaposi's sarcoma-associated herpesvirus IRES, a Hepatitis A IRES, a Hepatitis C IRES, a Pestivirus IRES, a Cripavirus IRES, a *Rhopalosiphum padi* virus IRES, and a Merek's disease virus IRES. In some embodiments, the IRES comprises a nucleic acid sequence at least 90% identical to SEQ ID NO: 12. In some embodiments, the IRES comprises SEQ ID NO: 12.

In further aspects, there are provided gene therapy vectors comprising a nucleic acid construct comprising, in 5' to 3' order: (a) an internal ribosomal entry sequence (IRES), and (b) a nucleic acid sequence encoding a therapeutic protein. In some embodiments, the IRES comprises an IRES selected from the group consisting of a cricket paralysis virus (CrPV) IRES, a picornavirus IRES, an Aphthovirus IRES, a Kaposi's sarcoma-associated herpesvirus IRES, a Hepatitis A IRES, a Hepatitis C IRES, a Pestivirus IRES, a Cripavirus IRES, a *Rhopalosiphum padi* virus IRES, and a Merek's disease virus IRES. In some embodiments, the IRES is a cricket paralysis virus (CrPV) IRES. In some embodiments, the IRES comprises a nucleic acid sequence at least 90% identical to SEQ ID NO: 12. In some embodiments, the IRES comprises SEQ ID NO: 12. In some embodiments, the nucleic acid construct further comprises a translation initiation sequence. In some embodiments, the translation initiation sequence comprises a Kozak sequence comprising AX₁X₂ATGA (SEQ ID NO: 28), wherein each of X₁ and X₂ is any nucleotide. In some embodiments, X₁ comprises A. In some embodiments, X₂ comprises G. In some embodiments, the Kozak sequence comprises a nucleic acid sequence at least 90% identical to AAGATGA (SEQ ID NO: 29). In some embodiments, the Kozak sequence comprises AAGATGA (SEQ ID NO: 29). In some embodiments the Kozak sequence comprises a nucleic acid sequence at least 85% identical to GCAAGATG (SEQ ID NO: 44). In some embodiments the Kozak sequence differs from the sequence of GCAAGATG (SEQ ID NO: 44) by one or two nucleotides. In some embodiments, the Kozak sequence comprises GCAAGATG (SEQ ID NO: 44). In some embodiments the Kozak sequence comprises a nucleic acid sequence at least 85% identical to CACCATG (SEQ ID NO: 47). In some embodiments the Kozak sequence differs from the sequence of CACCATG (SEQ ID NO: 47) by one or two nucleotides. In some embodiments, the Kozak sequence comprises CAC-CATG (SEQ ID NO: 47). In some embodiments, the nucleic acid construct further comprises a signal nucleic acid sequence encoding a signal peptide capable of increasing secretion of the therapeutic protein as compared to the therapeutic protein without the signal peptide. In some embodiments, the signal peptide is selected from a binding immunoglobulin protein (BiP) signal peptide and a *Gaussia* signal peptide. In some embodiments, the BiP signal peptide comprises an amino acid sequence at least 90% identical to an amino acid sequence selected from the group consisting of SEQ ID NOs: 13-17. In some embodiments, the BiP signal peptide comprises an amino acid sequence selected from the group consisting of SEQ ID NOs: 13-17. In some embodiments, the *Gaussia* signal peptide comprises an amino acid sequence at least 90% identical to SEQ ID NO: 32. In some embodiments, the *Gaussia* signal peptide comprises SEQ ID NO: 32.

In some embodiments, any of the nucleic acid constructs provided herein further comprise a nucleic acid sequence encoding a peptide that selectively binds to the CI-MPR with high affinity, wherein the therapeutic protein and the peptide that selectively binds to the CI-MPR are expressed as a fusion protein. In some embodiments, the nucleic acid construct further comprises a sequence encoding a linker peptide between the nucleic acid encoding the peptide that selectively binds to the CI-MPR nucleotide sequence and the nucleic acid sequence encoding the therapeutic protein. In some embodiments, the sequence of the linker peptide may overlap with the sequence of the therapeutic peptide or the sequence of the peptide that selectively binds to the CI-MPR, or both. In some embodiments, the peptide that binds to CI-MPR with high affinity is a variant IGF2 peptide (vIGF2). In some embodiments, the vIGF2 peptide facilitates uptake into the cells. In some embodiments, the vIGF2 peptide comprises an amino acid sequence at least 90% identical to an amino acid sequence selected from the group consisting of SEQ ID NOs: 1-11. In some embodiments, the vIGF2 peptide comprises an amino acid sequence selected from the group consisting of SEQ ID NOs: 2-11. In some embodiments, the vIGF2 nucleotide sequence is 5' to the nucleic acid sequence encoding a therapeutic protein. In some embodiments, the vIGF2 nucleotide sequence is 3' to the nucleic acid sequence encoding a therapeutic protein. In some embodiments, the nucleic acid construct further comprises a sequence encoding a linker peptide between the vIGF2 nucleotide sequence and the nucleic acid sequence encoding a therapeutic protein. In some embodiments, the linker peptide consists of 5-20 amino acids, 5-15 amino acids, 5-10 amino acids, 8-12 amino acids, or about 7, 8, 9, 10, 11, 12 or 13 amino acids. In some embodiments, the linker peptide comprises an amino acid sequence at least 90% identical to SEQ ID NO: 18-21, SEQ ID NO: 33 or SEQ ID NO: 37. In some embodiments, the linker peptide comprises SEQ ID NO: 18-21, SEQ ID NO: 33 or SEQ ID NO: 37. In some embodiments, the therapeutic protein is associated with a lysosomal storage disorder. In some embodiments, the therapeutic protein is a lysosomal enzyme or enzymatically active fragment thereof. In some embodiments, the therapeutic protein is selected from the group consisting of alpha-galactosidase (A or B), β-galactosidase, β-hexosaminidase (A or B), galactosylceramidase, arylsulfatase (A or B), β-glucocerebrosidase, glucocerebrosidase, lysosomal acid lipase, lysosomal enzyme acid sphingomyelinase, formylglycine-generating enzyme, iduronidase (e.g., alpha-L), acetyl-CoA:alpha-glucosaminide N-acetyltransferase, glycosaminoglycan alpha-L-iduronohydrolase, heparan N-sulfatase, N-acetyl-α-D-glucosaminidase (NAGLU), iduronate-2-sulfatase, galactosamine-6-sulfate sulfatase, N-acetylgalactosamine-6-sulfatase, glycosaminoglycan N-acetylgalactosamine 4-sulfatase, β-glucuronidase, hyaluronidase, alpha-N-acetyl neuraminidase (sialidase), ganglioside sialidase, phosphotransferase, alpha-glucosidase, alpha-D-mannosidase, beta-D-mannosidase, aspartylglucosaminidase, alpha-L-fucosidase, battenin, palmitoyl protein thioesterases, and other Batten-related proteins (e.g., ceroid-lipofuscinosis neuronal protein 6), or an enzymatically active fragment thereof. In some embodiments, the therapeutic protein is an alpha-galactosidase, or an enzymatically active fragment thereof. In some embodiments, the therapeutic protein is an alpha-glucosidase, or an enzymatically active fragment thereof. In some embodiments, the therapeutic protein is a palmitoyl protein thioesterase (PPT)—including palmitoyl protein thioesterase 1 and 2 (PPT1 and PPT2 respectively). In some embodiments, the therapeutic protein is palmitoyl protein thioesterase 1. In some embodiments, the therapeutic protein is N-acetyl-α-D-glucosaminidase (NAGLU). In some embodiments, the therapeutic protein is associated with a genetic disorder selected from the group consisting of CDKL5 deficiency disorder, cystic fibrosis, alpha- and beta-thalassemias, sickle cell anemia, Marfan syndrome, fragile X syndrome, Huntington's disease, hemochromatosis, Congenital Deafness (nonsyndromic), Tay-Sachs, Familial hypercholesterolemia, Duchenne muscular dystrophy, Stargardt disease, Usher syndrome, choroideremia, achromatopsia, X-linked retinoschisis, hemophilia, Wiskott-Aldrich syndrome, X-linked chronic granulomatous disease, aromatic L-amino acid decarboxylase deficiency, recessive dystrophic epidermolysis bullosa, alpha 1 antitrypsin deficiency, Hutchinson-Gilford progeria syndrome (HGPS), Noonan syndrome, X-linked severe combined immunodeficiency (X-SCID). In some embodiments, the therapeutic protein is selected from the group consisting of CDKL5, Connexin 26, hexosaminidase A, LDL receptor, Dystrophin, CFTR, beta-globulin, HFE, Huntington, ABCA4, myosin VIIA (MYO7A), Rab escort protein-1 (REP1), cyclic nucleotide gated channel beta 3 (CNGB3), retinoschisin 1 (RS1), hemoglobin subunit beta (HBB), Factor IX, WAS, cytochrome B-245 beta chain, dopa decarboxylase (DDC), collagen type VII alpha 1 chain (COL7A1), serpin family A member 1 (SERPINA1), LMNA, PTPN11, SOS1, RAF1, KRAS, and IL2 receptor γ gene. In some embodiments, the therapeutic protein is capable of replacing a defective or deficient protein associated with a genetic disorder in a subject having the genetic disorder. In some embodiments, the genetic disorder is a lysosomal storage disorder. In some embodiments, the genetic disorder is selected from the group consisting of aspartylglucosaminuria, Batten disease, cystinosis, Fabry disease, Gaucher disease type I, Gaucher disease type II, Gaucher disease type III, Pompe disease, Tay Sachs disease, Sandhoff disease, metachomatic leukodystrophy, mucolipidosis type I, mucolipidosis type II, mucolipidosis type III, mucolipidosis type IV, Hurler disease, Hunter disease, Sanfilippo disease type A, Sanfilippo disease type B, Sanfilippo disease type C, Sanfilippo disease type D, Morquio disease type A, Morquio disease type B, Maroteau-Lamy disease, Sly disease, Niemann-Pick disease type A, Niemann-Pick disease type B, Niemann-Pick disease type C1, Niemann-Pick disease type C2, Schindler disease type I, and Schindler disease type II. In some embodiments, the lysosomal storage disorder is selected from the group consisting of activator deficiency, GM2-gangliosidosis; GM2-gangliosidosis, AB variant; alpha-mannosidosis (type 2, moderate form; type 3, neonatal, severe); beta-mannosidosis; lysosomal acid lipase deficiency; cystinosis (late-onset juvenile or adolescent nephropathic type; infantile nephropathic); Chanarin-Dorfman syndrome; neutral lipid storage disease with myopathy; NLSDM; Danon disease; Fabry disease; Fabry disease type II, late-onset; Farber disease; Farber lipogranulomatosis; fucosidosis; galactosialidosis (combined neuraminidase & beta-galactosidase deficiency); Gaucher disease; type II Gaucher disease; type III Gaucher disease; type IIIC Gaucher disease; Gaucher disease, atypical, due to saposin C deficiency; GM1-gangliosidosis (late-infantile/juvenile GM1-gangliosidosis; adult/chronic GM1-gangliosidosis); Globoid cell leukodystrophy, Krabbe disease (Late infantile onset; Juvenile Onset; Adult Onset); Krabbe disease, atypical, due to saposin A deficiency; Metachromatic Leukodystrophy (juvenile; adult); partial cerebroside sulfate deficiency; pseudoarylsulfatase A deficiency; metachromatic leukodystrophy due to saposin B deficiency; Mucopolysaccharidoses disorders: MPS I, Hurler syndrome; MPS I, Hurler-Scheie syndrome; MPS I, Scheie syndrome; MPS II, Hunter syndrome; MPS II, Hunter syndrome; Sanfilippo syndrome Type A/MPS IIIA; Sanfilippo syndrome Type B/MPS IIIB; Sanfilippo syndrome Type C/MPS IIIC; Sanfilippo syndrome Type D/MPS IIID; Morquio syndrome, type A/MPS IVA; Morquio syndrome, type B/MPS IVB; MPS IX hyaluronidase deficiency; MPS VI Maroteaux-Lamy syndrome; MPS VII Sly syndrome; mucolipidosis I, sialidosis type II; I-cell disease, Leroy disease, mucolipidosis II; Pseudo-Hurler polydystrophy/mucolipidosis type III; mucolipidosis IIIC/ML III GAMMA; mucolipidosis type IV; multiple sulfatase deficiency; Niemann-Pick disease (type B; type C1/chronic neuronopathic form; type C2; type D/Nova Scotian type); Neuronal Ceroid Lipofuscinoses: CLN6 disease—Atypical Late Infantile, Late-Onset variant, Early Juvenile; Batten-Spielmeyer-Vogt/Juvenile NCL/CLN3 disease; Finnish Variant Late Infantile CLN5; Jansky-Bielschowsky disease/Late infantile CLN2/TPP1 Disease; Kufs/Adult-onset NCL/CLN4 disease (type B); Northern Epilepsy/variant late infantile CLN8; Santavuori-Haltia/Infantile CLN1/PPT disease; Pompe disease (glycogen storage disease type II); late-onset Pompe disease; Pycnodysostosis; Sandhoff disease/GM2 gangliosidosis; Sandhoff disease/GM2 gangliosidosis; Sandhoff disease/GM2 Gangliosidosis; Schindler disease (type III/intermediate, variable); Kanzaki disease; Salla disease; infantile free sialic acid storage disease (ISSD); spinal muscular atrophy with progressive myoclonic epilepsy (SMAPME); Tay-Sachs disease/GM2 gangliosidosis; juvenile-onset Tay-Sachs disease; late-onset Tay-Sachs disease; Christianson syndrome; Lowe oculocerebrorenal syndrome; Charcot-Marie-Tooth type 4J, CMT4J; Yunis-Varon syndrome; bilateral temporooccipital polymicrogyria (BTOP); X-linked hypercalciuric nephrolithiasis, Dent-1; and Dent disease 2, adenosine deaminase severe combined immunodeficiency (ADA-SCID), and neuronal ceroid lipofuscinosis. In some embodiments, the genetic disorder is Pompe disease. In some embodiments, the genetic disorder is neuronal ceroid lipofuscinosis. In some embodiments, the neuronal ceroid lipofuscinosis is selected from the group consisting of Infantile NCL (Santavuori-Haltia disease), Late Infantile NCL (Jansky-Bielschowsky disease), Batten disease, Adult NCL (Kufs disease), Finnish Late Infantile NCL, Variant Late Infantile NCL, CLN7, CLN8, Turkish Late Infantile NCL, NCL type 9, and CLN10. In some embodiments, the gene therapy vector is a viral vector. In some embodiments, the viral vector is an adeno-associated virus vector, a retrovirus vector, a lentivirus vector, a pox virus vector, a vaccinia virus vector, an adenovirus vector, or a herpes virus vector. In some embodiments, the viral vector is an AAV vector. In some embodiments, the AAV vector comprises inverted terminal repeats (ITRs). In some embodiments, the AAV vector is selected from the group consisting of an AAV1 vector, an AAV2 vector, an AAV3 vector, an AAV4 vector, an AAV5 vector, an AAV6 vector, an AAV7 vector, an AAV8 vector, an AAV9 vector, an AAVrhS vector, an AAVrh10 vector, an AAVrh33 vector, an AAVrh34 vector, an AAVrh74 vector, an AAV Anc80 vector, an AAVPHP.B vector, an AAVhu68 vector, and an AAV-DJ vector.

In certain aspects, there are provided gene therapy vectors, such as gene therapy vectors comprising: (a) a nucleic acid sequence encoding a therapeutic protein, and (b) a nucleic acid sequence encoding a peptide that binds to the CI-MPR with high affinity. In some embodiments, the peptide is a variant IGF2 (vIGF2) peptide. In some embodiments, the vIGF2 peptide comprises an amino acid sequence that is at least 90% identical to SEQ ID NO: 1 and having at least one substitution at one or more positions selected from the group consisting of positions 6, 26, 27, 43, 48, 49, 50, 54, 55, and 65 of SEQ ID NO: 1. In some embodiments, the at least one substitution is selected from the group consisting of E6R, F26S, Y27L, V43L, F48T, R49S, S50I, A54R, L55R, and K65R of SEQ ID NO: 1. In some embodiments, the vIGF2 peptide comprises at least two substitutions at two or more positions selected from the group consisting of positions 6, 26, 27, 43, 48, 49, 50, 54, and 55 of SEQ ID NO: 1. In some embodiments, the at least two substitutions are selected from the group consisting of E6R, F26S, Y27L, V43L, F48T, R49S, S50I, A54R, and L55R of SEQ ID NO: 1. In some embodiments, the vIGF2 peptide comprises an N-terminal deletion. In some embodiments, the vIGF2 peptide comprises an N-terminal deletion at position 1 of SEQ ID NO: 1. In some embodiments, the vIGF2 peptide comprises an N-terminal deletion of positions 1-2 of SEQ ID NO: 1. In some embodiments, the vIGF2 peptide comprises an N-terminal deletion of positions 1-3 of SEQ ID NO: 1. In some embodiments, the vIGF2 peptide comprises an N-terminal deletion of positions 1-4 of SEQ ID NO: 1. In some embodiments, the vIGF2 peptide comprises an N-terminal deletion of positions 1-4 of SEQ ID NO: 1 and substitutions of E6R, Y27L, and K65R. In some embodiments, the vIGF2 peptide comprises an N-terminal deletion of positions 1-4 of SEQ ID NO:1 and substitutions of E6R and Y27L. In some embodiments, the vIGF2 peptide comprises an N-terminal deletion of positions 1-5 of SEQ ID NO: 1. In some embodiments, the vIGF2 peptide comprises an N-terminal deletion at positions 1-6 of SEQ ID NO: 1. In some embodiments, the vIGF2 peptide comprises an N-terminal deletion at positions 1-7 of SEQ ID NO: 1. In some embodiments, the vIGF2 peptide has decreased or no affinity for the insulin receptor and IGF1R as compared to native IGF2 peptide. In some embodiments, the vIGF2 peptide is capable of facilitating uptake of the therapeutic protein into a cell. In some embodiments, the vIGF2 peptide is capable of facilitating uptake of the therapeutic protein into a lysosome. In some embodiments, the therapeutic protein is capable of replacing a defective or deficient protein associated with a genetic disorder in a subject having the genetic disorder. In some embodiments, the therapeutic protein is a lysosomal enzyme or enzymatically active fragment thereof. In some embodiments, the genetic disorder is a lysosomal storage disorder. In some embodiments, the genetic disorder is selected from the group consisting of aspartylglucosaminuria, Batten disease, cystinosis, Fabry disease, Gaucher disease type I, Gaucher disease type II, Gaucher disease type III, Pompe disease, Tay Sachs disease, Sandhoff disease, metachomatic leukodystrophy, mucolipidosis type I, mucolipidosis type II, mucolipidosis type III, mucolipidosis type IV, Hurler disease, Hunter disease, Sanfilippo disease type A, Sanfilippo disease type B, Sanfilippo disease type C, Sanfilippo disease type D, Morquio disease type A, Morquio disease type B, Maroteau-Lamy disease, Sly disease, Niemann-Pick disease type A, Niemann-Pick disease type B, Niemann-Pick disease type C1, Niemann-Pick disease type C2, Schindler disease type I, and Schindler disease type II. In some embodiments, the lysosomal storage disorder is selected from the group consisting of activator deficiency, GM2-gangliosidosis; GM2-gangliosidosis, AB variant; alpha-mannosidosis (type 2, moderate form; type 3, neonatal, severe); beta-mannosidosis; lysosomal acid lipase deficiency; cystinosis (late-onset juvenile or adolescent nephropathic type; infantile nephropathic); Chanarin-Dorfman syndrome; neutral lipid storage disease with myopathy; NLSDM; Danon disease; Fabry disease; Fabry disease type II, late-onset; Farber disease; Farber lipogranulomatosis; fucosidosis; galactosialidosis (combined neuraminidase & beta-galactosidase deficiency); Gaucher disease; type II Gaucher disease; type III Gaucher disease; type IIIC Gaucher disease; Gaucher disease, atypical, due to saposin C deficiency; GM1-gangliosidosis (late-infantile/juvenile GM1-gangliosidosis; adult/chronic GM1-gangliosidosis); Globoid cell leukodystrophy, Krabbe disease (Late infantile onset; Juvenile Onset; Adult Onset); Krabbe disease, atypical, due to saposin A deficiency; Metachromatic Leukodystrophy (juvenile; adult); partial cerebroside sulfate deficiency; pseudoarylsulfatase A deficiency; metachromatic leukodystrophy due to saposin B deficiency; Mucopolysaccharidoses disorders: MPS I, Hurler syndrome; MPS I, Hurler-Scheie syndrome; MPS I, Scheie syndrome; MPS II, Hunter syndrome; MPS II, Hunter syndrome; Sanfilippo syndrome Type A/MPS IIIA; Sanfilippo syndrome Type B/MPS IIIB; Sanfilippo syndrome Type C/MPS IIIC; Sanfilippo syndrome Type D/MPS IIID; Morquio syndrome, type A/MPS IVA; Morquio syndrome, type B/MPS IVB; MPS IX hyaluronidase deficiency; MPS VI Maroteaux-Lamy syndrome; MPS VII Sly syndrome; mucolipidosis I, sialidosis type II; I-cell disease, Leroy disease, mucolipidosis II; Pseudo-Hurler polydystrophy/mucolipidosis type III; mucolipidosis IIIC/ML III GAMMA; mucolipidosis type IV; multiple sulfatase deficiency; Niemann-Pick disease (type B; type C1/chronic neuronopathic form; type C2; type D/Nova Scotian type); Neuronal Ceroid Lipofuscinoses: CLN6 disease—Atypical Late Infantile, Late-Onset variant, Early Juvenile; Batten-Spielmeyer-Vogt/Juvenile NCL/CLN3 disease; Finnish Variant Late Infantile CLN5; Jansky-Bielschowsky disease/Late infantile CLN2/TPP1 Disease; Kufs/Adult-onset NCL/CLN4 disease (type B); Northern Epilepsy/variant late infantile CLN8; Santavuori-Haltia/Infantile CLN1/PPT disease; Pompe disease (glycogen storage disease type II); late-onset Pompe disease; Pycnodysostosis; Sandhoff disease/GM2 gangliosidosis; Sandhoff disease/GM2 gangliosidosis; Sandhoff disease/GM2 Gangliosidosis; Schindler disease (type III/intermediate, variable); Kanzaki disease; Salla disease; infantile free sialic acid storage disease (ISSD); spinal muscular atrophy with progressive myoclonic epilepsy (SMAPME); Tay-Sachs disease/GM2 gangliosidosis; juvenile-onset Tay-Sachs disease; late-onset Tay-Sachs disease; Christianson syndrome; Lowe oculocerebrorenal syndrome; Charcot-Marie-Tooth type 4J, CMT4J; Yunis-Varon syndrome; bilateral temporooccipital polymicrogyria (BTOP); X-linked hypercalciuric nephrolithiasis, Dent-1; and Dent disease 2, adenosine deaminase severe combined immunodeficiency (ADA-SCID), chronic granulomatous disease (CGD), and neuronal ceroid lipofuscinosis. In some embodiments, the genetic disorder is Pompe disease. In some embodiments, the genetic disorder is neuronal ceroid lipofuscinosis. In some embodiments, the neuronal ceroid lipofuscinosis is selected from the group consisting of Infantile NCL (Santavuori-Haltia disease), Late Infantile NCL (Jansky-Bielschowsky disease), Batten disease, Adult NCL (Kufs disease), Finnish Late Infantile NCL, Variant Late Infantile NCL, CLN7, CLN8, Turkish Late Infantile NCL, NCL type 9, and CLN10. In some embodiments, the therapeutic protein is a soluble lysosomal enzyme. In some embodiments, the therapeutic protein comprises an enzyme selected from the group consisting of alpha-galactosidase (A or B), β-galactosidase, β-hexosaminidase (A or B), galactosylceramidase, arylsulfatase (A or B), β-glucocerebrosidase, glucocerebrosidase, lysosomal acid lipase, lysosomal enzyme acid sphingomyelinase, formylglycine-generating enzyme, iduronidase (e.g., alpha-L), acetyl-CoA:alpha-glucosaminide N-acetyltransferase, glycosaminoglycan alpha-L-iduronohydrolase, heparan N-sulfatase, N-acetyl-α-D-glucosaminidase (NA-GLU), iduronate-2-sulfatase, galactosamine-6-sulfate sulfatase, N-acetylgalactosamine-6-sulfatase, glycosaminoglycan N-acetylgalactosamine 4-sulfatase, β-glucuronidase, hyaluronidase, alpha-N-acetyl neuraminidase (sialidase), ganglioside sialidase, phosphotransferase, alpha-glucosidase, alpha-D-mannosidase, beta-D-mannosidase, aspartylglucosaminidase, alpha-L-fucosidase, battenin, palmitoyl protein thioesterases, and other Batten-related proteins (e.g., ceroid-lipofuscinosis neuronal protein 6), or an enzymatically active fragment thereof. In some embodiments, the therapeutic protein is an alpha-glucosidase, or an enzymatically active fragment thereof. In some embodiments, the therapeutic protein is N-acetyl-α-D-glucosaminidase (NA-GLU). In some embodiments, the palmitoyl protein thioesterase is palmitoyl protein thioesterase 1 (PPT1) or 2 (PPT2). In some embodiments, the palmitoyl protein thioesterase is palmitoyl protein thioesterase 1. In some embodiments, the nucleic acid construct further comprises a translation initiation sequence. In some embodiments, the translation initiation sequence comprises a Kozak sequence. In some embodiments, the Kozak sequence comprises the sequence $AX_1X_2ATGA$ (SEQ ID NO: 28), wherein each of $X_1$ and $X_2$ is any nucleotide. In some embodiments, $X_1$ comprises A. In some embodiments, $X_2$ comprises G. In some embodiments, the Kozak sequence comprises a nucleic acid sequence at least 90% identical to AAGATGA (SEQ ID NO: 29). In some embodiments, the Kozak sequence comprises AAGATGA (SEQ ID NO: 29). In some embodiments the Kozak sequence comprises a nucleic acid sequence at least 85% identical to GCAAGATG (SEQ ID NO: 44). In some embodiments the Kozak sequence differs from the sequence of GCAAGATG (SEQ ID NO: 44) by one or two nucleotides. In some embodiments, the Kozak sequence comprises GCAAGATG (SEQ ID NO: 44). In some embodiments the Kozak sequence comprises a nucleic acid sequence at least 85% identical to CACCATG (SEQ ID NO: 47). In some embodiments the Kozak sequence differs from the sequence of CACCATG (SEQ ID NO: 47) by one or two nucleotides. In some embodiments, the Kozak sequence comprises CACCATG (SEQ ID NO: 47). In some embodiments, the nucleic acid construct further comprises a nucleic acid sequence encoding a signal peptide wherein the signal peptide is capable of increasing secretion of the therapeutic protein as compared to the therapeutic protein without the signal peptide. In some embodiments, the nucleic acid construct further comprises a nucleic acid sequence encoding a signal peptide wherein the signal peptide is capable of increasing secretion of the therapeutic protein as compared to the therapeutic protein with the natural signal peptide. In some embodiments, the nucleic acid construct comprises a nucleic acid sequence encoding a non-native signal peptide, wherein the non-native signal peptide is capable of increasing secretion of the therapeutic protein as compared to the native signal peptide for the therapeutic protein. In some embodiments, the signal peptide is selected from a binding immunoglobulin protein (BiP) signal peptide and a *Gaussia* signal peptide. In some embodiments, the BiP signal peptide comprises an amino acid sequence at least 90% identical to an amino acid sequence selected from the group consisting of SEQ ID NOs: 13-17. In some embodiments, the BiP signal peptide comprises an amino acid sequence selected from the group consisting of SEQ ID NOs: 13-17. In some embodiments, the signal peptide comprises a *Gaussia* signal peptide. In some embodiments, the *Gaussia* signal peptide comprises an amino acid sequence at least 90% identical to SEQ ID NO: 32. In some embodiments, the *Gaussia* signal peptide comprises SEQ ID NO: 32. In some embodiments, the vIGF2 nucleic acid sequence is 5' to the nucleic acid sequence encoding a therapeutic protein. In some embodiments, the vIGF2 nucleic acid sequence is 3' to the nucleic acid sequence encoding a therapeutic protein. In some embodiments, the nucleic acid construct further comprises a sequence encoding a linker peptide between the vIGF2 nucleotide sequence and the nucleic acid sequence encoding a therapeutic protein. In some embodiments, the linker consists of 5-20 amino acids, 5-15 amino acids, 5-10 amino acids, 8-12 amino acids, or about 7, 8, 9, 10, 11, 12 or 13 amino acids. In some embodiments, the linker peptide comprises SEQ ID NO: 18-21 or SEQ ID NO: 33. In some embodiments, the gene therapy vector is a virus vector. In some embodiments, the virus vector is an adenovirus vector, an adeno-associated virus (AAV) vector, a retrovirus vector, a lentivirus vector, or a herpes virus vector. In some embodiments, the virus vector is an AAV vector. In some embodiments, the AAV vector comprises inverted terminal repeats (ITRs). In some embodiments, the AAV vector is selected from the group consisting of an AAV1 vector, an AAV2 vector, an AAV3 vector, an AAV4 vector, an AAV5 vector, an AAV6 vector, an AAV7 vector, an AAV8 vector, an AAV9 vector, an AAVrhS vector, an AAVrh10 vector, an AAVrh33 vector, an AAVrh34 vector, an AAVrh74 vector, an AAV Anc80 vector, an AAVPHP.B vector, an AAVhu68 vector, and an AAV-DJ vector.

A gene therapy vector comprising a nucleic acid construct comprising: (a) a nucleic acid sequence encoding a therapeutic protein, and (b) a nucleic acid sequence encoding a peptide that increases endocytosis of the therapeutic protein. In some embodiments, the peptide that increases endocytosis of the therapeutic protein is a peptide that binds to the CI-MPR. In some embodiments, the peptide is a variant IGF2 (vIGF2) peptide, a HIRMab, or a TfRMab or other cell targeting peptide or protein. In some embodiments, the peptide is vIGF2. In some embodiments, the vIGF2 peptide comprises an amino acid sequence that is at least 90% identical to SEQ ID NO: 1 and having at least one substitution at one or more positions selected from the group consisting of positions 6, 26, 27, 43, 48, 49, 50, 54, 55, and 65 of SEQ ID NO: 1. In some embodiments, the at least one substitution is selected from the group consisting of E6R, F26S, Y27L, V43L, F48T, R49S, S50I, A54R, L55R, and K65R of SEQ ID NO: 1. In some embodiments, the at least one substitution is selected from the group consisting of E6R, F26S, Y27L, V43L, F48T, R49S, S50I, A54R, and L55R of SEQ ID NO: 1. In some embodiments, the vIGF2 peptide comprises at least two substitutions at two or more positions selected from the group consisting of positions 6, 26, 27, 43, 48, 49, 50, 54, and 55 of SEQ ID NO: 1. In some embodiments, the at least two substitutions are selected from the group consisting of E6R, F26S, Y27L, V43L, F48T, R49S, S50I, A54R, and L55R of SEQ ID NO: 1. In some embodiments, the vIGF2 peptide comprises an N-terminal deletion. In some embodiments, the vIGF2 peptide comprises an N-terminal deletion at position 1 of SEQ ID NO: 1. In some embodiments, the vIGF2 peptide comprises an N-terminal deletion at positions 1-6 of SEQ ID NO: 1. In some embodiments, the vIGF2 peptide comprises an N-terminal deletion of positions 1-2 of SEQ ID NO: 1. In some embodiments, the vIGF2 peptide comprises an N-terminal deletion of positions 1-3 of SEQ ID NO: 1. In some embodiments, the vIGF2 peptide comprises an N-terminal deletion of positions 1-4 of SEQ ID NO: 1. In some embodiments, the vIGF2 peptide comprises an N-terminal deletion of positions 1-4 of SEQ ID NO: 1 and a substitution of E6R, Y27L, and K65R. In some embodiments, the vIGF2 peptide comprises an N-terminal deletion of positions 1-4 of SEQ ID NO:1 and a substitution of E6R and Y27L. In some embodiments, the vIGF2 peptide comprises an N-terminal deletion of positions 1-5 of SEQ ID NO: 1. In some embodiments, the vIGF2 peptide comprises an N-terminal deletion of positions 1-6 of SEQ ID NO: 1. In some embodiments, the vIGF2 peptide comprises an N-terminal deletion at positions 1-7 of SEQ ID NO: 1. In some embodiments, the vIGF2 peptide has increased specificity for the cation-independent M6P receptor (CI-MPR) as compared to native IGF2 peptide. In some embodiments, the vIGF2 peptide is capable of facilitating uptake of the therapeutic protein into a lysosome in a cell. In some embodiments, the therapeutic protein is capable of replacing a defective or deficient protein associated with a genetic disorder in a subject having the genetic disorder. In some embodiments, the therapeutic protein is a lysosomal enzyme or enzymatically active fragment thereof. In some embodiments, the genetic disorder is a lysosomal storage disorder. In some embodiments, the genetic disorder is selected from the group consisting of aspartylglucosaminuria, Batten disease, cystinosis, Fabry disease, Gaucher disease type I, Gaucher disease type II, Gaucher disease type III, Pompe disease, Tay Sachs disease, Sandhoff disease, metachomatic leukodystrophy, mucolipidosis type I, mucolipidosis type II, mucolipidosis type III, mucolipidosis type IV, Hurler disease, Hunter disease, Sanfilippo disease type A, Sanfilippo disease type B, Sanfilippo disease type C, Sanfilippo disease type D, Morquio disease type A, Morquio disease type B, Maroteau-Lamy disease, Sly disease, Niemann-Pick disease type A, Niemann-Pick disease type B, Niemann-Pick disease type C1, Niemann-Pick disease type C2, Schindler disease type I, and Schindler disease type II. In some embodiments, the lysosomal storage disorder is selected from the group consisting of activator deficiency, GM2-gangliosidosis; GM2-gangliosidosis, AB variant; alpha-mannosidosis (type 2, moderate form; type 3, neonatal, severe); beta-mannosidosis; lysosomal acid lipase deficiency; cystinosis (late-onset juvenile or adolescent nephropathic type; infantile nephropathic); Chanarin-Dorfman syndrome; neutral lipid storage disease with myopathy; NLSDM; Danon disease; Fabry disease; Fabry disease type II, late-onset; Farber disease; Farber lipogranulomatosis; fucosidosis; galactosialidosis (combined neuraminidase & beta-galactosidase deficiency); Gaucher disease; type II Gaucher disease; type III Gaucher disease; type IIIC Gaucher disease; Gaucher disease, atypical, due to saposin C deficiency; GM1-gangliosidosis (late-infantile/juvenile GM1-gangliosidosis; adult/chronic GM1-gangliosidosis); Globoid cell leukodystrophy, Krabbe disease (Late infantile onset; Juvenile Onset; Adult Onset); Krabbe disease, atypical, due to saposin A deficiency; Metachromatic Leukodystrophy (juvenile; adult); partial cerebroside sulfate deficiency; pseudoarylsulfatase A deficiency; metachromatic leukodystrophy due to saposin B deficiency; Mucopolysaccharidoses disorders: MPS I, Hurler syndrome; MPS I, Hurler-Scheie syndrome; MPS I, Scheie syndrome; MPS II, Hunter syndrome; MPS II, Hunter syndrome; Sanfilippo syndrome Type A/MPS IIIA; Sanfilippo syndrome Type B/MPS IIIB; Sanfilippo syndrome Type C/MPS IIIC; Sanfilippo syndrome Type D/MPS IIID; Morquio syndrome, type A/MPS IVA; Morquio syndrome, type B/MPS IVB; MPS IX hyaluronidase deficiency; MPS VI Maroteaux-Lamy syndrome; MPS VII Sly syndrome; mucolipidosis I, sialidosis type II; I-cell disease, Leroy disease, mucolipidosis II; Pseudo-Hurler polydystrophy/mucolipidosis type III; mucolipidosis IIIC/ML III GAMMA; mucolipidosis type IV; multiple sulfatase deficiency; Niemann-Pick disease (type B; type C1/chronic neuronopathic form; type C2; type D/Nova Scotian type); Neuronal Ceroid Lipofuscinoses: CLN6 disease—Atypical Late Infantile, Late-Onset variant, Early Juvenile; Batten-Spielmeyer-Vogt/Juvenile NCL/CLN3 disease; Finnish Variant Late Infantile CLN5; Jansky-Bielschowsky disease/Late infantile CLN2/TPP1 Disease; Kufs/Adult-onset NCL/CLN4 disease (type B); Northern Epilepsy/variant late infantile CLN8; Santavuori-Haltia/Infantile CLN1/PPT disease; Pompe disease (glycogen storage disease type II); late-onset Pompe disease; Pycnodysostosis; Sandhoff disease/GM2 gangliosidosis; Sandhoff disease/GM2 gangliosidosis; Sandhoff disease/GM2 Gangliosidosis; Schindler disease (type III/intermediate, variable); Kanzaki disease; Salla disease; infantile free sialic acid storage disease (ISSD); spinal muscular atrophy with progressive myoclonic epilepsy (SMAPME); Tay-Sachs disease/GM2 gangliosidosis; juvenile-onset Tay-Sachs disease; late-onset Tay-Sachs disease; Christianson syndrome; Lowe oculocerebrorenal syndrome; Charcot-Marie-Tooth type 4J, CMT4J; Yunis-Varon syndrome; bilateral temporooccipital polymicrogyria (BTOP); X-linked hypercalciuric nephrolithiasis, Dent-1; and Dent disease 2, adenosine deaminase severe combined immunodeficiency (ADA-SCID), chronic granulomatous disease (CGD), and neuronal ceroid lipofuscinosis. In some embodiments, the genetic disorder is Pompe disease. In some embodiments, the genetic disorder is neuronal ceroid lipofuscinosis. In some embodiments, the neuronal ceroid lipofuscinosis is selected from the group consisting of Infantile NCL (Santavuori-Haltia disease), Late Infantile NCL (Jansky-Bielschowsky disease), Batten disease, Adult NCL (Kufs disease), Finnish Late Infantile NCL, Variant Late Infantile NCL, CLN7, CLN8, Turkish Late Infantile NCL, NCL type 9, and CLN10. In some embodiments, the therapeutic protein is a soluble lysosomal enzyme or an enzymatically active fragment thereof. In some embodiments, the therapeutic protein comprises an enzyme selected from the group consisting of alpha-galactosidase (A or B), β-galactosidase, β-hexosaminidase (A or B), galactosylceramidase, arylsulfatase (A or B), β-glucocerebrosidase, glucocerebrosidase, lysosomal acid lipase, lysosomal enzyme acid sphingomyelinase, formylglycine-generating enzyme, iduronidase (e.g., alpha-L), acetyl-CoA:alpha-glucosaminide N-acetyltransferase, glycosaminoglycan alpha-L-iduronohydrolase, heparan N-sulfatase, N-acetyl-α-D-glucosaminidase (NAGLU), iduronate-2-sulfatase, galactosamine-6-sulfate sulfatase, N-acetylgalactosamine-6-sulfatase, glycosaminoglycan N-acetylgalactosamine 4-sulfatase, β-glucuronidase, hyaluronidase, alpha-N-acetyl neuraminidase (sialidase), ganglioside sialidase, phosphotransferase, alpha-glucosidase, alpha-D-mannosidase, beta-D-mannosidase, aspartylglucosaminidase, alpha-L-fucosidase, battenin, palmitoyl protein thioesterases, and other Batten-related proteins (e.g., ceroid-lipofuscinosis neuronal protein 6), or an enzymatically active fragment thereof. In some embodiments, the therapeutic protein is an alpha-glucosidase, or an enzymatically active fragment thereof. In some embodiments, the therapeutic protein is N-acetyl-α-D-glucosaminidase (NAGLU). In some embodiments, the palmitoyl protein thioesterase is palmitoyl protein thioesterase 1 (PPT1) or 2 (PPT2). In some embodiments, the palmitoyl protein thioesterase is palmitoyl protein thioesterase 1. In some embodiments, the nucleic acid construct further comprises a translation initiation sequence. In some embodiments, the translation initiation sequence comprises a Kozak sequence. In some embodiments, the Kozak sequence comprises the sequence $AX_1X_2ATGA$ (SEQ ID NO: 28), wherein each of $X_1$ and $X_2$ is any nucleotide. In some embodiments, $X_1$ comprises A. In some embodiments, $X_2$ comprises G. In some embodiments, the Kozak sequence comprises a nucleic acid sequence at least 90% identical to AAGATGA (SEQ ID NO: 29). In some embodiments, the Kozak sequence comprises AAGATGA (SEQ ID NO: 29). In some embodiments the Kozak sequence comprises a nucleic acid sequence at least 85% identical to GCAAGATG (SEQ ID NO: 44). In some embodiments the Kozak sequence differs from the sequence of GCAAGATG (SEQ ID NO: 44) by one or two nucleotides. In some embodiments, the Kozak sequence comprises GCAAGATG (SEQ ID NO: 44). In some embodiments the Kozak sequence comprises a nucleic acid sequence at least 85% identical to CACCATG (SEQ ID NO: 47). In some embodiments the Kozak sequence differs from the sequence of CACCATG (SEQ ID NO: 47) by one or two nucleotides. In some embodiments, the Kozak sequence comprises CACCATG (SEQ ID NO: 47). In some embodiments, the nucleic acid construct further comprises a signal nucleic acid sequence encoding a signal peptide wherein the signal peptide is capable of increasing secretion of the therapeutic protein as compared to the therapeutic protein without the signal peptide. In some embodiments, the signal peptide is selected from a binding immunoglobulin protein (BiP) signal peptide and a *Gaussia* signal peptide. In some embodiments, the BiP signal peptide comprises an amino acid sequence at least 90% identical to an amino acid sequence selected from the group consisting of SEQ ID NOs: 13-17. In some embodiments, the BiP signal peptide comprises an amino acid sequence selected from the group consisting of SEQ ID NOs: 13-17. In some embodiments, the signal peptide comprises a *Gaussia* signal peptide. In some embodiments, the *Gaussia* signal peptide comprises an amino acid sequence at least 90% identical to SEQ ID NO: 32. In some embodiments, the *Gaussia* signal peptide comprises SEQ ID NO: 32. In some embodiments, the vIGF2 nucleic acid sequence is 5' to the nucleic acid sequence encoding a therapeutic protein. In some embodiments, the vIGF2 nucleic acid sequence is 3' to the nucleic acid sequence encoding a therapeutic protein. In some embodiments, the nucleic acid construct further comprises a linker sequence encoding a linker peptide between the vIGF2 nucleotide sequence and the nucleic acid sequence encoding a therapeutic protein. In some embodiments, the linker consists of 5-20 amino acids, 5-15 amino acids, 5-10 amino acids, 8-12 amino acids, or about 7, 8, 9, 10, 11, 12 or 13 amino acids. In some embodiments, the linker peptide comprises SEQ ID NO: 18-21 or SEQ ID NO: 33. In some embodiments, the gene therapy vector is a virus vector. In some embodiments, the virus vector is an adenovirus vector, an adeno-associated virus (AAV) vector, a retrovirus vector, a lentivirus vector, or a herpes virus vector. In some embodiments, the virus vector is an AAV vector. In some embodiments, the AAV vector comprises inverted terminal repeats (ITRs). In some embodiments, the AAV vector is selected from the group consisting of an AAV1 vector, an AAV2 vector, an AAV3 vector, an AAV4 vector, an AAV5 vector, an AAV6 vector, an AAV7 vector, an AAV8 vector, an AAV9 vector, an AAVrhS vector, an AAVrh10 vector, an AAVrh33 vector, an AAVrh34 vector, an AAVrh74 vector, an AAV Anc80 vector, an AAVPHP.B vector, an AAVhu68 vector, and an AAV-DJ vector.

In additional aspects, there are provided pharmaceutical composition comprising (i) a therapeutically effective amount of any one of the gene therapy vectors herein and (ii) a pharmaceutically acceptable carrier or excipient. In some embodiments, the carrier or excipient comprises a non-ionic, low-osmolar compound, a buffer, a polymer, a salt, or a combination thereof.

In further aspects, there are provided methods for treating a genetic disorder comprising administering to a subject in need thereof anyone of the gene therapy vectors provided herein or the any one of the pharmaceutical compositions provided herein. In some embodiments, the genetic disorder is a lysosomal storage disorder. In some embodiments, the genetic disorder is selected from the group consisting of aspartylglucosaminuria, Batten disease, cystinosis, Fabry disease, Gaucher disease type I, Gaucher disease type II, Gaucher disease type III, Pompe disease, Tay Sachs disease, Sandhoff disease, metachomatic leukodystrophy, mucolipidosis type I, mucolipidosis type II, mucolipidosis type III, mucolipidosis type IV, Hurler disease, Hunter disease, Sanfilippo disease type A, Sanfilippo disease type B, Sanfilippo disease type C, Sanfilippo disease type D, Morquio disease type A, Morquio disease type B, Maroteau-Lamy disease, Sly disease, Niemann-Pick disease type A, Niemann-Pick disease type B, Niemann-Pick disease type C1, Niemann-Pick disease type C2, Schindler disease type I, and Schindler disease type II. In some embodiments, the lysosomal storage disorder is selected from the group consisting of activator deficiency, GM2-gangliosidosis; GM2-gangliosidosis, AB variant; alpha-mannosidosis (type 2, moderate form; type 3, neonatal, severe); beta-mannosidosis; lysosomal acid lipase deficiency; cystinosis (late-onset juvenile or adolescent nephropathic type; infantile nephropathic); Chanarin-Dorfman syndrome; neutral lipid storage disease with myopathy; NLSDM; Danon disease; Fabry disease; Fabry disease type II, late-onset; Farber disease; Farber lipogranulomatosis; fucosidosis; galactosialidosis (combined neuraminidase & beta-galactosidase deficiency); Gaucher disease; type II Gaucher disease; type III Gaucher disease; type IIIC Gaucher disease; Gaucher disease, atypical, due to saposin C deficiency; GM1-gangliosidosis (late-infantile/juvenile GM1-gangliosidosis; adult/chronic GM1-gangliosidosis); Globoid cell leukodystrophy, Krabbe disease (Late infantile onset; Juvenile Onset; Adult Onset); Krabbe disease, atypical, due to saposin A deficiency; Metachromatic Leukodystrophy (juvenile; adult); partial cerebroside sulfate deficiency; pseudoarylsulfatase A deficiency; metachromatic leukodystrophy due to saposin B deficiency; Mucopolysaccharidoses disorders: MPS I, Hurler syndrome; MPS I, Hurler-Scheie syndrome; MPS I, Scheie syndrome; MPS II, Hunter syndrome; MPS II, Hunter syndrome; Sanfilippo syndrome Type A/MPS IIIA; Sanfilippo syndrome Type B/MPS IIIB; Sanfilippo syndrome Type C/MPS IIIC; Sanfilippo syndrome Type D/MPS IIID; Morquio syndrome, type A/MPS IVA; Morquio syndrome, type B/MPS IVB; MPS IX hyaluronidase deficiency; MPS VI Maroteaux-Lamy syndrome; MPS VII Sly syndrome; mucolipidosis I, sialidosis type II; I-cell disease, Leroy disease, mucolipidosis II; Pseudo-Hurler polydystrophy/mucolipidosis type III; mucolipidosis IIIC/ML III GAMMA; mucolipidosis type IV; multiple sulfatase deficiency; Niemann-Pick disease (type B; type C1/chronic neuronopathic form; type C2; type D/Nova Scotian type); Neuronal Ceroid Lipofuscinoses: CLN6 disease—Atypical Late Infantile, Late-Onset variant, Early Juvenile; Batten-Spielmeyer-Vogt/Juvenile NCL/CLN3 disease; Finnish Variant Late Infantile CLN5; Jansky-Bielschowsky disease/Late infantile CLN2/TPP1 Disease; Kufs/Adult-onset NCL/CLN4 disease (type B); Northern Epilepsy/variant late infantile CLN8; Santavuori-Haltia/Infantile CLN1/PPT disease; Pompe disease (glycogen storage disease type II); late-onset Pompe disease; Pycnodysostosis; Sandhoff disease/GM2 gangliosidosis; Sandhoff disease/GM2 gangliosidosis; Sandhoff disease/GM2 Gangliosidosis; Schindler disease (type III/intermediate, variable); Kanzaki disease; Salla disease; infantile free sialic acid storage disease (ISSD); spinal muscular atrophy with progressive myoclonic epilepsy (SMAPME); Tay-Sachs disease/GM2 gangliosidosis; juvenile-onset Tay-Sachs disease; late-onset Tay-Sachs disease; Christianson syndrome; Lowe oculocerebrorenal syndrome; Charcot-Marie-Tooth type 4J, CMT4J; Yunis-Varon syndrome; bilateral temporooccipital polymicrogyria (BTOP); X-linked hypercalciuric nephrolithiasis, Dent-1; and Dent disease 2, adenosine deaminase severe combined immunodeficiency (ADA-SCID), chronic granulomatous disease (CGD), CDKL5 deficiency disorder, and neuronal ceroid lipofuscinosis. In some embodiments, the genetic disorder is Pompe disease. In some embodiments, the genetic disorder is neuronal ceroid lipofuscinosis. In some embodiments, the neuronal ceroid lipofuscinosis is selected from the group consisting of Infantile NCL (Santavuori-Haltia disease), Late Infantile NCL (Jansky-Bielschowsky disease), Batten disease, Adult NCL (Kufs disease), Finnish Late Infantile NCL, Variant Late Infantile NCL, CLN7, CLN8, Turkish Late Infantile NCL, NCL type 9, and CLN10. In some embodiments, the administering is performed intrathecally, intraocularly, intravitreally, retinally, intravenously, intramuscularly, intraventricularly, intracerebrally, intracerebellarly, intracerebroventricularly, intraparenchymally, ocularly, subcutaneously, or a combination thereof. In some embodiments, the administering is performed intrathecally. In some embodiments, the administering is performed intraocularly, intravitreally, or retinally.

In additional aspects, there are provided pharmaceutical compositions comprising any one of the gene therapy vectors herein and a pharmaceutically acceptable carrier or excipient for use in treating a genetic disorder. In further aspects, there are provided pharmaceutical compositions comprising any one of the gene therapy vectors herein and a pharmaceutically acceptable carrier or excipient for use in preparation of a medicament for treatment of a genetic disorder. In some embodiments, the genetic disorder is a lysosomal storage disorder. In some embodiments, the genetic disorder is selected from the group consisting of aspartylglucosaminuria, Batten disease, cystinosis, Fabry disease, Gaucher disease type I, Gaucher disease type II, Gaucher disease type III, Pompe disease, Tay Sachs disease, Sandhoff disease, metachomatic leukodystrophy, mucolipidosis type I, mucolipidosis type II, mucolipidosis type III, mucolipidosis type IV, Hurler disease, Hunter disease, Sanfilippo disease type A, Sanfilippo disease type B, Sanfilippo disease type C, Sanfilippo disease type D, Morquio disease type A, Morquio disease type B, Maroteau-Lamy disease, Sly disease, Niemann-Pick disease type A, Niemann-Pick disease type B, Niemann-Pick disease type C1, Niemann-Pick disease type C2, Schindler disease type I, and Schindler disease type II. In some embodiments, the lysosomal storage disorder is selected from the group consisting of activator deficiency, GM2-gangliosidosis; GM2-gangliosidosis, AB variant; alpha-mannosidosis (type 2, moderate form; type 3, neonatal, severe); beta-mannosidosis; lysosomal acid lipase deficiency; cystinosis (late-onset juvenile or adolescent nephropathic type; infantile nephropathic); Chanarin-Dorfman syndrome; neutral lipid storage disease with myopathy; NLSDM; Danon disease; Fabry disease; Fabry disease type II, late-onset; Farber disease; Farber lipogranulomatosis; fucosidosis; galactosialidosis (combined neuraminidase & beta-galactosidase deficiency); Gaucher disease; type II Gaucher disease; type III Gaucher disease; type IIIC Gaucher disease; Gaucher disease, atypical, due to saposin C deficiency; GM1-gangliosidosis (late-infantile/juvenile GM1-gangliosidosis; adult/chronic GM1-gangliosidosis); Globoid cell leukodystrophy, Krabbe disease (Late infantile onset; Juvenile Onset; Adult Onset); Krabbe disease, atypical, due to saposin A deficiency; Metachromatic Leukodystrophy (juvenile; adult); partial cerebroside sulfate deficiency; pseudoarylsulfatase A deficiency; metachromatic leukodystrophy due to saposin B deficiency; Mucopolysaccharidoses disorders: MPS I, Hurler syndrome; MPS I, Hurler-Scheie syndrome; MPS I, Scheie syndrome; MPS II, Hunter syndrome; MPS II, Hunter syndrome; Sanfilippo syndrome Type A/MPS IIIA; Sanfilippo syndrome Type B/MPS IIIB; Sanfilippo syndrome Type C/MPS IIIC; Sanfilippo syndrome Type D/MPS IIID; Morquio syndrome, type A/MPS IVA; Morquio syndrome, type B/MPS IVB; MPS IX hyaluronidase deficiency; MPS VI Maroteaux-Lamy syndrome; MPS VII Sly syndrome; mucolipidosis I, sialidosis type II; I-cell disease, Leroy disease, mucolipidosis II; Pseudo-Hurler polydystrophy/mucolipidosis type III; mucolipidosis IIIC/ML III GAMMA; mucolipidosis type IV; multiple sulfatase deficiency; Niemann-Pick disease (type B; type C1/chronic neuronopathic form; type C2; type D/Nova Scotian type); Neuronal Ceroid Lipofuscinoses: CLN6 disease—Atypical Late Infantile, Late-Onset variant, Early Juvenile; Batten-Spielmeyer-Vogt/Juvenile NCL/CLN3 disease; Finnish Variant Late Infantile CLN5; Jansky-Bielschowsky disease/Late infantile CLN2/TPP1 Disease; Kufs/Adult-onset NCL/CLN4 disease (type B); Northern Epilepsy/variant late infantile CLN8; Santavuori-Haltia/Infantile CLN1/PPT disease; Pompe disease (glycogen storage disease type II); late-onset Pompe disease; Pycnodysostosis; Sandhoff disease/GM2 gangliosidosis; Sandhoff disease/GM2 gangliosidosis; Sandhoff disease/GM2 Gangliosidosis; Schindler disease (type III/intermediate, variable); Kanzaki disease; Salla disease; infantile free sialic acid storage disease (ISSD); spinal muscular atrophy with progressive myoclonic epilepsy (SMAPME); Tay-Sachs disease/GM2 gangliosidosis; juvenile-onset Tay-Sachs disease; late-onset Tay-Sachs disease; Christianson syndrome; Lowe oculocerebrorenal syndrome; Charcot-Marie-Tooth type 4J, CMT4J; Yunis-Varon syndrome; bilateral temporooccipital polymicrogyria (BTOP); X-linked hypercalciuric nephrolithiasis, Dent-1; and Dent disease 2, adenosine deaminase severe combined immunodeficiency (ADA-SCID), chronic granulomatous disease (CGD), CDKL5 deficiency disorder, and neuronal ceroid lipofuscinosis. In some embodiments, the genetic disorder is Pompe disease. In some embodiments, the genetic disorder is neuronal ceroid lipofuscinosis. In some embodiments, the neuronal ceroid lipofuscinosis is selected from the group consisting of Infantile NCL (Santavuori-Haltia disease), Late Infantile NCL (Jansky-Bielschowsky disease), Batten disease, Adult NCL (Kufs disease), Finnish Late Infantile NCL, Variant Late Infantile NCL, CLN7, CLN8, Turkish Late Infantile NCL, NCL type 9, and CLN10. In some embodiments, the composition is formulated for administration intrathecally, intraocularly, intravitreally, retinally, intravenously, intramuscularly, intraventricularly, intracerebrally, intracerebellarly, ocularly, or subcutaneously. In some embodiments, the composition is formulated for administration intrathecally. In some embodiments, the composition is formulated for administration intrathecally for treating a neurodegenerative disorder. In some embodiments, the composition is formulated for administration ocularly, intravitreally, or retinally.

Provided herein are gene therapy vectors comprising a nucleic acid construct encoding a polypeptide comprising: (a) a therapeutic protein; (b) a peptide that binds to the cation-independent mannose 6-phosphate (M6P) receptor (CI-MPR) with high affinity; and (c) a linker between the therapeutic protein and the peptide that binds CI-MPR. In some embodiments, the peptide is a variant IGF2 (vIGF2) peptide. In some embodiments, the vIGF2 peptide comprises an amino acid sequence that is at least 90% identical to SEQ ID NO: 1 and having at least one substitution at one or more positions selected from the group consisting of positions 6, 26, 27, 43, 48, 49, 50, 54, 55, and 65 of SEQ ID NO: 1. In some embodiments, the at least one substitution is selected from the group consisting of E6R, F26S, Y27L, V43L, F48T, R49S, S50I, A54R, L55R, and K65R of SEQ ID NO:1. In some embodiments, the vIGF2 peptide comprises at least two substitutions at two or more positions selected from the group consisting of positions 6, 26, 27, 43, 48, 49, 50, 54, 55, 65 of SEQ ID NO: 1. In some embodiments, the at least two substitutions are selected from the group consisting of E6R, F26S, Y27L, V43L, F48T, R49S, S50I, A54R, L55R, K65R of SEQ ID NO: 1. In some embodiments, the vIGF2 peptide comprises an N-terminal deletion at positions 1-4 of SEQ ID NO: 1. In some embodiments, wherein the vIGF2 peptide has decreased affinity for insulin receptor and IGF1R as compared to native IGF2 peptide. In some embodiments, the vIGF2 peptide is capable of facilitating uptake of the therapeutic protein into a cell. In some embodiments, the vIGF2 peptide is capable of facilitating uptake of the therapeutic protein into a lysosome. In some embodiments, the therapeutic protein is capable of replacing a defective or deficient protein associated with a genetic disorder in a subject having the genetic disorder. In some embodiments, genetic disorder is a lysosomal storage disorder. In some embodiments, the genetic disorder is selected from the group consisting of aspartylglucosaminuria, Batten disease, cystinosis, Fabry disease, Gaucher disease type I, Gaucher disease type II, Gaucher disease type III, Pompe disease, Tay Sachs disease, Sandhoff disease, metachomatic leukodystrophy, mucolipidosis type I, mucolipidosis type II, mucolipidosis type III, mucolipidosis type IV, Hurler disease, Hunter disease, Sanfilippo disease type A, Sanfilippo disease type B, Sanfilippo disease type C, Sanfilippo disease type D, Morquio disease type A, Morquio disease type B, Maroteau-Lamy disease, Sly disease, Niemann-Pick disease type A, Niemann-Pick disease type B, Niemann-Pick disease type C1, Niemann-Pick disease type C2, Schindler disease type I, Schindler disease type II, adenosine deaminase severe combined immunodeficiency (ADA-SCID), chronic granulomatous disease (CGD), and neuronal ceroid lipofuscinosis. In some embodiments, the genetic disorder is Pompe disease. In some embodiments, the genetic disorder is a CLN1 disease. In some embodiments, the therapeutic protein comprises a soluble lysosomal enzyme or an enzymatically active fragment thereof. In some embodiments, the therapeutic protein comprises a lysosomal enzyme or an enzymatically active fragment thereof, wherein the lysosomal enzyme is selected from the group consisting of alpha-galactosidase A, β-glucocerebrosidase, glucocerebrosidase, lysosomal acid lipase, glycosaminoglycan alpha-L-iduronohydrolase, iduronate-2-sulfatase, N-acetylgalactosamine-6-sulfatase, glycosaminoglycan N-acetylgalactosamine 4-sulfatase, palmitoyl protein thioesterases, cyclin dependent kinase like 5, and alpha-glucosidase. In some embodiments, the therapeutic protein is alpha-glucosidase or an enzymatically active fragment thereof. In some embodiments, the therapeutic protein is a palmitoyl protein thioesterase or an enzymatically active fragment thereof. In some embodiments, the therapeutic protein is palmitoyl protein thioesterase-1 or an enzymatically active fragment thereof. In some embodiments, the nucleic acid construct further comprises a translation initiation sequence. In some embodiments, the translation initiation sequence comprises a Kozak sequence. In some embodiments, the nucleic acid construct further comprises a nucleic acid sequence encoding a signal peptide wherein the signal peptide is capable of increasing secretion of the therapeutic protein as compared to the therapeutic protein without the signal peptide. In some embodiments, the signal peptide is selected from a binding immunoglobulin protein (BiP) signal peptide and a *Gaussia* signal peptide. In some embodiments, the BiP signal peptide comprises an amino acid sequence at least 90% identical to an amino acid sequence selected from the group consisting of SEQ ID NOs: 13-17. In some embodiments, the vIGF2 peptide comprises the sequence of SEQ ID NO:31. In some embodiments, the construct comprises SEQ ID NO:36. In some embodiments, the polypeptide comprises SEQ ID NO:23. In some embodiments, the construct comprises SEQ ID NO:38. In some embodiments, the vIGF2 at the N-terminus of the polypeptide. In some embodiments, the vIGF2 is at the C-terminus of the polypeptide. In some embodiments, the linker peptide comprises SEQ ID NO: 18-21 or SEQ ID NO: 33. In some embodiments, the gene therapy vector is a virus vector selected from the group consisting of an adenovirus vector, an adeno-associated virus (AAV) vector, a retrovirus vector, a lentivirus vector, a pox virus vector, a vaccinia virus vector, an adenovirus vector, and a herpes virus vector.

In certain aspects, there are provided fusion proteins, such as fusion proteins comprising a variant IGF2 peptide and a therapeutic protein. In some embodiments, the fusion protein further comprises a linker. In some embodiments, the linker consists of 5-20 amino acids, 5-15 amino acids, 5-10 amino acids, 8-12 amino acids, or about 7, 8, 9, 10, 11, 12 or 13 amino acids. In some embodiments, the linker comprises an amino acid sequence of GGGGSGGGG (SEQ ID NO: 18), GGGGS (SEQ ID NO: 19), GGGSGGGS (SEQ ID NO: 20), GGGGSGGGS (SEQ ID NO: 21), GGGGSGGGGS (SEQ ID NO: 37, also referred to herein as "2GS"), or GGSGSGSTS (SEQ ID NO: 33). In some embodiments, the fusion protein further comprises a signal peptide. In some embodiments, the signal peptide comprises a binding immunoglobulin protein (BiP) signal peptide. In some embodiments, the fusion protein is encoded by a nucleic acid comprising a cricket paralysis virus internal ribosome entry sequence (CrPV IRES). In some embodiments, the therapeutic protein comprises at least one enzyme of the group consisting of alpha-galactosidase (A or B), β-galactosidase, β-hexosaminidase (A or B), galactosylceramidase, arylsulfatase (A or B), β-glucocerebrosidase, glucocerebrosidase, lysosomal acid lipase, lysosomal enzyme acid sphingomyelinase, formylglycine-generating enzyme, iduronidase (e.g., alpha-L), acetyl-CoA:alpha-glucosaminide N-acetyltransferase, glycosaminoglycan alpha-L-iduronohydrolase, heparan N-sulfatase, N-acetyl-α-D-glucosaminidase (NAGLU), iduronate-2-sulfatase, galactosamine-6-sulfate sulfatase, N-acetylgalactosamine-6-sulfatase, glycosaminoglycan N-acetylgalactosamine 4-sulfatase, β-glucuronidase, hyaluronidase, alpha-N-acetyl neuraminidase (sialidase), ganglioside sialidase, phosphotransferase, alpha-glucosidase, alpha-D-mannosidase, beta-D-mannosidase, aspartylglucosaminidase, alpha-L-fucosidase, battenin, palmitoyl protein thioesterases, and other Batten-related proteins (e.g., ceroid-lipofuscinosis neuronal protein 6), or an enzymatically active fragment thereof. In some embodiments, the therapeutic protein comprises alpha-glucosidase, or an enzymatically active fragment thereof. In some embodiments, the therapeutic protein is N-acetyl-α-D-glucosaminidase (NAGLU). In some embodiments, the fusion protein is encoded by a nucleic acid comprising a Kozak sequence.

In additional aspects, there are provided fusion proteins comprising a signal peptide and a therapeutic protein, wherein the signal peptide is removed after translation upon secretion from the cell. In some embodiments, the signal peptide comprises a binding immunoglobulin protein (BiP) signal peptide. In some embodiments, the fusion protein further comprises a linker. In some embodiments, the linker consists of 5-20 amino acids, 5-15 amino acids, 5-10 amino acids, 8-12 amino acids, or about 7, 8, 9, 10, 11, 12 or 13 amino acids. In some embodiments, the linker comprises an amino acid sequence of GGGGSGGGG (SEQ ID NO: 18), GGGGS (SEQ ID NO: 19), GGGSGGGGS (SEQ ID NO: 20), GGGGSGGGS (SEQ ID NO: 21), GGGGSGGGGS (SEQ ID NO: 37), or GGSGSGSTS (SEQ ID NO: 33). In some embodiments, the fusion protein further comprises a variant IGF2 peptide. In some embodiments, the fusion protein is encoded by a nucleic acid comprising a cricket paralysis virus internal ribosome entry sequence (CrPV IRES). In some embodiments, the therapeutic protein comprises at least one enzyme of the group consisting of alpha-galactosidase (A or B), β-galactosidase, β-hexosaminidase (A or B), galactosylceramidase, arylsulfatase (A or B), β-glucocerebrosidase, glucocerebrosidase, lysosomal acid lipase, lysosomal enzyme acid sphingomyelinase, formylglycine-generating enzyme, iduronidase (e.g., alpha-L), acetyl-CoA:alpha-glucosaminide N-acetyltransferase, glycosaminoglycan alpha-L-iduronohydrolase, heparan N-sulfatase, N-acetyl-α-D-glucosaminidase (NAGLU), iduronate-2-sulfatase, galactosamine-6-sulfate sulfatase, N-acetylgalactosamine-6-sulfatase, glycosaminoglycan N-acetylgalactosamine 4-sulfatase, β-glucuronidase, hyaluronidase, alpha-N-acetyl neuraminidase (sialidase), ganglioside sialidase, phosphotransferase, alpha-glucosidase, alpha-D-mannosidase, beta-D-mannosidase, aspartyl-glucosaminidase, alpha-L-fucosidase, battenin, palmitoyl protein thioesterases, and other Batten-related proteins (e.g., ceroid-lipofuscinosis neuronal protein 6), or an enzymatically active fragment thereof. In some embodiments, the therapeutic protein comprises alpha-glucosidase, or an enzymatically active fragment thereof. In some embodiments, the therapeutic protein is N-acetyl-α-D-glucosaminidase (NAGLU). In some embodiments, the fusion protein is encoded by a nucleic acid comprising a Kozak sequence.

In further aspects, there are provided nucleic acid sequences encoding fusion proteins comprising a therapeutic protein, wherein the fusion protein is encoded by a nucleic acid comprising a cricket paralysis virus internal ribosome entry sequence (CrPV IRES). In some embodiments, the fusion protein further comprises a signal peptide. In some embodiments, the signal peptide comprises a binding immunoglobulin protein (BiP) signal peptide. In some embodiments, the fusion protein further comprises a variant IGF2 peptide. In some embodiments, the fusion protein further comprises a linker. In some embodiments, the linker consists of 5-20 amino acids, 5-15 amino acids, 5-10 amino acids, 8-12 amino acids, or about 7, 8, 9, 10, 11, 12 or 13 amino acids. In some embodiments, the linker comprises an amino acid sequence of GGGGSGGGG (SEQ ID NO: 18), GGGGS (SEQ ID NO: 19), GGGSGGGGS (SEQ ID NO: 20), GGGGSGGGS (SEQ ID NO: 21), GGGGSGGGGS (SEQ ID NO: 37), or GGSGSGSTS (SEQ ID NO: 33) In some embodiments, the therapeutic protein comprises at least one enzyme of the group consisting of alpha-galactosidase (A or B), β-galactosidase, β-hexosaminidase (A or B), galactosylceramidase, arylsulfatase (A or B), β-glucocerebrosidase, glucocerebrosidase, lysosomal acid lipase, lysosomal enzyme acid sphingomyelinase, formylglycine-generating enzyme, iduronidase (e.g., alpha-L), acetyl-CoA:alpha-glucosaminide N-acetyltransferase, glycosaminoglycan alpha-L-iduronohydrolase, heparan N-sulfatase, N-acetyl-α-D-glucosaminidase (NAGLU), iduronate-2-sulfatase, galactosamine-6-sulfate sulfatase, N-acetylgalactosamine-6-sulfatase, glycosaminoglycan N-acetylgalactosamine 4-sulfatase, β-glucuronidase, hyaluronidase, alpha-N-acetyl neuraminidase (sialidase), ganglioside sialidase, phosphotransferase, alpha-glucosidase, alpha-D-mannosidase, beta-D-mannosidase, aspartyl-glucosaminidase, alpha-L-fucosidase, battenin, palmitoyl protein thioesterases, and other Batten-related proteins (e.g., ceroid-lipofuscinosis neuronal protein 6), or an enzymatically active fragment thereof. In some embodiments, the therapeutic protein comprises alpha-glucosidase, or an enzymatically active fragment thereof. In some embodiments, the therapeutic protein is N-acetyl-α-D-glucosaminidase (NAGLU). In some embodiments, the fusion protein is encoded by a nucleic acid comprising a Kozak sequence.

In additional aspects, there are provided fusion proteins comprising a therapeutic protein, wherein the fusion protein is encoded by a nucleic acid comprising a Kozak sequence. In some embodiments, the fusion protein further comprises a linker. In some embodiments, the linker consists of 5-20 amino acids, 5-15 amino acids, 5-10 amino acids, 8-12 amino acids, or about 7, 8, 9, 10, 11, 12 or 13 amino acids. In some embodiments, the linker comprises an amino acid sequence of GGGGSGGGG (SEQ ID NO: 18), GGGGS (SEQ ID NO: 19), GGGSGGGGS (SEQ ID NO: 20), GGGGSGGGS (SEQ ID NO: 21), or GGSGSGSTS (SEQ ID NO: 33). In some embodiments, the fusion protein further comprises a signal peptide. In some embodiments, the signal peptide comprises a binding immunoglobulin protein (BiP) signal peptide. In some embodiments, the fusion protein further comprises a variant IGF2 peptide. In some embodiments, the therapeutic protein comprises at least one enzyme of the group consisting of alpha-galactosidase (A or B), β-galactosidase, β-hexosaminidase (A or B), galactosylceramidase, arylsulfatase (A or B), β-glucocerebrosidase, glucocerebrosidase, lysosomal acid lipase, lysosomal enzyme acid sphingomyelinase, formylglycine-generating enzyme, iduronidase (e.g., alpha-L), acetyl-CoA:alpha-glucosaminide N-acetyltransferase, glycosaminoglycan alpha-L-iduronohydrolase, heparan N-sulfatase, N-acetyl-α-D-glucosaminidase (NAGLU), iduronate-2-sulfatase, galactosamine-6-sulfate sulfatase, N-acetylgalactosamine-6-sulfatase, glycosaminoglycan N-acetylgalactosamine 4-sulfatase, β-glucuronidase, hyaluronidase, alpha-N-acetyl neuraminidase (sialidase), ganglioside sialidase, phosphotransferase, alpha-glucosidase, alpha-D-mannosidase, beta-D-mannosidase, aspartylglucosaminidase, alpha-L-fucosidase, battenin, palmitoyl protein thioesterases, and other Batten-related proteins (e.g., ceroid-lipofuscinosis neuronal protein 6), or an enzymatically active fragment thereof. In some embodiments, the therapeutic protein comprises alpha-glucosidase, or an enzymatically active fragment thereof. In some embodiments, the therapeutic protein is N-acetyl-α-D-glucosaminidase (NAGLU). In some embodiments, the fusion protein is encoded by a nucleic acid comprising a cricket paralysis virus internal ribosome entry sequence (CrPV IRES).

In additional aspects, there are provided nucleic acids encoding a fusion protein, such as nucleic acids encoding a fusion protein comprising a variant IGF2 peptide and a therapeutic protein. In some embodiments, the fusion protein further comprises a linker. In some embodiments, the linker consists of 5-20 amino acids, 5-15 amino acids, 5-10 amino acids, 8-12 amino acids, or about 7, 8, 9, 10, 11, 12 or 13 amino acids. In some embodiments, the linker comprises an amino acid sequence of GGGGSGGGG (SEQ ID NO: 18), GGGGS (SEQ ID NO: 19), GGGSGGGGS (SEQ ID NO: 20), GGGGSGGGS (SEQ ID NO: 21), GGGGSGGGGS (SEQ ID NO: 37), or GGSGSGSTS (SEQ ID NO: 33). In some embodiments, the fusion protein further comprises a signal peptide. In some embodiments, the signal peptide comprises a binding immunoglobulin protein (BiP) signal peptide. In some embodiments, the nucleic acid further comprises a cricket paralysis virus internal ribosome entry sequence (CrPV IRES). In some embodiments, the nucleic acid further comprises a Kozak sequence. In some embodiments, the therapeutic protein comprises at least one enzyme of the group consisting of alpha-galactosidase (A or B), β-galactosidase, β-hexosaminidase (A or B), galactosylceramidase, arylsulfatase (A or B), β-glucocerebrosidase, glucocerebrosidase, lysosomal acid lipase, lysosomal enzyme acid sphingomyelinase, formylglycine-generating enzyme, iduronidase (e.g., alpha-L), acetyl-CoA:alpha-glucosaminide N-acetyltransferase, glycosaminoglycan alpha-L-iduronohydrolase, heparan N-sulfatase, N-acetyl-α-D-glucosaminidase (NAGLU), iduronate-2-sulfatase, galactosamine-6-sulfate sulfatase, N-acetylgalactosamine-6-sulfatase, glycosaminoglycan N-acetylgalactosamine 4-sulfatase, β-glucuronidase, hyaluronidase, alpha-N-acetyl neuraminidase (sialidase), ganglioside sialidase, phosphotransferase, alpha-glucosidase, alpha-D-mannosidase, beta-D-mannosidase, aspartylglucosaminidase, alpha-L-fucosidase, battenin, palmitoyl protein thioesterases, and other Batten-related proteins (e.g., ceroid-lipofuscinosis neuronal protein 6), or an enzymatically active fragment thereof. In some embodiments, the therapeutic protein comprises alpha-glucosidase, or an enzymatically active fragment thereof. In some embodiments, the therapeutic protein is N-acetyl-α-D-glucosaminidase (NAGLU). In some embodiments, the nucleic acid further comprises a promoter. In some embodiments, the nucleic acid is comprised within a viral vector. In some embodiments, the viral vector comprises a retrovirus, an adenovirus, an adeno associated virus, a lentivirus, or a herpes virus.

In further aspects, there are provided nucleic acids encoding a fusion protein comprising a signal peptide and a therapeutic protein. In some embodiments, the signal peptide comprises a binding immunoglobulin protein (BiP) signal peptide. In some embodiments, the fusion protein further comprises a linker. In some embodiments, the linker consists of 5-20 amino acids, 5-15 amino acids, 5-10 amino acids, 8-12 amino acids, or about 7, 8, 9, 10, 11, 12 or 13 amino acids. In some embodiments, the linker comprises an amino acid sequence of GGGGSGGGG (SEQ ID NO: 18), GGGGS (SEQ ID NO: 19), GGGSGGGGS (SEQ ID NO: 20), GGGGSGGGS (SEQ ID NO: 21), GGGGSGGGGS (SEQ ID NO: 37), or GGSGSGSTS (SEQ ID NO: 33). In some embodiments, the fusion protein further comprises a variant IGF2 peptide. In some embodiments, the nucleic acid further comprises a cricket paralysis virus internal ribosome entry sequence (CrPV IRES). In some embodiments, the nucleic acid further comprises a Kozak sequence. In some embodiments, the therapeutic protein comprises at least one enzyme of the group consisting of alpha-galactosidase (A or B), β-galactosidase, β-hexosaminidase (A or B), galactosylceramidase, arylsulfatase (A or B), β-glucocerebrosidase, glucocerebrosidase, lysosomal acid lipase, lysosomal enzyme acid sphingomyelinase, formylglycine-generating enzyme, iduronidase (e.g., alpha-L), acetyl-CoA:alpha-glucosaminide N-acetyltransferase, glycosaminoglycan alpha-L-iduronohydrolase, heparan N-sulfatase, N-acetyl-α-D-glucosaminidase (NAGLU), iduronate-2-sulfatase, galactosamine-6-sulfate sulfatase, N-acetylgalactosamine-6-sulfatase, glycosaminoglycan N-acetylgalactosamine 4-sulfatase, β-glucuronidase, hyaluronidase, alpha-N-acetyl neuraminidase (sialidase), ganglioside sialidase, phosphotransferase, alpha-glucosidase, alpha-D-mannosidase, beta-D-mannosidase, aspartylglucosaminidase, alpha-L-fucosidase, battenin, palmitoyl protein thioesterases, and other Batten-related proteins (e.g., ceroid-lipofuscinosis neuronal protein 6), or an enzymatically active fragment thereof. In some embodiments, the therapeutic protein comprises alpha-glucosidase, or an enzymatically active fragment thereof. In some embodiments, the therapeutic protein is N-acetyl-α-D-glucosaminidase (NAGLU). In some embodiments, the nucleic acid further comprises a promoter. In some embodiments, the nucleic acid is comprised within a viral vector. In some embodiments, the viral vector comprises a retrovirus, an adenovirus, an adeno associated virus, a lentivirus, or a herpes virus.

In additional aspects, there are provided nucleic acids encoding a fusion protein comprising a therapeutic protein, wherein the nucleic acid further comprises a cricket paralysis virus internal ribosome entry sequence (CrPV IRES). In some embodiments, the nucleic acid further comprises a Kozak sequence. In some embodiments, the fusion protein further comprises a linker. In some embodiments, the linker consists of 5-20 amino acids, 5-15 amino acids, 5-10 amino acids, 8-12 amino acids, or about 7, 8, 9, 10, 11, 12 or 13 amino acids. In some embodiments, the linker comprises an amino acid sequence of GGGGSGGGG (SEQ ID NO: 18), GGGGS (SEQ ID NO: 19), GGGSGGGGS (SEQ ID NO: 20), GGGGSGGGS (SEQ ID NO: 21), GGGGSGGGGS (SEQ ID NO: 37), or GGSGSGSTS (SEQ ID NO: 33). In some embodiments, the fusion protein further comprises a signal peptide. In some embodiments, the signal peptide comprises a binding immunoglobulin protein (BiP) signal peptide. In some embodiments, the fusion protein further comprises a variant IGF2 peptide. In some embodiments, the therapeutic protein comprises at least one enzyme of the group consisting of alpha-galactosidase (A or B), β-galactosidase, β-hexosaminidase (A or B), galactosylceramidase, arylsulfatase (A or B), β-glucocerebrosidase, glucocerebrosidase, lysosomal acid lipase, lysosomal enzyme acid sphingomyelinase, formylglycine-generating enzyme, iduronidase (e.g., alpha-L), acetyl-CoA:alpha-glucosaminide N-acetyltransferase, glycosaminoglycan alpha-L-iduronohydrolase, heparan N-sulfatase, N-acetyl-α-D-glucosaminidase (NAGLU), iduronate-2-sulfatase, galactosamine-6-sulfate sulfatase, N-acetylgalactosamine-6-sulfatase, glycosaminoglycan N-acetylgalactosamine 4-sulfatase, β-glucuronidase, hyaluronidase, alpha-N-acetyl neuraminidase (sialidase), ganglioside sialidase, phosphotransferase, alpha-glucosidase, alpha-D-mannosidase, beta-D-mannosidase, aspartylglucosaminidase, alpha-L-fucosidase, battenin, palmitoyl protein thioesterases, and other Batten-related proteins (e.g., ceroid-lipofuscinosis neuronal protein 6), or an enzymatically active fragment thereof. In some embodiments, the therapeutic protein comprises alpha-glucosidase, or an enzymatically active fragment thereof. In some embodiments, the therapeutic protein is N-acetyl-α-D-glucosaminidase (NAGLU). In some embodiments, the nucleic acid further comprises a promoter. In some embodiments, the nucleic acid is comprised within a viral vector. In some embodiments, the viral vector comprises a retrovirus, an adenovirus, an adeno associated virus, a lentivirus, or a herpes virus.

In further aspects, there are provided nucleic acids encoding a fusion protein comprising a therapeutic protein, wherein the nucleic acid further comprises a Kozak sequence. In some embodiments, the nucleic acid further comprises a Kozak sequence. In some embodiments, the fusion protein further comprises a linker. In some embodiments, the linker consists of 5-20 amino acids, 5-15 amino acids, 5-10 amino acids, 8-12 amino acids, or about 7, 8, 9, 10, 11, 12 or 13 amino acids. In some embodiments, the linker comprises an amino acid sequence of GGGGSGGGG (SEQ ID NO: 18), GGGGS (SEQ ID NO: 19), GGGSGGGGS (SEQ ID NO: 20), GGGGSGGGS (SEQ ID NO: 21), GGGGSGGGGS (SEQ ID NO: 37), or GGSGSGSTS (SEQ ID NO: 33). In some embodiments, the fusion protein further comprises a signal peptide. In some embodiments, the signal peptide comprises a binding immunoglobulin protein (BiP) signal peptide. In some embodiments, the fusion protein further comprises a variant IGF2 peptide. In some embodiments, the therapeutic protein comprises at least one enzyme of the group consisting of alpha-galactosidase (A or B), β-galactosidase, β-hexosaminidase (A or B), galactosylceramidase, arylsulfatase (A or B), β-glucocerebrosidase, glucocerebrosidase, lysosomal acid lipase, lysosomal enzyme acid sphingomyelinase, formylglycine-generating enzyme, iduronidase (e.g., alpha-L), acetyl-CoA:alpha-glucosaminide N-acetyltransferase, glycosaminoglycan alpha-L-iduronohydrolase, heparan N-sulfatase, N-acetyl-α-D-glucosaminidase (NAGLU), iduronate-2-sulfatase, galactosamine-6-sulfate sulfatase, N-acetylgalactosamine-6-sulfatase, glycosaminoglycan N-acetylgalactosamine 4-sulfatase, β-glucuronidase, hyaluronidase, alpha-N-acetyl neuraminidase (sialidase), ganglioside sialidase, phosphotransferase, alpha-glucosidase, alpha-D-mannosidase, beta-D-mannosidase, aspartylglucosaminidase, alpha-L-fucosidase, battenin, palmitoyl protein thioesterases, and other Batten-related proteins (e.g., ceroid-lipofuscinosis neuronal protein 6), or an enzymatically active fragment thereof. In some embodiments, the therapeutic protein comprises alpha-glucosidase, or an enzymatically active fragment thereof. In some embodiments, the therapeutic protein is N-acetyl-α-D-glucosaminidase (NAGLU). In some embodiments, the nucleic acid further comprises a promoter. In some embodiments, the nucleic acid is comprised within a viral vector. In some embodiments, the viral vector comprises a retrovirus, an adenovirus, an adeno associated virus, a lentivirus, or a herpes virus.

In additional aspects, there are provided compositions comprising (a) a nucleic acid encoding a fusion protein comprising a variant IGF2 peptide and a therapeutic protein; and (b) a buffer or excipient suitable for gene therapy. In some embodiments, the fusion protein further comprises a linker. In some embodiments, the linker consists of 5-20 amino acids, 5-15 amino acids, 5-10 amino acids, 8-12 amino acids, or about 7, 8, 9, 10, 11, 12 or 13 amino acids. In some embodiments, the linker comprises an amino acid sequence of GGGGSGGGG (SEQ ID NO: 18), GGGGS (SEQ ID NO: 19), GGGSGGGGS (SEQ ID NO: 20), GGGGSGGGS (SEQ ID NO: 21), GGGGSGGGGS (SEQ ID NO: 37), or GGSGSGSTS (SEQ ID NO: 33). In some embodiments, the fusion protein further comprises a signal peptide. In some embodiments, the signal peptide comprises a binding immunoglobulin protein (BiP) signal peptide. In some embodiments, the nucleic acid further comprises a cricket paralysis virus internal ribosome entry sequence (CrPV IBES). In some embodiments, the nucleic acid further comprises a Kozak sequence. In some embodiments, the therapeutic protein comprises at least one enzyme of the group consisting of alpha-galactosidase (A or B), β-galactosidase, β-hexosaminidase (A or B), galactosylceramidase, arylsulfatase (A or B), β-glucocerebrosidase, glucocerebrosidase, lysosomal acid lipase, lysosomal enzyme acid sphingomyelinase, formylglycine-generating enzyme, iduronidase (e.g., alpha-L), acetyl-CoA:alpha-glucosaminide N-acetyltransferase, glycosaminoglycan alpha-L-iduronohydrolase, heparan N-sulfatase, N-acetyl-α-D-glucosaminidase (NAGLU), iduronate-2-sulfatase, galactosamine-6-sulfate sulfatase, N-acetylgalactosamine-6-sulfatase, glycosaminoglycan N-acetylgalactosamine 4-sulfatase, β-glucuronidase, hyaluronidase, alpha-N-acetyl neuraminidase (sialidase), ganglioside sialidase, phosphotransferase, alpha-glucosidase, alpha-D-mannosidase, beta-D-mannosidase, aspartylglucosaminidase, alpha-L-fucosidase, battenin, palmitoyl protein thioesterases, and other Batten-related proteins (e.g., ceroid-lipofuscinosis neuronal protein 6), or an enzymatically active fragment thereof. In some embodiments, the therapeutic protein comprises alpha-glucosidase, or an enzymatically active fragment thereof. In some embodiments, the therapeutic protein is N-acetyl-α-D-glucosaminidase (NAGLU). In some embodiments, the nucleic acid further comprises a promoter. In some embodiments, the nucleic acid is comprised within a viral vector. In some embodiments, the viral vector comprises a retrovirus, an adenovirus, an adeno associated virus, a lentivirus, or a herpes virus. In some embodiments, the buffer or excipient suitable for gene therapy comprises a liposome, a nanoparticle, or a cell-penetrating peptide. In some embodiments, the buffer or excipient suitable for gene therapy comprises a viral coat protein. In some embodiments, the viral coat protein is selected from the group consisting of a vesicular stomatitis virus coat protein, an adenovirus coat protein, an adeno-associated virus coat protein, a murine leukemia virus coat protein, an HIV coat protein, and an influenza virus coat protein.

In additional aspects, there are provided compositions comprising (a) a nucleic acid encoding a fusion protein comprising a signal peptide and a therapeutic protein; and (b) a buffer or excipient suitable for gene therapy. In some embodiments, the signal peptide comprises a binding immunoglobulin protein (BiP) signal peptide. In some embodiments, the fusion protein further comprises a variant IGF2 peptide. In some embodiments, the fusion protein further comprises a linker. In some embodiments, the linker consists of 5-20 amino acids, 5-15 amino acids, 5-10 amino acids, 8-12 amino acids, or about 7, 8, 9, 10, 11, 12 or 13 amino acids. In some embodiments, the linker comprises an amino acid sequence of GGGGSGGGG (SEQ ID NO: 18), GGGGS (SEQ ID NO: 19), GGGSGGGGS (SEQ ID NO: 20), GGGGSGGGS (SEQ ID NO: 21), GGGGSGGGGS (SEQ ID NO: 37), or GGSGSGSTS (SEQ ID NO: 33). In some embodiments, the nucleic acid further comprises a cricket paralysis virus internal ribosome entry sequence (CrPV IBES). In some embodiments, the nucleic acid further comprises a Kozak sequence. In some embodiments, the therapeutic protein comprises at least one enzyme of the group consisting of alpha-galactosidase (A or B), β-galactosidase, β-hexosaminidase (A or B), galactosylceramidase, arylsulfatase (A or B), β-glucocerebrosidase, glucocerebrosidase, lysosomal acid lipase, lysosomal enzyme acid sphingomyelinase, formylglycine-generating enzyme, iduronidase (e.g., alpha-L), acetyl-CoA:alpha-glucosaminide N-acetyltransferase, glycosaminoglycan alpha-L-iduronohydrolase, heparan N-sulfatase, N-acetyl-α-D-glucosaminidase (NAGLU), iduronate-2-sulfatase, galactosamine-6-sulfate sulfatase, N-acetylgalactosamine-6-sulfatase, glycosaminoglycan N-acetylgalactosamine 4-sulfatase, β-glucuronidase, hyaluronidase, alpha-N-acetyl neuraminidase (sialidase), ganglioside sialidase, phosphotransferase, alpha-glucosidase, alpha-D-mannosidase, beta-D-mannosidase, aspartylglucosaminidase, alpha-L-fucosidase, battenin, palmitoyl protein thioesterases, and other Batten-related proteins (e.g., ceroid-lipofuscinosis neuronal protein 6), or an enzymatically active fragment thereof. In some embodiments, the therapeutic protein comprises alpha-glucosidase, or an enzymatically active fragment thereof. In some embodiments, the therapeutic protein is N-acetyl-α-D-glucosaminidase (NAGLU). In some embodiments, the nucleic acid further comprises a promoter. In some embodiments, the nucleic acid is comprised within a viral vector. In some embodiments, the viral vector comprises a retrovirus, an adenovirus, an adeno associated virus, a lentivirus, or a herpes virus. In some embodiments, the buffer or excipient suitable for gene therapy comprises a liposome, a nanoparticle, or a cell-penetrating peptide. In some embodiments, the buffer or excipient suitable for gene therapy comprises a viral coat protein. In some embodiments, the viral coat protein is selected from the group consisting of a vesicular stomatitis virus coat protein, an adenovirus coat protein, an adeno-associated virus coat protein, a murine leukemia virus coat protein, an HIV coat protein, and an influenza virus coat protein.

In further aspects, there are provided compositions comprising (a) a nucleic acid encoding a fusion protein comprising a therapeutic protein; and (b) a buffer or excipient suitable for gene therapy, wherein the nucleic acid further comprises a cricket paralysis virus internal ribosome entry sequence (CrPV IBES). In some embodiments, the nucleic acid further comprises a Kozak sequence. In some embodiments, the fusion protein further comprises a linker. In some embodiments, the linker consists of 5-20 amino acids, 5-15 amino acids, 5-10 amino acids, 8-12 amino acids, or about 7, 8, 9, 10, 11, 12 or 13 amino acids. In some embodiments, the linker comprises an amino acid sequence of GGGGSGGGG (SEQ ID NO: 18), GGGGS (SEQ ID NO: 19), GGGSGGGGS (SEQ ID NO: 20), GGGGSGGGS (SEQ ID NO: 21), GGGGSGGGGS (SEQ ID NO: 37), or GGSGSGSTS (SEQ ID NO: 33). In some embodiments, the fusion protein further comprises a signal peptide. In some embodiments, the signal peptide comprises a binding immunoglobulin protein (BiP) signal peptide. In some embodiments, the fusion protein further comprises a variant IGF2 peptide. In some embodiments, the therapeutic protein comprises at least one enzyme of the group consisting of alpha-galactosidase (A or B), β-galactosidase, β-hexosaminidase (A or B), galactosylceramidase, arylsulfatase (A or B), β-glucocerebrosidase, glucocerebrosidase, lysosomal acid lipase, lysosomal enzyme acid sphingomyelinase, formylglycine-generating enzyme, iduronidase (e.g., alpha-L), acetyl-CoA:alpha-glucosaminide N-acetyltransferase, glycosaminoglycan alpha-L-iduronohydrolase, heparan N-sulfatase, N-acetyl-α-D-glucosaminidase (NAGLU), iduronate-2-sulfatase, galactosamine-6-sulfate sulfatase, N-acetylgalactosamine-6-sulfatase, glycosaminoglycan N-acetylgalactosamine 4-sulfatase, β-glucuronidase, hyaluronidase, alpha-N-acetyl neuraminidase (sialidase), ganglioside sialidase, phosphotransferase, alpha-glucosidase, alpha-D-mannosidase, beta-D-mannosidase, aspartylglucosaminidase, alpha-L-fucosidase, battenin, palmitoyl protein thioesterases, and other Batten-related proteins (e.g., ceroid-lipofuscinosis neuronal protein 6), or an enzymatically active fragment thereof. In some embodiments, the therapeutic protein comprises alpha-glucosidase, or an enzymatically active fragment thereof. In some embodiments, the therapeutic protein is N-acetyl-α-D-glucosaminidase (NAGLU). In some embodiments, the nucleic acid further comprises a promoter. In some embodiments, the nucleic acid is comprised within a viral vector. In some embodiments, the viral vector comprises a retrovirus, an adenovirus, an adeno associated virus, a lentivirus, or a herpes virus. In some embodiments, the buffer or excipient suitable for gene therapy comprises a liposome, a nanoparticle, or a cell-penetrating peptide. In some embodiments, the buffer or excipient suitable for gene therapy comprises a viral coat protein. In some embodiments, the viral coat protein is selected from the group consisting of a vesicular stomatitis virus coat protein, an adenovirus coat protein, an adeno-associated virus coat protein, a murine leukemia virus coat protein, an HIV coat protein, and an influenza virus coat protein.

In further aspects, there are provided compositions comprising (a) a nucleic acid encoding a fusion protein comprising a therapeutic protein; and (b) a buffer or excipient suitable for gene therapy, wherein the nucleic acid further comprises a Kozak sequence. In some embodiments, the nucleic acid further comprises a cricket paralysis virus internal ribosome entry sequence (CrPV IBES). In some embodiments, the fusion protein further comprises a linker. In some embodiments, the linker consists of 5-20 amino acids, 5-15 amino acids, 5-10 amino acids, 8-12 amino acids, or about 7, 8, 9, 10, 11, 12 or 13 amino acids. In some embodiments, the linker comprises an amino acid sequence of GGGGSGGGG (SEQ ID NO: 18), GGGGS (SEQ ID NO: 19), GGGSGGGGS (SEQ ID NO: 20), GGGGSGGGS (SEQ ID NO: 21), GGGGSGGGGS (SEQ ID NO: 37), or GGSGSGSTS (SEQ ID NO: 33). In some embodiments, the fusion protein further comprises a signal peptide. In some embodiments, the signal peptide comprises a binding immunoglobulin protein (BiP) signal peptide. In some embodiments, the fusion protein further comprises a variant IGF2 peptide. In some embodiments, the therapeutic protein comprises at least one enzyme of the group consisting of alpha-galactosidase (A or B), β-galactosidase, β-hexosaminidase (A or B), galactosylceramidase, arylsulfatase (A or B), β-glucocerebrosidase, glucocerebrosidase, lysosomal acid lipase, lysosomal enzyme acid sphingomyelinase, formylglycine-generating enzyme, iduronidase (e.g., alpha-L), acetyl-CoA:alpha-glucosaminide N-acetyltransferase, glycosaminoglycan alpha-L-iduronohydrolase, heparan N-sulfatase, N-acetyl-α-D-glucosaminidase (NA-GLU), iduronate-2-sulfatase, galactosamine-6-sulfate sulfatase, N-acetylgalactosamine-6-sulfatase, glycosaminoglycan N-acetylgalactosamine 4-sulfatase, β-glucuronidase, hyaluronidase, alpha-N-acetyl neuraminidase (sialidase), ganglioside sialidase, phosphotransferase, alpha-glucosidase, alpha-D-mannosidase, beta-D-mannosidase, aspartylglucosaminidase, alpha-L-fucosidase, battenin, palmitoyl protein thioesterases, and other Batten-related proteins (e.g., ceroid-lipofuscinosis neuronal protein 6), or an enzymatically active fragment thereof. In some embodiments, the therapeutic protein comprises alpha-glucosidase, or an enzymatically active fragment thereof. In some embodiments, the therapeutic protein is N-acetyl-α-D-glucosaminidase (NA-GLU). In some embodiments, the nucleic acid further comprises a promoter. In some embodiments, the nucleic acid is comprised within a viral vector. In some embodiments, the viral vector comprises a retrovirus, an adenovirus, an adeno associated virus, a lentivirus, or a herpes virus. In some embodiments, the buffer or excipient suitable for gene therapy comprises a liposome, a nanoparticle, or a cell-penetrating peptide. In some embodiments, the buffer or excipient suitable for gene therapy comprises a viral coat protein. In some embodiments, the viral coat protein is selected from the group consisting of a vesicular stomatitis virus coat protein, an adenovirus coat protein, an adeno-associated virus coat protein, a murine leukemia virus coat protein, an HIV coat protein, and an influenza virus coat protein.

In additional aspects, there are provided methods of treating a genetic disorder in an individual comprising administering a composition comprising (a) a nucleic acid encoding a fusion protein comprising a variant IGF2 peptide and a therapeutic protein; and (b) a buffer or excipient suitable for gene therapy. In some embodiments, the fusion protein further comprises a linker. In some embodiments, the linker consists of 5-20 amino acids, 5-15 amino acids, 5-10 amino acids, 8-12 amino acids, or about 7, 8, 9, 10, 11, 12 or 13 amino acids. In some embodiments, the linker comprises an amino acid sequence of GGGGSGGGG (SEQ ID NO: 18), GGGGS (SEQ ID NO: 19), GGGSGGGGS (SEQ ID NO: 20), GGGGSGGGS (SEQ ID NO: 21), GGGGSGGGGS (SEQ ID NO: 37), or GGSGSGSTS (SEQ ID NO: 33). In some embodiments, the fusion protein further comprises a signal peptide. In some embodiments, the signal peptide comprises a binding immunoglobulin protein (BiP) signal peptide. In some embodiments, the nucleic acid further comprises a cricket paralysis virus internal ribosome entry sequence (CrPV IBES). In some embodiments, the nucleic acid further comprises a Kozak sequence. In some embodiments, the therapeutic protein comprises at least one enzyme of the group consisting of alpha-galactosidase (A or B), β-galactosidase, β-hexosaminidase (A or B), galactosylceramidase, arylsulfatase (A or B), β-glucocerebrosidase, glucocerebrosidase, lysosomal acid lipase, lysosomal enzyme acid sphingomyelinase, formylglycine-generating enzyme, iduronidase (e.g., alpha-L), acetyl-CoA:alpha-glucosaminide N-acetyltransferase, glycosaminoglycan alpha-L-iduronohydrolase, heparan N-sulfatase, N-acetyl-α-D-glucosaminidase (NA-GLU), iduronate-2-sulfatase, galactosamine-6-sulfate sulfatase, N-acetylgalactosamine-6-sulfatase, glycosaminoglycan N-acetylgalactosamine 4-sulfatase, β-glucuronidase, hyaluronidase, alpha-N-acetyl neuraminidase (sialidase), ganglioside sialidase, phosphotransferase, alpha-glucosidase, alpha-D-mannosidase, beta-D-mannosidase, aspartylglucosaminidase, alpha-L-fucosidase, battenin, palmitoyl protein thioesterases, and other Batten-related proteins (e.g., ceroid-lipofuscinosis neuronal protein 6), or an enzymatically active fragment thereof. In some embodiments, the therapeutic protein comprises alpha-glucosidase, or an enzymatically active fragment thereof. In some embodiments, the therapeutic protein is N-acetyl-α-D-glucosaminidase (NA-GLU). In some embodiments, the nucleic acid further comprises a promoter. In some embodiments, the nucleic acid is comprised within a viral vector. In some embodiments, the viral vector comprises a retrovirus, an adenovirus, an adeno associated virus, a lentivirus, or a herpes virus. In some embodiments, the buffer or excipient suitable for gene therapy comprises a liposome, a nanoparticle, or a cell-penetrating peptide. In some embodiments, the buffer or excipient suitable for gene therapy comprises a viral coat protein. In some embodiments, the viral coat protein is selected from the group consisting of a vesicular stomatitis virus coat protein, an adenovirus coat protein, an adeno-associated virus coat protein, a murine leukemia virus coat protein, an HIV coat protein, and an influenza virus coat protein. In some embodiments, the genetic disorder is a lysosomal storage disorder. In some embodiments, the genetic disorder is selected from the group consisting of aspartylglucosaminuria, Batten disease, cystinosis, Fabry disease, Gaucher disease type I, Gaucher disease type II, Gaucher disease type III, Pompe disease, Tay Sachs disease, Sandhoff disease, metachomatic leukodystrophy, mucolipidosis type I, mucolipidosis type II, mucolipidosis type III, mucolipidosis type IV, Hurler disease, Hunter disease, Sanfilippo disease type A, Sanfilippo disease type B, Sanfilippo disease type C, Sanfilippo disease type D, Morquio disease type A, Morquio disease type B, Maroteau-Lamy disease, Sly disease, Niemann-Pick disease type A, Niemann-Pick disease type B, Niemann-Pick disease type C1, Niemann-Pick disease type C2, Schindler disease type I, Schindler disease type II, adenosine deaminase severe combined immunodeficiency (ADA-SCID), and chronic granulomatous disease (CGD). In some embodiments, cells from the individual are treated ex vivo and administered to the individual after ex vivo treatment.

In additional aspects, there are provided methods of treating a genetic disorder in an individual comprising administering a composition comprising (a) a nucleic acid encoding a fusion protein comprising a signal peptide and a therapeutic protein; and (b) a buffer or excipient suitable for gene therapy. In some embodiments, the signal peptide comprises a binding immunoglobulin protein (BiP) signal peptide. In some embodiments, the fusion protein further comprises a linker. In some embodiments, the linker consists of 5-20 amino acids, 5-15 amino acids, 5-10 amino acids, 8-12 amino acids, or about 7, 8, 9, 10, 11, 12 or 13 amino acids. In some embodiments, the linker comprises an amino acid sequence of GGGGSGGGG (SEQ ID NO: 18), GGGGS (SEQ ID NO: 19), GGGSGGGGS (SEQ ID NO:

20), GGGGSGGGS (SEQ ID NO: 21), GGGGSGGGGS (SEQ ID NO: 37), or GGSGSGSTS (SEQ ID NO: 33). In some embodiments, the fusion protein further comprises a variant IGF2 peptide. In some embodiments, the nucleic acid further comprises a cricket paralysis virus internal ribosome entry sequence (CrPV IBES). In some embodiments, the nucleic acid further comprises a Kozak sequence. In some embodiments, the therapeutic protein comprises at least one enzyme of the group consisting of alpha-galactosidase (A or B), β-galactosidase, β-hexosaminidase (A or B), galactosylceramidase, arylsulfatase (A or B), β-glucocerebrosidase, glucocerebrosidase, lysosomal acid lipase, lysosomal enzyme acid sphingomyelinase, formylglycine-generating enzyme, iduronidase (e.g., alpha-L), acetyl-CoA: alpha-glucosaminide N-acetyltransferase, glycosaminoglycan alpha-L-iduronohydrolase, heparan N-sulfatase, N-acetyl-α-D-glucosaminidase (NAGLU), iduronate-2-sulfatase, galactosamine-6-sulfate sulfatase, N-acetylgalactosamine-6-sulfatase, glycosaminoglycan N-acetylgalactosamine 4-sulfatase, β-glucuronidase, hyaluronidase, alpha-N-acetyl neuraminidase (sialidase), ganglioside sialidase, phosphotransferase, alpha-glucosidase, alpha-D-mannosidase, beta-D-mannosidase, aspartylglucosaminidase, alpha-L-fucosidase, battenin, palmitoyl protein thioesterases, and other Batten-related proteins (e.g., ceroid-lipofuscinosis neuronal protein 6), or an enzymatically active fragment thereof. In some embodiments, the therapeutic protein comprises alpha-glucosidase, or an enzymatically active fragment thereof. In some embodiments, the therapeutic protein is N-acetyl-α-D-glucosaminidase (NAGLU). In some embodiments, the nucleic acid further comprises a promoter. In some embodiments, the nucleic acid is comprised within a viral vector. In some embodiments, the viral vector comprises a retrovirus, an adenovirus, an adeno associated virus, a lentivirus, or a herpes virus. In some embodiments, the buffer or excipient suitable for gene therapy comprises a liposome, a nanoparticle, or a cell-penetrating peptide. In some embodiments, the buffer or excipient suitable for gene therapy comprises a viral coat protein. In some embodiments, the viral coat protein is selected from the group consisting of a vesicular stomatitis virus coat protein, an adenovirus coat protein, an adeno-associated virus coat protein, a murine leukemia virus coat protein, an HIV coat protein, and an influenza virus coat protein. In some embodiments, the genetic disorder is a lysosomal storage disorder. In some embodiments, the genetic disorder is selected from the group consisting of aspartylglucosaminuria, Batten disease, cystinosis, Fabry disease, Gaucher disease type I, Gaucher disease type II, Gaucher disease type III, Pompe disease, Tay Sachs disease, Sandhoff disease, metachomatic leukodystrophy, mucolipidosis type I, mucolipidosis type II, mucolipidosis type III, mucolipidosis type IV, Hurler disease, Hunter disease, Sanfilippo disease type A, Sanfilippo disease type B, Sanfilippo disease type C, Sanfilippo disease type D, Morquio disease type A, Morquio disease type B, Maroteau-Lamy disease, Sly disease, Niemann-Pick disease type A, Niemann-Pick disease type B, Niemann-Pick disease type C1, Niemann-Pick disease type C2, Schindler disease type I, Schindler disease type II, adenosine deaminase severe combined immunodeficiency (ADA-SCID), and chronic granulomatous disease (CGD). In some embodiments, cells from the individual are treated ex vivo and administered to the individual after ex vivo treatment.

In further aspects, there are provided methods of treating a genetic disorder in an individual comprising administering a composition comprising (a) a nucleic acid encoding a fusion protein comprising a therapeutic protein and a targeting peptide; and (b) a buffer or excipient suitable for gene therapy, wherein the nucleic acid further comprises a cricket paralysis virus internal ribosome entry sequence (CrPV IBES). In some embodiments, the nucleic acid further comprises a Kozak sequence. In some embodiments, the fusion protein further comprises a linker. In some embodiments, the linker consists of 5-20 amino acids, 5-15 amino acids, 5-10 amino acids, 8-12 amino acids, or about 7, 8, 9, 10, 11, 12 or 13 amino acids. In some embodiments, the linker comprises an amino acid sequence of GGGGSGGGG (SEQ ID NO: 18), GGGGS (SEQ ID NO: 19), GGGSGGGGS (SEQ ID NO: 20), GGGGSGGGS (SEQ ID NO: 21), GGGGSGGGGS (SEQ ID NO: 37), or GGSGSGSTS (SEQ ID NO: 33). In some embodiments, the fusion protein further comprises a signal peptide. In some embodiments, the signal peptide comprises a binding immunoglobulin protein (BiP) signal peptide. In some embodiments, the fusion protein further comprises a variant IGF2 peptide. In some embodiments, the therapeutic protein comprises at least one enzyme of the group consisting of alpha-galactosidase (A or B), β-galactosidase, β-hexosaminidase (A or B), galactosylceramidase, arylsulfatase (A or B), β-glucocerebrosidase, glucocerebrosidase, lysosomal acid lipase, lysosomal enzyme acid sphingomyelinase, formylglycine-generating enzyme, iduronidase (e.g., alpha-L), acetyl-CoA:alpha-glucosaminide N-acetyltransferase, glycosaminoglycan alpha-L-iduronohydrolase, heparan N-sulfatase, N-acetyl-α-D-glucosaminidase (NAGLU), iduronate-2-sulfatase, galactosamine-6-sulfate sulfatase, N-acetylgalactosamine-6-sulfatase, glycosaminoglycan N-acetylgalactosamine 4-sulfatase, β-glucuronidase, hyaluronidase, alpha-N-acetyl neuraminidase (sialidase), ganglioside sialidase, phosphotransferase, alpha-glucosidase, alpha-D-mannosidase, beta-D-mannosidase, aspartylglucosaminidase, alpha-L-fucosidase, battenin, palmitoyl protein thioesterases, and other Batten-related proteins (e.g., ceroid-lipofuscinosis neuronal protein 6), or an enzymatically active fragment thereof. In some embodiments, the therapeutic protein comprises alpha-glucosidase, or an enzymatically active fragment thereof. In some embodiments, the therapeutic protein is N-acetyl-α-D-glucosaminidase (NAGLU). In some embodiments, the nucleic acid further comprises a promoter. In some embodiments, the nucleic acid is comprised within a viral vector. In some embodiments, the viral vector comprises a retrovirus, an adenovirus, an adeno associated virus, a lentivirus, or a herpes virus. In some embodiments, the buffer or excipient suitable for gene therapy comprises a liposome, a nanoparticle, or a cell-penetrating peptide. In some embodiments, the buffer or excipient suitable for gene therapy comprises a viral coat protein. In some embodiments, the viral coat protein is selected from the group consisting of a vesicular stomatitis virus coat protein, an adenovirus coat protein, an adeno-associated virus coat protein, a murine leukemia virus coat protein, an HIV coat protein, and an influenza virus coat protein. In some embodiments, the genetic disorder is a lysosomal storage disorder. In some embodiments, the genetic disorder is selected from the group consisting of aspartylglucosaminuria, Batten disease, cystinosis, Fabry disease, Gaucher disease type I, Gaucher disease type II, Gaucher disease type III, Pompe disease, Tay Sachs disease, Sandhoff disease, metachomatic leukodystrophy, mucolipidosis type I, mucolipidosis type II, mucolipidosis type III, mucolipidosis type IV, Hurler disease, Hunter disease, Sanfilippo disease type A, Sanfilippo disease type B, Sanfilippo disease type C, Sanfilippo disease type D, Morquio disease type A, Morquio disease type B, Maroteau-Lamy disease, Sly disease, Niemann-Pick disease type A, Niemann-Pick disease type B, Niemann-Pick disease type C1, Niemann-Pick disease type C2, Schindler disease type I, Schindler disease type II, adenosine deaminase severe combined immunodeficiency (ADA-SCID), and chronic granulomatous disease (CGD). In some embodiments, cells from the individual are treated ex vivo and administered to the individual after ex vivo treatment.

In additional aspects, there are provided methods of treating a genetic disorder in an individual comprising administering a composition comprising (a) a nucleic acid encoding a fusion protein comprising a therapeutic protein; and (b) a buffer or excipient suitable for gene therapy, wherein the nucleic acid further comprises a Kozak sequence. In some embodiments, the nucleic acid further comprises a cricket paralysis virus internal ribosome entry sequence (CrPV IBES). In some embodiments, the fusion protein further comprises a signal peptide. In some embodiments, the signal peptide comprises a binding immunoglobulin protein (BiP) signal peptide. In some embodiments, the fusion protein further comprises a variant IGF2 peptide. In some embodiments, the therapeutic protein comprises at least one enzyme of the group consisting of alpha-galactosidase (A or B), β-galactosidase, hexosaminidase (A or B), galactosylceramidase, arylsulfatase (A or B), β-glucocerebrosidase, glucocerebrosidase, lysosomal acid lipase, lysosomal enzyme acid sphingomyelinase, formylglycine-generating enzyme, iduronidase (e.g., alpha-L), acetyl-CoA:alpha-glucosaminide N-acetyltransferase, glycosaminoglycan alpha-L-iduronohydrolase, heparan N-sulfatase, N-acetyl-α-D-glucosaminidase (NAGLU), iduronate-2-sulfatase, galactosamine-6-sulfate sulfatase, N-acetylgalactosamine-6-sulfatase, glycosaminoglycan N-acetylgalactosamine 4-sulfatase, β-glucuronidase, hyaluronidase, alpha-N-acetyl neuraminidase (sialidase), ganglioside sialidase, phosphotransferase, alpha-glucosidase, alpha-D-mannosidase, beta-D-mannosidase, aspartylglucosaminidase, alpha-L-fucosidase, battenin, palmitoyl protein thioesterases, and other Batten-related proteins (e.g., ceroid-lipofuscinosis neuronal protein 6), or an enzymatically active fragment thereof. In some embodiments, the therapeutic protein comprises alpha-glucosidase, or an enzymatically active fragment thereof. In some embodiments, the therapeutic protein is N-acetyl-α-D-glucosaminidase (NAGLU). In some embodiments, the nucleic acid further comprises a promoter. In some embodiments, the nucleic acid is comprised within a viral vector. In some embodiments, the viral vector comprises a retrovirus, an adenovirus, an adeno associated virus, a lentivirus, or a herpes virus. In some embodiments, the buffer or excipient suitable for gene therapy comprises a liposome, a nanoparticle, or a cell-penetrating peptide. In some embodiments, the buffer or excipient suitable for gene therapy comprises a viral coat protein. In some embodiments, the viral coat protein is selected from the group consisting of a vesicular stomatitis virus coat protein, an adenovirus coat protein, an adeno-associated virus coat protein, a murine leukemia virus coat protein, an HIV coat protein, and an influenza virus coat protein. In some embodiments, the genetic disorder is a lysosomal storage disorder. In some embodiments, the genetic disorder is selected from the group consisting of aspartylglucosaminuria, Batten disease, cystinosis, Fabry disease, Gaucher disease type I, Gaucher disease type II, Gaucher disease type III, Pompe disease, Tay Sachs disease, Sandhoff disease, metachomatic leukodystrophy, mucolipidosis type I, mucolipidosis type II, mucolipidosis type III, mucolipidosis type IV, Hurler disease, Hunter disease, Sanfilippo disease type A, Sanfilippo disease type B, Sanfilippo disease type C, Sanfilippo disease type D, Morquio disease type A, Morquio disease type B, Maroteau-Lamy disease, Sly disease, Niemann-Pick disease type A, Niemann-Pick disease type B, Niemann-Pick disease type C1, Niemann-Pick disease type C2, Schindler disease type I, Schindler disease type II, adenosine deaminase severe combined immunodeficiency (ADA-SCID), and chronic granulomatous disease (CGD). In some embodiments, cells from the individual are treated ex vivo and administered to the individual after ex vivo treatment.

In further aspects, there are provided methods of treating a genetic disorder in an individual comprising administering a cell comprising a nucleic acid encoding a fusion protein comprising a variant IGF2 peptide and a therapeutic protein. In some embodiments, the fusion protein further comprises a linker. In some embodiments, the linker consists of 5-20 amino acids, 5-15 amino acids, 5-10 amino acids, 8-12 amino acids, or about 7, 8, 9, 10, 11, 12 or 13 amino acids. In some embodiments, the linker comprises an amino acid sequence of GGGGSGGGG (SEQ ID NO: 18), GGGGS (SEQ ID NO: 19), GGGSGGGGS (SEQ ID NO: 20), GGGGSGGGS (SEQ ID NO: 21), GGGGSGGGGS (SEQ ID NO: 37), or GGSGSGSTS (SEQ ID NO: 33). In some embodiments, the fusion protein further comprises a signal peptide. In some embodiments, the signal peptide comprises a binding immunoglobulin protein (BiP) signal peptide. In some embodiments, the nucleic acid further comprises a cricket paralysis virus internal ribosome entry sequence (CrPV IBES). In some embodiments, the nucleic acid further comprises a Kozak sequence. In some embodiments, the therapeutic protein comprises at least one enzyme of the group consisting of alpha-galactosidase (A or B), β-galactosidase, β-hexosaminidase (A or B), galactosylceramidase, arylsulfatase (A or B), β-glucocerebrosidase, glucocerebrosidase, lysosomal acid lipase, lysosomal enzyme acid sphingomyelinase, formylglycine-generating enzyme, iduronidase (e.g., alpha-L), acetyl-CoA:alpha-glucosaminide N-acetyltransferase, glycosaminoglycan alpha-L-iduronohydrolase, heparan N-sulfatase, N-acetyl-α-D-glucosaminidase (NAGLU), iduronate-2-sulfatase, galactosamine-6-sulfate sulfatase, N-acetylgalactosamine-6-sulfatase, glycosaminoglycan N-acetylgalactosamine 4-sulfatase, β-glucuronidase, hyaluronidase, alpha-N-acetyl neuraminidase (sialidase), ganglioside sialidase, phosphotransferase, alpha-glucosidase, alpha-D-mannosidase, beta-D-mannosidase, aspartylglucosaminidase, alpha-L-fucosidase, battenin, palmitoyl protein thioesterases, and other Batten-related proteins (e.g., ceroid-lipofuscinosis neuronal protein 6), or an enzymatically active fragment thereof. In some embodiments, the therapeutic protein comprises alpha-glucosidase, or an enzymatically active fragment thereof. In some embodiments, the therapeutic protein is N-acetyl-α-D-glucosaminidase (NAGLU). In some embodiments, the nucleic acid further comprises a promoter. In some embodiments, the nucleic acid is comprised within a viral vector. In some embodiments, the viral vector comprises a retrovirus, an adenovirus, an adeno associated virus, a lentivirus, or a herpes virus. In some embodiments, the buffer or excipient suitable for gene therapy comprises a liposome, a nanoparticle, or a cell-penetrating peptide. In some embodiments, the buffer or excipient suitable for gene therapy comprises a viral coat protein. In some embodiments, the viral coat protein is selected from the group consisting of a vesicular stomatitis virus coat protein, an adenovirus coat protein, an adeno-associated virus coat protein, a murine leukemia virus coat protein, an HIV coat protein, and an influenza virus coat protein. In some embodiments, the genetic disorder is a lysosomal storage disorder. In some embodiments, the genetic disorder is selected from the group consisting of aspartylglucosaminuria, Batten disease, cystinosis, Fabry disease, Gaucher disease type I, Gaucher disease type II, Gaucher disease type III, Pompe disease, Tay Sachs disease, Sandhoff disease, metachomatic leukodystrophy, mucolipidosis type I, mucolipidosis type II, mucolipidosis type III, mucolipidosis type IV, Hurler disease, Hunter disease, Sanfilippo disease type A, Sanfilippo disease type B, Sanfilippo disease type C, Sanfilippo disease type D, Morquio disease type A, Morquio disease type B, Maroteau-Lamy disease, Sly disease, Niemann-Pick disease type A, Niemann-Pick disease type B, Niemann-Pick disease type C1, Niemann-Pick disease type C2, Schindler disease type I, Schindler disease type II, adenosine deaminase severe combined immunodeficiency (ADA-SCID), and chronic granulomatous disease (CGD). In some embodiments, the cells are derived from the individual.

In additional aspects, there are provided methods of treating a genetic disorder in an individual comprising administering a cell comprising a nucleic acid encoding a fusion protein comprising a signal peptide and a therapeutic protein. In some embodiments, the signal peptide comprises a binding immunoglobulin protein (BiP) signal peptide. In some embodiments, the fusion protein further comprises a linker. In some embodiments, the linker consists of 5-20 amino acids, 5-15 amino acids, 5-10 amino acids, 8-12 amino acids, or about 7, 8, 9, 10, 11, 12 or 13 amino acids. In some embodiments, the linker comprises an amino acid sequence of GGGGSGGGG (SEQ ID NO: 18), GGGGS (SEQ ID NO: 19), GGGSGGGGS (SEQ ID NO: 20), GGGGSGGGS (SEQ ID NO: 21), GGGGSGGGGS (SEQ ID NO: 37), or GGSGSGSTS (SEQ ID NO: 33). In some embodiments, the fusion protein further comprises a variant IGF2 peptide. In some embodiments, the nucleic acid further comprises a cricket paralysis virus internal ribosome entry sequence (CrPV IBES). In some embodiments, the nucleic acid further comprises a Kozak sequence. In some embodiments, the therapeutic protein comprises at least one enzyme of the group consisting of alpha-galactosidase (A or B), β-galactosidase, β-hexosaminidase (A or B), galactosylceramidase, arylsulfatase (A or B), β-glucocerebrosidase, glucocerebrosidase, lysosomal acid lipase, lysosomal enzyme acid sphingomyelinase, formylglycine-generating enzyme, iduronidase (e.g., alpha-L), acetyl-CoA:alpha-glucosaminide N-acetyltransferase, glycosaminoglycan alpha-L-iduronohydrolase, heparan N-sulfatase, N-acetyl-α-D-glucosaminidase (NAGLU), iduronate-2-sulfatase, galactosamine-6-sulfate sulfatase, N-acetylgalactosamine-6-sulfatase, glycosaminoglycan N-acetylgalactosamine 4-sulfatase, β-glucuronidase, hyaluronidase, alpha-N-acetyl neuraminidase (sialidase), ganglioside sialidase, phosphotransferase, alpha-glucosidase, alpha-D-mannosidase, beta-D-mannosidase, aspartylglucosaminidase, alpha-L-fucosidase, battenin, palmitoyl protein thioesterases, and other Batten-related proteins (e.g., ceroid-lipofuscinosis neuronal protein 6), or an enzymatically active fragment thereof. In some embodiments, the therapeutic protein comprises alpha-glucosidase, or an enzymatically active fragment thereof. In some embodiments, the therapeutic protein is N-acetyl-α-D-glucosaminidase (NAGLU). In some embodiments, the nucleic acid further comprises a promoter. In some embodiments, the nucleic acid is comprised within a viral vector. In some embodiments, the viral vector comprises a retrovirus, an adenovirus, an adeno associated virus, a lentivirus, or a herpes virus. In some embodiments, the buffer or excipient suitable for gene therapy comprises a liposome, a nanoparticle, or a cell-penetrating peptide. In some embodiments, the buffer or excipient suitable for gene therapy comprises a viral coat protein. In some embodiments, the viral coat protein is selected from the group consisting of a vesicular stomatitis virus coat protein, an adenovirus coat protein, an adeno-associated virus coat protein, a murine leukemia virus coat protein, an HIV coat protein, and an influenza virus coat protein. In some embodiments, the genetic disorder is a lysosomal storage disorder. In some embodiments, the genetic disorder is selected from the group consisting of aspartylglucosaminuria, Batten disease, cystinosis, Fabry disease, Gaucher disease type I, Gaucher disease type II, Gaucher disease type III, Pompe disease, Tay Sachs disease, Sandhoff disease, metachomatic leukodystrophy, mucolipidosis type I, mucolipidosis type II, mucolipidosis type III, mucolipidosis type IV, Hurler disease, Hunter disease, Sanfilippo disease type A, Sanfilippo disease type B, Sanfilippo disease type C, Sanfilippo disease type D, Morquio disease type A, Morquio disease type B, Maroteau-Lamy disease, Sly disease, Niemann-Pick disease type A, Niemann-Pick disease type B, Niemann-Pick disease type C1, Niemann-Pick disease type C2, Schindler disease type I, Schindler disease type II, adenosine deaminase severe combined immunodeficiency (ADA-SCID), and chronic granulomatous disease (CGD). In some embodiments, the cells are derived from the individual.

In additional aspects, there are provided methods of treating a genetic disorder in an individual comprising administering a cell comprising a nucleic acid encoding a fusion protein comprising a therapeutic protein, wherein the nucleic acid further comprises a cricket paralysis virus internal ribosome entry sequence (CrPV IBES). In some embodiments, the nucleic acid further comprises a Kozak sequence. In some embodiments, the fusion protein further comprises a linker. In some embodiments, the linker consists of 5-20 amino acids, 5-15 amino acids, 5-10 amino acids, 8-12 amino acids, or about 7, 8, 9, 10, 11, 12 or 13 amino acids. In some embodiments, the linker comprises an amino acid sequence of GGGGSGGGG (SEQ ID NO: 18), GGGGS (SEQ ID NO: 19), GGGSGGGGS (SEQ ID NO: 20), GGGGSGGGS (SEQ ID NO: 21), GGGGSGGGGS (SEQ ID NO: 37), or GGSGSGSTS (SEQ ID NO: 33). In some embodiments, the fusion protein further comprises a signal peptide. In some embodiments, the signal peptide comprises a binding immunoglobulin protein (BiP) signal peptide. In some embodiments, the fusion protein further comprises a variant IGF2 peptide. In some embodiments, the therapeutic protein comprises at least one enzyme of the group consisting of alpha-galactosidase (A or B), β-galactosidase, β-hexosaminidase (A or B), galactosylceramidase, arylsulfatase (A or B), β-glucocerebrosidase, glucocerebrosidase, lysosomal acid lipase, lysosomal enzyme acid sphingomyelinase, formylglycine-generating enzyme, iduronidase (e.g., alpha-L), acetyl-CoA:alpha-glucosaminide N-acetyltransferase, glycosaminoglycan alpha-L-iduronohydrolase, heparan N-sulfatase, N-acetyl-α-D-glucosaminidase (NAGLU), iduronate-2-sulfatase, galactosamine-6-sulfate sulfatase, N-acetylgalactosamine-6-sulfatase, glycosaminoglycan N-acetylgalactosamine 4-sulfatase, β-glucuronidase, hyaluronidase, alpha-N-acetyl neuraminidase (sialidase), ganglioside sialidase, phosphotransferase, alpha-glucosidase, alpha-D-mannosidase, beta-D-mannosidase, aspartylglucosaminidase, alpha-L-fucosidase, battenin, palmitoyl protein thioesterases, and other Batten-related proteins (e.g., ceroid-lipofuscinosis neuronal protein 6), or an enzymatically active fragment thereof. In some embodiments, the therapeutic protein comprises alpha-glucosidase, or an enzymatically active fragment thereof. In some embodiments, the therapeutic protein is N-acetyl-α-D-glucosaminidase (NAGLU). In some embodiments, the nucleic acid further comprises a promoter. In some embodiments, the nucleic acid is comprised within a viral vector. In some embodiments, the viral vector comprises a retrovirus, an adenovirus, an adeno associated virus, a lentivirus, or a herpes virus. In some embodiments, the buffer or excipient suitable for gene therapy comprises a liposome, a nanoparticle, or a cell-penetrating peptide. In some embodiments, the buffer or excipient suitable for gene therapy comprises a viral coat protein. In some embodiments, the viral coat protein is selected from the group consisting of a vesicular stomatitis virus coat protein, an adenovirus coat protein, an adeno-associated virus coat protein, a murine leukemia virus coat protein, an HIV coat protein, and an influenza virus coat protein. In some embodiments, the genetic disorder is a lysosomal storage disorder. In some embodiments, the genetic disorder is selected from the group consisting of aspartylglucosaminuria, Batten disease, cystinosis, Fabry disease, Gaucher disease type I, Gaucher disease type II, Gaucher disease type III, Pompe disease, Tay Sachs disease, Sandhoff disease, metachomatic leukodystrophy, mucolipidosis type I, mucolipidosis type II, mucolipidosis type III, mucolipidosis type IV, Hurler disease, Hunter disease, Sanfilippo disease type A, Sanfilippo disease type B, Sanfilippo disease type C, Sanfilippo disease type D, Morquio disease type A, Morquio disease type B, Maroteau-Lamy disease, Sly disease, Niemann-Pick disease type A, Niemann-Pick disease type B, Niemann-Pick disease type C1, Niemann-Pick disease type C2, Schindler disease type I, Schindler disease type II, adenosine deaminase severe combined immunodeficiency (ADA-SCID), and chronic granulomatous disease (CGD). In some embodiments, the cells are derived from the individual.

In further aspects, there are provided methods of treating a genetic disorder in an individual comprising administering a cell comprising a nucleic acid encoding a fusion protein comprising a therapeutic protein, wherein the nucleic acid further comprises a Kozak sequence. In some embodiments, the nucleic acid further comprises a cricket paralysis virus internal ribosome entry sequence (CrPV IBES). In some embodiments, the fusion protein further comprises a linker. In some embodiments, the linker consists of 5-20 amino acids, 5-15 amino acids, 5-10 amino acids, 8-12 amino acids, or about 7, 8, 9, 10, 11, 12 or 13 amino acids. In some embodiments, the linker comprises an amino acid sequence of GGGGSGGGG (SEQ ID NO: 18), GGGGS (SEQ ID NO: 19), GGGSGGGS (SEQ ID NO: 20), GGGGSGGGS (SEQ ID NO: 21), GGGGSGGGGS (SEQ ID NO: 37), or GGSGSGSTS (SEQ ID NO: 33). In some embodiments, the fusion protein further comprises a signal peptide. In some embodiments, the signal peptide comprises a binding immunoglobulin protein (BiP) signal peptide. In some embodiments, the fusion protein further comprises a variant IGF2 peptide. In some embodiments, the therapeutic protein comprises at least one enzyme of the group consisting of alpha-galactosidase (A or B), β-galactosidase, β-hexosaminidase (A or B), galactosylceramidase, arylsulfatase (A or B), β-glucocerebrosidase, glucocerebrosidase, lysosomal acid lipase, lysosomal enzyme acid sphingomyelinase, formylglycine-generating enzyme, iduronidase (e.g., alpha-L), acetyl-CoA:alpha-glucosaminide N-acetyltransferase, glycosaminoglycan alpha-L-iduronohydrolase, heparan N-sulfatase, N-acetyl-α-D-glucosaminidase (NA-GLU), iduronate-2-sulfatase, galactosamine-6-sulfate sulfatase, N-acetylgalactosamine-6-sulfatase, glycosaminoglycan N-acetylgalactosamine 4-sulfatase, β-glucuronidase, hyaluronidase, alpha-N-acetyl neuraminidase (sialidase), ganglioside sialidase, phosphotransferase, alpha-glucosidase, alpha-D-mannosidase, beta-D-mannosidase, aspartylglucosaminidase, alpha-L-fucosidase, battenin, palmitoyl protein thioesterases, and other Batten-related proteins (e.g., ceroid-lipofuscinosis neuronal protein 6), or an enzymatically active fragment thereof. In some embodiments, the therapeutic protein comprises alpha-glucosidase, or an enzymatically active fragment thereof. In some embodiments, the therapeutic protein is N-acetyl-α-D-glucosaminidase (NAGLU). In some embodiments, the nucleic acid further comprises a promoter. In some embodiments, the nucleic acid is comprised within a viral vector. In some embodiments, the viral vector comprises a retrovirus, an adenovirus, an adeno associated virus, a lentivirus, or a herpes virus. In some embodiments, the buffer or excipient suitable for gene therapy. In some embodiments, the buffer or excipient suitable for gene therapy comprises a viral coat protein. In some embodiments, the viral coat protein is selected from the group consisting of a vesicular stomatitis virus coat protein, an adenovirus coat protein, an adeno-associated virus coat protein, a murine leukemia virus coat protein, an HIV coat protein, and an influenza virus coat protein. In some embodiments, the genetic disorder is a lysosomal storage disorder. In some embodiments, the genetic disorder is selected from the group consisting of aspartylglucosaminuria, Batten disease, cystinosis, Fabry disease, Gaucher disease type I, Gaucher disease type II, Gaucher disease type III, Pompe disease, Tay Sachs disease, Sandhoff disease, metachomatic leukodystrophy, mucolipidosis type I, mucolipidosis type II, mucolipidosis type III, mucolipidosis type IV, Hurler disease, Hunter disease, Sanfilippo disease type A, Sanfilippo disease type B, Sanfilippo disease type C, Sanfilippo disease type D, Morquio disease type A, Morquio disease type B, Maroteau-Lamy disease, Sly disease, Niemann-Pick disease type A, Niemann-Pick disease type B, Niemann-Pick disease type C1, Niemann-Pick disease type C2, Schindler disease type I, Schindler disease type II, adenosine deaminase severe combined immunodeficiency (ADA-SCID), and chronic granulomatous disease (CGD). In some embodiments, the cells are derived from the individual.

Further provided herein is a fusion protein comprising a native signal peptide, an ER proteolytic cleavage domain, a variant IGF2 peptide, and an alpha-glucosidase lacking its native signal peptide, wherein the fusion protein is encoded by a nucleic acid comprising a Kozak sequence.

Additionally provided herein is a fusion protein comprising a binding immunoglobulin protein (BiP) signal peptide, a variant IGF2 peptide, and an alpha-glucosidase, wherein the fusion protein is encoded by a nucleic acid comprising a Kozak sequence.

Additionally provided herein is a fusion protein comprising a binding immunoglobulin protein (BiP) signal peptide, a variant IGF2 peptide, and an alpha-glucosidase lacking its native signal peptide, wherein the fusion protein is encoded by a nucleic acid comprising a cricket paralysis virus internal ribosome entry sequence (CrPV IRES).

Additionally provided herein is a nucleic acid encoding a fusion protein comprising a native signal peptide, an ER proteolytic cleavage domain, a variant IGF2 peptide, and an alpha-glucosidase lacking its native signal peptide.

Additionally provided herein is a nucleic acid encoding a fusion protein comprising a binding immunoglobulin protein (BiP) signal peptide, a variant IGF2 peptide and an alpha-glucosidase lacking its native signal peptide, wherein the nucleic acid further comprises a Kozak sequence.

Additionally provided herein is a nucleic acid encoding a fusion protein comprising a variant IGF2 peptide and an alpha-glucosidase, wherein the nucleic acid further comprises a cricket paralysis virus internal ribosome entry sequence (CrPV IRES).

Additionally provided herein is a composition comprising (a) a nucleic acid encoding a fusion protein comprising a native signal peptide, an ER proteolytic cleavage domain, a variant IGF2 peptide, and an alpha-glucosidase lacking its native signal peptide; and (b) a buffer or excipient suitable for gene therapy.

Additionally provided herein is a composition comprising (a) a nucleic acid encoding a fusion protein comprising a binding immunoglobulin protein (BiP) signal peptide, a variant IGF2 peptide and an alpha-glucosidase lacking its native signal peptide, wherein the nucleic acid further comprises a Kozak sequence; and (b) a buffer or excipient suitable for gene therapy.

Additionally provided herein is a composition comprising (a) a nucleic acid encoding a fusion protein comprising a variant IGF2 peptide and an alpha-glucosidase, wherein the nucleic acid further comprises a cricket paralysis virus internal ribosome entry sequence (CrPV IRES); and (b) a buffer or excipient suitable for gene therapy.

Additionally provided herein is a method of treating Pompe disease in an individual comprising administering a composition comprising (a) a nucleic acid encoding a fusion protein comprising a native signal peptide, an ER proteolytic cleavage domain, a variant IGF2 peptide, and an alpha-glucosidase lacking its native signal peptide; and (b) a buffer or excipient suitable for gene therapy.

Additionally provided herein is a method of treating Pompe disease in an individual comprising administering a composition comprising (a) a nucleic acid encoding a fusion protein comprising a binding immunoglobulin protein (BiP) signal peptide, a variant IGF2 peptide and an alpha-glucosidase lacking its native signal peptide, wherein the nucleic acid further comprises a Kozak sequence; and (b) a buffer or excipient suitable for gene therapy.

Additionally provided herein is a method of treating Pompe disease in an individual comprising administering a composition comprising (a) a nucleic acid encoding a fusion protein comprising a variant IGF2 peptide and an alpha-glucosidase, wherein the nucleic acid further comprises a cricket paralysis virus internal ribosome entry sequence (CrPV IRES); and (b) a buffer or excipient suitable for gene therapy.

Additionally provided herein is a method of treating Pompe disease in an individual comprising administering a cell comprising a nucleic acid encoding a fusion protein comprising a native signal peptide, an ER proteolytic cleavage domain, a variant IGF2 peptide, and an alpha-glucosidase lacking its native signal peptide.

Additionally provided herein is a method of treating Pompe disease in an individual comprising administering a cell comprising a nucleic acid encoding a fusion protein comprising a binding immunoglobulin protein (BiP) signal peptide, a variant IGF2 peptide and an alpha-glucosidase, or an enzymatically active fragment thereof, wherein the nucleic acid further comprises a Kozak sequence.

Additionally provided herein is a method of treating Pompe disease in an individual comprising administering a cell comprising a nucleic acid encoding a fusion protein comprising a variant IGF2 peptide and an alpha-glucosidase, wherein the nucleic acid further comprises a cricket paralysis virus internal ribosome entry sequence (CrPV IRES).

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The patent application file contains at least one drawing executed in color. Copies of this patent application with color drawing(s) will be provided by the Office upon request and payment of the necessary fee. An understanding of the features and advantages of the present disclosure will be obtained by reference to the following detailed description that sets forth illustrative embodiments, in which the principles of the disclosure are utilized, and the accompanying drawings of which:

FIG. 1 shows the proportion of commercial ERT that is able to bind to the CI-MPR. The first peak is the rhGAA that lack any M6P containing glycans and thus unable to be taken up and delivered to the lysosome. The second peak is the fraction that contains at least one phosphorylated glycan and has the potential to be taken up by the cell and delivered to the lysosome for hydrolysis of glycogen.

DETAILED DESCRIPTION

Figure 1:
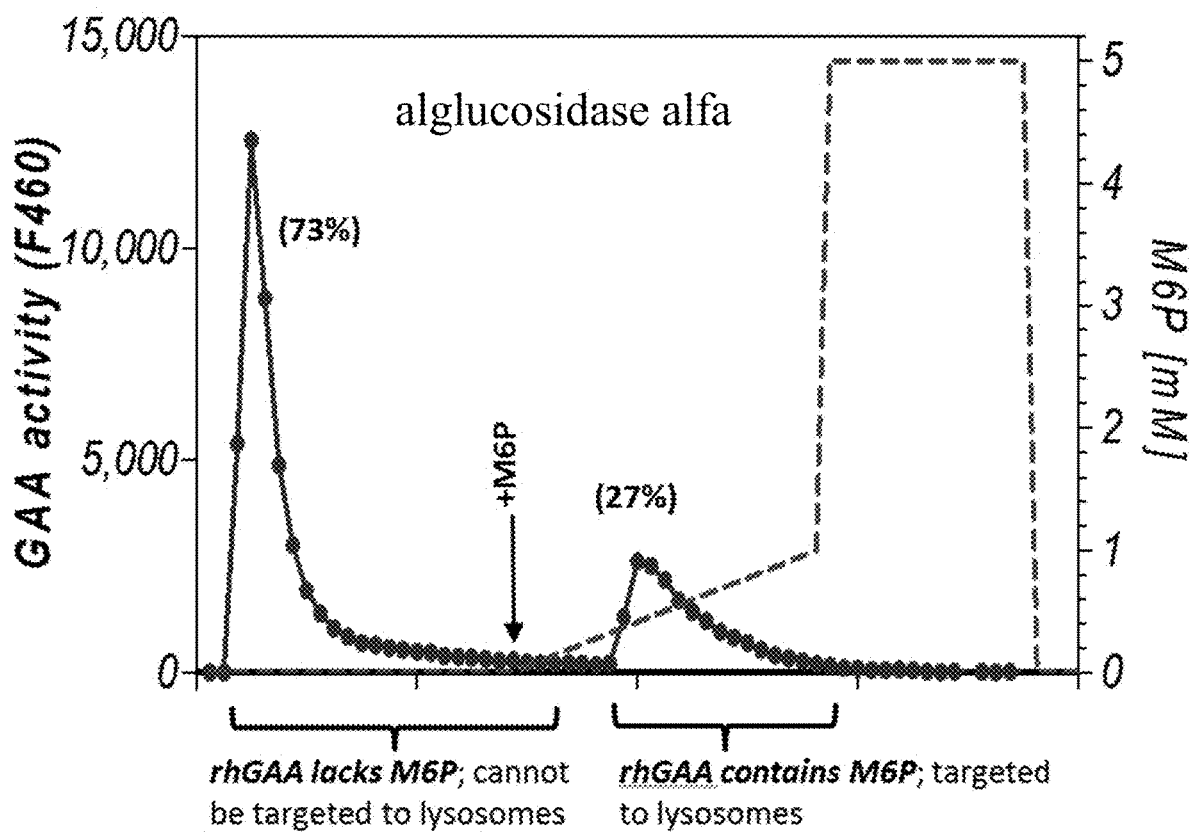
FIG. 1 shows GAA activity of alglucosidase-alfa rhGAA with and without M6P.

Gene therapy for single gene genetic disorders presents a potential one-time treatment for diseases and disorders, some of which have devastating symptoms that can appear early in life and sometimes lead to life-long disability. Neurologic genetic disorders, such as lysosomal storage disorders, are often treated with enzyme replacement therapies which administer to the patient a therapeutic protein that is an active form of the protein that is defective or deficient in the disease or disorder state. However, there are challenges for current therapies, including frequent treatments, development of an immune response to the therapeutic protein, and difficulty targeting the therapeutic protein to the affected tissue, cell, or subcellular compartment. Gene therapy offers advantages including a reduced number of treatments and long lasting efficacy.

Provided herein are components for gene therapy vectors that offer improvements to gene therapy, such as providing more therapeutic protein where it is needed, thus improving treatment efficacy. Such challenges are addressed herein by improving expression and cellular uptake or delivery and intracellular or subcellular targeting of therapeutic proteins. Specific tools or components provided herein include but are not limited to signal peptides (e.g., binding immunoglobulin protein (BiP) and *Gaussia* signal peptides) for increasing secretion and peptides that increase endocytosis of the therapeutic protein (e.g., peptides that bind to the CI-MPR with high affinity for increasing cellular uptake and lysosomal delivery). Such peptides are fused to therapeutic proteins encoded by gene therapy vectors. In some embodiments, the peptides are IGF2 (Insulin Like growth factor 2) peptides or variants thereof. Gene therapy vectors provided herein are contemplated to comprise, in some embodiments, a nucleic acid encoding a therapeutic protein fused to a peptide that bind to the CI-MPR with high affinity for optimizing efficacy of gene therapy.

Gene therapy constructs for enzyme replacement gene therapy were designed. A translation initiation sequence, including, but not limited to a Kozak sequence or an IRES sequence, such as CrPV IRES, located at the 5' end of the construct, followed by a nucleic acid encoding a signal peptide selected from one or more of a GAA signal peptide, a nucleic acid encoding an anti-trypsin inhibitor, and a nucleic acid encoding BiP sequence. These are followed by a nucleic acid encoding a cell targeting domain which can be a vIGF-2, a HIRMab, or a TfRMab or other cell targeting peptide or protein. The gene therapy construct further comprises a nucleic acid encoding a linker and a nucleic acid encomding a corrective enzyme or enzymatically active fragment thereof, wherein the linker connects the cell targeting domain to the corrective enzyme, or enzymatically active fragment thereof. Suitable corrective enzymes include but are not limited to alpha-glucosidase (GAA), alpha-galactosidase (GLA), iduronidase (IDUA), iduroniate-2-sulfatase (IDS), PPT1, or enzymatically active fragments thereof, and other enzymes found deficient in an individual.

Intracellular Targeting of Therapeutic Proteins

N-linked carbohydrates of most lysosomal proteins are modified to contain a specialized carbohydrate structure called mannose 6-phosphate (M6P). M6P is the biological signal that enables transport of lysosomal proteins to lysosomes via membrane-bound M6P receptors. Enzyme replacement therapies for lysosomal storage disorders utilize M6P receptors for uptake and delivery of therapeutic proteins to lysosomes. Certain therapeutics do not utilize M6P receptors including Cerezyme® and other versions of recombinant human GCase, utilize the mannose receptor that is able to bind terminal mannose on protein glycans and deliver to the lysosome. A problem facing certain enzyme replacement therapeutics is there are low amounts of M6P present on the enzyme therapeutic which necessitate higher doses to reach therapeutic efficacy. This leads to substantially longer infusion times, higher probability of developing immune responses to the therapeutic, and higher drug demand, requiring increased protein manufacturing resulting in increased costs.

Figure 2:
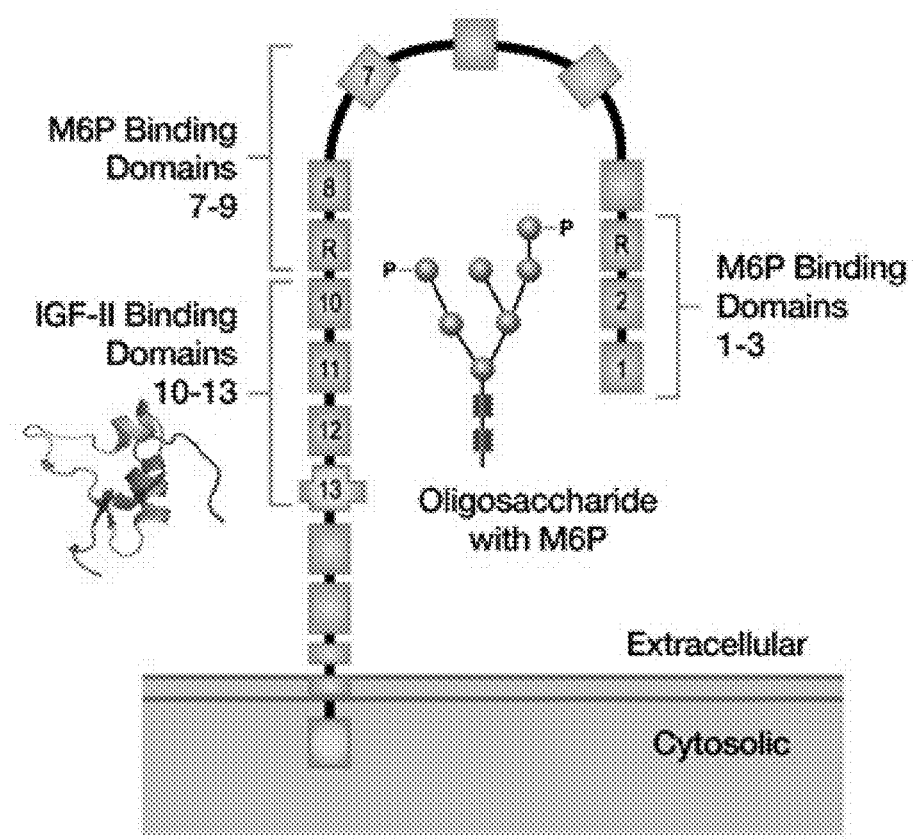
FIG. 2 shows structure of the CI-MPR including the different binding domains for the IGF2 and for mono- and bis-phosphorylated oligosaccharides.
Figure 3:
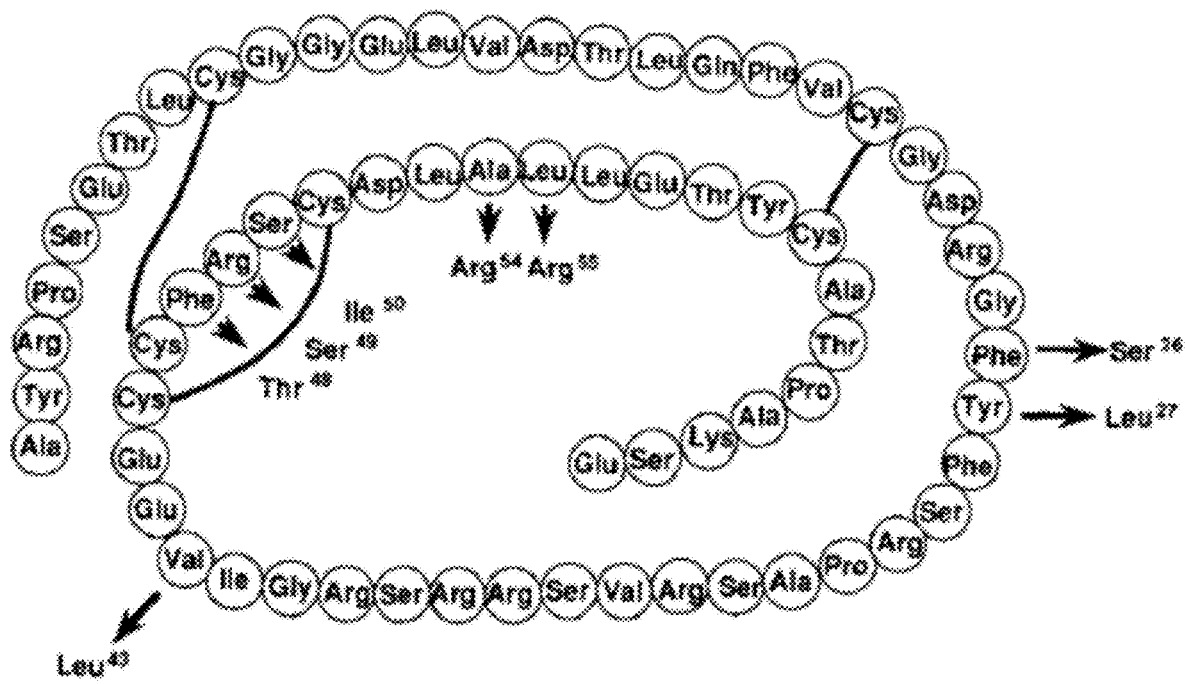
FIG. 3 shows the sequence and structure of the mature, human IGF2 peptide (SEQ ID NO: 1). Site specific amino acid substitutions (SEQ ID NOS 2-9) are proposed to influence binding of other receptors.

The CI-MPR captures M6P-containing lysosomal enzymes from circulation. The receptor has distinct binding domains for M6P and insulin-like growth factor (domains 1-3 and 7-9, see FIG. 2) and therefore is also known as the IGF2/Mannose-6-phosphate receptor or IGF2/CI-MPR. This receptor can be utilized for targeting M6P- or IGF2- or IGF2 variant-containing enzyme replacement therapeutics. Binding affinity of this receptor for these ligands including insulin-like growth factor is provided in Table 1. Notably, IGF2 peptide has a higher binding affinity for CI-MPR than mono- or bis-phosphorylated oligosaccharides.

TABLE 1

Ligands for CI-MPR

| Ligand | Binding Affinity (Apparent Kd; nM) |
| --- | --- |
| IGF2 | 0.03-0.2 |
| [Leu27]IGF2 | 0.05 |
| Bis-M6P | 2 |
| Beta-galactosidase | 20 |
| Pentamannose-M6P | 6,000 |
| Free M6P | 7,000 |

Therapeutic Fusion Proteins for Gene Therapy

Therapeutic fusion proteins produced from gene therapy vectors are provided herein. In some embodiments the fusion protein is secreted by cells transduced with the gene therapy vector encoding the fusion protein. In some embodiments, the transduced cells are within a tissue or organ (e.g., liver). Once secreted from a cell, the fusion protein is transported through a patient's vascular system and reaches the tissue of interest. In some embodiments, the therapeutic fusion protein is engineered to have improved secretion. In some embodiments, the fusion protein comprises a signal peptide for improving the secretion level as compared to the corresponding therapeutic protein or a fusion protein comprising the therapeutic protein but lacking a signal peptide.

The provided gene therapy vectors are, in some embodiments, engineered to address issues with gene therapy with regard to delivery of the therapeutic protein. For example, in some instances gene therapy may not achieve the intended treatment by merely generating a sufficient amount of a therapeutic protein in the body of the patient if an insufficient amount of the therapeutic protein is delivered into the cells in need of the therapeutic protein, due to, for example, physical and/or biological barriers that impede distribution of the therapeutic protein to the site where needed. As such, even if a gene therapy is capable of flooding blood or a tissue, to a point of saturation, with a high concentration of a therapeutic protein, the gene therapy may not be sufficiently therapeutic. Additionally, non-productive clearance pathways may remove the vast majority of the therapeutic protein. Even if the therapeutic protein is transported out of the vasculature to the interstitial space within the tissue (e.g., muscle fibers), adequate therapeutic effects are not assured. For effective treatment of lysosomal storage disorders, a therapeutically effective amount of the therapeutic protein must undergo cellular endocytosis and lysosomal delivery to result in a meaningful efficacy. The present disclosure addresses these issues by providing gene therapy vectors encoding fusion proteins comprising a peptide that enables endocytosis of the therapeutic protein into a target cell for treatment resulting in efficacious treatment. In some embodiments, the peptide that enables endocytosis is a peptide that binds the CI-MPR. In some embodiments, the peptide that binds the CI-MPR is a vIGF2 peptide.

Provided herein are gene therapy vectors encoding fusion proteins comprising a peptide that enables endocytosis the therapeutic protein into a target cell for treatment. In some embodiments, the gene therapy vectors encode fusion proteins comprising a therapeutic protein and a peptide that binds the CI-MPR. Such fusion proteins when expressed from a gene therapy vector target therapeutic proteins, such as enzyme replacement therapeutics, to the cells where they are needed, increase delivery into or cellular uptake by such cells and target the therapeutic protein to a subcellular location (e.g., a lysosome). In some embodiments, the peptide is an IGF2 peptide or variant thereof, which can target a therapeutic protein to the lysosome. Fusion proteins herein also, in some embodiments, further comprise a signal peptide that increases secretion, such as a BiP signal peptide or a Gaussia signal peptide. In some embodiments, fusion proteins comprise a linker sequence. In some embodiments, nucleic acids encoding fusion proteins herein, comprise internal ribosomal entry sequences.

Therapeutic proteins for gene therapy comprising a vIGF2 peptide are provided herein. Exemplary proteins are provided in Table 2 below.

TABLE 2

Amino Acid Sequences

| | | SEQ ID NO |
| --- | --- | --- |
| Natural hGAA | MGVRHPPCSHRLLAVCALVSLATAALLGHILLHDFLLVPRELSGSSPVLEE THPAHQQGASRPGPRDAQAHPGRPRAVPTQCDVPPNSRFDCAPDKAITQE QCEARGCCYIPAKQGLQGAQMGQPWCFFPPSYPSYKLENLSSSEMGYTAT LTRTTPTFFPKDILTLRLDVMMETENRLHFTIKDPANRRYEVPLETPHVSR APSPLYSVEFSEEPFGVIVRRQLDGRVLLNTTVAPLFFADQFLQLSTSLPSQ YITGLAEHLSPLMLSTSWTRITLWNRDLAPTPGANLYGSHPFYLALEDGGS AHGVFLLNSNAMDVVLQPSPALSWRSTGGILDVYIFLGPEPKSVVQQYLD VVGYPFMPPYWGLGFHLCRWGYSSTAITRQVVENMTRAHFPLDVQWND LDYMDSRRDFTFNKDGFRDFPPAMVQELHQGGRRYMMIVDPAISSSGPAGS YRPYDEGLRRGVFITNETGQPLIGKVWPGSTAFPDFTNPTALAWWEDMVA | 22 |

TABLE 2-continued

Amino Acid Sequences

| | | SEQ ID NO |
|---|---|---|
| | EFHDQVPFDGMWIDMNEPSNFIRGSEDGCPNNELENPPYVPGVVGGTLQA ATICASSHQFLSTHYNLHNLYGLTEAIASHRALVKARGTRPFVISRSTFAGH GRYAGHWTGDVWSSWEQLASSVPEILQFNLLGVPLVGADVCGFLGNTSE ELCVRWTQLGAFYPFMRNHNSLLSLPQEPYSFSEPAQQAMRKALTLRYAL LPHLYTLFHQAHVAGETVARPLFLEFPKDSSTWTVDHQLLWGEALLITPVL QAGKAEVTGYFPLGTWYDLQTVPVEALGSLPPPPAAPREPAIHSEGQWVT LPAPLDTINVHLRAGYIIPLQGPGLTTTESRQQPMALAVALTKGGEARGEL FWDDGESLEVLERGAYTQVIFLARNNTIVNELVRVTSEGAGLQLQKVTVL GVATAPQQVLSNGVPVSNFTYSPDTKVLDICVSLLMGEQFLVSWC | |
| Engineered hGAA (BiP-vIGF2-GAA) | MKLSLVAAMLLLLSAARASRTLCGGELVDTLQFVCGDRGFLFSRPASRVS RRSRGIVEECCFRSCDLALLETYCATPARSEGGGGSGGGGSRPGPRDAQAH PGRPRAVPTQCDVPPNSRFDCAPDKAITQEQCEARGCCYIPAKQGLQGAQ MGQPWCFFPPSYPSYKLENLSSSEMGYTATLTRTTPTFFPKDILTLRLDVM METENRLHFTIKDPANRRYEVPLETPHVHSRAPSPLYSVEFSEEPFGVIVRR QLDGRVLLNTTVAPLFFADQFLQLSTSLPSQYITGLAEHLSPLMLSTSWTRI TLWNRDLAPTPGANLYGSHPFYLALEDGGSAHGVFLLNSNAMDVVLQPS PALSWRSTGGILDVYIFLGPEPKSVVQQYLDVVGYPFMPPYWGLGFHLCR WGYSSTAITRQVVENMTRAHFPLDVQWNDLDYMDSRRDFTFNKDGFRDF PAMVQELHQGGRRYMMIVDPAISSSGPAGSYRPYDEGLRRGVFITNETGQ PLIGKVWPGSTAFPDFTNPTALAWWEDMVAEFHDQVPFDGMWIDMNEPS NFIRGSEDGCPNNELENPPYVPGVVGGTLQAATICASSHQFLSTHYNLHNL YGLTEAIASHRALVKARGTRPFVISRSTFAGHGRYAGHWTGDVWSSWEQ LASSVPEILQFNLLGVPLVGADVCGFLGNTSEELCVRWTQLGAFYPFMRN HNSLLSLPQEPYSFSEPAQQAMRKALTLRYALLPHLYTLFHQAHVAGETV ARPLFLEFPKDSSTWTVDHQLLWGEALLITPVLQAGKAEVTGYFPLGTWY DLQTVPVEALGSLPPPPAAPREPAIHSEGQWVTLPAPLDTINVHLRAGYIIP LQGPGLTTTESRQQPMALAVALTKGGEARGELFWDDGESLEVLERGAYT QVIFLARNNTIVNELVRVTSEGAGLQLQKVTVLGVATAPQQVLSNGVPVS NFTYSPDTKVLDICVSLLMGEQFLVSWC | 23 |
| hGAA Δ1-60 | SRPGPRDAQAHPGRPRAVPTQCDVPPNSRFDCAPDKAITQEQCEARGCCYI PAKQGLQGAQMGQPWCFFPPSYPSYKLENLSSSEMGYTATLTRTTPTFFPK DILTLRLDVMMETENRLHFTIKDPANRRYEVPLETPHVHSRAPSPLYSVEFS EEPFGVIVRRQLDGRVLLNTTVAPLFFADQFLQLSTSLPSQYITGLAEHLSP LMLSTSWTRITLWNRDLAPTPGANLYGSHPFYLALEDGGSAHGVFLLNSN AMDVVLQPSPALSWRSTGGILDVYIFLGPEPKSVVQQYLDVVGYPFMPPY WGLGFHLCRWGYSSTAITRQVVENMTRAHFPLDVQWNDLDYMDSRRDF TFNKDGFRDFPAMVQELHQGGRRYMMIVDPAISSSGPAGSYRPYDEGLRR GVFITNETGQPLIGKVWPGSTAFPDFTNPTALAWWEDMVAEFHDQVPFDG MWIDMNEPSNFIRGSEDGCPNNELENPPYVPGVVGGTLQAATICASSHQFL STHYNLHNLYGLTEAIASHRALVKARGTRPFVISRSTFAGHGRYAGHWTG DVWSSWEQLASSVPEILQFNLLGVPLVGADVCGFLGNTSEELCVRWTQLG AFYPFMRNHNSLLSLPQEPYSFSEPAQQAMRKALTLRYALLPHLYTLFHQ AHVAGETVARPLFLEFPKDSSTWTVDHQLLWGEALLITPVLQAGKAEVTG YFPLGTWYDLQTVPVEALGSLPPPPAAPREPAIHSEGQWVTLPAPLDTINV HLRAGYIIPLQGPGLTTTESRQQPMALAVALTKGGEARGELFWDDGESLE VLERGAYTQVIFLARNNTIVNELVRVTSEGAGLQLQKVTVLGVATAPQQV LSNGVPVSNFTYSPDTKVLDICVSLLMGEQFLVSWC | 46 |
| wt-PPT1 | MASPGCLWLLAVALLPWTCASRALQHLDPPAPLPLVIWHGMGDSCCNPL SMGAIKKMVEKKIPGIYVLSLEIGKTLMEDVENSFFLNVNSQVTTVCQALA KDPKLQQGYNAMGFSQGGQFLRAVAQRCPSPPMINLISVGGQHQGVFGLP RCPGESSHICDFIRKTLNAGAYSKVVQERLVQAEYWHDPIKEDVYRNHSIF LADINQERGINESYKKNLMALKKFVMVKFLNDSIVDPVDSEWFGFYRSGQ AKETIPLQETSLYTQDRLGLKEMDNAGQLVFLATEGDHLQLSEEWFYAHII PFLG | 24 |
| PPT1-2 (vIGF2-PPT1) | MASPGCLWLLAVALLPWTCASRALQHLSRTLCGGELVDTLQFVCGDRGF LFSRPASRVSRRSRGIVEECCFRSCDLALLETYCATPARSEGGGGSGGGGS RPRAVPTQDPPAPLPLVIWHGMGDSCCNPLSMGAIKKMVEKKIPGIYVLSL EIGKTLMEDVENSFFLNVNSQVTTVCQALAKDPKLQQGYNAMGFSQGGQ FLRAVAQRCPSPPMINLISVGGQHQGVFGLPRCPGESSHICDFIRKTLNAGA YSKVVQERLVQAEYWHDPIKEDVYRNHSIFLADINQERGINESYKKNLMA LKKFVMVKFLNDSIVDPVDSEWFGFYRSGQAKETIPLQETSLYTQDRLGLK EMDNAGQLVFLATEGDHLQLSEEWFYAHIIPFLG | 25 |
| PPT1-29 (BiP2aa-vIGF2-PPT1) | MKLSLVAAMLLLLWVALLLLSAARAASRTLCGGELVDTLQFVCGDRGF LFSRPASRVSRRSRGIVEECCFRSCDLALLETYCATPARSEGGGGSGGGGS RPRAVPTQDPPAPLPLVIWHGMGDSCCNPLSMGAIKKMVEKKIPGIYVLSL EIGKTLMEDVENSFFLNVNSQVTTVCQALAKDPKLQQGYNAMGFSQGGQ FLRAVAQRCPSPPMINLISVGGQHQGVFGLPRCPGESSHICDFIRKTLNAGA | 26 |

TABLE 2-continued

Amino Acid Sequences

| | SEQ ID NO |
|---|---|
| YSKVVQERLVQAEYWHDPIKEDVYRNHSIFLADINQERGINESYKKNLMA LKKFVMVKFLNDSIVDPVDSEWFGFYRSGQAKETIPLQETSLYTQDRLGLK EMDNAGQLVFLATEGDHLQLSEEWFYAHIIPFLG | |

Components of fusion proteins provided herein are further described below.

Peptides that Bind CI-MPR (e.g., vIGF2 Peptides)

Provided herein are peptides that bind CI-MPR. Fusion proteins comprising such peptides and a therapeutic protein, when expressed from a gene therapy vector, target the therapeutic protein to the cells where it is needed, increase cellular uptake by such cells and target the therapeutic protein to a subcellular location (e.g., a lysosome). In some embodiments, the peptide is fused to the N-terminus of the therapeutic peptide. In some embodiments, the peptide is fused to the C-terminus of the therapeutic protein. In some embodiments, the peptide is a vIGF2 peptide. Some vIGF2 peptides maintain high affinity binding to CI-MPR while their affinity for IGF1 receptor, insulin receptor, and IGF binding proteins (IGFBP) is decreased or eliminated. Thus, some variant IGF2 peptides are substantially more selective and have reduced safety risks compared to wt IGF2. vIGF2 peptides herein include those having the amino acid sequence of SEQ ID NO: 31. Variant IGF2 peptides further include those with variant amino acids at positions 6, 26, 27, 43, 48, 49, 50, 54, 55, or 65 compared to wt IGF2 (SEQ ID NO: 1). In some embodiments, the vIGF2 peptide has a sequence having one or more substitutions from the group consisting of E6R, F26S, Y27L, V43L, F48T, R49S, S50I, A54R, L55R, and K65R. In some embodiments, the vIGF2 peptide has a sequence having a substitution of E6R. In some embodiments, the vIGF2 peptide has a sequence having a substitution of F26S. In some embodiments, the vIGF2 peptide has a sequence having a substitution of Y27L. In some embodiments, the vIGF2 peptide has a sequence having a substitution of V43L. In some embodiments, the vIGF2 peptide has a sequence having a substitution of F48T. In some embodiments, the vIGF2 peptide has a sequence having a substitution of R49S. In some embodiments, the vIGF2 peptide has a sequence having a substitution of S50I. In some embodiments, the vIGF2 peptide has a sequence having a substitution of A54R. In some embodiments, the vIGF2 peptide has a sequence having a substitution of L55R. In some embodiments, the vIGF2 peptide has a sequence having a substitution of K65R. In some embodiments, the vIGF2 peptide has a sequence having a substitution of E6R, F26S, Y27L, V43L, F48T, R49S, S50I, A54R, and L55R. In some embodiments, the vIGF2 peptide has an N-terminal deletion. In some embodiments, the vIGF2 peptide has an N-terminal deletion of one amino acid. In some embodiments, the vIGF2 peptide has an N-terminal deletion of two amino acids. In some embodiments, the vIGF2 peptide has an N-terminal deletion of three amino acids. In some embodiments, the vIGF2 peptide has an N-terminal deletion of four amino acids. In some embodiments, the vIGF2 peptide has an N-terminal deletion of four amino acids and a substitution of E6R, Y27L, and K65R. In some embodiments, the vIGF2 peptide has an N-terminal deletion of four amino acids and a substitution of E6R and Y27L. In some embodiments, the vIGF2 peptide has an N-terminal deletion of five amino acids. In some embodiments, the vIGF2 peptide has an N-terminal deletion of six amino acids. In some embodiments, the vIGF2 peptide has an N-terminal deletion of seven amino acids. In some embodiments, the vIGF2 peptide has an N-terminal deletion of seven amino acids and a substitution of Y27L and K65R.

TABLE 3

IGF2 Amino Acid Sequences (variant residues are underlined)

| Peptide | Sequence | SEQ ID NO |
|---|---|---|
| Wildtype | AYRPSETLCGGELVDTLQFVCGDRGFYFSRPASR VSRRSRGIVEECCFRSCDLALLETYCATPAKSE | 1 |
| F26S | AYRPSETLCGGELVDTLQFVCGDRGSYFSRPASR VSRRSRGIVEECCFRSCDLALLETYCATPAKSE | 2 |
| Y27L | AYRPSETLCGGELVDTLQFVCGDRGFLFSRPASRV SRRSRGIVEECCFRSCDLALLETYCATPAKSE | 3 |
| V43L | AYRPSETLCGGELVDTLQFVCGDRGFYFSRPASR VSRRSRGILEECCFRSCDLALLETYCATPAKSE | 4 |
| F48T | AYRPSETLCGGELVDTLQFVCGDRGFYFSRPASR VSRRSRGIVEECCTRSCDLALLETYCATPAKSE | 5 |
| R49S | AYRPSETLCGGELVDTLQFVCGDRGFYFSRPASR VSRRSRGIVEECCFSSCDLALLETYCATPAKSE | 6 |
| S50I | AYRPSETLCGGELVDTLQFVCGDRGFYFSRPASR VSRRSRGIVEECCFRICDLALLETYCATPAKSE | 7 |
| A54R | AYRPSETLCGGELVDTLQFVCGDRGFYFSRPASR VSRRSRGIVEECCFRSCDLRLLETYCATPAKSE | 8 |
| L55R | AYRPSETLCGGELVDTLQFVCGDRGFYFSRPASR VSRRSRGIVEECCFRSCDLARLETYCATPAKSE | 9 |
| F26S, Y27L, V43L, F48T, R49S, S50I, A54R, L55R | AYRPSETLCGGELVDTLQFVCGDRGSLFSRPASRV SRRSRGILEECCTSICDLRRLETYCATPAKSE | 10 |
| Δ1-6, Y27L, K65R | TLCGGELVDTLQFVCGDRGFLFSRPASRVSRRSRG IVEECCFRSCDLALLETYCATPARSE | 11 |
| Δ1-7, Y27L, K65R | LCGGELVDTLQFVCGDRGFLFSRPASRVSRRSRGI VEECCFRSCDLALLETYCATPARSE | 30 |
| Δ1-4, E6R, Y27L, K65R | SRTLCGGELVDTLQFVCGDRGFLFSRPASRVSRRS RGIVEECCFRSCDLALLETYCATPARSE | 31 |
| Δ1-4, E6R, Y27L | SRTLCGGELVDTLQFVCGDRGFLFSRPASRVSRRS RGIVEECCFRSCDLALLETYCATPAKSE | 34 |
| E6R | AYRPSRTLCGGELVDTLQFVCGDRGFYFSRPASR VSRRSRGIVEECCFRSCDLALLETYCATPAKSE | 35 |

TABLE 4

IGF2 DNA Coding Sequences

| Peptide | DNA Sequence | SEQ ID NO |
|---|---|---|
| Mature WT IGF2 | GCTTACCGCCCCAGTGAGACCCTGTGCGGCGGG GAGCTGGTGGACACCCTCCAGTTCGTCTGTGGG GACCGCGGCTTCTACTTCAGCAGGCCCGCAAGC CGTGTGAGCCGTCGCAGCCGTGGCATCGTTGAG GAGTGCTGTTTCCGCAGCTGTGACCTGGCCCTC CTGGAGACGTACTGTGCTACCCCCGCCAAGTCC GAG | 48 |
| vIGF2 Δ1-4, E6R, Y27L, K65R | TCTAGAACACTGTGCGGAGGGGAGCTTGTAGAC ACTCTTCAGTTCGTGTGTGGAGATCGCGGGTTC CTCTTCTCTCGCCCCGCTTCCAGAGTTTCACGGA GGTCTAGGGGTATAGTAGAGGAGTGTTGTTTCA GGTCCTGTGACTTGGCGCTCCTCGAGACCTATT GCGCGACGCCAGCCAGGTCCGAA | 36 |

Internal Ribosomal Entry Sequences

Provided herein are gene therapy constructs useful in treating a disorder further comprising an internal ribosome entry sequence (IRES) for increasing gene expression by bypassing the bottleneck of translation initiation. Suitable internal ribosomal entry sequences for optimizing expression for gene therapy include but are not limited to a cricket paralysis virus (CrPV) IRES, a picornavirus IRES, an Aphthovirus IRES, a Kaposi's sarcoma-associated herpesvirus IRES, a Hepatitis A IRES, a Hepatitis C IRES, a Pestivirus IRES, a Cripavirus IRES, a Rhopalosiphum padi virus IRES, a Merek's disease virus IRES, and other suitable IRES sequences. In some embodiments, the gene therapy construct comprises a CrPV IRES. In some embodiments, the CrPV IRES has a nucleic acid sequence of AAAAATGTGATCTTGCTTGTAAATACAATTTTGAGAGGTTAATAAATTACAAGTAGTGCTAT TTTTGTATTTAGGTTAGCTATTTAGCTTTACGTTCCAGGATGCCTAGTGGCAGCCCCACAATA TCCAGGAAGCCCTCTCTGCGGTTTTTCAGATTAGGTAGTCGAAAAACCTAAGAAATTTACCT GCT (SEQ ID NO: 12). In some embodiments, the CrPV IRES sequence is at least 90%, at least 91%, at least 92%, at least 93%, at least 94%, at least 95%, at least 96%, at least 97%, at least 98%, or at least 99% identical to SEQ ID NO: 12.

Signal Peptides

Gene therapy constructs provided herein, in some embodiments, further comprise a signal peptide, which improves secretion of the therapeutic protein from the cell transduced with the gene therapy construct. The signal peptide in some embodiments improves protein processing of therapeutic proteins, and facilitates translocation of the nascent polypeptide-ribosome complex to the ER and ensuring proper co-translational and post-translational modifications. In some embodiments, the signal peptide is located (i) in an upstream position of the signal translation initiation sequence, (ii) in between the translation initiation sequence and the therapeutic protein, or (iii) a downstream position of the therapeutic protein. Signal peptides useful in gene therapy constructs include but are not limited to binding immunoglobulin protein (BiP) signal peptide from the family of HSP70 proteins (e.g., HSPA5, heat shock protein family A member 5) and Gaussia signal peptides, and variants thereof. These signal peptides have ultrahigh affinity to the signal recognition particle. Examples of BiP and Gaussia amino acid sequences are provided in Table 5 below. In some embodiments, the signal peptide has an amino acid sequence that is at least 90% identical to a sequence selected from the group consisting of SEQ ID Nos: 13-17. In some embodiments, the signal peptide differs from a sequence selected from the group consisting of SEQ ID Nos: 13-17 by 5 or fewer, 4 or fewer, 3 or fewer, 2 or fewer, or 1 amino acid.

TABLE 5

Signal Peptide Sequences

| Signal Peptide | Amino Acid Sequence | SEQ ID NO: |
|---|---|---|
| Native human BiP | MKLSLVAAMLLLLSAARA | 13 |
| Modified BiP-1 | MKLSLVAAMLLLLSLVAAMLLLLSAARA | 14 |
| Modified BiP-2 | MKLSLVAAMLLLWVALLLLSAARA | 15 |
| Modified BiP-3 | MKLSLVAAMLLLLSLVALLLLSAARA | 16 |
| Modified BiP-4 | MKLSLVAAMLLLLALVALLLLSAARA | 17 |
| Gaussia | MGVKVLFALICIAVAEA | 32 |

Figure 20:
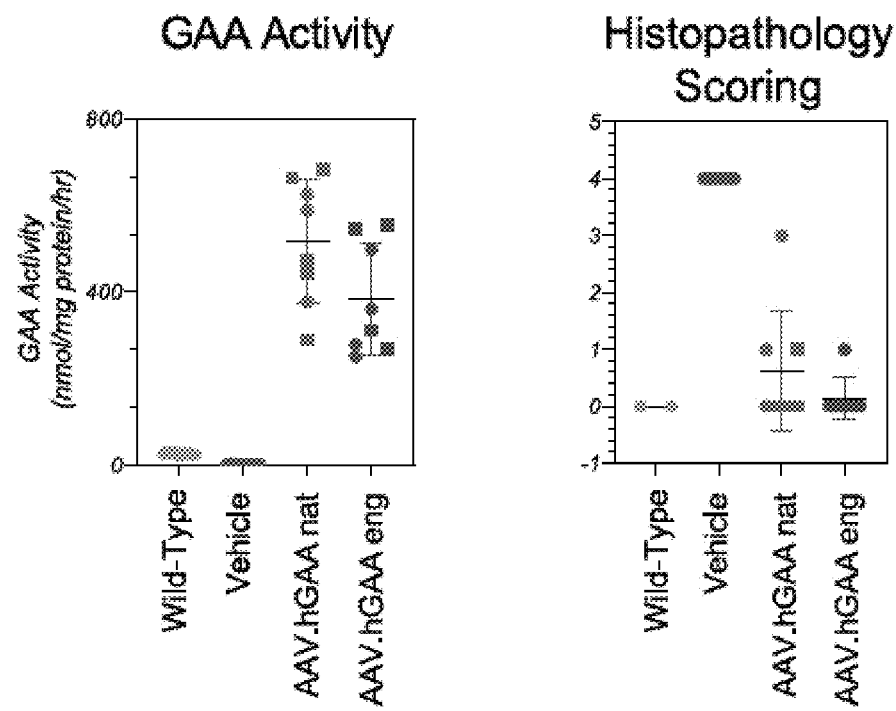
FIG. 20 shows GAA activity, and quad glycogen histopathology score for tibialis antierior of untreated wild type ("Normal") mice or GAA knockout mice treated with gene therapy vectors or vehicle as indicated.

The BiP signal peptide-signal recognition particle (SRP) interaction facilitates translocation to the ER. This interaction is illustrated in FIG. 20.

The Gaussia signal peptide is derived from the luciferase from Gaussia princeps and directs increased protein synthesis and secretion of therapeutic proteins fused to this signal peptide. In some embodiments, the Gaussia signal peptide has an amino acid sequence that is at least 90% identical to SEQ ID NO: 32. In some embodiments, the signal peptide differs from SEQ ID NO: 32 by 5 or fewer, 4 or fewer, 3 or fewer, 2 or fewer, or 1 amino acid.

Linker

Gene therapy constructs provided herein, in some embodiments, comprise a linker between the targeting peptide and the therapeutic protein. Such linkers, in some embodiments, maintain correct spacing and mitigate steric clash between the vIGF2 peptide and the therapeutic protein. Linkers, in some embodiments, comprise repeated glycine residues, repeated glycine-serine residues, and combinations thereof. In some embodiments, the linker consists of 5-20 amino acids, 5-15 amino acids, 5-10 amino acids, 8-12 amino acids, or about 5, 6, 7, 8, 9, 10, 11, 12 or 13 amino acids. Suitable linkers for gene therapy constructs herein include but are not limited to those provided in Table 6 below.

TABLE 6

Linker Sequences

| Sequence | SEQ ID NO: |
|---|---|
| GGGGSGGGG | 18 |
| GGGGS | 19 |
| GGGSGGGGS | 20 |
| GGGGSGGGS | 21 |
| GGSGSGSTS | 33 |
| GGGGSGGGGS | 37 |

Translation Initiation Sequence

Gene therapy constructs provided herein comprise a nucleic acid having a translation initiation sequence, such as a Kozak sequence which aids in initiation of translation of the mRNA. Kozak sequences contemplated herein have a consensus sequence of (gcc)RccATGG (SEQ ID NO: 27) where a lowercase letter denotes the most common base at the position and the base varies, uppercase letters indicate highly conserved bases that only vary rarely change. R indicates that a purine (adenine or guanine) is always observed at that position. The sequence in parentheses (gcc) is of uncertain significance. In some embodiments, the Kozak sequence comprises the sequence $AX_1X_2ATGA$ (SEQ ID NO: 28), wherein each of $X_1$ and $X_2$ is any nucleotide. In some embodiments, $X_1$ comprises A. In some embodiments, $X_2$ comprises G. In some embodiments, the Kozak sequence comprises a nucleic acid sequence at least 85% identical to AAGATGA (SEQ ID NO: 29). In some embodiments, the Kozak sequence differs from the sequence of AAGATGA (SEQ ID NO: 29) by one or two nucleotides. In some embodiments, Kozak sequences provided herein have a sequence of AAGATGA (SEQ ID NO: 29). In some embodiments the Kozak sequence comprises a nucleic acid sequence at least 85% identical to GCAAGATG (SEQ ID NO: 44). In some embodiments the Kozak sequence differs from the sequence of GCAAGATG (SEQ ID NO: 44) by one or two nucleotides. In some embodiments, the Kozak sequence comprises GCAAGATG (SEQ ID NO: 44). In some embodiments the Kozak sequence comprises a nucleic acid sequence at least 85% identical to CACCATG (SEQ ID NO: 47). In some embodiments the Kozak sequence differs from the sequence of CACCATG (SEQ ID NO: 47) by one or two nucleotides. In some embodiments, the Kozak sequence comprises CACCATG (SEQ ID NO: 47).

Therapeutic Protein

Gene therapy constructs provided herein comprise a nucleic acid encoding a therapeutic protein for treating a genetic disorder due to a genetic defect in an individual resulting in an absent or defective protein. The therapeutic protein expressed from the gene therapy construct replaces the absent or defective protein. Therapeutic proteins, therefore, are chosen based on the genetic defect in need of treatment in an individual. In some embodiments, the therapeutic protein is a structural protein. In some embodiments, the therapeutic protein is an enzyme. In some embodiments, the therapeutic protein is a regulatory protein. In some embodiments, the therapeutic protein is a receptor. In some embodiments, the therapeutic protein is a peptide hormone. In some embodiments, the therapeutic protein is a cytokine or a chemokine.

In some embodiments, gene therapy constructs herein encode an enzyme, such as an enzyme having a genetic defect in an individual with a lysosomal storage disorder. In some embodiments, gene therapy constructs encode a lysosomal enzyme, such as a glycosidase, a protease, or a sulfatase. In some embodiments, enzymes encoded by gene therapy constructs provided herein include but are not limited to α-D-mannosidase; N-aspartyl-β-glucosaminidase; β-galactosidase; ceramidase; fucosidase; galactocerebrosidase; arylsulfatase A; N-acetylglucosamine-1-phosphotransferase; iduronate sulfatase; N-acetylglucosaminidase; acetyl-CoA:α-glucosaminide acetyltransferase; N-acetylglucosamine 6-sulfatase; β-glucuronidase; hyaluronidase; sialidase; sulfatase; sphingomyelinase; acid β-mannosidase; cathepsin K; 3-hexosaminidase A; β-hexosaminidase B; α-N-acetylgalactosaminidase; sialin; hexosaminidase A; beta-glucosidase; α-iduronidase; α-galactosidase A; β-glucocerebrosidase; lysosomal acid lipase; glycosaminoglycan alpha-L-iduronohydrolase; iduronate-2-sulfatase; N-acetylgalactosamine-6-sulfatase; glycosaminoglycan N-acetylgalactosamine 4-sulfatase; alpha-glucosidase; heparan sulfamidase; gp-91 subunit of NADPH oxidase; adenosine deaminase; cyclin dependent kinase like 5; and palmitoyl protein thioesterase 1. In some embodiments, enzymes encoded by gene therapy constructs provided herein comprise alpha-glucosidase. In some embodiments, the therapeutic protein is associated with a genetic disorder selected from the group consisting of CDKL5 deficiency disorder, cystic fibrosis, alpha- and beta-thalassemias, sickle cell anemia, Marfan syndrome, fragile X syndrome, Huntington's disease, hemochromatosis, Congenital Deafness (nonsyndromic), Tay-Sachs, Familial hypercholesterolemia, Duchenne muscular dystrophy, Stargardt disease, Usher syndrome, choroideremia, achromatopsia, X-linked retinoschisis, hemophilia, Wiskott-Aldrich syndrome, X-linked chronic granulomatous disease, aromatic L-amino acid decarboxylase deficiency, recessive dystrophic epidermolysis bullosa, alpha 1 antitrypsin deficiency, Hutchinson-Gilford progeria syndrome (HGPS), Noonan syndrome, X-linked severe combined immunodeficiency (X-SCID). In some embodiments, the therapeutic protein is selected from the group consisting of CDKL5, Connexin 26, hexosaminidase A, LDL receptor, Dystrophin, CFTR, beta-globulin, HFE, Huntington, ABCA4, myosin VIIA (MYO7A), Rab escort protein-1 (REP1), cyclic nucleotide gated channel beta 3 (CNGB3), retinoschisin 1 (RS1), hemoglobin subunit beta (HBB), Factor IX, WAS, cytochrome B-245 beta chain, dopa decarboxylase (DDC), collagen type VII alpha 1 chain (COL7A1), serpin family A member 1 (SERPINA1), LMNA, PTPN11, SOS1, RAF1, KRAS, and IL2 receptor γ gene.

Gene Therapy Vector Examples

Gene Therapy Vectors and Compositions

Provided herein are gene therapy vectors in which a nucleic acid, such as a DNA, encoding a therapeutic fusion protein, such as a vIGF2 fusion, optionally having a signal peptide. The gene therapy vector optionally comprises an internal ribosomal entry sequence. Vectors derived from retroviruses such as the lentivirus are suitable tools to achieve long-term gene transfer since they allow long-term, stable integration of a transgene and its propagation in daughter cells. Lentiviral and adeno-associated viral vectors have the added advantage over vectors derived from oncoretroviruses such as murine leukemia viruses in that they are capable of transducing non-proliferating cells, such as hepatocytes and neurons. They also have the added advantage of low immunogenicity.

Exemplary gene therapy vectors herein encode therapeutic proteins and therapeutic fusion proteins comprising a vIGF2 peptide. Nucleic acids encoding exemplary fusion protein amino acid sequences are provided in Table 7 below.

TABLE 7

DNA Sequences

| Construct | DNA Sequence | SEQ ID NO |
|---|---|---|
| Kozak-hGAA (Natural GAA) | GCAAGATGGGAGTGAGGCACCCGCCCTGCTCCCACCGGCTCCTGGCCG<br>TCTGCGCCCTCGTGTCCTTGGCAACCGCTGCACTCCTGGGGCACATCCT<br>ACTCCATGATTTCCTGCTGGTTCCCCGAGAGCTGAGTGGCTCCTCCCCA<br>GTCCTGGAGGAGACTCACCCAGCTCACCAGCAGGGAGCCAGTAGACCA<br>GGGCCCCGGGATGCCCAGGCACACCCCGGCCGTCCCAGAGCAGTGCCC<br>ACACAGTGCGACGTCCCCCCCAACAGCCGCTTCGATTGCGCCCCTGAC<br>AAGGCCATCACCCAGGAACAGTGCGAGGCCCGCGGCTGTTGCTACATC<br>CCTGCAAAGCAGGGGCTGCAGGGAGCCCAGATGGGGCAGCCCTGGTGC<br>TTCTTCCCACCCAGCTACCCCAGCTACAAGCTGGAGAACCTGAGCTCCT<br>CTGAAATGGGCTACACGGCCACCCTGACCCGTACCACCCCCACCTTCTT<br>CCCCAAGGACATCCTGACCCTGCGGCTGGACGTGATGATGGAGACTGA<br>GAACCGCCTCCACTTCACGATCAAAGATCCAGCTAACAGGCGCTACGA<br>GGTGCCCTTGGAGACCCCGCATGTCCACAGCCGGGCACCGTCCCCACT<br>CTACAGCGTGGAGTTCTCCGAGGAGCCCTTCGGGGTGATCGTGCGCCG<br>GCAGCTGGACGGCCGCGTGCTGCTGAACACGACGGTGGCGCCCCTGTT<br>CTTTGCGGACCAGTTCCTTCAGCTGTCCACCTCGCTGCCCTCGCAGTAT<br>ATCACAGGCCTCGCCGAGCACCTCAGTCCCCTGATGCTCAGCACCAGCT<br>GGACCAGGATCACCCTGTGGAACCGGGACCTTGCGCCCACGCCCGGTG<br>CGAACCTCTACGGGTCTCACCCTTTCTACCTGGCGCTGGAGGACGGCGG<br>GTCGGCACACGGGGTGTTCCTGCTAAACAGCAATGCCATGGATGTGGT<br>CCTGCAGCCGAGCCCTGCCCTTAGCTGGAGGTCGACAGGTGGGATCCT<br>GGATGTCTACATCTTCCTGGGCCCAGAGCCCAAGAGCGTGGTGCAGCA<br>GTACCTGGACGTTGTGGGATACCCGTTCATGCCGCCATACTGGGGCCTG<br>GGCTTCCACCTGTGCCGCTGGGGCTACTCCTCCACCGCTATCACCCGCC<br>AGGTGGTGGAGAACATGACCAGGGCCCACTTCCCCCTGGACGTCCAGT<br>GGAACGACCTGGACTACATGGACTCCCGGAGGGACTTCACGTTCAACA<br>AGGATGGCTTCCGGGACTTCCCGGCCATGGTGCAGGAGCTGCACCAGG<br>GCGGCCGGCGCTACATGATGATCGTGGATCCTGCCATCAGCAGCTCGG<br>GCCCTGCCGGGAGCTACAGGCCCTACGACGAGGGTCTGCGGAGGGGG<br>TTTTCATCACCAACGAGACCGGCCAGCCGCTGATTGGGAAGGTATGGC<br>CCGGGTCCACTGCCTTCCCCGACTTCACCAACCCCACAGCCCTGGCCTG<br>GTGGGAGGACATGGTGGCTGAGTTCCATGACCAGGTGCCCTTCGACGG<br>CATGTGGATTGACATGAACGAGCCTTCCAACTTCATCAGGGGCTCTGA<br>GGACGGCTGCCCCAACAATGAGCTGGAGAACCCACCCTACGTGCCTGG<br>GGTGGTTGGGGGGACCCTCCAGGCGGCCACCATCTGTGCCTCCAGCCA<br>CCAGTTTCTCTCCACACACTACAACCTGCACAACCTCTACGGCCTGACC<br>GAAGCCATCGCCTCCCACAGGGCGCTGGTGAAGGCTCGGGGGACACGC<br>CCATTTGTGATCTCCCGCTCGACCTTTGCTGGCCACGGCCGATACGCCG<br>GCCACTGGACGGGGACGTGTGGAGCTCCTGGGAGCAGCTCGCCTCCT<br>CCGTGCCAGAAATCCTGCAGTTTAACCTGCTGGGGGTGCCTCTGGTCGG<br>GGCCGACGTCTGCGGCTTCCTGGGCAACACCTCAGAGGAGCTGTGTGT<br>GCGCTGGACCCAGCTGGGGGCTTCTACCCCTTCATGCGGAACCACAA<br>CAGCCTGCTCAGTCTGCCCCAGGAGCCGTACAGCTTCAGCGAGCCGGC<br>CCAGCAGGCCATGAGGAAGGCCCTCACCCTGCGCTACGCACTCCTCCC<br>CCACCTCTACACACTGTTCCACCAGGCCCACGTCGCGGGGAGACCGT<br>GGCCCGGCCCCTCTTCCTGGAGTTCCCCAAGGACTCTAGCACCTGGACT<br>GTGGACCACCAGCTCCTGTGGGGGGAGGCCCTGCTCATCACCCCAGTG<br>CTCCAGGCCGGGAAGGCCGAAGTGACTGGCTACTTCCCCTTGGGCACA<br>TGGTACGACCTGCAGACGGTGCCAGTAGAGGCCCTTGGCAGCCTCCCA<br>CCCCCACCTGCAGCTCCCCGTGAGCCAGCCATCCACAGCGAGGGGCAG<br>TGGGTGACGCTGCCGGCCCCCTGGACACCATCAACGTCCACCTCCGG<br>GCTGGGTACATCATCCCCTGCAGGGCCCTGGCCTCACAACCACAGAG<br>TCCCGCCAGCAGCCCATGGCCTGGCTGTGGCCCTGACCAAGGGTGGG<br>GAGGCCCGAGGGGAGCTTTTCTGGGACGATGGAGAGAGCCTGGAAGTG<br>CTGGAGCGAGGGGCCTACACACAGGTCATCTTCCTGGCCAGGAATAAC<br>ACGATCGTGAATGAGCTGGTACGTGTGACCAGTGAGGGAGCTGGCCTG<br>CAGCTGCAGAAGGTGACTGTCCTGGGCGTGGCCACGGCGCCCCAGCAG<br>GTCCTCTCCAACGGTGTCCCTGTCTCCAACTTCACCTACAGCCCCGACA<br>CCAAGGTCCTGGACATCTGTGTCTCGCTGTTGATGGGAGAGCAGTTTCT<br>CGTCAGCTGGTGTTAG | 45 |
| Kozak BiP-vIGF2-GAA ("Engineered hGAA") | GCAAGATGAAGCTCTCCCTGGTGGCCGCGATGCTGCTGCTGCTCAGCG<br>CGGCGCGGGCCTCTAGAACACTGTGCGGAGGGGAGCTTGTAGACACTC<br>TTCAGTTCGTGTGTGGAGATCGCGGGTTCCTCTTCTCTCGCCCCGCTTCC<br>AGAGTTTCACGGAGGTCTAGGGGTATAGTAGAGGAGTGTTGTTTCAGG<br>TCCTGTGACTTGGCGCTCCTCGAGACCTATTGCGCGACGCCAGCCAGGT<br>CCGAAGGGGCGGTGGCTCAGGTGGTGGAGGTAGCAGACCAGGGCC<br>CGGGATGCCCAGGCACACCCCGGCCGTCCCAGAGCAGTGCCCACACAG<br>TGCGACGTCCCCCCCAACAGCCGCTTCGATTGCGCCCCTGACAAGGCC<br>ATCACCCAGGAACAGTGCGAGGCCCGCGGCTGTTGCTACATCCCTGCA<br>AAGCAGGGGCTGCAGGGAGCCCAGATGGGGCAGCCCTGGTGCTTCTTC<br>CCACCCAGCTACCCCAGCTACAAGCTGGAGAACCTGAGCTCCTCTGAA<br>ATGGGCTACACGGCCACCCTGACCCGTACCACCCCCACCTTCTTCCCCA<br>AGGACATCCTGACCCTGCGGCTGGACGTGATGATGGAGACTGAGAACC<br>GCCTCCACTTCACGATCAAAGATCCAGCTAACAGGCGCTACGAGGTGC | 38 |

TABLE 7-continued

DNA Sequences

| Construct | DNA Sequence | SEQ ID NO |
|---|---|---|
| | CCTTGGAGACCCCGCATGTCCACAGCCGGGCACCGTCCCCACTCTACA<br>GCGTGGAGTTCTCCGAGGAGCCCTTCGGGGTGATCGTGCGCCGGCAGC<br>TGGACGGCCGCGTGCTGCTGAACACGACGGTGGCGCCCCTGTTCTTTGC<br>GGACCAGTTCCTTCAGCTGTCCACCTCGCTGCCCTCGCAGTATATCACN<br>GGCCTCGCCGAGCACCTCAGTCCCCTGATGCTCAGCACCAGCTGGACC<br>AGGATCACCCTGTGGAACCGGGACCTTGCGCCCACGCCCGGTGCGAAC<br>CTCTACGGGTCTCACCCTTTCTACCTGGCGCTGGAGGACGGCGGGTCGG<br>CACACGGGGTGTTCCTGCTAAACAGCAATGCCATGGATGTGGTCCTGC<br>AGCCGAGCCCTGCCCTTAGCTGGAGGTCGACAGGTGGGATCCTGGATG<br>TCTACATCTTCCTGGGCCCAGAGCCCAAGAGCGTGGTGCAGCAGTACC<br>TGGACGTTGTGGGATACCCGTTCATGCCGCCATACTGGGGCCTGGGCTT<br>CCACCTGTGCCGCTGGGGCTACTCCTCCACCGCTATCACCCGCCAGGTG<br>GTGGAGAACATGACCAGGGCCCACTTCCCCCTGGACGTCCAGTGGAAC<br>GACCTGGACTACATGGACTCCCGGAGGGACTTCACGTTCAACAAGGAT<br>GGCTTCCGGGACTTCCCGGCCATGGTGCAGGAGCTGCACCAGGGCGGC<br>CGGCGCTACATGATGATCGTGGATCCTGCCATCAGCAGCTCGGGCCCT<br>GCCGGGAGCTACAGGCCCTACGACGAGGGTCTGCGGAGGGGGGTTTTC<br>ATCACCAACGAGACCGGCCAGCCGCTGATTGGGAAGGTATGCCCCGGG<br>TCCACTGCCTTCCCCGACTTCACCAACCCCACAGCCCTGGCCTGGTGGG<br>AGGACATGGTGGCTGAGTTCCATGACCAGGTGCCCTTCGACGGCATGT<br>GGATTGACATGAACGAGCCTTCCAACTTCATCAGGGGCTCTGAGGACG<br>GCTGCCCCAACAATGAGCTGGAGAACCCACCCTACGTGCCTGGGGTGG<br>TTGGGGGGACCCTCCAGGCGGCCACCATCTGTGCCTCCAGCCACCAGTT<br>TCTCTCCACACACTACAACCTGCACAACCTCTACGGCCTGACCGAAGCC<br>ATCGCCTCCCACAGGGCGCTGGTGAAGGCTCGGGGGACACGCCCATTT<br>GTGATCTCCCGCTCGACCTTTGCTGGCCACGGCCGATACGCCGGCCACT<br>GGACGGGGGACGTGTGGAGCTCCTGGGAGCAGCTCGCCTCCTCCGTGC<br>CAGAAATCCTGCAGTTTAACCTGCTGGGGGTGCCTCTGGTCGGGGCCG<br>ACGTCTGCGGCTTCCTGGGCAACACCTCAGAGGAGCTGTGTGTGCGCT<br>GGACCCAGCTGGGGGCCTTCTACCCCTTCATGCGGAACCACAACAGCC<br>TGCTCAGTCTGCCCCAGGAGCCGTACAGCTTCAGCGAGCCGGCCCAGC<br>AGGCCATGAGGAAGGCCCTCACCCTGCGCTACGCACTCCTCCCCCACCT<br>CTACACACTGTTCCACCAGGCCCACGTCGCGGGGGAGACCGTGGCCCG<br>GCCCCTCTTCCTGGAGTTCCCCAAGGACTCTAGCACCTGGACTGTGGAC<br>CACCAGCTCCTGTGGGGGGAGGCCCTGCTCATCACCCCAGTGCTCCAG<br>GCCGGGAAGGCCGAAGTGACTGGCTACTTCCCCTTGGGCACATGGTAC<br>GACCTGCAGACGGTGCCAGTAGAGGCCCTTGGCAGCCTCCCACCCCCA<br>CCTGCAGCTCCCCGTGAGCCAGCCATCCACAGCGAGGGGCAGTGGGTG<br>ACGCTGCCGGCCCCCTGGACACCATCAACGTCCACCTCCGGGCTGGG<br>TACATCATCCCCCTGCAGGGCCCTGGCCTCACAACCACAGAGTCCCGCC<br>AGCAGCCCATGGCCCTGGCTGTGGCCCTGACCAAGGGTGGGGAGGCCC<br>GAGGGGAGCTGTTCTGGGACGATGGAGAGAGCCTGGAAGTGCTGGAG<br>CGAGGGGCCTACACACAGGTCATCTTCCTGGCCAGGAATAACACGATC<br>GTGAATGAGCTGGTACGTGTGACCAGTGAGGGAGCTGGCCTGCAGCTG<br>CAGAAGGTGACTGTCCTGGGCGTGGCCACGGCGCCCCAGCAGGTCCTC<br>TCCAACGGTGTCCCTGTCTCCAACTTCACCTACAGCCCCGACACCAAGG<br>TCCTGGACATCTGTGTCTCGCTGTTGATGGGAGAGCAGTTTCTCGTCAG<br>CTGGTGTTAG | |
| Cricket<br>Paralysis<br>Virus IRES<br>(underlined)-<br>BiP-vIGF2-<br>GAA | AAAAATGTGATCTTGCTTGTAAATACAATTTTGAGAGGTTAATAAATTACAAGT<br>AGTGCTATTTTTGTATTTAGGTTAGCTATTTAGCTTTACGTTCCAGGATGCCTA<br>GTGGCAGCCCCACAATATCCAGGAAGCCCTCTCTGCGGTTTTTCAGATTAGG<br>TAGTCGAAAAACCTAAGAAATTTACCTGCTATGAAGCTCTCCCTGTGGCC<br>GCGATGCTGCTGCTGCAGCGCGGCGCGGGCCTCTAGAACACTGTGC<br>GGAGGGGAGCTTGTAGACACTCTTCAGTTCGTGTGTGGAGATCGCGGG<br>TTCCTCTTCTCTCGCCCCGCTTCCAGAGTTTCACGGAGGTCTAGGGGTA<br>TAGTAGAGGAGTGTTGTTTCAGGTCCTGTGACTTGGCGCTCCTCGAGAC<br>CTATTGCGCGACGCCAGCCAGGTCCGAAGGGGGCGGTGGCTCAGGTGG<br>TGGAGGTAGCAGACCAGGGCCCCGGGATGCCCAGGCACACCCCGGCCG<br>TCCCAGAGCAGTGCCCACACAGTGCGACGTCCCCCCCAACAGCCGCTT<br>CGATTGCGCCCCTGACAAGGCCATCACCCAGGAACAGTGCGAGGC*CCG<br>CGG*CTGTTGCTACATCCCTGCAAAGCAGGGGCTGCAGGGAGCCCAGAT<br>GGGGCAGCCCTGGTGCTTCTTCCCACCCAGCTACCCCAGCTACAAGCTG<br>GAGAACCTGAGCTCCTCTGAAATGGGCTACACGGCCACCCTGACCCGT<br>ACCACCCCCACCTTCTTCCCCAAGGACATCCTGACCCTGCGGCTGGACG<br>TGATGATGGAGACTGAGAACCGCCTCACTTCACGATCAAAGATCCAG<br>CTAACAGGCGCTACGAGGTGCCCTTGGAGACCCCGCATGTCCACAGCC<br>GGGCACCGTCCCCACTCTACAGCGTGGAGTTCTCCGAGGAGCCCTTCG<br>GGGTGATCGTGCGCCGGCAGCTGGACGGCCGCGTGCTGCTGAACACGA<br>CGGTGGCGCCCCTGTTCTTTGCGGACCAGTTCCTTCAGCTGTCCACCTC<br>GCTGCCCTCGCAGTATATCACAGGCCTCGCCGAGCACCTCAGTCCCCTG<br>ATGCTCAGCACCAGCTGGACCAGGATCACCCTGTGGAACGGGACCTT<br>GCGCCCACGCCCGGTGCGAACCTCTACGGGTCTCACCCTTTCTACCTGG<br>CGCTGGAGGACGGCGGGTCGGCACACGGGGTGTTCCTGCTAAACAGCA<br>ATGCCATGGATGTGGTCCTGCAGCCGAGCCCTGCCCTTAGCTGGAGGTC | 39 |

TABLE 7-continued

DNA Sequences

| Construct | DNA Sequence | SEQ ID NO |
|---|---|---|
| | GACAGGTGGGATCCTGGATGTCTACATCTTCCTGGGCCCAGAGCCCAA<br>GAGCGTGGTGCAGCAGTACCTGGACGTTGTGGGATACCCGTTCATGCC<br>GCCATACTGGGGCCTGGGCTTCCACCTGTGCCGCTGGGGCTACTCCTCC<br>ACCGCTATCACCCGCCAGGTGGTGGAGAACATGACCAGGGCCCACTTC<br>CCCCTGGACGTCCAGTGGAACGACCTGGACTACATGGACTCCCGGAGG<br>GACTTCACGTTCAACAAGGATGGCTTCCGGGACTTCCCGGCCATGGTGC<br>AGGAGCTGCACCAGGGCGGCCGGCGCTACATGATGATCGTGGATCCTG<br>CCATCAGCAGCTCGGGCCCTGCCGGGAGCTACAGGCCCTACGACGAGG<br>GTCTGCGGAGGGGGGTTTTCATCACCAACGAGACCGGCCAGCCGCTGA<br>TTGGGAAGGTATGGCCCGGGTCCACTGCCTTCCCCGACTTCACCAACCC<br>CACAGCCCTGGCCTGGTGGGAGGACATGGTGGCTGAGTTCCATGACCA<br>GGTGCCCTTCGACGGCATGTGGATTGACATGAACGAGCCTTCCAACTTC<br>ATCAGGGGCTCTGAGGACGGCTGCCCCAACAATGAGCTGGAGAACCCA<br>CCCTACGTGCCTGGGGTGGTTGGGGGGACCCTCCAGGCGGCCACCATC<br>TGTGCCTCCAGCCACCAGTTTCTCTCCACACACTACAACCTGCACAACC<br>TCTACGGCCTGACCGAAGCCATCGCCTCCCACAGGGCGCTGGTGAAGG<br>CTCGGGGGACACGCCCATTTGTGATCTCCCGCTCGACCTTTGCTGGCCA<br>CGGCCGATACGCCGGCCACTGGACGGGGACGTGTGGAGCTCCTGGGA<br>GCAGCTCGCCTCCTCCGTGCCAGAAATCCTGCAGTTTAACCTGCTGGGG<br>GTGCCTCTGGTCGGGGCCGACGTCTGCGGCTTCCTGGGCAACACCTCAG<br>AGGAGCTGTGTGTGCGCTGGACCCAGCTGGGGGCCTTCTACCCCTTCAT<br>GCGGAACCACAACAGCCTGCTCAGTCTGCCCCAGGAGCCGTACAGCTT<br>CAGCGAGCCGGCCCAGCAGGCCATGAGGAAGGCCCTCACCCTGCGCTA<br>CGCACTCCTCCCCCACCTCTACACACTGTTCCACCAGGCCCACGTCGCG<br>GGGGAGACCGTGGCCCGGCCCCTCTTCCTGGAGTTCCCCAAGGACTCT<br>AGCACCTGGACTGTGGACCACCAGCTCCTGTGGGGGAGGCCCTGCTC<br>ATCACCCCAGTGCTCCAGGCCGGGAAGGCCGAAGTGACTGGCTACTTC<br>CCCTTGGGCACATGGTACGACCTGCAGACGGTGCCAGTAGAGGCCCTT<br>GGCAGCCTCCCACCCCCACCTGCAGCTCCCCGTGAGCCAGCCATCCAC<br>AGCGAGGGGCAGTGGGTGACGCTGCCGGCCCCCCTGGACACCATCAAC<br>GTCCACCTCCGGGCTGGGTACATCATCCCCCTGCAGGGCCCTGGCCTCA<br>CAACCACAGAGTCCCGCCAGCAGCCCATGGCCCTGGCTGTGGCCCTGA<br>CCAAGGGTGGGGAGGCCCGAGGGGAGCTGTTCTGGGACGATGGAGAG<br>AGCCTGGAAGTGCTGGAGCGAGGGGCCTACACACAGGTCATCTTCCTG<br>GCCAGGAATAACACGATCGTGAATGAGCTGGTACGTGTGACCAGTGAG<br>GGAGCTGGCCTGCAGCTGCAGAAGGTGACTGTCCTGGGCGTGGCCACG<br>GCGCCCCAGCAGGTCCTCTCCAACGGTGTCCCTGTCTCCAACTTCACCT<br>ACAGCCCCGACACCAAGGTCCTGGACATCTGTGTCTCGCTGTTGATGGG<br>AGAGCAGTTTCTCGTCAGCTGGTGTTAG | |
| wt-PPT1<br>IDT codon<br>optimized | ATGGCATCACCGGGTTGCCTCTGGTTGTTGGCCGTTGCGTTGCTTCCGT<br>GGACATGTGCATCAAGAGCTCTTCAACATCTGGATCCCCCAGCTCCCT<br>GCCGCTCGTAATCTGGCACGGGATGGGGGATTCATGTTGTAACCCGTTG<br>TCAATGGGCGCGATAAAAAAGATGGTTGAAAAGAAGATTCCAGGCATC<br>TACGTTCTGTCCCTGGAAATCGGTAAGACACTGATGAAGACGTGGAG<br>AACTCCTTCTTTCTCAACGTCAATAGTCAGGTCACTACCGTCTGTCAAG<br>CATTGGCAAAGGACCCTAAACTTCAGCAGGGGTACAATGCGATGGGGT<br>TTAGCCAGGGCGGACAGTTTCTTAGAGCCGTCGCACAGCGCTGTCCATC<br>TCCCCCGATGATTAACCTTATATCTGTCGGGGGACAACACCAGGGTGTT<br>TTTGGTCTTCCTCGCTGTCCTGGTGAAAGCTCCCACATCTGTGATTTCAT<br>ACGCAAAACGTTGAACGCAGGAGCTTATAGTAAAGTCGTCCAAGAACG<br>GCTTGTTCAAGCGGAGTATTGGCATGACCCAATAAAAGAAGACGTTTA<br>TAGGAATCACTCTATCTTCTTGGCCGATATCAACCAAGAACGCGGAATC<br>AACGAAAGCTACAAAAAGAATCTTATGGCTCTCAAGAAATTTGTTATG<br>GTGAAATTCCTTAATGACTCTATAGTAGATCCTGTCGATTCAGAATGGT<br>TCGGGTTCTACAGGTCTGGCCAGGCGAAGGAGACTATTCCCCTCCAAG<br>AAACGTCTCTCTATACACAAGACAGACTCGGACTGAAAGAGATGGATA<br>ATGCGGGCCAGTTGGTCTTCTTGGCTACGGAAGGCGATCATCTCCAACT<br>CTCCGAAGAGTGGTTCTATGCCCATATAATCCCGTTCCTGGGCTAA | 40 |
| PPT 1-2 (wt-<br>vIGF2-PPT1;<br>Codon<br>optimized by<br>IDT codon<br>optimization<br>tool) | ATGGCATCCCCCGGATGTTTGTGGCTGCTGGCGGTTGCGCTTCTGCCAT<br>GGACGTGCGCCTCCCGAGCCCTCCAACACCTGCTCCAGGACACTTTGCG<br>GCGGAGAGTTGGTCGATACGCTTCAATTCGTGTGTGGGGATAGAGGCT<br>TCCTTTTTTCTCGGCCCGCTAGCCGCGTGTCCCGAAGGTCCCGGGGTAT<br>CGTTGAGGAATGCTGTTTCCGGTCCTGCGATCTTGCACTGTTGGAGACA<br>TACTGTGCTACGCCTGCGAGAAGCGAGGGTGGAGGGGTTCTGGAGGT<br>GGAGGGAGCCGGCTCGGGCGGTTCCCACCCAGGATCCTCCAGCTCCT<br>CTGCCCTCTGGTCATCTGGCATGGGATGGGGACTCATGTTGTAACCCGC<br>TGAGTATGGGGCAATTAAAAAATGGTTGAAAAGAAAATTCCAGGTA<br>TTTATGTCCTCTCTCTTGAAATCGGTAAGACACTTATGGAGGATGTGGA<br>AAACTCCTTTTTCCTTAATGTCAATTCTCAGGTCACAACAGTTTGTCAG<br>GCTCTGGCAAGGATCCTAAGCTGCAGCAAGGCTACAACGCCATGGGT<br>TTTTCCCAGGGAGGCCAATTTCTCAGAGCGGTAGCTCAGCGATGTCCAT<br>CACCACCGATGATAAATCTGATCAGTGTCGGCGGACAACACCAGGGAG<br>TTTTCGGGCTGCCCAGGTGTCCGGGGGAATCTAGTCACATATGTGACTT | 41 |

TABLE 7-continued

DNA Sequences

| Construct | DNA Sequence | SEQ ID NO |
|---|---|---|
| | CATTCGCAAGACCCTTAACGCCGGCGCTTACTCAAAGGTGGTTCAAGA<br>ACGGCTTGTGCAGGCTGAATACTGGCACGATCCCATCAAGGAAGATGT<br>ATATAGGAACCACAGTATCTTTCTGGCAGACATAAATCAGGAAAGGGG<br>TATTAACGAAAGCTACAAGAAAAATCTCATGGCCCTGAAGAAATTTGT<br>AATGGTTAAGTTTTTGAACGATTCTATAGTAGATCCTGTTGACTCCGAG<br>TGGTTCGGGTTCTATCGATCTGGTCAAGCCAAGGAGACGATTCCGCTTC<br>AGGAAACTTCACTGTACACACAGGATCGGCTGGGACTCAAGGAGATGG<br>ACAATGCGGGCCAGTTGGTGTTTCTGGCTACAGAGGGAGACCATCTCC<br>AGTTGAGTGAAGAATGGTTCTATGCACATATTATCCCATTCCTCGGCTA<br>A | |
| PPT1-29<br>(BiP2aa-<br>vIGF2-PPT1;<br>native human<br>sequence) | ATGAAGCTCTCCCTGGTGGCCGCGATGCTGCTGCTGCTCTGGGTGGCAC<br>TGCTGCTGCTCAGCGCGGCGAGGGCCGCCGCGAGTCGCACGTTGTGTG<br>GAGGTGAACTCGTCGACACCCTTCAGTTCGTATGTGGAGATCGCGGTTT<br>CCTCTTCTCACGCCCAGCTTCCAGAGTTTCCCGAAGATCACGAGGAATA<br>GTTGAGGAGTGCTGTTTTCGGTCTTGTGATCTGGCTCTCCTCGAGACTT<br>ATTGTGCTACGCCGGCCCGCTCTGAAGGAGGTGGTGGCAGTGGAGGAG<br>GAGGGAGTCGGCCTAGGGCAGTCCCAACCCAGGACCCGCCGGCGCCGC<br>TGCCGTTGGTGATCTGGCATGGGATGGGAGACAGCTGTTGCAATCCCTT<br>AAGCATGGGTGCTATTAAAAAAATGGTGGAGAAGAAAATACCTGGAAT<br>TTACGTCTTATCTTTAGAGATTGGGAAGACCCTGATGGAGGACGTGGA<br>GAACAGCTTCTTCTTGAATGTCAATTCCCAAGTAACAACAGTGTGTCAG<br>GCACTTGCTAAGGATCCTAAATTGCAGCAAGGCTACAATGCTATGGGA<br>TTCTCCCAGGGAGGCCAATTTCTGAGGGCAGTGGCTCAGAGATGCCCTT<br>CACCTCCCATGATCAATCTGATCTCGGTTGGGGGACAACATCAAGGTGT<br>TTTTGGACTCCCTCGATGCCCAGGAGAGAGCTCTCACATCTGTGACTTC<br>ATCCGAAAAACACTGAATGCTGGGGCGTACTCCAAAGTTGTTCAGGAA<br>CGCCTCGTGCAAGCCGAATACTGGCATGACCCCATAAAGGAGGATGTG<br>TATCGCAACCACAGCATCTTCTTGGCAGATATAAATCAGGAGCGGGGT<br>ATCAATGAGTCCTACAAGAAAAACCTGATGGCCCTGAAGAAGTTTGTG<br>ATGGTGAAATTCCTCAATGATTCCATTGTGGACCCTGTAGATTCGGAGT<br>GGTTTGGATTTTACAGAAGTGGCCAAGCCAAGGAAACCATTCCCTTAC<br>AGGAGACCTCCCTGTACACACAGGACCGCCTGGGGCTAAAGGAAATGG<br>ACAATGCAGGACAGCTAGTGTTTCTGGCTACAGAAGGGGACCATCTTC<br>AGTTGTCTGAAGAATGGTTTTATGCCCACATCATACCATTCCTTGGATG<br>A | 42 |

In some embodiments, the vector comprising the nucleic acid encoding the desired therapeutic fusion protein, such as a vIGF2 fusion or a signal peptide fusion, optionally having an internal ribosomal entry sequence, provided herein is an adeno-associated viral vector (A5/35).

In some embodiments, the nucleic acid encoding the therapeutic fusion protein, such as a vIGF2 fusion, optionally having an internal ribosomal entry sequence, is cloned into a number of types of vectors. For example, in some embodiments, the nucleic acid is cloned into a vector including, but not limited to a plasmid, a phagemid, a phage derivative, an animal virus, and a cosmid. Vectors of particular interest include expression vectors, replication vectors, probe generation vectors, and sequencing vectors.

Further, the expression vector encoding the therapeutic fusion protein, such as a vIGF2 fusion or a signal peptide fusion, optionally having an internal ribosomal entry sequence, in some embodiments, is provided to a cell in the form of a viral vector. Viral vector technology is described, e.g., in Sambrook et al., 2012, Molecular Cloning: A Laboratory Manual, volumes 1-4, Cold Spring Harbor Press, NY), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers (e.g., WO 01/96584; WO 01/29058; and U.S. Pat. No. 6,326,193).

Also provided herein are compositions and systems for gene transfer. A number of virally based systems have been developed for gene transfer into mammalian cells. For example, retroviruses provide a convenient platform for gene delivery systems. A selected gene, in some embodiments, is inserted into a vector and packaged in retroviral particles using suitable techniques. The recombinant virus is then isolated and delivered to cells of the subject either in vivo or ex vivo. A number of retroviral systems are suitable for gene therapy. In some embodiments, adenovirus vectors are used. A number of adenovirus vectors are suitable for gene therapy. In some embodiments, adeno-associated virus vectors are used. A number of adeno-associated viruses are suitable for gene therapy. In one embodiment, lentivirus vectors are used.

Gene therapy constructs provided herein comprise a vector (or gene therapy expression vector) into which the gene of interest is cloned or otherwise which includes the gene of interest in a manner such that the nucleotide sequences of the vector allow for the expression (constitutive or otherwise regulated in some manner) of the gene of interest. The vector constructs provided herein include any suitable gene expression vector that is capable of being delivered to a tissue of interest and which will provide for the expression of the gene of interest in the selected tissue of interest.

In some embodiments, the vector is an adeno-associated virus (AAV) vector because of the capacity of AAV vectors to cross the blood-brain barrier and transduction of neuronal tissue. In methods provided herein, AAV of any serotype is contemplated to be used. The serotype of the viral vector used in certain embodiments is selected from the group consisting of an AAV1 vector, an AAV2 vector, an AAV3 vector, an AAV4 vector, an AAV5 vector, an AAV6 vector, an AAV7 vector, an AAV8 vector, an AAV9 vector, an AAVrhS vector, an AAVrh10 vector, an AAVrh33 vector, an AAVrh34 vector, an AAVrh74 vector, an AAV Anc80 vector, an AAVPHP.B vector, an AAVhu68 vector, an AAV-DJ vector, and others suitable for gene therapy.

AAV vectors are DNA parvoviruses that are nonpathogenic for mammals. Briefly, AAV-based vectors have the rep and cap viral genes that account for 96% of the viral genome removed, leaving the two flanking 145 base pair inverted terminal repeats (ITRs) which are used to initiate viral DNA replication, packaging, and integration.

Further embodiments include use of other serotype capsids to create an AAV1 vector, an AAV2 vector, an AAV3 vector, an AAV4 vector, an AAV5 vector, an AAV6 vector, an AAV7 vector, an AAV8 vector, an AAV9 vector, an AAVrhS vector, an AAVrh10 vector, an AAVrh33 vector, an AAVrh34 vector, an AAVrh74 vector, an AAV Anc80 vector, an AAVPHP.B vector, an AAV-DJ vector, and others suitable for gene therapy. Optionally, the AAV viral capsid is AAV2/9, AAV9, AAVrhS, AAVrh10, AAVAnc80, or AAV PHP.B.

Additional promoter elements, e.g., enhancers, regulate the frequency of transcriptional initiation. Typically, these are located in the region 30-110 bp upstream of the start site, although a number of promoters have been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements is often increased to 50 bp apart before activity begins to decline. Depending on the promoter, it appears that individual elements function either cooperatively or independently to activate transcription.

An example of a promoter that is capable of expressing a therapeutic fusion protein, such as a vIGF2 fusion or a signal peptide fusion, optionally having an internal ribosomal entry sequence, transgene in a mammalian T-cell is the EF1a promoter. The native EF1a promoter drives expression of the alpha subunit of the elongation factor-1 complex, which is responsible for the enzymatic delivery of aminoacyl tRNAs to the ribosome. The EF1a promoter has been extensively used in mammalian expression plasmids and has been shown to be effective in driving expression from transgenes cloned into a lentiviral vector (see, e.g., Milone et al., Mol. Ther. 17(8): 1453-1464 (2009)). Another example of a promoter is the immediate early cytomegalovirus (CMV) promoter sequence. This promoter sequence is a strong constitutive promoter sequence capable of driving high levels of expression of any polynucleotide sequence operatively linked thereto. However, other constitutive promoter sequences are sometimes also used, including, but not limited to the chicken β actin promoter, the P546 promoter, the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the elongation factor-1a promoter, the hemoglobin promoter, and the creatine kinase promoter. Further, gene therapy vectors are not contemplated to be limited to the use of constitutive promoters. Inducible promoters are also contemplated here. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline-regulated promoter.

In order to assess the expression of a therapeutic fusion protein, such as a vIGF fusion or a signal peptide fusion, optionally having an internal ribosomal entry sequence, or portions thereof, the expression vector to be introduced into a cell often contains either a selectable marker gene or a reporter gene or both to facilitate identification and selection of expressing cells from the population of cells sought to be transfected or infected through viral vectors. In other aspects, the selectable marker is often carried on a separate piece of DNA and used in a co-transfection procedure. Both selectable markers and reporter genes are sometimes flanked with appropriate regulatory sequences to enable expression in the host cells. Useful selectable markers include, for example, antibiotic-resistance genes, such as neo and the like.

Methods and compositions for introducing and expressing genes into a cell are suitable for methods herein. In the context of an expression vector, the vector is readily introduced into a host cell, e.g., mammalian, bacterial, yeast, or insect cell by any method in the art. For example, the expression vector is transferred into a host cell by physical, chemical, or biological means.

Physical methods and compositions for introducing a polynucleotide into a host cell include calcium phosphate precipitation, lipofection, particle bombardment, microinjection, gene gun, electroporation, and the like. Methods for producing cells comprising vectors and/or exogenous nucleic acids are suitable for methods herein (see, e.g., Sambrook et al., 2012, Molecular Cloning: A Laboratory Manual, volumes 1-4, Cold Spring Harbor Press, NY). One method for the introduction of a polynucleotide into a host cell is calcium phosphate transfection.

Chemical means and compositions for introducing a polynucleotide into a host cell include colloidal dispersion systems, such as macromolecule complexes, nanocapsules, microspheres, beads, and lipid-based systems including oil-in-water emulsions, micelles, mixed micelles, nucleic acid-lipid particles, and liposomes. An exemplary colloidal system for use as a delivery vehicle in vitro and in vivo is a liposome (e.g., an artificial membrane vesicle). Other methods of state-of-the-art targeted delivery of nucleic acids are available, such as delivery of polynucleotides with targeted nanoparticles or other suitable sub-micron sized delivery system.

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid is associated with a lipid. The nucleic acid associated with a lipid, in some embodiments, is encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, in some embodiments, they are present in a bilayer structure, as micelles, or with a "collapsed" structure. Alternately, they are simply be interspersed in a solution, possibly forming aggregates that are not uniform in size or shape. Lipids are fatty substances which are, in some embodiments, naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Lipids suitable for use are obtained from commercial sources. For example, in some embodiments, dimyristyl phosphatidylcholine ("DMPC") is obtained from Sigma, St. Louis, Mo.; in some embodiments, dicetyl phosphate ("DCP") is obtained from K & K Laboratories (Plainview, N.Y.); cholesterol ("Choi"), in some embodiments, is obtained from Calbiochem-Behring; dimyristyl phosphatidylglycerol ("DMPG") and other lipids are often obtained from Avanti Polar Lipids, Inc. (Birmingham, Ala.). Stock solutions of lipids in chloroform or chloroform/methanol are often stored at about −20° C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes are often characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 Glycobiology 5: 505-10). However, compositions that have different structures in solution than the normal vesicular structure are also encompassed. For example, the lipids, in some embodiments, assume a micellar structure or merely exist as non-uniform aggregates of lipid molecules. Also contemplated are lipofectamine-nucleic acid complexes.

Regardless of the method used to introduce exogenous nucleic acids into a host cell or otherwise expose a cell to the therapeutic fusion protein, such as a vIGF2 fusion or a signal peptide fusion, optionally having an internal ribosomal entry sequence, provided herein, in order to confirm the presence of the recombinant DNA sequence in the host cell, a variety of assays are contemplated to be performed. Such assays include, for example, "molecular biological" assays suitable for methods herein, such as Southern and Northern blotting, RT-PCR and PCR; "biochemical" assays, such as detecting the presence or absence of a particular peptide, e.g., by immunological means (ELISAs and western blots) or by assays described herein to identify agents falling within the scope herein.

The present disclosure further provides a vector comprising a therapeutic fusion protein, such as a vIGF2 fusion or a signal peptide fusion, optionally having an internal ribosomal entry sequence, encoding nucleic acid molecule. In one aspect, a therapeutic fusion protein vector is capable of being directly transduced into a cell. In one aspect, the vector is a cloning or expression vector, e.g., a vector including, but not limited to, one or more plasmids (e.g., expression plasmids, cloning vectors, minicircles, minivectors, double minute chromosomes), retroviral and lentiviral vector constructs. In one aspect, the vector is capable of expressing the vIGF2-therapeutic fusion protein construct in mammalian cells. In one aspect, the mammalian cell is a human cell.

Uses and Methods of Treatment

Also provided herein are methods of treating genetic disorders using gene therapy comprising administering to an individual a nucleic acid encoding a therapeutic fusion protein (such as a vIGF2 fusion or a signal peptide fusion or a signal peptide-vIGF2 fusion), optionally having an internal ribosomal entry sequence, disclosed herein. Genetic disorders suitable for treatment using methods herein comprise disorders in an individual caused by one or more mutations in the genome causing lack of expression or expression of a dysfunctional protein by the mutant gene.

Further provided herein are pharmaceutical compositions comprising a gene therapy vector, such as a gene therapy vector comprising a nucleic acid encoding a therapeutic fusion protein (such as a vIGF2 fusion or a signal peptide fusion or a signal peptide-vIGF2 fusion), optionally having an internal ribosomal entry sequence, disclosed herein and a pharmaceutically acceptable carrier or excipient for use in preparation of a medicament for treatment of a genetic disorder.

Genetic disorders suitable for treatment by methods herein include but are not limited to Achondroplasia, Alpha-1 Antitrypsin Deficiency, Antiphospholipid Syndrome, Autosomal Dominant Polycystic Kidney Disease, Charcot-Marie-Tooth, Colon cancer, Cri du chat, Crohn's Disease, Cystic fibrosis, Dercum Disease, Duane Syndrome, Duchenne Muscular Dystrophy, Factor V Leiden Thrombophilia, Familial Hypercholesterolemia, Familial Mediterranean Fever, Fragile X Syndrome, Gaucher Disease, Hemochromatosis, Hemophilia, Holoprosencephaly, Huntington's disease, Klinefelter syndrome, Marfan syndrome, Myotonic Dystrophy, Neurofibromatosis, Noonan Syndrome, Osteogenesis Imperfecta, Parkinson's disease, Phenylketonuria, Poland Anomaly, Porphyria, Progeria, Retinitis Pigmentosa, Severe Combined Immunodeficiency (SCID), Sickle cell disease, Spinal Muscular Atrophy, Tay-Sachs disease, Thalassemia, Trimethylaminuria, Turner Syndrome, Velocardiofacial Syndrome, WAGR Syndrome, or Wilson Disease. In some embodiments, the genetic disorder is selected from the group consisting of CDKL5 deficiency disorder, cystic fibrosis, alpha- and beta-thalassemias, sickle cell anemia, Marfan syndrome, fragile X syndrome, Huntington's disease, hemochromatosis, Congenital Deafness (nonsyndromic), Tay-Sachs, Familial hypercholesterolemia, Duchenne muscular dystrophy, Stargardt disease, Usher syndrome, choroideremia, achromatopsia, X-linked retinoschisis, hemophilia, Wiskott-Aldrich syndrome, X-linked chronic granulomatous disease, aromatic L-amino acid decarboxylase deficiency, recessive dystrophic epidermolysis bullosa, alpha 1 antitrypsin deficiency, Hutchinson-Gilford progeria syndrome (HGPS), Noonan syndrome, X-linked severe combined immunodeficiency (X-SCID).

In some embodiments, genetic disorders suitable for treatment using methods provided herein are lysosomal storage disorder. In some embodiments, lysosomal storage disorders are treated herein using gene therapy to deliver missing or defective enzymes to the patient. In some embodiments, methods herein deliver an enzyme fused to a vIGF2 or fused to a signal peptide to the patient in order to deliver the enzyme to the cell where it is needed. In some embodiments, the lysosomal storage disorders is selected from the group consisting of aspartylglucosaminuria, Batten disease, cystinosis, Fabry disease, Gaucher disease type I, Gaucher disease type II, Gaucher disease type III, Pompe disease, Tay Sachs disease, Sandhoff disease, metachomatic leukodystrophy, mucolipidosis type I, mucolipidosis type II, mucolipidosis type III, mucolipidosis type IV, Hurler disease, Hunter disease, Sanfilippo disease type A, Sanfilippo disease type B, Sanfilippo disease type C, Sanfilippo disease type D, Morquio disease type A, Morquio disease type B, Maroteau-Lamy disease, Sly disease, Niemann-Pick disease type A, Niemann-Pick disease type B, Niemann-Pick disease type C1, Niemann-Pick disease type C2, Schindler disease type I, and Schindler disease type II. In some embodiments, the lysosomal storage disorder is selected from the group consisting of activator deficiency, GM2-gangliosidosis; GM2-gangliosidosis, AB variant; alpha-mannosidosis (type 2, moderate form; type 3, neonatal, severe); beta-mannosidosis; aspartylglucosaminuria; lysosomal acid lipase deficiency; cystinosis (late-onset juvenile or adolescent nephropathic type; infantile nephropathic); Chanarin-Dorfman syndrome; neutral lipid storage disease with myopathy; NLSDM; Danon disease; Fabry disease; Fabry disease type II, late-onset; Farber disease; Farber lipogranulomatosis; fucosidosis; galactosialidosis (combined neuraminidase & beta-galactosidase deficiency); Gaucher disease; type II Gaucher disease; type III Gaucher disease; type IIIC Gaucher disease; Gaucher disease, atypical, due to saposin C deficiency; GM1-gangliosidosis (late-infantile/juvenile GM1-gangliosidosis; adult/chronic GM1-gangliosidosis); Globoid cell leukodystrophy, Krabbe disease (Late infantile onset; Juvenile Onset; Adult Onset); Krabbe disease, atypical, due to saposin A deficiency; Metachromatic Leukodystrophy (juvenile; adult); partial cerebroside sulfate deficiency; pseudoarylsulfatase A deficiency; metachromatic leukodystrophy due to saposin B deficiency; Mucopolysaccharidoses disorders: MPS I, Hurler syndrome; MPS I, Hurler-Scheie syndrome; MPS I, Scheie syndrome; MPS II, Hunter syndrome; MPS II, Hunter syndrome; Sanfilippo syndrome Type A/MPS IIIA; Sanfilippo syndrome Type B/MPS IIIB; Sanfilippo syndrome Type C/MPS IIIC; Sanfilippo syndrome Type D/MPS IIID; Morquio syndrome, type A/MPS IVA; Morquio syndrome, type B/MPS IVB; MPS IX hyaluronidase deficiency; MPS VI Maroteaux-Lamy syndrome; MPS VII Sly syndrome; mucolipidosis I, sialidosis type II; I-cell disease, Leroy disease, mucolipidosis II; Pseudo-Hurler polydystrophy/mucolipidosis type III; mucolipidosis IIIC/ML III GAMMA; mucolipidosis type IV; multiple sulfatase deficiency; Niemann-Pick disease (type B; type C1/chronic neuronopathic form; type C2; type D/Nova Scotian type); Neuronal Ceroid Lipofuscinoses: CLN6 disease—Atypical Late Infantile, Late-Onset variant, Early Juvenile; Batten-Spielmeyer-Vogt/Juvenile NCL/CLN3 disease; Finnish Variant Late Infantile CLN5; Jansky-Bielschowsky disease/Late infantile CLN2/TPP1 Disease; Kufs/Adult-onset NCL/CLN4 disease (type B); Northern Epilepsy/variant late infantile CLN8; Santavuori-Haltia/Infantile CLN1/PPT disease; Pompe disease (glycogen storage disease type II); late-onset Pompe disease; Pycnodysostosis; Sandhoff disease/GM2 gangliosidosis; Sandhoff disease/GM2 gangliosidosis; Sandhoff disease/GM2 Gangliosidosis; Schindler disease (type III/intermediate, variable); Kanzaki disease; Salla disease; infantile free sialic acid storage disease (ISSD); spinal muscular atrophy with progressive myoclonic epilepsy (SMAPME); Tay-Sachs disease/GM2 gangliosidosis; juvenile-onset Tay-Sachs disease; late-onset Tay-Sachs disease; Christianson syndrome; Lowe oculocerebrorenal syndrome; Charcot-Marie-Tooth type 4J, CMT4J; Yunis-Varon syndrome; bilateral temporooccipital polymicrogyria (BTOP); X-linked hypercalciuric nephrolithiasis, Dent-1; and Dent disease 2. In some embodiments, the therapeutic protein is associated with a lysosomal storage disorder and the therapeutic protein is selected from the group consisting of GM2-activator protein; α-mannosidase; MAN2B1; lysosomal ß-mannosidase; glycosylasparaginase; lysosomal acid lipase; cystinosin; CTNS; PNPLA2; lysosome-associated membrane protein-2; α-galactosidase A; GLA; acid ceramidase; α-L-fucosidase; protective protein/cathepsin A; acid ß-glucosidase; GBA; PSAP; ß-galactosidase-1; GLB1; galactosylceramide ß-galactosidase; GALC; PSAP; arylsulfatase A; ARSA; α-L-iduronidase; iduronate 2-sulfatase; heparan N-sulfatase; N-α-acetylglucosaminidase; heparan acetyl CoA: α-glucosaminide acetyltransferase; N-acetylglucosamine ß-sulfatase; galactosamine-6-sulfate sulfatase; ß-galactosidase; hyaluronidase; arylsulfatase B; ß-glucuronidase; neuraminidase; NEU1; gamma subunit of N-acetylglucosamine-1-phosphotransferase; mucolipin-1; sulfatase-modifying factor-1; acid sphingomyelinase; SMPD1; NPC1; and NPC2.

In some embodiments, treatment via methods herein delivers a gene encoding a therapeutic protein to a cell in need of the therapeutic protein. In some embodiments, the treatment delivers the gene to all somatic cells in the individual. In some embodiments, the treatment replaces the defective gene in the targeted cells. In some embodiments, cells treated ex vivo to express the therapeutic protein are delivered to the individual.

Gene therapy for disorders disclosed herein provides superior treatment outcomes to conventional treatments, including enzyme replacement therapy, because it does not require long infusion treatments. In addition, it has reduced risk of the individual developing an immune response to the therapeutic protein, which is often experienced in individuals receiving enzyme replacement therapy.

Definitions

As used herein "ex vivo gene therapy" refers to methods where patient cells are genetically modified outside the subject, for example to express a therapeutic gene. Cells with the new genetic information are then returned to the subject from whom they were derived.

As used herein "in vivo gene therapy" refers to methods where a vector carrying the therapeutic gene(s) is directly administered to the subject.

As used herein "fusion protein" and "therapeutic fusion protein" are used interchangeably herein and refer to a therapeutic protein having at least one additional protein, peptide, or polypeptide, linked to it. In some instances, fusion proteins are a single protein molecule containing two or more proteins or fragments thereof, covalently linked via peptide bond within their respective peptide chains, without chemical linkers. In some embodiments, the fusion protein comprises a therapeutic protein and a signal peptide, a peptide that increases endocytosis of the fusion protein, or both. In some embodiments, the peptide that increases endocytosis is a peptide that binds CI-MPR.

As used herein "vector", or "gene therapy vector", used interchangeably herein, refers to gene therapy delivery vehicles, or carriers, that deliver therapeutic genes to cells. A gene therapy vector is any vector suitable for use in gene therapy, e.g., any vector suitable for the therapeutic delivery of nucleic acid polymers (encoding a polypeptide or a variant thereof) into target cells (e.g., sensory neurons) of a patient. In some embodiments, the gene therapy vector delivers the nucleic acid encoding a therapeutic protein or therapeutic fusion protein to a cell where the therapeutic protein or fusion is expressed and secreted from the cell. The vector may be of any type, for example it may be a plasmid vector or a minicircle DNA. Typically, the vector is a viral vector. These include both genetically disabled viruses such as adenovirus and nonviral vectors such as liposomes. The viral vector may for example be derived from an adeno-associated virus (AAV), a retrovirus, a lentivirus, a herpes simplex virus, or an adenovirus. AAV derived vectors. The vector may comprise an AAV genome or a derivative thereof.

"Construct" as used herein refers to a nucleic acid molecule or sequence that encodes a therapeutic protein or fusion protein and optionally comprises additional sequences such as a translation initiation sequence or IRES sequence.

As used herein "plasmid" refers to circular, double-stranded unit of DNA that replicates within a cell independently of the chromosomal DNA.

As used herein "promoter" refers to a site on DNA to which the enzyme RNA polymerase binds and initiates the transcription of DNA into RNA.

As used herein "somatic therapy" refers to methods where the manipulation of gene expression in cells that will be corrective to the patient but not inherited by the next generation. Somatic cells include all the non-reproductive cells in the human body As used herein "somatic cells" refers to all body cells except the reproductive cells.

As used herein "tropism" refers to preference of a vector, such as a virus for a certain cell or tissue type. Various factors determine the ability of a vector to infect a particular cell. Viruses, for example, must bind to specific cell surface receptors to enter a cell. Viruses are typically unable to infect a cell if it does not express the necessary receptors.

The term "transduction" is used to refer to the administration/delivery of the nucleic acid encoding the therapeutic protein to a target cell either in vivo or in vitro, via a replication-deficient rAAV of the disclosure resulting in expression of a functional polypeptide by the recipient cell. Transduction of cells with a gene therapy vector such as a rAAV of the disclosure results in sustained expression of polypeptide or RNA encoded by the rAAV. The present disclosure thus provides methods of administering/delivering to a subject a gene therapy vector such as an rAAV encoding a therapeutic protein by an intrathecal, intraretinal, intraocular, intravitreous, intracerebroventricular, intraparechymal, or intravenous route, or any combination thereof "Intrathecal" delivery refers to delivery into the space under the arachnoid membrane of the brain or spinal cord. In some embodiments, intrathecal administration is via intracisternal administration.

The terms "recipient", "individual", "subject", "host", and "patient", are used interchangeably herein and in some cases, refer to any mammalian subject for whom diagnosis, treatment, or therapy is desired, particularly humans. "Mammal" for purposes of treatment refers to any animal classified as a mammal, including humans, domestic and farm animals, and laboratory, zoo, sports, or pet animals, such as dogs, horses, cats, cows, sheep, goats, pigs, mice, rats, rabbits, guinea pigs, monkeys etc. In some embodiments, the mammal is human.

As used herein, the terms "treatment," "treating," "ameliorating a symptom," and the like, in some cases, refer to administering an agent, or carrying out a procedure, for the purposes of obtaining a therapeutic effect, including inhibiting, attenuating, reducing, preventing or altering at least one aspect or marker of a disorder, in a statistically significant manner or in a clinically significant manner. The term "ameliorate" or "treat" does not state or imply a cure for the underlying condition. "Treatment," or "to ameliorate" (and like) as used herein, may include treating a mammal, particularly in a human, and includes: (a) preventing the disorder or a symptom of a disorder from occurring in a subject which may be predisposed to the disorder but has not yet been diagnosed as having it (e.g., including disorders that may be associated with or caused by a primary disorder; (b) inhibiting the disorder, i.e., arresting its development; (c) relieving the disorder, i.e., causing regression of the disorder; and (d) improving at least one symptom of the disorder. Treating may refer to any indicia of success in the treatment or amelioration or prevention of a disorder, including any objective or subjective parameter such as abatement; remission; diminishing of symptoms or making the disorder condition more tolerable to the patient; slowing in the rate of degeneration or decline; or making the final point of degeneration less debilitating. The treatment or amelioration of symptoms is based on one or more objective or subjective parameters; including the results of an examination by a physician. Accordingly, the term "treating" includes the administration of the compounds or agents of the present invention to prevent or delay, to alleviate, or to arrest or inhibit development of the symptoms or conditions associated with the disorder. The term "therapeutic effect" refers to the reduction, elimination, or prevention of the disorder, symptoms of the disorder, or side effects of the disorder in the subject.

The term "affinity" refers to the strength of binding between a molecule and its binding partner or receptor.

As used herein, the phrase "high affinity" refers to, for example, a therapeutic fusion containing such a peptide that binds CI-MPR which has an affinity to CI-MPR that is about 100 to 1,000 times or 500 to 1,000 times higher than that of the therapeutic protein without the peptide. In some embodiments, the affinity is at least 100, at least 500, or at least 1000 times higher than without the peptide. For example, where the therapeutic protein and CI-MPR are combined in relatively equal concentration, the peptide of high affinity will bind to the available CI-MPR so as to shift the equilibrium toward high concentration of the resulting complex.

"Secretion" as used herein refers to the release of a protein from a cell into, for example, the bloodstream to be carried to a tissue of interest or a site of action of the therapeutic protein. When a gene therapy product is secreted into the interstitial space of an organ, secretion can allow for cross-correction of neighboring cells.

"Delivery" as used herein means drug delivery. In some embodiments, the process of delivery means transporting a drug substance (e.g., therapeutic protein or fusion protein produced from a gene therapy vector) from outside of a cell (e.g., blood, tissue, or interstitial space) into a target cell for therapeutic activity of the drug substance.

"Engineering" or "protein engineering" as used here in refers to the manipulation of the structures of a protein by providing appropriate a nucleic acid sequence that encodes for the protein as to produce desired properties, or the synthesis of the protein with particular structures.

A "therapeutically effective amount" in some cases means the amount that, when administered to a subject for treating a disorder, is sufficient to effect treatment for that disorder.

As used herein, the term "about" a number refers to a range spanning that from 10% less than that number through 10% more than that number, and including values within the range such as the number itself.

As used herein, the term "comprising" an element or elements of a claim refers to those elements but does not preclude the inclusion of an additional element or elements.

EXAMPLES

The following examples are given for the purpose of illustrating various embodiments of the invention and are not meant to limit the present invention in any fashion. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Example 1: Binding of Variant IGF2 Peptide to CI-MPRReceptor

Figure 4:
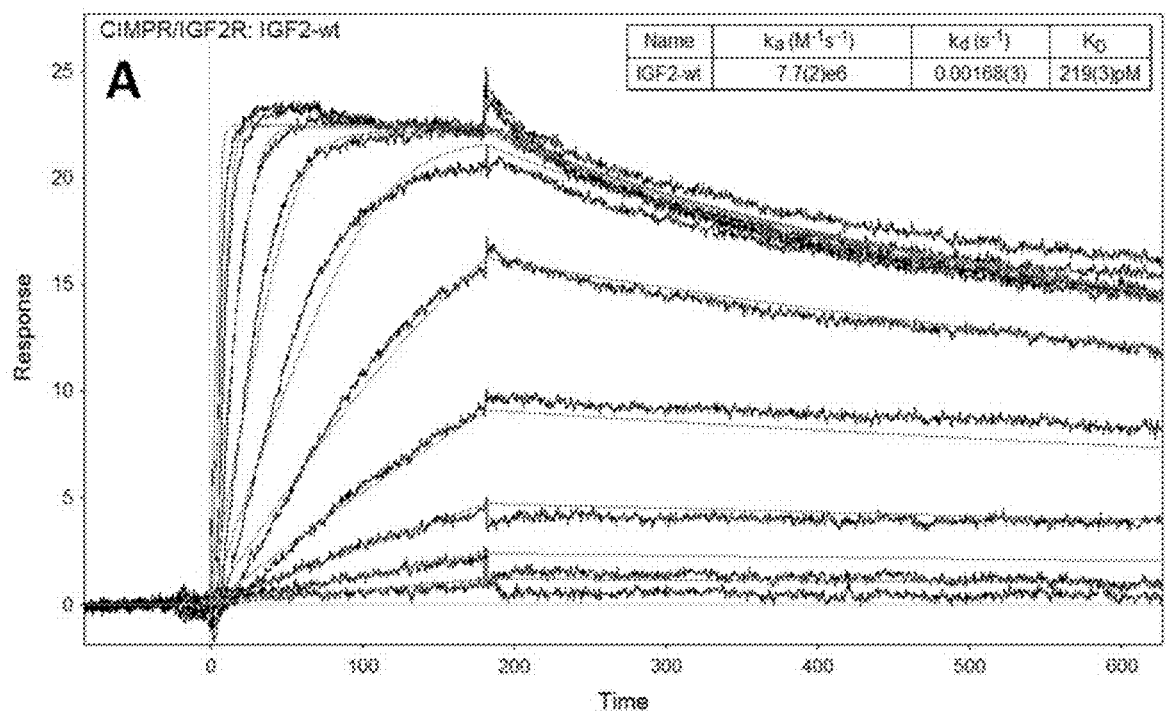
FIG. 4 shows binding of the wild-type IGF2 (wtIGF2) peptide to CI-MPR as measured by surface plasmon resonance
Figure 5:
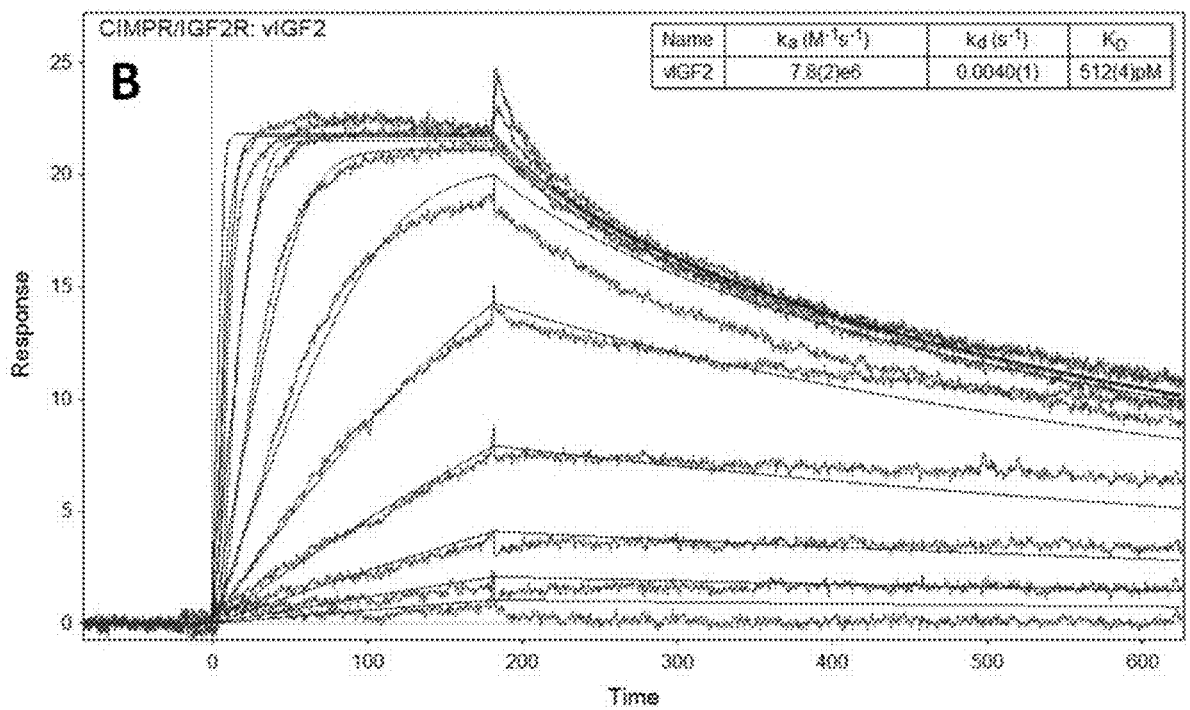
FIG. 5 shows binding of the variant IGF2 (vIGF2) peptide binding to CI-MPR as measured by surface plasmon resonance.

Surface plasmon resonance (SPR) experiments were conducted using Biacore to measure binding of wildtype and variant IGF2 (vIGF2) to the CI-MPR receptor. The wildtype, human mature IGF2 peptide (wt IGF2) has the sequence set forth in SEQ ID NO: 1. The vIGF2 sequence differs from wt IGF2 in that it lacks residues 1-4 and contains the following mutations: E6R, Y27L, and K65R. It has the amino sequence: SRTLCGGELVDTLQFVCGDRGFLFSRPASRVSRRSRGIVEECCFRSCDLALLETYCATPARSE (SEQ ID NO: 31). vIGF2 also has an N-terminal linker with the sequence GGGGSGGGG (SEQ ID NO: 18). The combined sequence is GGGGSGGGGSRTLCGGELVDTLQFVCGDRGFLFSRPASRVSRRSR-GIVEECCFRSCDLALLETYC ATPARSE SEQ ID NO: 43). FIG. 4 shows that as expected, the wildtype IGF2 peptide binds to the CI-MPRreceptor with high affinity (0.2 nM). FIG. 5 shows that the variant IGF2 peptide (vIGF2) also binds to the CI-MPRreceptor with high affinity (0.5 nM). These data indicate that vIGF2 peptide has high affinity for the intended CI-MPRreceptor for targeting therapeutics to lysosomes.

Figure 8:
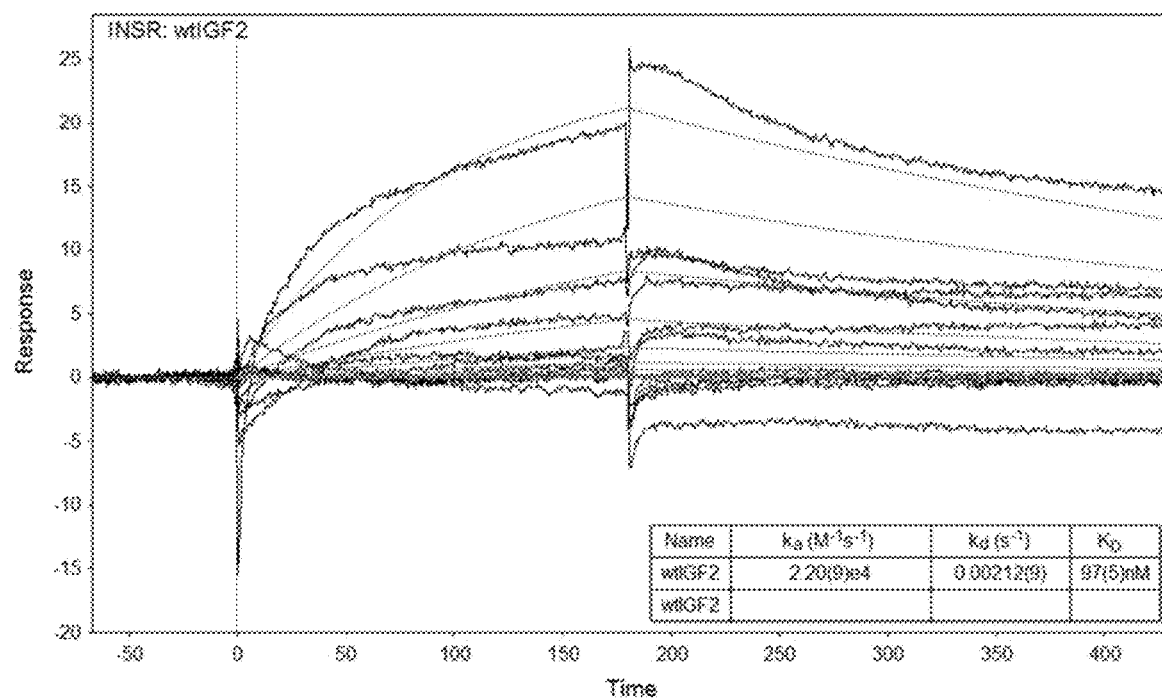
FIG. 8 shows binding of wildtype human IGF2 to insulin receptor.
Figure 9:
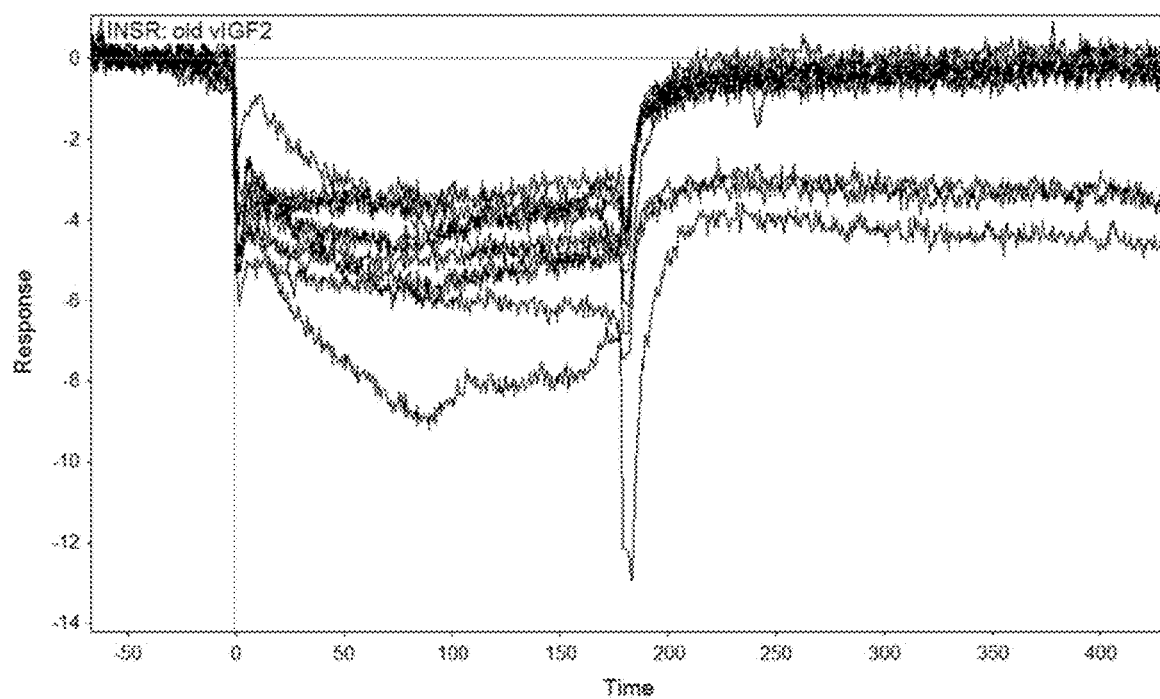
FIG. 9 shows no detectable binding of vIGF2 to insulin receptor.

SPR was utilized to measure peptide binding to the Insulin Receptor to assess potential side effects. Insulin binds the Insulin Receptor with high affinity (~8 nM; data not shown). Wildtype IGF2 and a vIGF2 were tested, where the vIGF2 had the sequence SRTLCGGELVDTLQFVCGDRGFLFSRPASRVSRRSR-GIVEECCFRSCDLALLETYCATPARSE (SEQ ID NO: 31) having an N-terminal linker with a sequence GGGGSGGGG (SEQ ID NO: 18). FIG. 8 shows that wildtype IGF2 also binds the Insulin Receptor with relatively high affinity (~100 nM). IGF2 peptide from Biomarin/Zystor IGF2-GAA fusion protein (BMN-701) also binds the Insulin Receptor with high affinity and was shown to cause hypoglycemia in clinical trials. FIG. 9 shows no measurable binding of vIGF2 peptide to the insulin receptor. These data show that vIGF2 peptide confers a superior safety profile compared with wt IGF2 peptide fusions.

Figure 10:
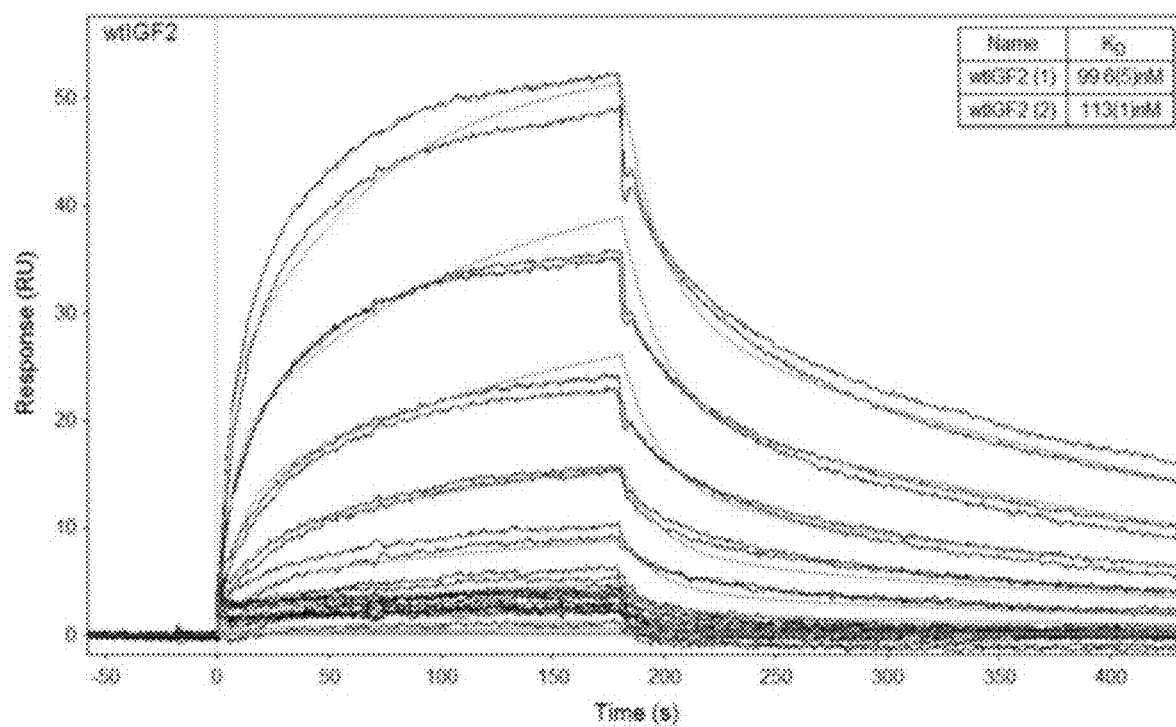
FIG. 10 shows binding of wildtype IGF2 to insulin-like growth factor 1 receptor.
Figure 11:
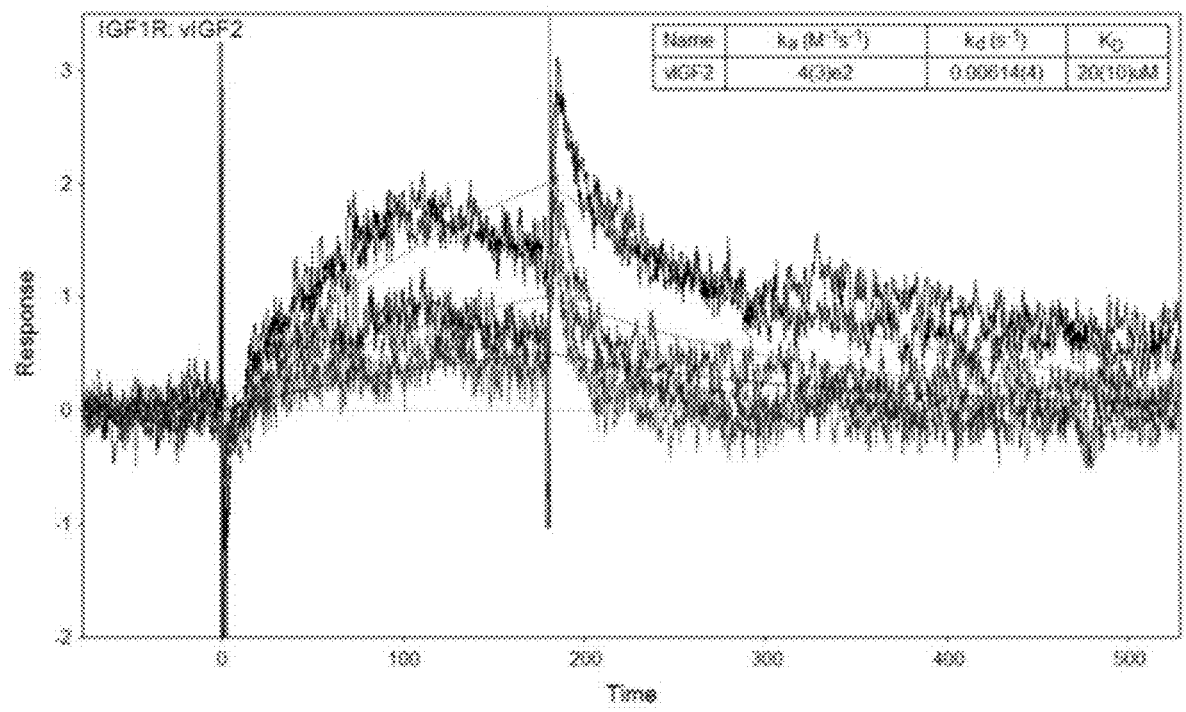
FIG. 11 shows decreased binding of vIGF2 peptide to insulin-like growth factor 1 receptor, as compared to wild-type IGF2.

The same SPR binding analysis was utilized to characterize vIGF2 peptide interaction with the IGF1 Receptor. FIG. 10 shows that the wildtype IGF2 peptide binds IGF1 receptor with relatively high affinity (~100 nM). FIG. 11 shows no measurable binding of vIGF2 peptide to the IGF1 Receptor, showing an improved safety profile compared to wt IGF2.

TABLE 8

| SPR Affinity Results | | |
|---|---|---|
| Receptor | wt IGF2 Kd (nM) | vIGF2 Kd (nM) |
| CI-MPR | 0.2 | 0.5 |
| Insulin Receptor | 100 | No Binding Detected |
| IGF1 Receptor | 100 | No Binding Detected |

Example 2: vIGF2 Converts Low Affinity Ligand to High Affinity ERT for CI-MPR

Figure 6:
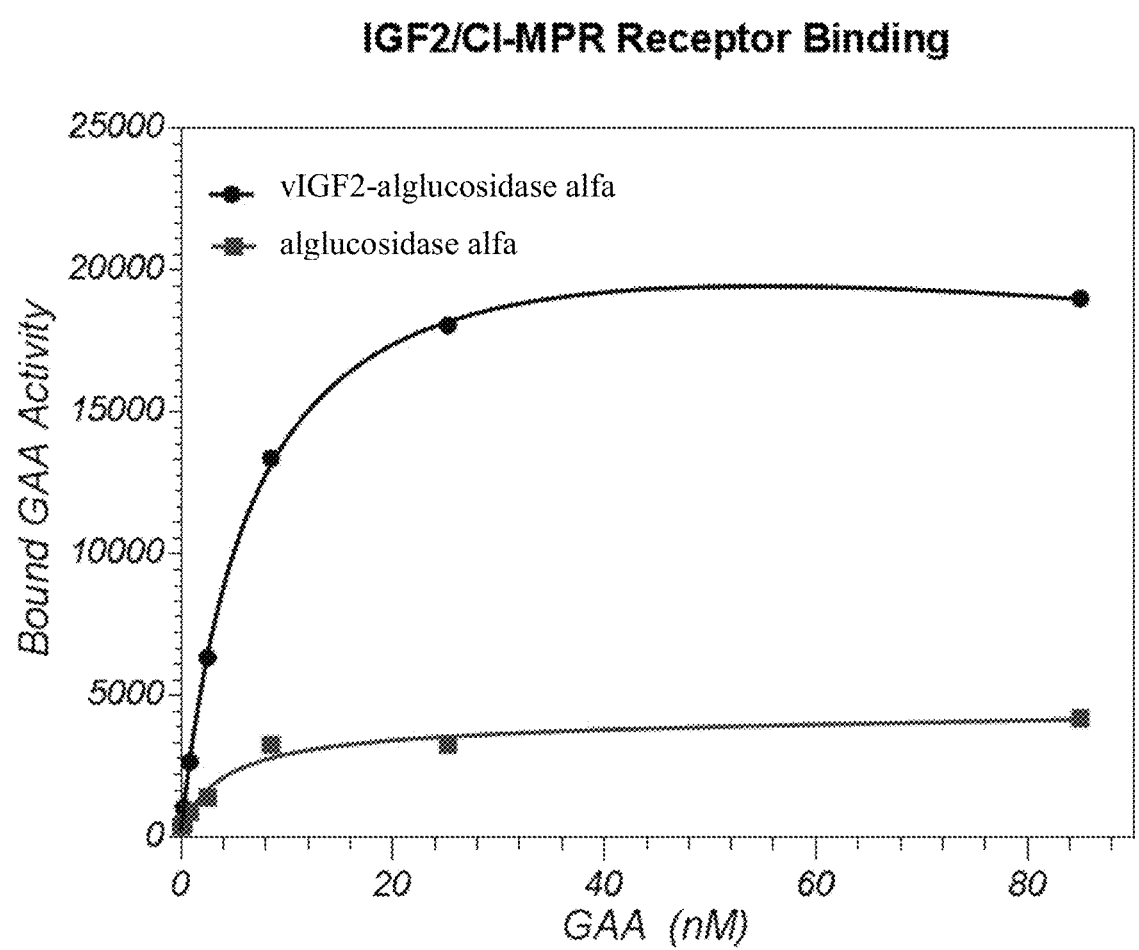
FIG. 6 shows benefit of adding vIGF2 to aluglucisidase alfa to increase the binding to the IGF2/CI-MPR.

The vIGF2 peptide (SEQ ID NO: 31) with an N-terminal linker (SEQ ID NO: 18) was chemically coupled to alglucosidase-alfa, designated here as vIGF2-alglucosidase-alfa, to determine whether the vIGF2 peptide could improve affinity for CI-MPR. As shown in FIG. 6, binding affinities of alglucosidase-alfa and vIGF2-alglucosidase-alfa were directly compared using CI-MPR plate binding assays in 96-well ELISA plates coated with CI-MPR. Unbound enzyme was washed away prior to measuring bound enzyme activity. Varying concentrations of both enzyme preparations were used with or without free WT IGF2 peptide. vIGF2 substantially improved the affinity for CI-MPR. Further, binding of vIGF2-alglucosidase-alfa was blocked by free WT IGF2 indicating that binding was IGF2-dependent. (Data not shown.) Coupling of vIGF2 peptide did not impair GAA enzyme activity.

Figure 7:
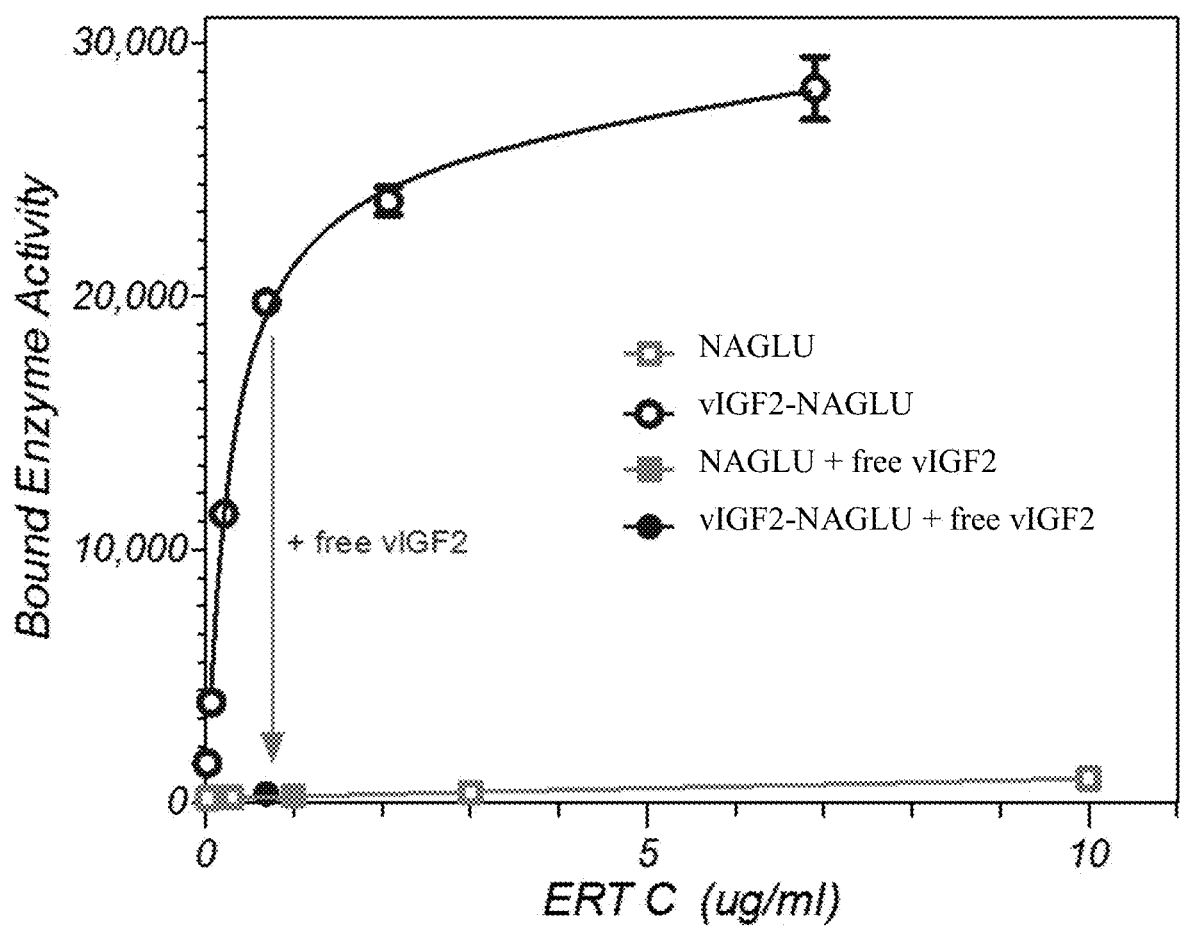
FIG. 7 shows the benefit of adding a vIGF2 to recombinant human N-acetyl-α-D-glucosaminidase (rhNAGLU) to increase the binding to the IGF2/CI-MPR.

The vIGF2 was coupled to recombinant human N-acetyl-α-D-glucosaminidase (rhNAGLU). RrhNAGLU, a lysosomal enzyme lacking M6P, to determine whether peptide can convert a non-ligand to high affinity ligand for CI-MPR. In this experiment, rhNAGLU and vIGF2-rhNAGLU were directly compared using CI-MPRplate binding assays, utilizing CI-MPR-coated plates. Unbound enzyme was washed away prior to measuring bound enzyme activity. Varying concentrations of both enzyme preparations were used with or without free vIGF2 peptide. As shown in FIG. 7, vIGF2-rhNAGLU has significantly higher affinity for CI-MPR than rhNAGLU lacking vIGF2. Further, vIGF2-rhNAGLU binding was blocked by free vIGF2 peptide indicating that receptor binding was specific for IGF2 peptide. These results show that vIGF2 peptide can be utilized to improve drug targeting to lysosomes.

Example 3: Myoblast Uptake of vIGF2-GAA Fusion Proteins vIGF2-GAA fusion proteins (same sequences as in Examples 1-2) were administered and L6 myoblast uptake of the enzyme was measured. FIG. 6 shows superior uptake of the vIGF2-rhGAA compared to rhGAA and M6P-GAA. Therefore, vIGF2 is effective at targeting GAA to the cells.

Example 4: Constructs for ERT Delivered by Gene Therapy

Figure 12:
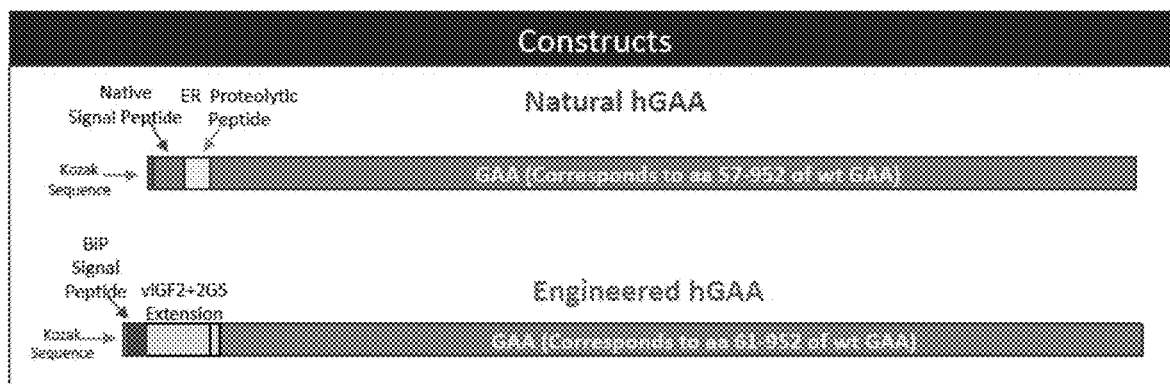
FIG. 12 shows two examples of gene therapy expression cassettes encoding Natural hGAA and Engineered hGAA. Natural hGAA has poor phosphorylation leading to poor CIMPR binding and cellular uptake. Engineered hGAA has element added for improved CIMPR binding (vIGF2), a 2GS linker that reduces steric hinderance of the vIGF2-GAA protein with CIMPR, and a BiP signal peptide to improve secretion.

Two different constructs are illustrated in FIG. 12. In the top panel is a construct which contains a Kozak sequence and a nucleic acid encoding a recombinant human GAA with the native signal peptide (SEQ ID NO: 45), encoding "natural hGAA" (SEQ ID NO: 45). In the middle panel is the construct Kozak-BiP-vIGF2-2GS-GAA, encoding "engineered hGAA" (SEQ ID NO: 23). This construct is characterized by a Kozak sequence, a nucleic acid encoding BiP signal peptide, a nucleic acid encoding the vIGF2 peptide having the sequence set forth in SEQ ID NO: 31, and a nucleic acid encoding a 2GS linker (SEQ ID NO:18) followed by a nucleic acid encoding a recombinant human GAA with the N-terminal 60 amino acids removed (SEQ ID NO:46) to prevent premature processing and removal of the vIGF2.

Example 5: Enhanced Secretion of Gene Therapy Constructs

Figure 15:
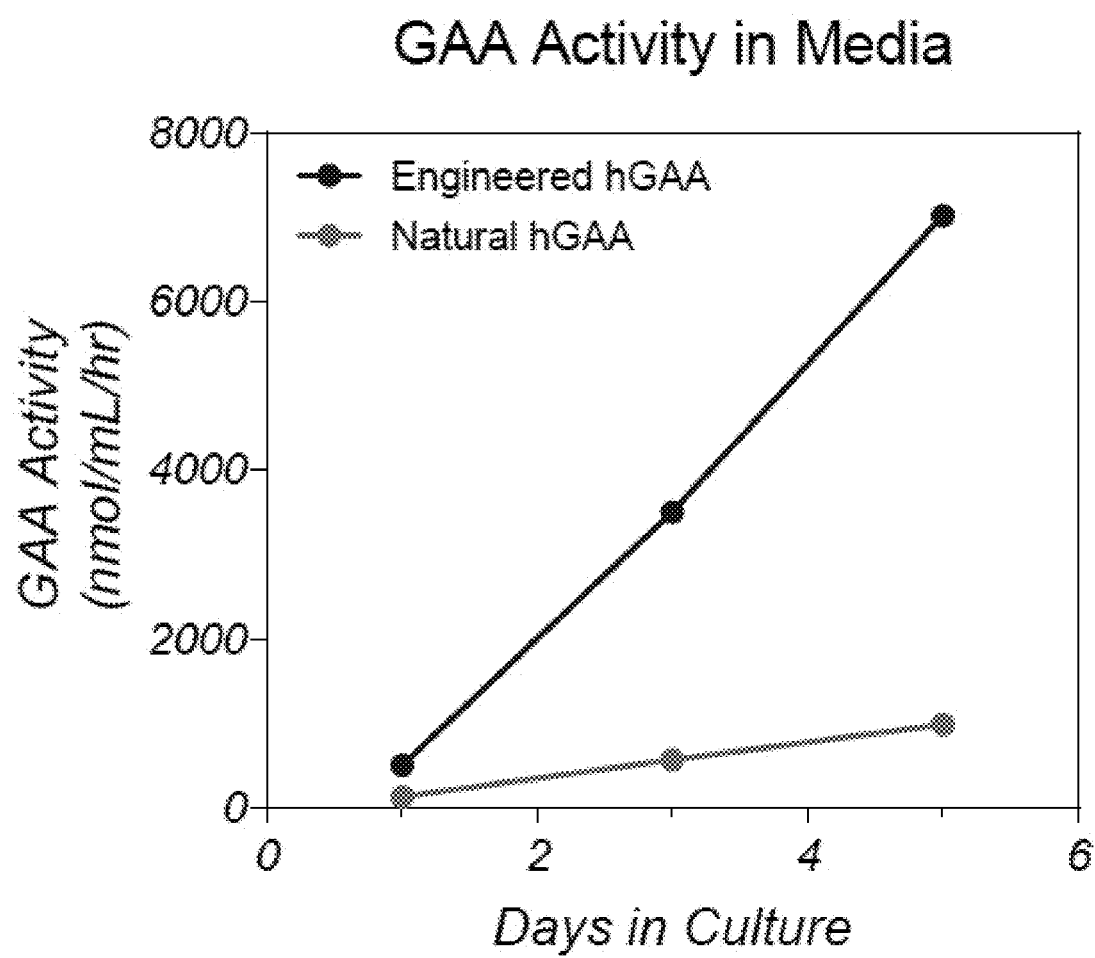
FIG. 15 shows GAA activity in conditioned media of CHO cells expressing engineered or natural hGAA.

Engineered hGAA has greater secretion and is able to interact with a cell surface receptor appropriate for cellular uptake and lysosomal targeting CHO expressing engineered hGAA, described in more detail below, or natural hGAA were cultured and conditioned media was collected for measurement of GAA activity. FIG. 15 shows the relative activity of engineered and natural hGAA showing that engineered hGAA has increased activity compared to natural hGAA, indicative of more efficient secretion of engineered hGAA.

Example 6: Analysis of PPT1 in Conditioned Media

Cloning of PPT1 Constructs

PPT1 constructs were cloned into the pcDNA3.1 expression vector (ThermoFisher cat #V79020), which contains a CMV promoter. The tested constructs included PPT1-1 (WT-PPT1) (SEQ ID NO: 24); PPT1-2 (WT-vIGF2-PPT1) (SEQ ID NO: 25); PPT1-29 (BiP2aa-vIGF2-PPT1) (SEQ ID NO: 26).

PPT1 Secretion & Binding

Figure 13:
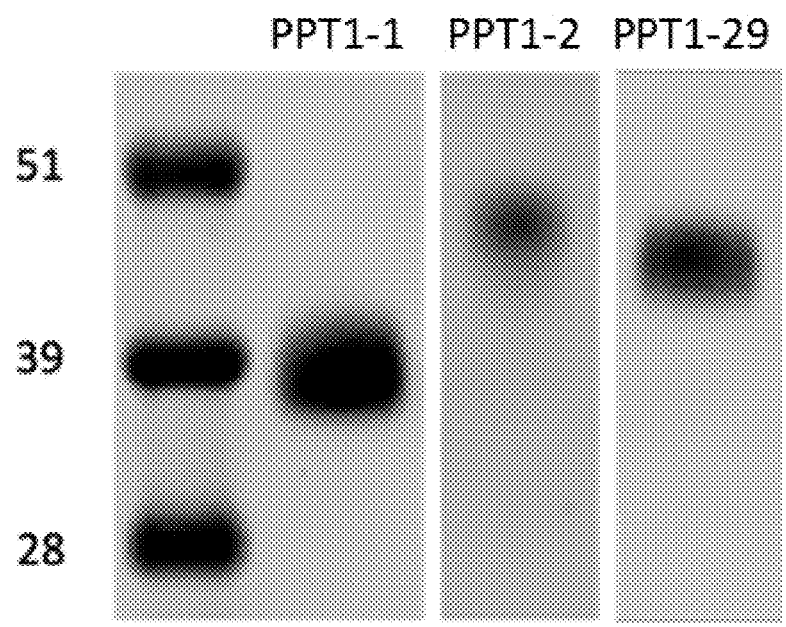
FIG. 13 shows a Western blot of PPT1 from cells expressing recombinant human PPT1 (PPT1-1), recombinant human PPT1 having a vIGF2 targeting domain (PPT1-2) and recombinant human PPT1 having a vIGF2 targeting domain and a BiP signal sequence (PPT1-29).
Figure 14:
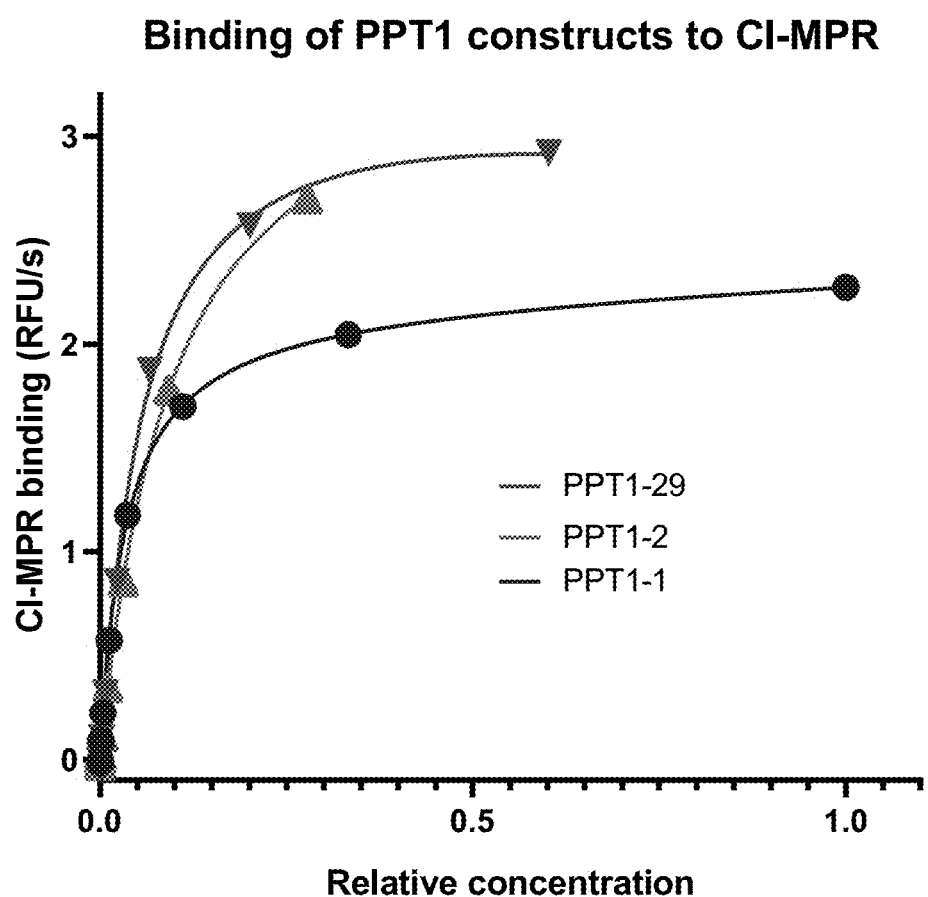
FIG. 14 shows binding of PPT1 constructs to CI-MPR.

The PPT1 constructs were transiently expressed in HEK293T cells for 3 days and the PPT1 secreted into the media. Secreted PPT1 was quantified by Western Blotting, and assayed for CI-MPR binding using established methods. Secreted PPT1 is shown in FIG. 13. CI-MPR binding is shown in FIG. 14.

Example 7: Testing Gene Therapy Vectors in an Animal Model of Pompe Disease

Pompe Gene Therapy: Preclinical Proof of Concept Study Design

Figure 16:
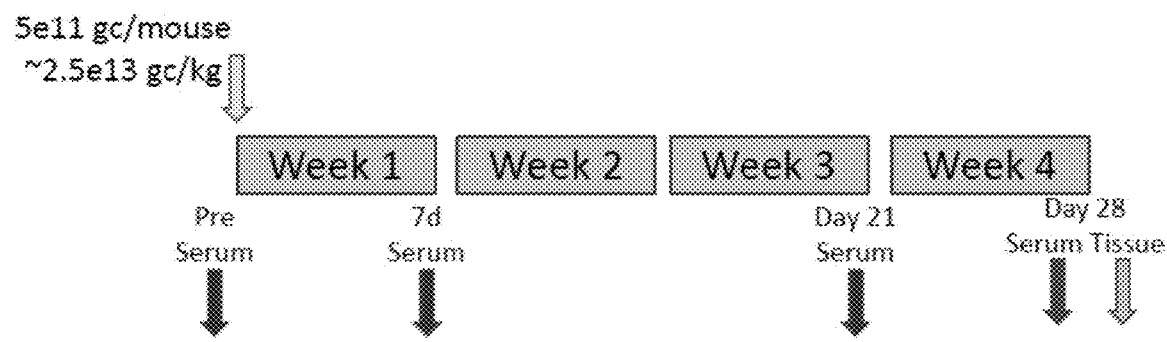
FIG. 16 shows the study design of a 4 week mouse study of gene therapy in a GAA knockout mouse.

A preclinical study was conducted in GAA knockout (GAA KO) mice using a high dose for initial comparison of constructs. The constructs are shown in FIG. 12. Mice were treated with vehicle or one of two constructs, Natural—hGAA or Engineered—hGAA. Mice were administered 5e11 gc/mouse (approximately 2.5e13 gc/kg). GAA knockout mice were used at age 2 months. Normal (wildtype) mice were used as a control. The study design is outlined in FIG. 16.

Pompe Gene Therapy: Plasma

Figure 17:
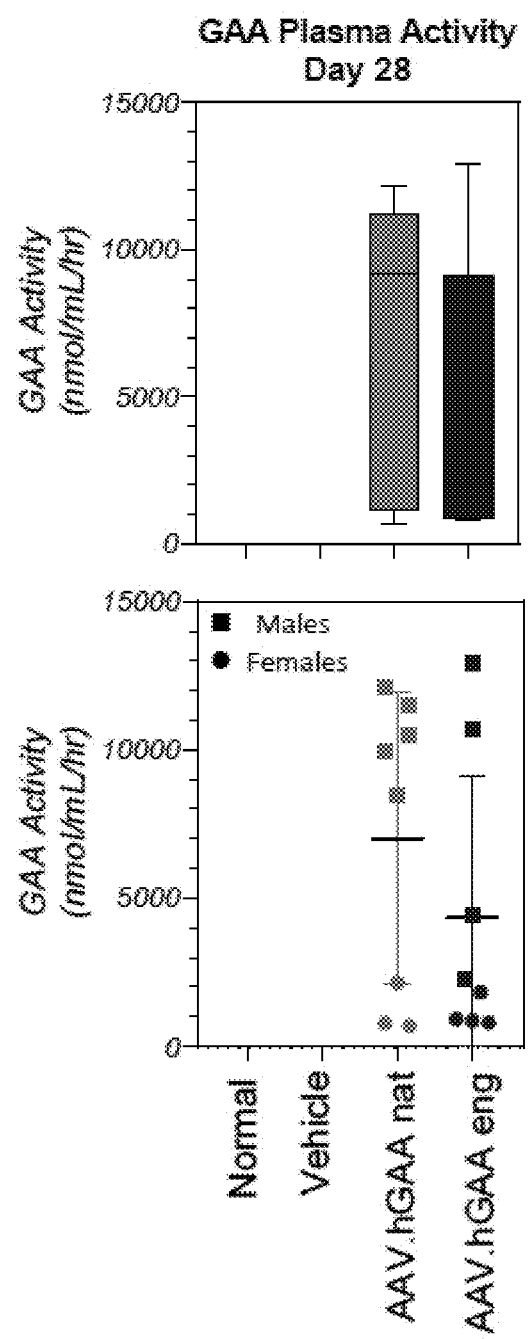
FIG. 17 shows GAA plasma activity in untreated wild type ("Normal") mice or GAA knockout mice treated with gene therapy vectors or vehicle as indicated.
Figure 18:
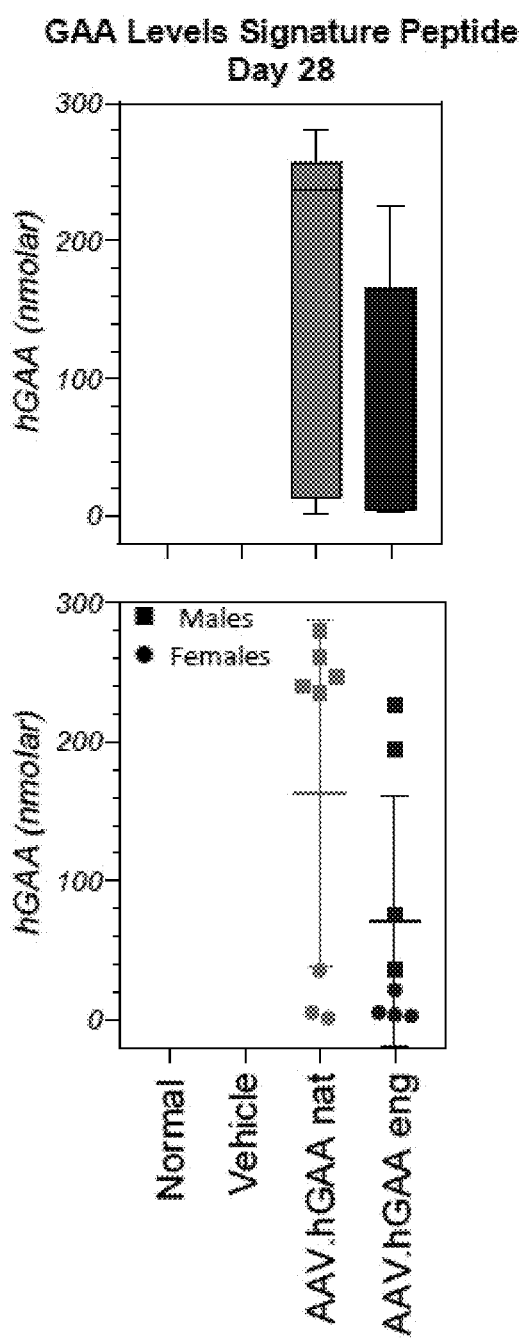
FIG. 18 shows GAA levels measured in untreated wild type ("Normal") mice or GAA knockout mice treated with gene therapy vectors or vehicle as indicated.
Figure 19:
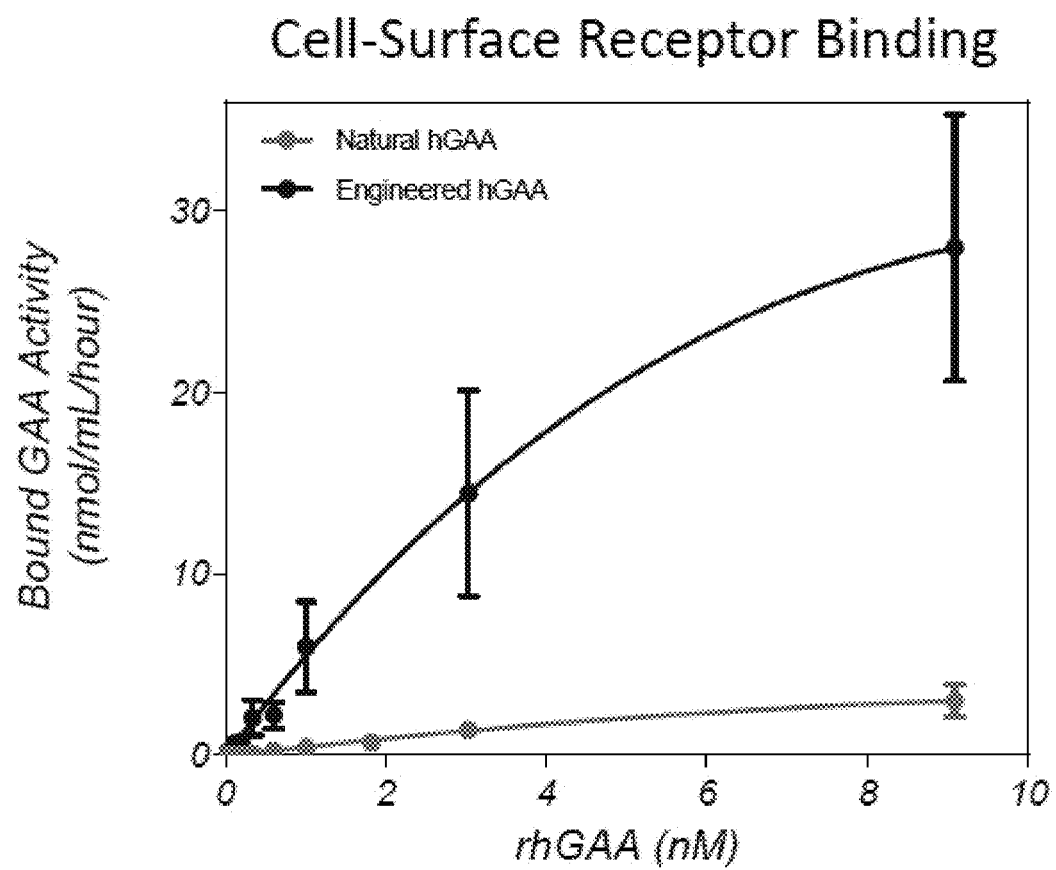
FIG. 19 shows cell surface receptor binding of rhGAA from plasma samples obtained from treated mice as indicated.
Figure 27:
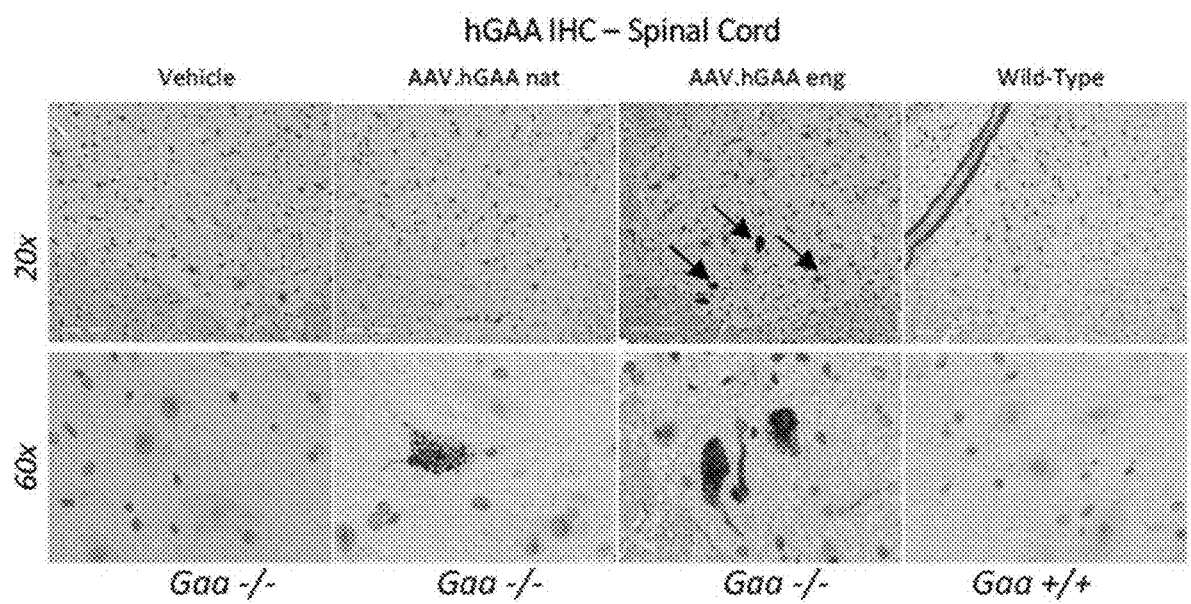
FIG. 27 shows hGAA immunohistochemistry of spinal cord from untreated wild type mice or GAA knockout mice treated with gene therapy vectors or vehicle as indicated.

Plasma was collected from wild type (normal) mice or GAA KO mice treated with vehicle or a gene therapy vector as indicated and GAA activity and cell surface binding was measured. Data are summarized in FIG. 17, FIG. 27, and FIG. 19. Similar high GAA levels were seen in mice treated with gene therapy vectors (FIG. 17, FIG. 18). However, greater cell targeting receptor binding was observed with the engineered construct (FIG. 19).

Pompe Gene Therapy: Quadriceps

Figure 28:
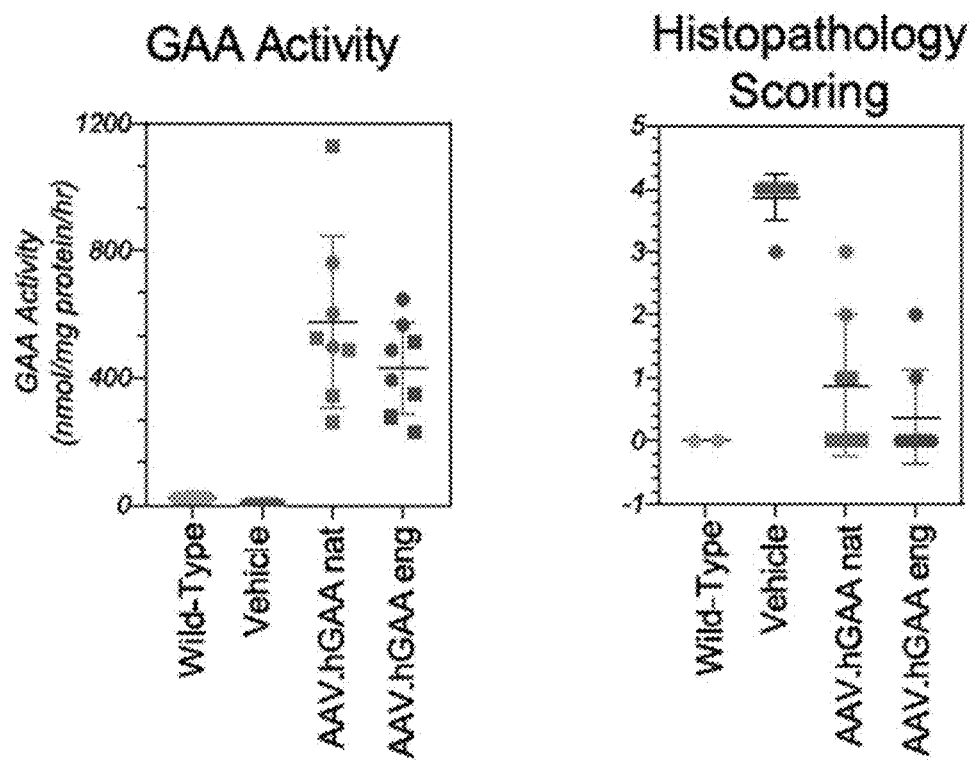
FIG. 28 shows quadriceps GAA activity and glycogen histopathology scoring from untreated wild type ("Normal") mice or GAA knockout mice treated with gene therapy vectors or vehicle as indicated.
Figure 29:
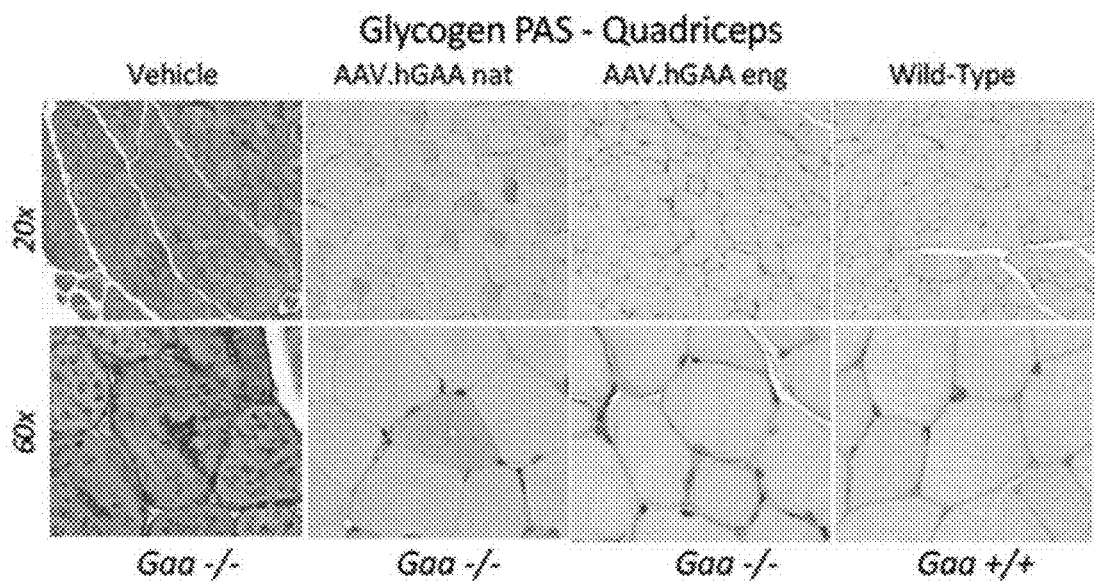
FIG. 29 shows glycogen luxol/PAS for quadriceps from untreated wild type mice or GAA knockout mice treated with gene therapy vectors or vehicle as indicated.
Figure 30:
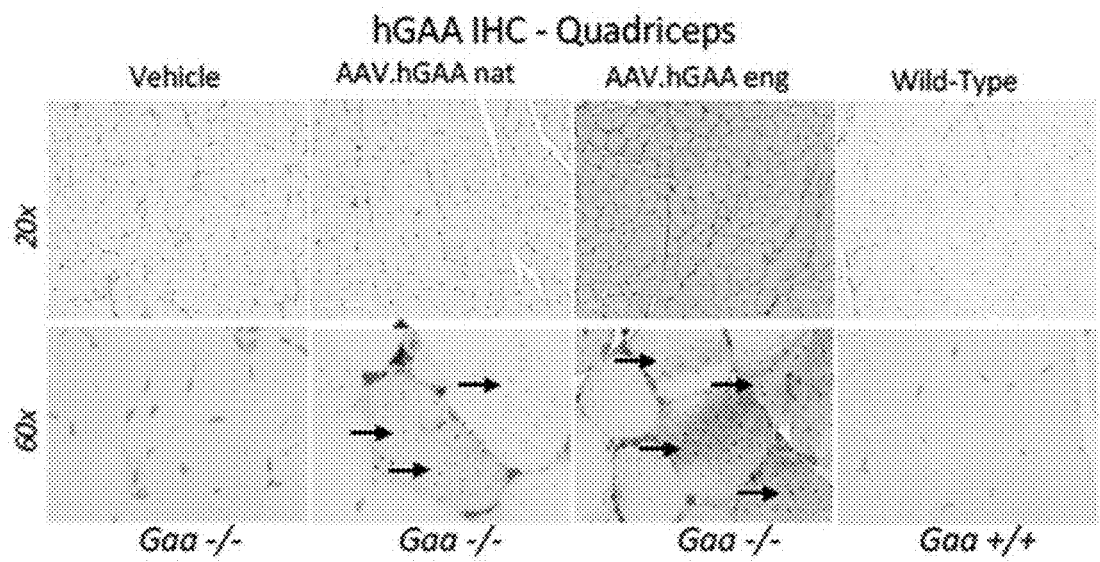
FIG. 30 shows hGAA immunohistochemistry of quadriceps from untreated wild type mice or GAA knockout mice treated with gene therapy vectors or vehicle as indicated.

GAA activity, and glycogen storage/cytoplasmic vacuolization were assessed in normal (wild type) mice and treated GAA KO mice (FIG. 28). GAA activity in the quadriceps was about 20 fold higher than wild type. Glycogen PAS (FIG. 29) and immunohistochemistry (FIG. 30) were also assessed. Immunohistochemistry showed greater lysosomal targeting of engineered hGAA compared to wild type. Glycogen reduction was more consistent for engineered hGAA by PAS staining.

Pompe Gene Therapy: Triceps

Figure 31:
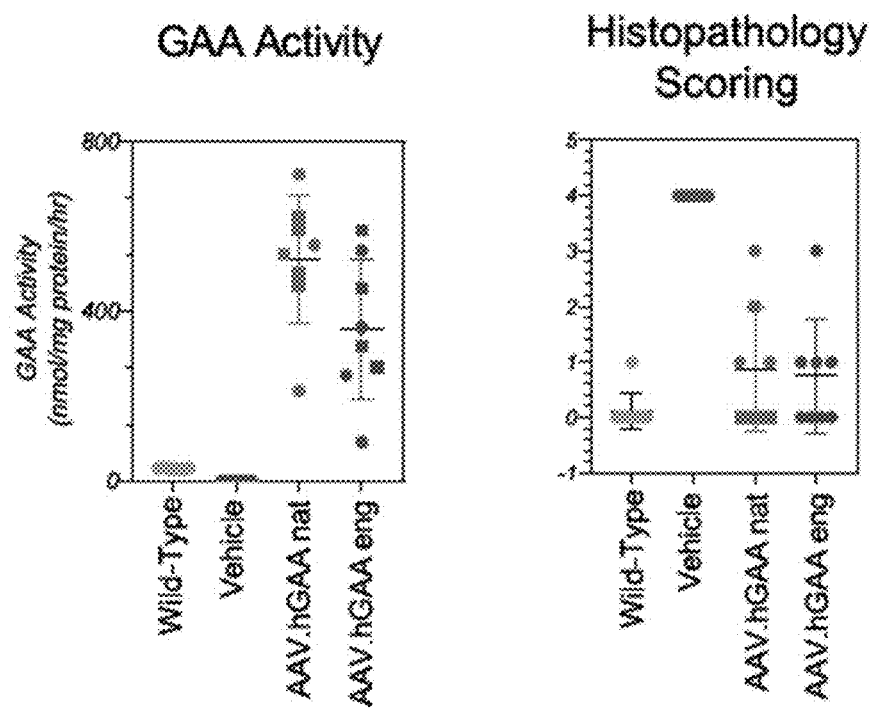
FIG. 31 shows triceps GAA activity and histopathology scoring for untreated wild type ("Normal") mice or GAA knockout mice treated with gene therapy vectors or vehicle as indicated.
Figure 32:
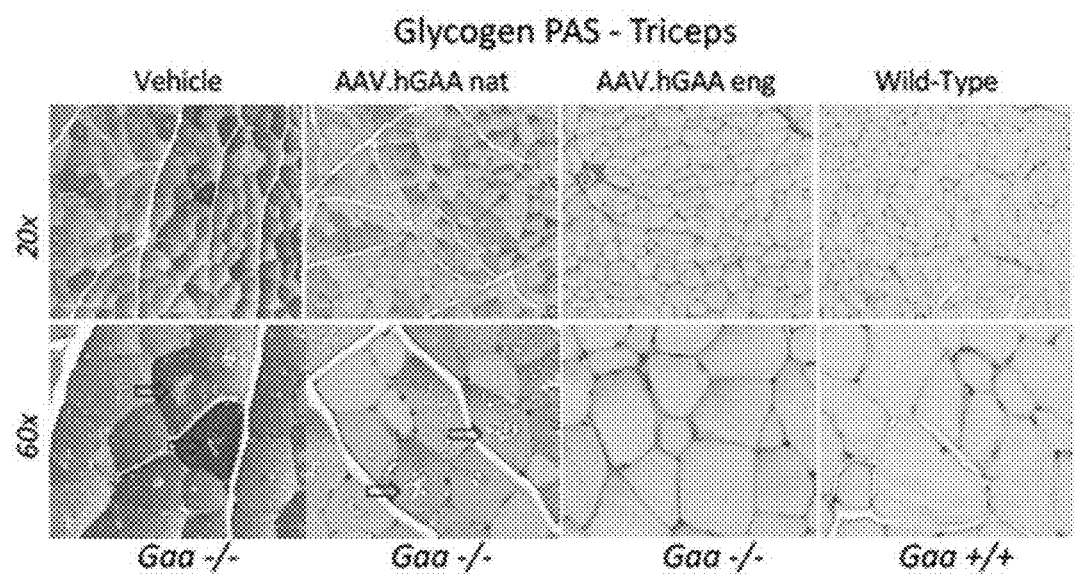
FIG. 32 shows glycogen luxol/PAS of triceps from untreated wild type mice or GAA knockout mice treated with gene therapy vectors or vehicle as indicated.
Figure 33:
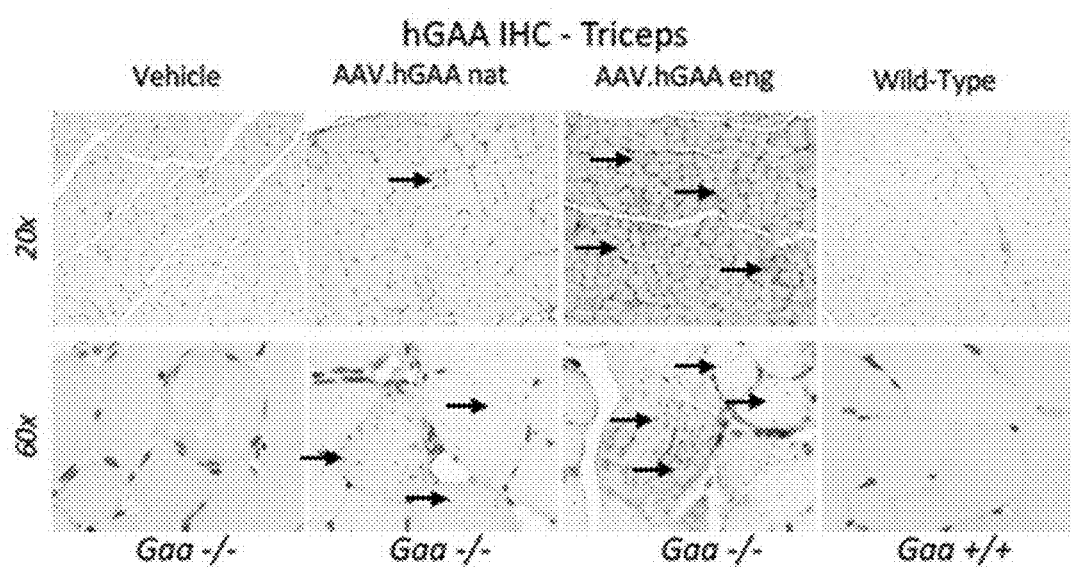
FIG. 33 shows hGAA immunohistochemistry of triceps from untreated wild type mice or GAA knockout mice treated with gene therapy vectors or vehicle as indicated.

GAA activity, and glycogen storage/cytoplasmic vacuolization were assessed in normal (wild type) mice and in treated GAA KO mice (FIG. 31). GAA activity was about 10-15 fold higher than wild type. Immunohistochemistry and glycogen PAS were also assessed (FIG. 32 and FIG. 33). Immunohistochemistry illustrated greater lysosomal targeting of engineered hGAA compared to wildtype GAA. Glycogen reduction was more consistent for engineered hGAA as measured by PAS staining.

Pompe Gene Therapy: Tibialis Anterior (TA)

Figure 21:
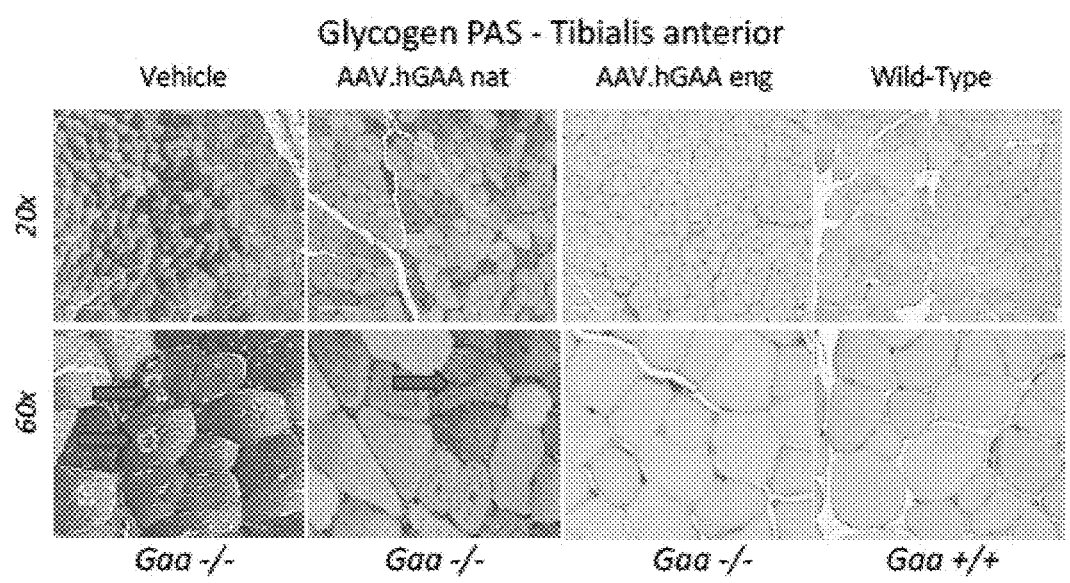
FIG. 21 shows glycogen PAS of tibialis antierior from untreated wild type mice or GAA knockout mice treated with gene therapy vectors or vehicle as indicated.
Figure 22:
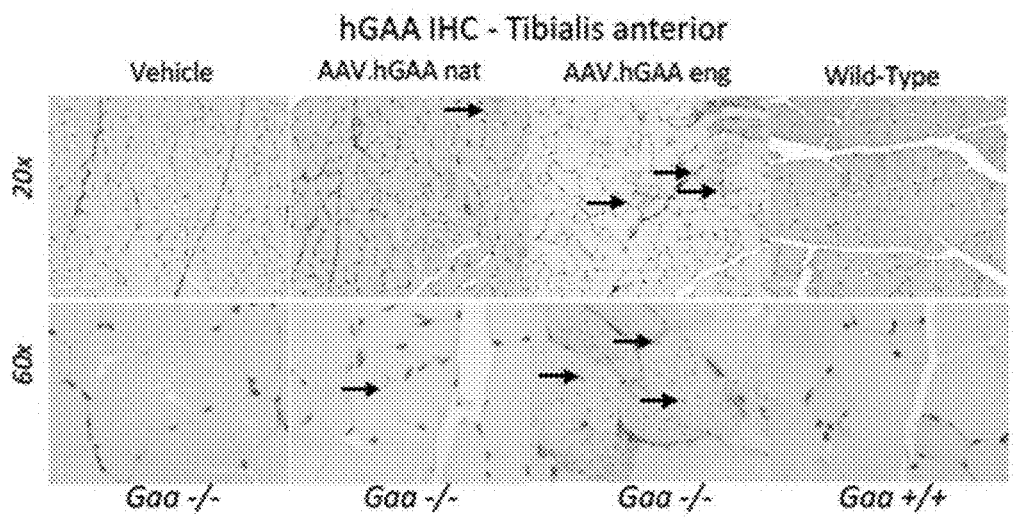
FIG. 22 shows hGAA immunohistochemistry of tibialis antierior from untreated wild type mice or GAA knockout mice treated with gene therapy vectors or vehicle as indicated.

GAA activity, and glycogen storage/cytoplasmic vacuolization were assessed in normal (wild type) and treated GAA KO mice (FIG. 20). GAA activity in the TA was about 15-20 fold higher than wild type. Immunohistochemistry and glycogen PAS were also assessed (FIG. 21 and FIG. 22). Immunohistochemistry illustrated greater lysosomal targeting of engineered hGAA compared to wildtype GAA. Glycogen levels were close to wildtype levels. Glycogen reduction was more consistent for engineered hGAA by PAS staining.

Pompe Gene Therapy: Brain and Spinal Cord

Figure 23:
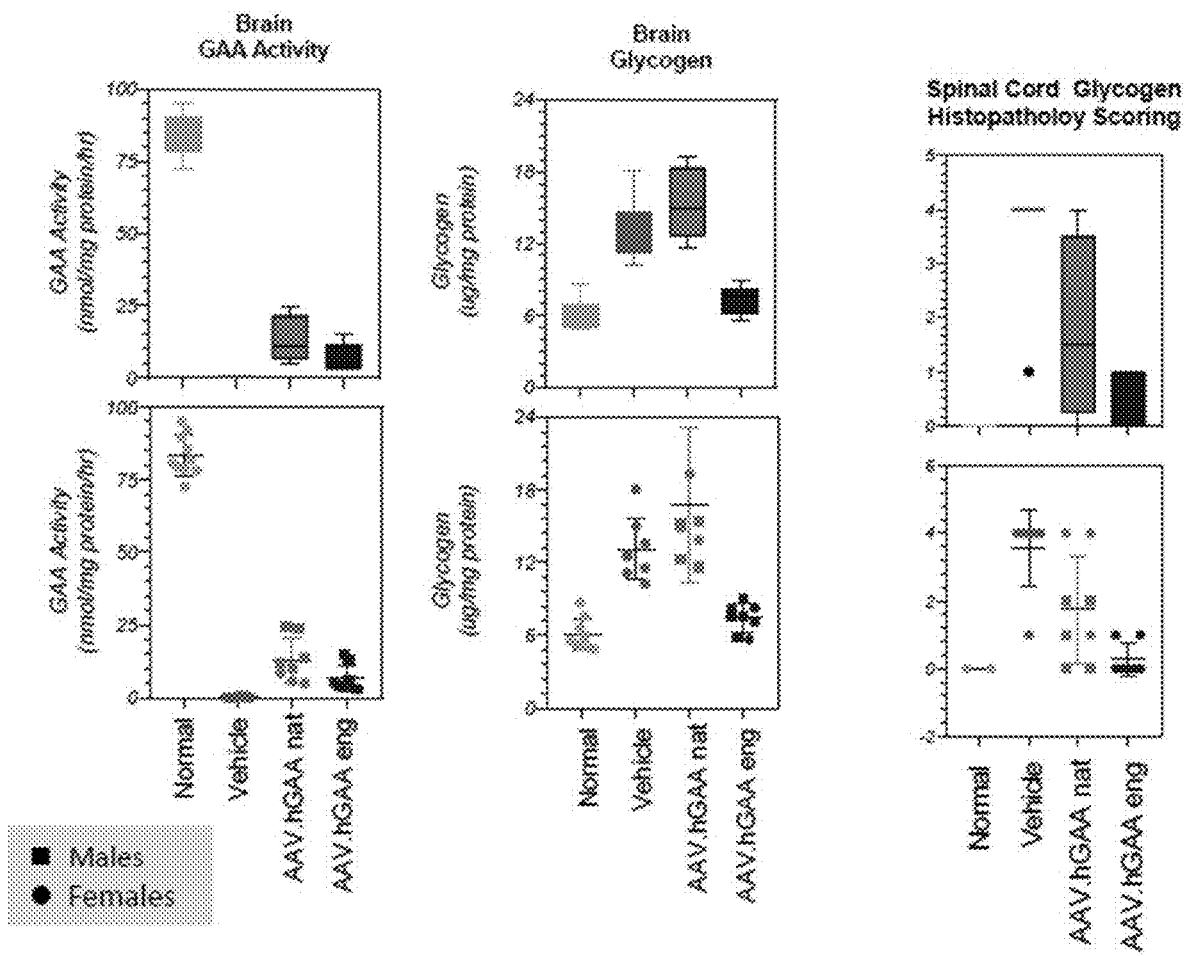
FIG. 23 shows brain GAA activity, brain glycogen, and spinal cord glycogen histopathology scoring for brain and spinal cord from untreated wild type ("Normal") mice or GAA knockout mice treated with gene therapy vectors or vehicle as indicated.
Figure 24:
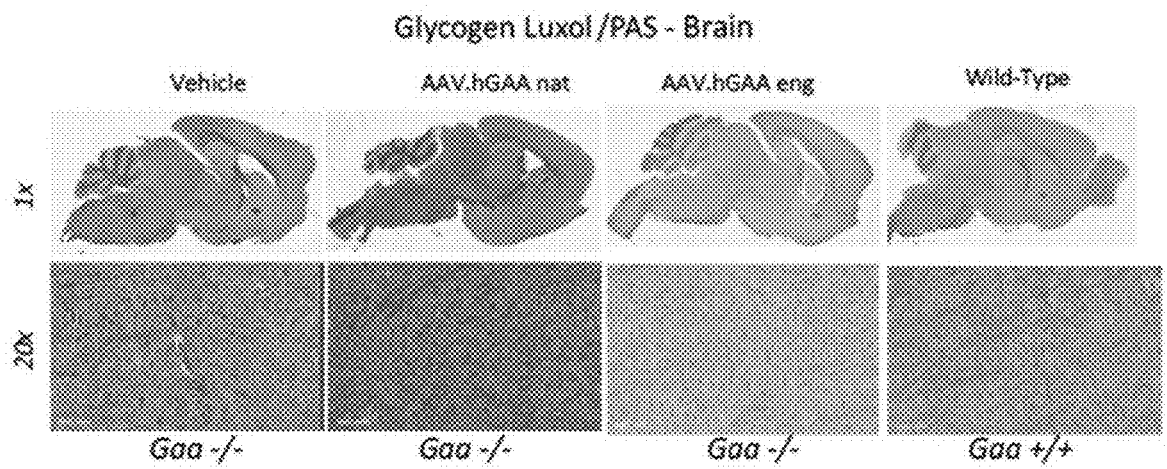
FIG. 24 shows glycogen PAS of brain from untreated wild type mice or GAA knockout mice treated with gene therapy vectors or vehicle as indicated.
Figure 25:
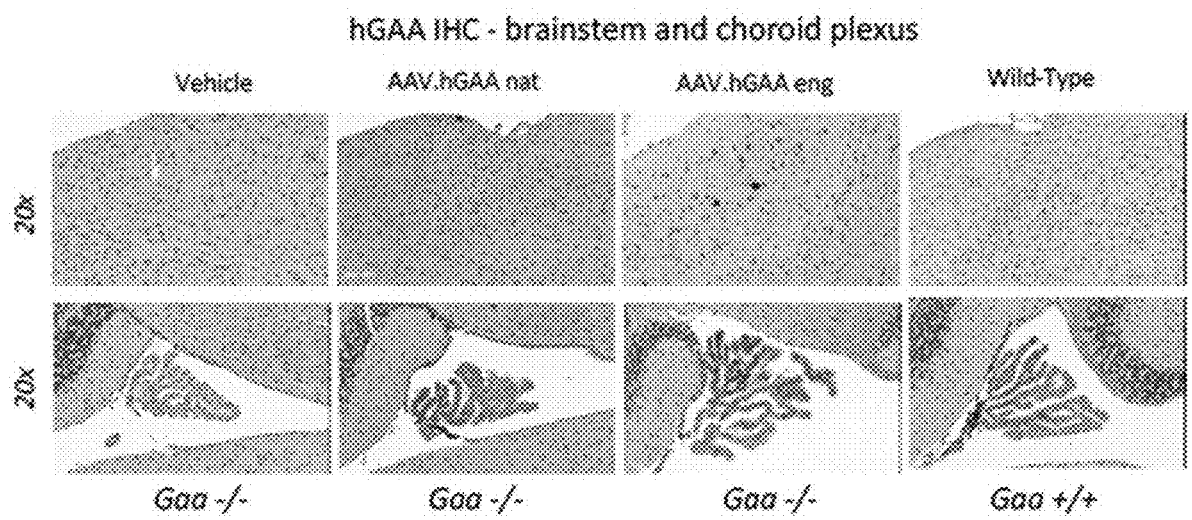
FIG. 25 shows hGAA immunohistochemistry of brainstem and choroid plexus from untreated wild type ("Normal") mice or GAA knockout mice treated with gene therapy vectors or vehicle as indicated.
Figure 26:
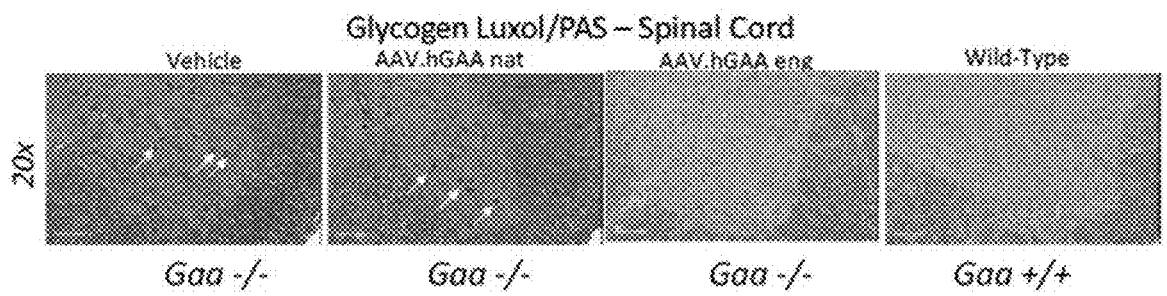
FIG. 26 shows glycogen PAS of spinal cord from untreated wild type mice or GAA knockout mice treated with gene therapy vectors or vehicle as indicated.

GAA activity, glycogen content, and glycogen storage/cytoplasmic vacuolization were assessed in normal (wild type) mice and treated GAA KO mice (FIG. 23). GAA activity in the brain was about 5 fold lower than wildtype. Immunohistochemistry and glycogen PAS were also assessed (FIG. 24, FIG. 25, FIG. 26, FIG. 27). Immunohistochemistry indicated that there may be a direct transduction of some cells. However, little to no glycogen clearance was obtained with the natural construct. Glycogen levels were close to wild type levels for the engineered construct even though activity was only 20% of wild type. PAS staining in the spinal cord shows little to no glycogen clearance with the natural construct. Glycogen levels close to wild type for engineered construct was observed in the ventral horn including motor neurons. Immunohistochemistry demonstrated direct transduction in spinal cord neurons. Engineered hGAA produced by the choroid plexus and neuronal cells was able to reduce glycogen by cross correction in the spinal cord while little glycogen reduction was observed for natural hGAA.

Conclusions

Overall the data in this example demonstrated that the engineered gene therapy constructs have dramatically better uptake into tissues and glycogen reduction than the wildtype GAA used in conventional treatments, including effects in the brain and spinal cord.

Example 8: Animal Study Protocols

AAVhu68 vectors were produced and titrated by the Penn Vector Core as described. (Lock, Alvira et al. 2010, "Rapid, simple, and versatile manufacturing of recombinant adeno-associated viral vectors at scale." Hum Gene Ther 21(10): 1259-1271).

*Mus musculus*, Pompe mice Gaa knock-out, in a C57BL/6/129 background founders were purchased at Jackson Labs (stock #004154, also known as 6neo mice).

Mice received $5 \times 10^{11}$ GCs (approximately $2.5 \times 10^{13}$ GC/kg) of AAVhu68.CAG.hGAA (comprising either natural hGAA (SEQ ID NO: 45) or engineered hGAA (SEQ ID NO:

38) in 0.1 mL via the lateral tail vein, were bled on Day 7 and Day 21 post vector dosing for serum isolation, and were terminally bled (for plasma isolation) and euthanized by exsanguination 28 days post injection. Tissues were promptly collected, starting with brain.

GAA Activity

Plasma was mixed with 5.6 mM 4-MU-α-glucopyranoside pH 4.0 and incubated for three hours at 37° C. The reaction was stopped with 0.4 M sodium carbonate, pH 11.5. Relative fluorescence units, RFUs were measured using a Victor3 fluorimeter, ex 355 nm and emission at 460 nm. Activity in units of nmol/mL/hr was calculated by interpolation from a standard curve of 4-MU. Activity in individual tissue samples were further normalized based on total protein content in the homogenate.

GAA Signature Peptide by LC/MS

Plasma was precipitated in 100% methanol and centrifuged. Supernatants were discarded. The pellet was spiked with a stable isotope-labeled peptide unique to hGAA as an internal standard and resuspended with trypsin and incubated at 37° C. for one hour. The digestion was stopped with 10% formic acid. Tryptic peptides were separated by C-18 reverse phase chromatography and Identified and quantified by ESI-mass spectroscopy. The total GAA concentration in plasma was calculated from the signature peptide concentration.

Cell Surface Receptor Binding Assay

A 96-well plate was coated with receptor, washed, and blocked with BSA. 28 day plasma from AAV treated mice was serially diluted to give a series of decreasing concentrations and incubated with coupled receptor. After incubation the plate was washed to remove any unbound hGAA and 4-MU-α-glucopyranoside added for one hour at 37° C. The reaction was stopped with 1.0 M glycine, pH 10.5 and RFUs were read by a Spectramax fluorimeter; ex 370, emission 460. RFU's for each sample were converted to activity (nmol/mL/hr) by interpolation from a standard curve of 4-MU. Nonlinear regression was done using GraphPad Prism.

Histology

Tissues were formalin fixed and paraffin embedded. Muscle slides were stained with PAS; CNS slides with luxol fast blue/Periodic Acid-Schiff (PAS). A board certified veterinary pathologist (JH) blindly reviewed histological slides. A semi-quantitative estimation of the total percentage of cells with glycogen storage and cytoplasmic vacuolization was done on scanned slides. A score from 0 to 4 was attributed as described in table below.

TABLE 9

Histology Scoring

| | Storage/Vacuolization |
|---|---|
| 0 | 0 |
| 1 | 1 to 9% |
| 2 | 10 to 49% |
| 3 | 50 to 74% |
| 4 | 75 to 100% |

Immuno-Histochemistry (IHC)

We studied transgene expression and cellular localization from slides immunostained using an anti-human GAA antibody (Sigma HPA029126).

Example 9: Histology-Tissue Processing-Protocols and Results in an Animal Model of Pompe Disease All tissues were fixed in 10% NBF (neutral buffered formalin). The assays (PAS and IHC) are routinely used in the field.

PAS Staining of Quadriceps and Triceps (FIG. 29 and FIG. 32)—

Tissues were fixed in 10% NBF and embedded in paraffin. Sections were post-fixed in 1% periodic acid and stained with Schiff's reagent. Afterwards, sections were counterstained with hematoxylin. Glycogen appears as magenta aggregates (lysosomal bound) or diffused pink (cytosolic); nuclei are blue. Based on the images and assuming each is representative of a group, the ranking order in terms of glycogen clearance is: Engineered hGAA >Natural hGAA. The Engineered hGAA construct produced more staining across the entire image compared to the rest, showing an improved endocytosis of GAA protein mediated through the binding of vIGF2 to CI-MPR.

PAS Staining of Spinal Cord (FIG. 26)—

Tissues were fixed in 10% NBF. Post-fixation in 1% periodic acid could have been done prior to or after paraffin embedding. Sections were stained with Schiff's reagent and counterstained likely with methylene blue. Glycogen appears as magenta aggregates (lysosomal bound); nerve fibers appear blue. The images focused on the ventral horn of the spinal cord and glycogen accumulation in the motor neurons. Engineered hGAA appeared most effective in glycogen reduction among the constructs.

GAA IHC (FIG. 22, FIG. 25, FIG. 27, FIG. 30, and FIG. 35)—

Tissues were fixed in 10% NBF and embedded in paraffin. Sections were incubated with an anti-GAA primary antibody, followed by a secondary antibody that recognizes the primary antibody and carries an enzyme tag—HRP. Subsequently, an enzymatic reaction was carried out and a brown-colored precipitating product was formed. Sections were then counterstained with hematoxylin. The constructs showed GAA uptake into muscle fibers (FIG. 31). Engineered hGAA >Natural hGAA. The BiP-vIGF2 construct had more diffused staining across the entire image compared to the rest.

Compared to other vectors, engineered hGAA produced more GAA IHC signals with a punctum-like appearance inside the muscle fibers, showing a much more efficient lysosomal targeting (FIG. 22).

In all, engineered hGAA consistently demonstrated superiority in tissue uptake, lysosomal targeting, and glycogen reduction in various tissues among the constructs.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments described herein may be employed. It is intended that the following claims define the scope of the invention and that methods and structures within the scope of these claims and their equivalents be covered thereby.

What is claimed is:

1. A gene therapy vector comprising a nucleic acid construct encoding a polypeptide comprising:
   (a) a therapeutic protein;
   (b) a peptide that binds to the cation-independent mannose 6-phosphate (M6P) receptor (CI-MPR), wherein the peptide is a variant (vIGF2) peptide comprising the sequence of SEQ ID NO: 31;
   (c) a linker between the therapeutic protein and the peptide that binds CI-MPR; and
   (d) a signal peptide selected from a binding immunoglobulin protein (BiP) signal peptide and a *Gaussia* signal peptide.

2. The gene therapy vector of claim 1, wherein the therapeutic protein is capable of replacing a defective or deficient protein associated with a genetic disorder in a subject having the genetic disorder.

3. The gene therapy vector of claim 2, wherein the genetic disorder is a lysosomal storage disorder.

4. The gene therapy vector of claim 2, wherein the genetic disorder is selected from the group consisting of aspartylglucosaminuria, Batten disease, cystinosis, Fabry disease, Gaucher disease type I, Gaucher disease type II, Gaucher disease type III, Pompe disease, Tay Sachs disease, Sandhoff disease, metachomatic leukodystrophy, mucolipidosis type I, mucolipidosis type II, mucolipidosis type III, mucolipidosis type IV, Hurler disease, Hunter disease, Sanfilippo disease type A, Sanfilippo disease type B, Sanfilippo disease type C, Sanfilippo disease type D, Morquio disease type A, Morquio disease type B, Maroteau-Lamy disease, Sly disease, Niemann-Pick disease type A, Niemann-Pick disease type B, Niemann-Pick disease type C1, Niemann-Pick disease type C2, Schindler disease type I, Schindler disease type II, adenosine deaminase severe combined immunodeficiency (ADA-SCID), chronic granulomatous disease (CGD), and neuronal ceroid lipofuscinosis.

5. The gene therapy vector of claim 2, wherein the genetic disorder is Pompe disease.

6. The gene therapy vector of claim 2, wherein the genetic disorder is a CLN1 disease.

7. The gene therapy vector of claim 1, wherein the therapeutic protein comprises a soluble lysosomal enzyme.

8. The gene therapy vector of claim 1, wherein the therapeutic protein comprises a lysosomal enzyme, wherein the lysosomal enzyme is selected from the group consisting of alpha-galactosidase A, β-glucocerebrosidase, glucocerebrosidase, lysosomal acid lipase, glycosaminoglycan alpha-L-iduronohydrolase, iduronate-2-sulfatase, N-acetylgalactosamine-6-sulfatase, glycosaminoglycan N-acetylgalactosamine 4-sulfatase, palmitoyl protein thioesterase, cyclin dependent kinase like 5, and alpha-glucosidase.

9. The gene therapy vector of claim 8, wherein the therapeutic protein is alpha-glucosidase.

10. The gene therapy vector of claim 8, wherein the therapeutic protein is palmitoyl protein thioesterase.

11. The gene therapy vector of claim 1, wherein the nucleic acid construct further comprises a translation initiation sequence.

12. The gene therapy vector of claim 1, wherein the construct comprises SEQ ID NO:36.

13. The gene therapy vector of claim 1, wherein the polypeptide comprises SEQ ID NO:23.

14. The gene therapy vector of claim 1, wherein the construct comprises SEQ ID NO:38.

15. The gene therapy vector of claim 1, wherein the vIGF2 peptide is at the N-terminus of the polypeptide.

16. The gene therapy vector of claim 1, wherein the vIGF2 peptide is at the C-terminus of the polypeptide.

17. The gene therapy vector of claim 1, wherein the linker peptide comprises SEQ ID NO: 18-21 or SEQ ID NO: 33.

18. The gene therapy vector of claim 1, wherein the gene therapy vector is a virus vector selected from the group consisting of an adenovirus vector, an adeno-associated virus (AAV) vector, a retrovirus vector, a lentivirus vector, a pox virus vector, a vaccinia virus vector, an adenovirus vector, and a herpes virus vector.

19. The gene therapy vector of claim 1, wherein the therapeutic protein is selected from the group consisting of N-acetyl-α-D-glucosaminidase, alpha-glucosidase and palmitoyl protein thioesterase.

* * * * *